US012806087B2

(12) United States Patent
Smet et al.

(10) Patent No.: US 12,806,087 B2
(45) Date of Patent: Nov. 24, 2026

(54) ABSORBENT ARTICLE WITH CHANNELS AND METHOD FOR MANUFACTURING THEREOF

(71) Applicant: Drylock Technologies NV, Zele (BE)

(72) Inventors: Steven Smet, Zele (BE); Werner Van Ingelgem, Zele (BE); Tom Derycke, Zele (BE)

(73) Assignee: Drylock Technologies NV, Zele (BE)

( * ) Notice: Subject to any disclaimer, the term of this patent is extended or adjusted under 35 U.S.C. 154(b) by 993 days.

(21) Appl. No.: 15/733,591

(22) PCT Filed: Mar. 7, 2019

(86) PCT No.: PCT/EP2019/055685
§ 371 (c)(1),
(2) Date: Sep. 8, 2020

(87) PCT Pub. No.: WO2019/170801
PCT Pub. Date: Sep. 12, 2019

(65) Prior Publication Data
US 2021/0000660 A1 Jan. 7, 2021

(30) Foreign Application Priority Data
Mar. 9, 2018 (EP) .................................... 18161032

(51) Int. Cl.
*A61F 13/535* (2006.01)
*A61F 13/15* (2006.01)
(Continued)

(52) U.S. Cl.
CPC ...... *A61F 13/535* (2013.01); *A61F 13/15577* (2013.01); *A61F 13/511* (2013.01); *A61F 13/514* (2013.01); *A61F 2013/5349* (2013.01)

(58) Field of Classification Search
CPC .............. A61F 13/53; A61F 2013/5349; A61F 13/49001; A61F 2013/5315; A61F 13/5323
See application file for complete search history.

(56) References Cited

U.S. PATENT DOCUMENTS 5,433,715 A 7/1995 Tanzer et al.
7,750,203 B2 7/2010 Becker et al.
(Continued)

FOREIGN PATENT DOCUMENTS

EP 3329889 A1 6/2018
EP 3403630 A1 11/2018
(Continued)

OTHER PUBLICATIONS

"Russian Application Serial No. 2020133174, Non-Final Office Action mailed on May 27, 2022", w English Translation, 13 pages.
(Continued)

*Primary Examiner* — Andrew J Mensh
*Assistant Examiner* — Meagan Ngo
(74) *Attorney, Agent, or Firm* — Schwegman Lundberg & Woessner, P.A.

(57) ABSTRACT

An absorbent core comprising an absorbent material between a top core wrap sheet and a back core wrap sheet, said absorbent core having a first and second longitudinal edge and a first and second transverse edge, wherein the absorbent core is provided with at least a first elongated channel, said first channel zone has a first width (w1) at a first position and a second width (w2) at a second position, wherein the first width is larger than the second width.

14 Claims, 87 Drawing Sheets

(51) Int. Cl.

| | |
|---|---|
| *A61F 13/511* | (2006.01) |
| *A61F 13/514* | (2006.01) |
| *A61F 13/534* | (2006.01) |

(56) References Cited

U.S. PATENT DOCUMENTS

| | | | | |
|---|---|---|---|---|
| 2009/0270825 | A1 | 10/2009 | Wciorka et al. | |
| 2015/0173968 | A1* | 6/2015 | Joseph | A61F 13/532 604/361 |
| 2015/0342798 | A1* | 12/2015 | Jackels | A61F 13/5323 604/366 |
| 2016/0058630 | A1* | 3/2016 | Roe | A61F 13/49001 604/385.101 |
| 2016/0206482 | A1 | 7/2016 | Nishikawa et al. | |
| 2016/0235594 | A1* | 8/2016 | Ehrnsperger | A61F 13/494 |
| 2016/0235595 | A1* | 8/2016 | Ehrnsperger | A61F 13/536 |
| 2017/0246047 | A1* | 8/2017 | Ryu | A61F 13/15593 |
| 2018/0116880 | A1* | 5/2018 | Garcia | A61F 13/537 |
| 2020/0352799 | A1* | 11/2020 | Sillerström | A61F 13/15203 |

FOREIGN PATENT DOCUMENTS

| | | | |
|---|---|---|---|
| EP | 3527183 | A1 | 8/2019 |
| RU | 2294727 | | 3/2007 |
| WO | WO-2017022532 | A1 | 2/2017 |
| WO | WO-2018122234 | A1 | 7/2018 |

OTHER PUBLICATIONS

"International Application Serial No. PCT/EP2019/055685, International Search Report mailed Apr. 24, 2019", (Apr. 24, 2019), 3 pgs.
"International Application Serial No. PCT/EP2019/055685, Written Opinion mailed Apr. 24, 2019", (Apr. 24, 2019), 6 pgs.
"Amended claims filed after receipt of European search report", (Feb. 4, 2020), 3 pgs.
"Amended Claims with Annotations", (Feb. 14, 2020), 4 pgs.
"Amended claims with annotations", (Jun. 12, 2020), 3 pgs.
"Amended Description filed after Receipt of European Search Report", (Feb. 14, 2020), 4 pgs.
"Amended Description with Annotations", (Feb. 14, 2020), 4 pgs.
"Amended Description with Annotations", (Jun. 12, 2020), 6 pgs.
"Amended Paragraphs B1 publication for Auxiliary Requests 12-14", (Mar. 10, 2023), 5 pgs.
"Amended Paragraphs B1 publication for Auxiliary Requests 12-14 with Edits", (Mar. 10, 2023), 5 pgs.
"Amended Paragraphs B1 publication for Auxiliary Requests 15-17", (Mar. 10, 2023), 6 pgs.
"Amended Paragraphs B1 publication for Auxiliary Requests 15-17 with Edits", (Mar. 10, 2023). 6 pgs.
"Amended Paragraphs B1 publication for Auxiliary Requests 18-20", (Mar. 10, 2023), 5 pgs.
"Amended Paragraphs B1 publication for Auxiliary Requests 18-20 with Edits", (Mar. 10, 2023), 6 pgs.
"Amended Paragraphs B1 publication for Auxiliary Requests 21-23", (Mar. 10, 2023), 6 pgs.
"Amended Paragraphs B1 publication for Auxiliary Requests 21-23 with Edits", (Mar. 10, 2023), 7 pgs.
"Amended Paragraphs B1 publication for Auxiliary Requests 24-26", (Mar. 10, 2023), 6 pgs.
"Amended Paragraphs B1 publication for Auxiliary Requests 24-26 with Edits", (Mar. 10, 2023), 6 pgs.
"Amended Paragraphs B1 publication for Auxiliary Requests 27-29", (Mar. 10, 2023), 8 pgs.
"Amended Paragraphs B1 publication for Auxiliary Requests 27-29with Edits", (Mar. 10, 2023), 18 pgs.
"Amended Paragraphs B1 publication for Auxiliary Requests 3-5", (Mar. 10, 2023), 3 pgs.
"Amended Paragraphs B1 publication for Auxiliary Requests 9-11", (Mar. 10, 2023), 2 pgs.
"Amended Paragraphs B1 publication for Auxiliary Requests 9-11 with Edits", (Mar. 10, 2023), 12 pgs.
"Amendments Received Before Examination", (Feb. 14, 2020), 5 pgs.
"Annex to the communication—opposition", (Oct. 13, 2022), 9 pgs.
"Annex to the communication—opposition", (Mar. 11, 2020), 2 pgs.
"Auxiliary Request 1", (Jun. 14, 2023), 2 pgs.
"Auxiliary Request 1", (Mar. 21, 2022), 2 pgs.
"Auxiliary Request 10", (Mar. 10, 2023), 2 pgs.
"Auxiliary Request 10 with edits", (Mar. 10, 2023), 3 pgs.
"Auxiliary Request 11", (Mar. 10, 2023), 2 pgs.
"Auxiliary Request 11 with edits", 3 pgs.
"Auxiliary Request 12", (Mar. 10, 2023), 2 pgs.
"Auxiliary Request 12 with edits", (Mar. 10, 2013), 3 pgs.
"Auxiliary Request 13", (Mar. 10, 2023), 2 pgs.
"Auxiliary Request 13 with edits", (Mar. 10, 2023), 3 pgs.
"Auxiliary Request 14", (Mar. 10, 2023), 2 pgs.
"Auxiliary Request 14 with edits", (Mar. 10, 2023), 3 pgs.
"Auxiliary Request 15", (Mar. 10, 2023), 2 pgs.
"Auxiliary Request 15", (May 10, 2023), 2 pgs.
"Auxiliary Request 15 with edits", (Mar. 10, 2023), 3 pgs.
"Auxiliary Request 16", (Mar. 10, 2023), 2 pgs.
"Auxiliary Request 16 with edits", (Mar. 10, 2023), 3 pgs.
"Auxiliary Request 17", (Mar. 10, 2023), 2 pgs.
"Auxiliary Request 17 with edits", (Mar. 10, 2023), 3 pgs.
"Auxiliary Request 18", (Mar. 10, 2023), 2 pgs.
"Auxiliary Request 18 with edits", (Mar. 10, 2023), 3 pgs.
"Auxiliary Request 19", (Mar. 10, 2023), 2 pgs.
"Auxiliary Request 19 with edits", (Mar. 10, 2023), 1 pg.
"Auxiliary Request 2", (Mar. 21, 2022), 2 pgs.
"Auxiliary Request 2 version 2", (Jun. 14, 2023), 2 pgs.
"Auxiliary Request 20", (Mar. 10, 2023), 2 pgs.
"Auxiliary Request 20 with edits", (Mar. 10, 2023), 1 pg.
"Auxiliary Request 21", (Mar. 10, 2023), 2 pgs.
"Auxiliary Request 21 with edits", (Mar. 10, 2023), 3 pgs.
"Auxiliary Request 22", (Mar. 10, 2023), 2 pgs.
"Auxiliary Request 22 with edits", (Mar. 10, 2023), 3 pgs.
"Auxiliary Request 23", (Mar. 10, 2023), 2 pgs.
"Auxiliary Request 23 with edits", (Mar. 10, 2023), 3 pgs.
"Auxiliary Request 24", (Mar. 10, 2023), 2 pgs.
"Auxiliary Request 25", (Mar. 10, 2023), 2 pgs.
"Auxiliary Request 25 with edits", (Mar. 10, 2023), 3 pgs.
"Auxiliary Request 26", (Mar. 10, 2023), 2 pgs.
"Auxiliary Request 26 with edits", (Mar. 10, 2023), 3 pgs.
"Auxiliary Request 27", (Mar. 10, 2023), 1 pg.
"Auxiliary Request 27 with edits", (Mar. 10, 2023), 3 pgs.
"Auxiliary Request 28", (Mar. 10, 2023), 2 pgs.
"Auxiliary Request 28 with edits", 3 pgs.
"Auxiliary Request 29", (Mar. 10, 2023), 2 pgs.
"Auxiliary Request 29 with edits", (Mar. 10, 2023), 3 pgs.
"Auxiliary Request 3", (Mar. 10, 2023), 2 pgs.
"Auxiliary Request 3", (Mar. 21, 2022), 2 pgs.
"Auxiliary Request 3 with Edits", (Mar. 10, 2023), 2 pgs.
"Auxiliary Request 4", (Mar. 10, 2023), 2 pgs.
"Auxiliary Request 4", (Mar. 21, 2022), 2 pgs.
"Auxiliary Request 4 version 2", (Jun. 14, 2023), 2 pgs.
"Auxiliary Request 4 with Edits", (Mar. 10, 2023), 2 pgs.
"Auxiliary Request 5", (Mar. 10, 2023), 2 pgs.
"Auxiliary Request 5", (Mar. 21, 2022), 3 pgs.
"Auxiliary Request 5 version 2", (Jun. 14, 2023), 2 pgs.
"Auxiliary Request 5 with Edits", (Mar. 10, 2023), 2 pgs.
"Auxiliary Request 6", (Mar. 10, 2023), 2 pgs.
"Auxiliary Request 6", (Mar. 21, 2022), 3 pgs.
"Auxiliary Request 6 version 2", (Jun. 14, 2023), 2 pgs.
"Auxiliary Request 6 with Edits", (Mar. 10, 2023), 2 pgs.
"Auxiliary Request 7", (Mar. 10, 2023), 2 pgs.
"Auxiliary Request 7", (Mar. 21, 2022), 3 pgs.
"Auxiliary Request 7 version 2", (Mar. 10, 2023), 2 pgs.
"Auxiliary Request 7 with Edits", (Mar. 10, 2023), 2 pgs.
"Auxiliary Request 8", (Mar. 10, 2023), 2 pgs.
"Auxiliary Request 8", (Mar. 21, 2022), 3 pgs.
"Auxiliary Request 8 version 2", (Jun. 14, 2023), 2 pgs.
"Auxiliary Request 8 with edits", (Mar. 10, 2023), 2 pgs.

(56) References Cited

OTHER PUBLICATIONS

"Auxiliary Request 9", (Mar. 10, 2023), 2 pgs.
"Auxiliary Request 9", (Mar. 21, 2022), 3 pgs.
"Auxiliary Request 9 version 2", (Jun. 14, 2023), 2 pgs.
"Auxiliary Request 9 with edits", (Mar. 10, 2023), 3 pgs.
"Brief communication—Opposition proceedings", (Apr. 21, 2022), 14 pgs.
"Brief communication—Opposition proceedings", (Jan. 24, 2022), 3 pgs.
"Brief communication—Opposition proceedings", (Jun. 14, 2021), 5 pgs.
"Brief communication—Opposition proceedings", (Mar. 17, 2023), 8 pgs.
"Brief communication—Opposition proceedings", (Mar. 24, 2022), 61 pgs.
"Brief communication—Opposition proceedings 2", (Mar. 17, 2023), 14 pgs.
"Claims", (Jun. 12, 2020), 2 pgs.
"Communication about Intention to Grant a European Patent", (Sep. 16, 2021), 5 pgs.
"Communication from the Examining Division", (Mar. 11, 2020), 2 pgs.
"Communication of a notice of opposition", (May 18, 2021), 24 pgs.
"Communication of amended entries", (Jan. 24, 2022), 2 pgs.
"Consolidated List", (Jun. 8, 2021), 1 pg.
"Decision to Grant a European Patent", (Jan. 14, 2021), 2 pgs.
"Description", (Jun. 12, 2020), 6 pgs.
"Document Annexed to the Extended European Search Report", (May 23, 2018), 26 pgs.
"Electric Receipt", (Apr. 13, 2022), 1 pg.
"Electric Receipt", (Oct. 18, 2022), 1 pg.
"Electric Receipt", (May 11, 2021), 1 pg.
"Electronic receipt", (Jun. 8, 2021), 1 pg.
"Electronic receipt", (Mar. 10, 2023), 1 pg.
"Electronic receipt", (Mar. 9, 2023), 1 pg.
"EP 35326294 application", (Jan. 27, 2021), 2 pgs.
"European Application No. 18161032 Brief Communication for Opposition mailed on Mar. 17, 2023", (Mar. 17, 2023), 8 pgs.
"European Search Opinion", (May 23, 2018), 3 pgs.
"European Search Report", (May 23, 2018), 2 pgs.
"Information about the result of oral proceedings", (May 10, 2023), 2 pgs.
"Information on Search Strategy", (May 23, 2018), 1 pg.
"Intention to Grant Signatures", (Sep. 16, 2021), 1 pg.
"Letter accompanying subsequently filed items", (Mar. 8, 2023), 1 pg.
"Letter accompanying subsequently filed items", (Mar. 13, 2019), 1 pg.
"Letter accompanying subsequently filed items", (Jun. 12, 2020), 1 pg.
"Letter accompanying subsequently filed items", (Apr. 13, 2022), 1 pg.
"Letter accompanying subsequently filed items", (Jun. 8, 2021), 1 pg.
"Letter accompanying subsequently filed items", (May 11, 2021), 2 pgs.
"Letter regarding the opposition procedure", (Apr. 13, 2022), 13 pgs.
"Letter regarding the opposition procedure (no time limit)", (Jun. 8, 2021), 4 pgs.
"Notice of further oppositions to opponent(s)", (Nov. 9, 2021), 2 pgs.
"Notice of Opposition", (May 11, 2021), 18 pgs.
"Notice of Opposition to a European Patent", (May 11, 2021), 5 pgs.
"Opposition against EP patent No. 3536294", (Mar. 10, 2023), 7 pgs.
"Partial set of Drawings Filed in Response to Formal Objections", (Mar. 13, 2019), 1 pg.
"Receipt", (Mar. 21, 2022), 2 pgs.
"Reply of the patent proprietor to the notice(s) of opposition", (Mar. 21, 2022), 1 pg.
"Reply of the patent proprietor to the notices of opposition", (Mar. 21, 2022), 17 pgs.
"Reply to Communication from the Examining Division", (Jun. 12, 2020), 7 pgs.
"Request concerning representative opponent", (Oct. 25, 2021), 1 pg.
"Request for Correction of Errors in Filed Documents", (Mar. 13, 2019), 1 pg.
"Submission in Opposition Proceedings", (Mar. 21, 2022), 2 pgs.
"Summons to attend oral proceedings", (Jan. 3, 2023), 1 pg.
"Summons to attend oral proceedings", (Oct. 13, 2022), 1 pg.
"Text Intended to Grant Clean Copy", (Sep. 16, 2021), 179 pgs.
"Transmission Certificate for EP Patent Pursuant to Rule 74 EPC", (Feb. 8, 2021), 1 pg.
"Transmittal of decision—summons—opposition", (Mar. 10, 2023), 15 pgs.
"Transmittal of decision—summons—opposition 2H_2WK16_SC", (Mar. 10, 2023), 15 pgs.
"Written submission in preparation to-during oral proceedings", (Mar. 9, 2023), 13 pgs.

* cited by examiner

ABSORBENT ARTICLE WITH CHANNELS AND METHOD FOR MANUFACTURING THEREOF

PRIORITY APPLICATIONS

This application is a U.S. National Stage Filing under 35 U.S.C. § 371 from International Application No. PCT/EP2019/055685, filed on Mar. 7, 2019, and published as WO2019/170801 on Sep. 12, 2019, which claims the benefit of priority to European Application No. 18161032.0, filed on Mar. 9, 2018; the benefit of priority of each of which is hereby claimed herein, and which applications and publication are hereby incorporated herein by reference in their entireties.

TECHNICAL FIELD

The present invention pertains to the technical field of absorbent articles, more preferably disposable personal care articles such as diapers, baby pants, adult incontinent garments, and the like, and to absorbent structures for use in such absorbent articles. More specifically the present invention relates to an absorbent structure comprising an absorbent core between a topsheet and a backsheet. The present invention also relates to a method and apparatus for manufacturing such an absorbent article.

BACKGROUND

Absorbent articles such as diapers, baby pants, adult incontinent garments and the like, typically comprise an absorbent core, positioned in between a liquid permeable or pervious, hydrophilic or semi hydrophilic topsheet and a liquid impermeable or impervious backsheet. The absorbent core comprises absorbent material that is able to absorb fluid and liquid bodily excretions of the user of the absorbent article.

The absorbent material of the absorbent core may be an absorbent particulate polymer material which is dispersed in a matrix of cellulose fibers or fluff pulp in order to prevent the particulate material from aggregating, as well as to prevent gel blocking. Gel blocking can occur when the absorbent particulate polymer material absorbs liquid, as they tend to typically swell and form a gel structure. This gel structure often blocks the further transfer of liquid into the remaining absorbent core. As a result, the liquid may be unable to reach the remaining absorbent particulate polymer material and the efficiency of the overall absorbent article decreases significantly. Existing fluff pulp materials are not suited to cope with rapid, subsequent insults of fluid since they possess limited distribution capacities. Moreover existing fluff pulp materials exhibit a limited capacity of overall liquid intake. Furthermore, existing absorbent cores containing fluff pulp have a limited wet integrity, which leads to the shape and fit of the absorbent article being deformed when e.g. an absorbent article is being worn by a baby which moves around.

In recent years, there has been a strong demand for more flexible, thinner, light-weight, absorbent articles to resolve various problems associated with manufacturing, marketing, design, fit, wearing comfort, distribution, garbage disposal, material and energy consumption, transport and storage costs and the like. This lead to the search for and the development and production of absorbent articles of which the absorbent cores contains little to no cellulose fibers or fluff pulp, as the latter tend to be quite bulky, thus rendering generally more thick absorbent cores which reduces the overall wearing comfort of the user of the absorbent article.

Hence, various absorbent cores containing little to no cellulose fibers or fluff pulp were developed in the past few years to try and overcome the above drawbacks, whereby the relative high amounts of absorbent polymer materials necessary to replace the absorption, distribution and retention capacity of the excluded cellulose fibers and/or fluff pulp were loaded, distributed and immobilized within these new absorbent cores according to several techniques. However given the ability and capacity of the absorbent core to absorb, transport and retain fluid and liquids is heavily dependent upon the form, position and/or manner wherein these absorbent polymer materials are incorporated within the absorbent core several drawback remained unsolved. In general the substantially heterogeneously distributed absorbent cores having non-continuous compartments and/or clusters of absorbent polymer material have in general proven to be better in coping with the above mentioned problems, nevertheless they also proved to remain unsatisfactory within most of the available absorbent articles. Especially problematic however, were the substantially homogenously distributed absorbent structures having continuous layers of absorbent polymer particulate material given they exhibit a substantially homogenous swollen absorbent polymer material area for second, third and next liquid insults wherein the dry and/or wetted absorbent polymer material layer may actually act as a liquid barrier. These problems and complications are especially prevalent within very flexible, thin, lightweight absorbent structures wherein high amounts of absorbent polymer material are distributed within the absorbent core of the absorbent article. Adding even more, thicker and larger overlying acquisition and dispersing layers did not at all resolve the above cited absorption, distribution and retention problems and moreover made the absorbent articles commercially unviable, environmentally unsustainable and more difficult to manufacture, store and transport.

Furthermore an existing problem which has been associated with such absorbent cores containing no or little cellulose fibers or fluff pulp is related to the migration, loss and leakage of the absorbent particulate polymer material from the absorbent article during dry and/or wet state, which leads to irritation, skin problems and overall discomfort for the user. This again is also especially true in the more homogenously distributed absorbent structures given their immobilization and liquid distribution properties remain unsatisfactory to date. This lack of effective and efficient immobilization and liquid distribution leads to dysfunctional absorbent articles due to lowered uptake capacity, gel blocking, enhanced rewet values, leakages and the creation of ruptures and/or pinholes through the liquid pervious topsheet and/or liquid impervious backsheet of such absorbent articles.

Absorbent cores generally have a high absorbent capacity and the absorbent core may expand several times its weight and volume. These increases may cause the absorbent article to deform and/or to sag in the crotch region as they become saturated with liquid. This may cause leaks to occur via a longitudinal and/or transversal edge of the absorbent article.

SUMMARY

The object of embodiments of the invention is to provide an absorbent article of the type stated in the preamble, with improved liquid distribution and absorption capacities.

According to an aspect of the invention, there is provided an absorbent core comprising an absorbent material between a top core wrap sheet and a back core wrap sheet. The absorbent core has a first and second longitudinal edge and a first and second transverse edge. The absorbent core is provided with at least a first elongated channel zone, in particular an attachment zone. The first channel zone has a first width (w1) at a first position and a second width (w2) at a second position. The first width is larger than the second width. At the first elongate channel zone any one of the following conditions or any combination thereof is fulfilled: less absorbent material is present as compared to other regions of the absorbent core, substantially no absorbent material is present, the top core wrap sheet is attached to the back core wrap sheet.

By providing a first elongate channel zone which has a first width (w1) at a first position and a second width (w2) at a second position, upon wetting of the absorbent core an elongate channel is created such that liquid can be distributed and absorbed in an improved manner. The first channel zone has a first width (w1) at a first position and a second width (w2) at a second position, in which the first width is larger than the second width. In that manner, immediately after wetting, the created elongate channel is wider at the position according to the first position of the first elongate channel zone, and as a result a larger quantity of liquid can be temporarily held there. Because a larger quantity of liquid is held and the liquid is distributed quickly, the chance of liquid overflow and leakage during a liquid insult is decreased. Thanks to the channel zones and associated channels the liquid is evenly spread, resulting in the formation of tubes which provide a tub shape to the absorbent core. Such a tub shape adapts perfectly to the body. However when too much liquid is absorbed, the channel might be closed by the over-welling tubes, preventing further liquid from entering the channel. As the channel is less wide in the second position, the channel at the second position may not be closed even when the tubes are over-swelling. As a result, the liquid distribution over the absorbent core is further improved and the risk of liquid overflow is further reduced, even during an eventual second liquid insult, a third liquid insult and a fourth liquid insult. On the other hand, the channel is less wide in the second position, allowing improving the shape of the elongated channel and tubes adjacent to the channel, compared to prior art solution where the channel has a constant width. In that manner, the fitting of the absorbent article to the body of the wearer can be further improved, especially in the wetted state, reducing leakage risks. In addition, it allows a better customization of absorbent cores according to gender, age, and body size of the wearers.

In an exemplary embodiment, the width of the first channel zone increases from the second position to the first position. In this manner the width of the created channel accordingly increases from the second position to the first position, allowing for a more smooth distribution of liquid over the channel.

In an exemplary embodiment, the width of the first channel zone is measured perpendicularly to a center line of the first channel zone. The center line is a line which is at the same distance of opposite edges of the first elongate channel zone. Preferably the opposite edges extend in a length direction of the elongate channel zone. Preferably the center line of the first channel zone is a straight line, or a curve, or a polyline.

In an exemplary embodiment, the first width is at least 2% larger than the second width, preferably 4% larger, more preferably 6% larger, even more preferably 8% larger, e.g. 10% larger or even 20% larger. The first width may also be much larger than the second width, e.g. 50% larger, 60% larger, 70% larger, 100% larger (i.e. the double of the second width), 200% larger, etc. Also, the second width may be very small or zero, i.e. the elongate first channel zone may e.g. end in a point.

In an exemplary embodiment, the distance between the first position and the second position along the center line of the first channel zone is larger than 4% of the length of the absorbent core, preferably 8% larger, more preferably 12% larger, even more preferably 16% larger, most preferably 20% larger, e.g. 30% or 40% or 50% or 60% or 70% or even 100% of the length of the absorbent core.

In an exemplary embodiment, the first position is at a first end of the first channel zone and the second position is at a second end of the first channel zone. The width of the channel zone may then gradually or discontinuously vary between the first end and the second end. It is noted that between the first end and the second end the width may vary in any manner, and may e.g. increase first to decrease afterwards. This allows creating a width pattern creating an improved compromise between a good liquid distribution and a good anatomical fit, reducing leakage. Because of the swelling of the core material of absorbent core upon wetting, the outer bands of absorbent core will rotate around channels inward, making the absorbent article the shape of a tub or cup, such that any liquid which would not yet be absorbed by the absorbent material is maintained in the tub shape.

The varying width of the channel in combination with the tub or cup shape of the channel provides an absorbent article fitting perfectly to the body and a better protection against leakage. Hence the absorbent article creates more freedom of movement for the wearer of a wetted diaper.

In an exemplary embodiment, the first channel zone extends from a crotch region in the direction of the first and/or second transverse edge, which allows a better liquid distribution between crotch region and front and/or back portion of absorbent article.

In an exemplary embodiment, the first channel zone further has a third width (w3) at a third position, wherein the second position is located between the first position and the third position, wherein the third width is larger than the second width, and the width of the first channel zone increases from the second position to the third position, preferably the second position is in a crotch region of the absorbent core. In that manner it allows a larger quantity of liquid to be held at the front and rear portions of the absorbent core, and better liquid distribution over the absorbent core. This embodiment may be advantageous for male wearer as more liquid is expected at a front and a rear portion of the absorbent core during a liquid insult. Therefore, the tubes formed at the first and third position of the channel may not close-up the channel, even when large amount of liquid is absorbed and the tubes are heavily swelling. As a result, the liquid holding and distribution capacities of the channel during further liquid insults are improved, and the risks of liquid overflow and leakage are decreased.

In an exemplary embodiment, the first channel zone further has a third width at a third position, wherein the first position is located between the second position and the third position, wherein the third width is smaller than the first width, and the width of the first channel zone decreases from the first position to the third position, preferably the first position is in a crotch region of the absorbent core. In that manner it allows a larger quantity of liquid to be held at the crotch region of the absorbent core, and better liquid distribution over the absorbent core. This embodiment is particularly advantageous for female wearer, as more liquid is expected at the crotch region of the absorbent core during a liquid insult. Therefore, the tubes formed at the first position of the channel may not close-up the channel, even when large amount of liquid is absorbed and the tubes are heavily swelling. As a result, the liquid holding and distribution capacities of the channel during further liquid insults are improved, and the risks of liquid overflow and leakage are decreased.

In an exemplary embodiment, in the first channel zone substantially no absorbent material is present between the top core wrap sheet and the back core wrap sheet, preferably the first channel zone is a continuous zone with substantially no absorbent material present between the top core wrap sheet and the back core wrap sheet, which allows a better liquid distribution throughout the entire channel of the absorbent core, enabling better liquid absorbance.

In an exemplary embodiment, the first channel zone comprises a plurality of sections which have substantially no absorbent material between the top core wrap sheet and the back core wrap sheet, and absorbent material is present in area in-between adjacent said sections, between the top core wrap sheet and the back core wrap sheet. It allows a better liquid flow and distribution between absorbent material on both sides of the first channel zone.

In an exemplary embodiment, a contour of the first channel zone is adjacent to absorbent material.

In an exemplary embodiment, the length of the first channel zone is larger than 10% of the length of the absorbent core, preferably larger than 20%, more preferably larger than 30%, even more preferably larger than 40%, most preferably larger than 50%, e.g. 60% or 70% or even 100% of the length of the absorbent core, which allows a better liquid distribution over a large area of the absorbent core.

In an exemplary embodiment, the first width is at least 3 mm, preferably at least 5 mm, more preferably at least 7 mm, even more preferably at least 9 mm, most preferably at least 11 mm; and/or the second width is preferably at least 2 mm, more preferably at least 4 mm, even more preferably at least 6 mm, most preferably at least 8 mm. The first width may also be much larger than the second width, e.g. 4 mm larger, 6 mm larger, 8 mm larger, 10 mm larger, 15 mm larger, etc. Also, the second width may be very small or zero, i.e. the elongate first channel zone may e.g. end in a point.

In an exemplary embodiment, said first channel zone is a permanent channel zone, in particular a permanent attachment zone, which remains intact when wetted, which allows the channel to distribute liquid during further liquid insults, e.g. during a second liquid insult, a third liquid insult, a fourth liquid insult, etc. The first attachment zone may remain intact in various manners. For example, when channel zone is an attachment zone and the top core wrap sheet is attached to the back core wrap sheet in the first attachment zone when dry, the top core wrap sheet may remain attached to the back core wrap sheet when wetted. Alternatively or in addition, when substantially no or less absorbent material is present in the first channel zone when dry, such distribution may remain substantially unaltered such that substantially no or less absorbent material is present in the first channel zone when wetted.

In an exemplary embodiment, the absorbent core is provided with a plurality of channel zones, in particular attachment zones, wherein the plurality of channel zones further comprises at least a second elongate channel zone, preferably the plurality of channel zones further comprises a third elongate channel zone, more preferably the plurality of channel zones further comprises a fourth elongate channel zone. In this manner the quantity of liquid that can be temperately held is further increased. In addition, as the total area of the channel zones increases accordingly, and the liquid can be more evenly distributed over the entire absorbent core. At each channel zone of the plurality of channel zones any one of the following conditions or any combination thereof is fulfilled: less absorbent material is present as compared to other regions of the absorbent core, substantially no absorbent material is present, the top core wrap sheet is attached to the back core wrap sheet. It is clear to the skilled person that at different channel zones of the plurality of channel zones mutually similar conditions or mutually different conditions may be fulfilled.

In an exemplary embodiment, said first and second channel zone extend next to each other from the crotch region in the direction of the first and/or the second transverse edge, which allows a better liquid distribution between crotch region and front and/or back portion of absorbent article.

In an exemplary embodiment, the first channel zone crosses the second channel zone at a crossing point, preferably the crossing point is on a longitudinal center line of the absorbent core extending between the first and second transverse edge, which allows a better liquid distribution and communication between the first and second channels.

In an exemplary embodiment, the first and second channel zone together form a substantially X-shaped zone. In that manner, immediately after wetting, liquid is guided in the first and/or second elongate channel from left to right and/or from right to left, respectively, whilst flowing towards the crotch region or away from the crotch region, improving the liquid distribution, whereupon the liquid can be absorbed by the absorbent material. Further, by making the first and second channel zones cross the longitudinal center line, the zones may be longer compared to similar zones extending parallel to the longitudinal center line, resulting in a larger liquid distribution zone. Optionally the legs of the "X" may be interrupted to create one or more bridge zones as defined below.

In an exemplary embodiment, the plurality of channel zones is arranged symmetrically with respect to the longitudinal center line of the absorbent core.

In an exemplary embodiment, the absorbent core comprises a bridge zone (B) allowing a liquid flow between the first and the second longitudinal edge by capillary action through the absorbent material and/or by mass flow, such that upon wetting of the absorbent material, a front and rear channel are created, wherein the bridge zone extends between said front and rear channel; wherein a minimum distance between said front and rear channel is preferably larger than 3 mm, more preferably larger than 5 mm, even more preferably larger than 7 mm, most preferably larger than 10 mm. In that manner a capillary bridge is created between the first and second channel zones. It improves liquid flow between absorbent material from a right portion and a left portion of the absorbent core, as a result liquid can be better distributed over the entire absorbent core. It is noted that the liquid path through the bridge zone may be any path going from an area near the first side edge to an area near the second edge. It may be a straight transverse zone, but it may also be a curved zone, or a partially straight and partially curved zone. This minimum distance (which is related to the capillary flow and/or mass flow) may be varied depending on the size of the absorbent article. In a preferred embodiment the bridge zone is configured to cause a capillary flow so that a flow against the gravity force is possible.

In an exemplary embodiment, said bridge zone comprises one or more temporary attachments between the top and back core wrap sheet which are configured to detach when wetted; and/or said bridge zone comprises at least one permanent channel zone, in particular a permanent attachment zone, in a direction from the first to the second side edge; and/or said bridge zone comprises absorbent material. In this manner, upon wetting the one or more temporary attachments may first function to guide a mass flow of the liquid, whereupon, after loosening a capillary flow through the absorbent material is made possible.

In an exemplary embodiment, the first channel zone is connected to the second channel zone through at least one semi-permanent channel zone, in particular a semi-permanent attachment zone, preferably extending in a transverse direction. Said at least one semi-permanent channel zone may be configured to release or disappear after having been in contact with liquid for a predetermined period of time, wherein said predetermined period of time is preferably smaller than 30 s. It allows a better liquid distribution in a transverse direction through the absorbent material of the absorbent core after the absorbent core is wetted.

In an exemplary embodiment, the absorbent material comprises cellulosic fluff pulp and/or superabsorbent particles.

In an exemplary embodiment, the first transverse edge is a front edge intended to be positioned at a front side of a person, and the second transverse edge is a rear edge intended to be positioned at a rear side of a person; wherein the first portion of the absorbent core is a front portion, and the second portion a rear portion; or wherein the first transverse edge is a rear edge intended to be positioned at a rear side of a person, and the second transverse edge is a front edge intended to be positioned at a front side of a person; wherein the first portion of the absorbent core is a rear portion, and the second portion a front portion.

According to another aspect of the invention, there is provided an absorbent article comprising a liquid pervious topsheet, a liquid impervious backsheet, and an absorbent core. The absorbent core may be according to any one of the embodiments disclosed above.

In an exemplary embodiment, a position and/or shape of the at least first elongated channel zone is indicated by means of a distinguishable color and/or colored pattern. Such embodiments have the advantage that, on the one hand the channel zones result in an improved liquid distribution and absorption of the liquid, and on the other hand, the color and/or pattern allows a user to easily distinguish e.g. a front and a rear portion of the absorbent article or between different sizes, or between different types of absorbent articles, such absorbent articles for male or female persons. Indeed, by giving e.g. the first channel zone a color and/or pattern which is different from the color and/or pattern of the second channel zone, a user can remember easily e.g. which color has to be on the left or right side. The person skilled in the art understands that many color and/or pattern variants are possible which will allow a user to easily recognize e.g. a front and a rear portion. In addition to or alternative to allow a user to easily recognize the correct orientation of the absorbent article, the color and/or pattern which indicate the position and/or shape of the channel zones may be utilized to provide more information to a user about the absorbent article by linking a particular color and/or pattern of the visual indication to a certain characteristic of the absorbent article such as size, type (e.g. diaper versus pants), etc.

In an exemplary embodiment, the position and/or shape of the at least first elongated channel zone is indicated by means of a printed ink layer.

In an exemplary embodiment, the distinguishable color and/or colored pattern is provided on at least one of the topsheet, the top core wrap sheet, the backsheet and the back core wrap sheet. The color and/or colored pattern may be provided on either side of the topsheet, the top core wrap sheet, the backsheet and/or the back core wrap sheet. In addition or alternatively, the color and/or colored pattern is provided on an acquisition and/or a distribution layer of the absorbent article.

According to an embodiment the absorbent core has a longitudinal center line dividing the absorbent core in a first longitudinal portion and a second longitudinal portion on either side of the longitudinal center line, and a transverse crotch line dividing the absorbent core in a front portion and a rear portion on either side of the transverse crotch line. The absorbent core is provided with a plurality of channel zones. The plurality of channel zones comprises a first and second elongate channel zone, said first and second elongate channel zone extending next to each other from a crotch region in the direction of the first and/or second transverse edge. The first elongate channel zone crosses the longitudinal center line in a first crossing point, from the first longitudinal portion to the second longitudinal portion; and the second elongate channel zone crosses the longitudinal center line in a second crossing point, from the second longitudinal portion to the first longitudinal portion. The first and second crossing point may be the same point or a different point, and may be located in the front portion or in the rear portion or on the transverse crotch line between connecting the front portion to the rear portion. The first and second channel zone may each have a first width (w1) at a first position and a second width (w2) at a second position. The first width is larger than the second width. The various embodiments disclosed above for the channel zones with different widths may equally apply in this embodiment.

By providing a first and a second elongate channel zone which are crossing the longitudinal center line, upon wetting of the absorbent core two elongate channels are created. The first elongate channel extends from a first left position to a second right side, where the first left position is closer to the first transverse edge than the second right position. Similarly, the second elongate channel extends from a second right position to a first left position, where the second right position is closer to the first transverse edge than the first left position. In that manner, immediately after wetting, liquid is guided in the first and/or second elongate channel from left to right and/or from right to left, respectively, whilst flowing towards the crotch region or away from the crotch region, improving the liquid distribution, whereupon the liquid can be absorbed by the absorbent material. Further, by making the first and second channel zones cross the longitudinal center line and by appropriately adjusting the width of the channel zones, the zones may be longer and better optimized compared to similar zones extending parallel to the longitudinal center line, resulting in a larger liquid distribution zone.

The first and second crossing point may correspond with substantially the same point located on the longitudinal center line. In that manner a connection between the first and the second channel zone is realized further enhancing the liquid distribution.

In another embodiment, the first and second crossing point may be different points, and the first and the second channel zone may cross each other at a distance of the longitudinal center line. In such an embodiment third and fourth elongate channel zone arranged symmetrically with respect to the first and second elongate channel zones may be provided, such that the first and second channel zone cross each other at one side of the longitudinal center line and the third and fourth channel zone cross each other at another side of the longitudinal center line. Also the third and fourth channel zones may each have a first width (w1) at a first position and a second width (w2) at a second position. The first width is larger than the second width.

Preferably, the first and/or second crossing point are located at a distance of the transverse crotch line. For example, the first and/or second crossing point may be located in a front portion. In that way the position of the first and/or second can be optimized e.g. in function of whether the absorbent article is intended for a male or female person. However, in other embodiments, the first and/or second crossing point may be located on the transverse crotch line.

When at a distance of the transverse crotch line, preferably, the distance between the first and/or second crossing point and the transverse crotch line is larger than 1% of the length of the absorbent core, preferably larger than 2%, even more preferably larger than 3%.

In certain embodiments with multiple first crossing points and multiple second crossing points may be provided, wherein these multiple first crossing points may be located a different distances of the transverse crotch line, e.g. two first crossing points, one in the front portion and one in the rear portion, and two second crossing points, one in the front portion (optionally corresponding with the first crossing point in the front portion), and one in the rear portion (optionally corresponding with the first crossing point in the rear portion), see e.g. FIG. 17P.

Preferably, a distance between the transverse crotch line and a transverse center line extending perpendicular on the longitudinal direction of the absorbent core, through the middle of the absorbent core, is smaller than 10%, more preferably smaller than 5% of the length of the absorbent core.

Preferably, the first elongate channel zone extends both in the front portion and in the rear portion; and the second elongate channel zone extends both in the front portion and in the rear portion. In that manner a good liquid distribution from left to right and from front to rear can be obtained.

In an exemplary embodiment a maximum distance between the first and the second channel zone in the front portion is different from a maximum distance between the first and the second channel zone in the rear portion. In that manner the liquid distribution zone may be better adapted to the type of person wearing the absorbent article. For example, for a male person, a maximum distance between the distance between the first and the second channel zone near a front transverse edge may be larger than a maximum distance between the first and the second channel zone in a rear portion, whilst for a female person the maximum distance may be larger in the rear portion than in the front portion. Further it is possible to optimize the difference between the front and the rear portion for obtaining a unisex absorbent article.

Preferably, the first and second channel zone each extends, seen in the transverse direction of the absorbent core, over the transverse distance which is at least 1 mm, preferably at least 3 mm, more preferably at least 4 mm, even more preferably at least 5 mm, most preferably at least 6 mm. In that manner the channels created upon wetting will be sufficiently wide to cause a good liquid distribution.

According to an exemplary embodiment, the first and second transverse edge correspond with a front and rear transverse edge, and the plurality of channel zones further comprises at least one connecting channel zone connecting said first channel zone with said second channel zone.

By providing a first and a second elongate channel zone which are interconnected by at least one connecting channel zone, upon wetting of the absorbent core two elongate channels are created which are interconnected by at least one interconnecting channel which is in liquid communication with the first and second elongate channel. In that manner, immediately after wetting, liquid can flow from the first elongate channel to the second elongate channel and vice versa, improving the liquid distribution, whereupon the liquid can be absorbed by the absorbent material.

According to an exemplary embodiment the at least one connecting channel zone comprises at least one of:

- a front connecting channel zone which connects a front end portion of the first channel zone to a corresponding front end portion of the second attachment zone;
- a rear connecting channel zone which connects a rear end portion of the first channel zone to a corresponding rear end portion of the second channel zone.

In that manner a good distribution is obtained in the front portion and/or in the back portion. Especially for a male person, it may be desirable to have a front connecting channel zone. Preferably, the front connecting channel zone is located in the front portion and/or the rear connecting channel zone is located in the rear portion.

In an exemplary embodiment a connecting channel zone extends substantially in a transverse direction of the absorbent core. This may be advantageous when the first and second elongate channel extend substantially parallel. In that manner an absorbent core is obtained which may be substantially symmetrical with respect to a longitudinal center axis. In other symmetrical embodiments the connecting channel zone may be substantially V-shaped or U-shaped, wherein the V-shape or U-shape is arranged such that it is symmetrical with respect to the longitudinal center axis of the absorbent core.

In an exemplary embodiment, upon wetting of the absorbent material, a first and second channel are created at said first and second elongate channel zone, respectively, and the first and second channel are directly connected to each other through the at least one connecting channel zone; wherein a first, second, and at least one connecting channel are created at said first, second, and at least one connecting channel zone, respectively.

In an exemplary embodiment the at least one connecting channel zone comprises one or more straight portions, and/or one or more curved portions.

In an exemplary embodiment the first channel zone, the second channel zone, and the at least one connecting channel zone collectively form a substantially "U" shaped zone, or a substantially "V" shaped zone. A U-shape or V-shape provides for a good guidance of the liquid. Moreover, with a U-shaped channel zone sharp angles may be avoided further improving a good liquid transport from a first elongate channel zone (one leg) of the U-shaped channel zone to the second elongate channel zone (the other leg) of the U-shaped channel zone. Further, with a V-shape, liquid may be guided from e.g. a left and right front portion to a center portion in the crotch region.

In an exemplary embodiment, the first channel zone, the second channel zone, and the at least one connecting channel zone collectively delimit a substantially enclosed region. For example, the substantially enclosed region may be a substantially "O" shaped region, or a substantially polygon shaped region, such as a substantially rectangular shaped region, a substantially triangular shaped region, a diamond shaped region, a substantially hexagonal shaped region. In that manner liquid can be distributed around the boundary of the enclosed region, such that it can be absorbed from the entire boundary by the absorbent material in the enclosed region and by the absorbent material in a region surrounding the enclosed region.

In an exemplary embodiment, the first channel zone and the second channel zone are substantially parallel and extend in a longitudinal direction of the absorbent core. In another exemplary embodiment, an angle between the first channel zone and a longitudinal direction of the absorbent core and an angle between the second channel zone and the longitudinal direction of the absorbent core is smaller than 5°. For example the first and second front channel zones may diverge in the direction of the first zone.

In an exemplary embodiment, the maximum distance between the first and the second channel zone in the transverse direction is between 15 and 70% of the width of the absorbent core, more preferably between 20 and 50%; wherein preferably the maximum distance between the first and the second channel zone in the transverse direction is between 10 mm and 100 mm, more preferably between 20 mm and 80 mm, even more preferably between 30 mm and 70 mm.

In an exemplary embodiment, the first and second channel zones are permanent channel zones which remain intact upon wetting, or semi-permanent channel zones configured to disappear or dissolve after having been in contact with liquid for a predetermined period of time, wherein said predetermined period of time is preferably smaller than 30 s. The permanent channel zones may remain intact in various manners. For example, when the top core wrap sheet is attached to the back core wrap sheet in the permanent attachment zones when dry, the top core wrap sheet may remain attached to the back core wrap sheet when wetted. Alternatively or in addition, when substantially no or less absorbent material is present in the permanent channel zones when dry, such distribution may remain substantially unaltered such that substantially no or less absorbent material is present in the channel attachment zones when wetted.

The first transverse edge may be the front edge or the rear edge, and the second transverse edge may be the rear edge or the front edge, respectively. The absorbent core has a first portion and a second portion on either side of the transverse crotch line. The first and the second elongate channel zone may extend next to each other, at least in the first portion of the absorbent core in the direction of the first transverse edge. The plurality of channel zones may further comprise a third and a fourth elongate channel zone extending next to each other, at least in the second portion of the absorbent core, in the direction of the second transverse edge. Optionally the third and fourth elongate channel zone may be connected by a connecting channel zone.

In another possible embodiment, the plurality of channel zones may further comprise a third channel zone extending from the crotch region in the direction of the second transverse edge, wherein seen in a projection on a transverse direction the third channel zone is located between the first and the second channel zone. By having a first and a second channel zone in the front or rear portion and a third channel zone in the rear or front portion, respectively, said third channel zone being such that it is between the first and the second channel zone, seen in a projection as defined above, it is possible to tailor the absorbent article to the wearer. For example, for a male person the first and second channel zone may be in the front portion and the third channel zone may be in the rear portion, whilst for a female person the first and second channel zone may be in the rear portion and the third channel zone in the front portion. Further it is possible to optimize the difference between the front and the rear portion for obtaining a unisex absorbent article.

For an embodiment with a third and fourth channel zone, the first distance between the first and the second channel zone may be at least 5%, preferably at least 10% bigger, even more preferably at least 20% bigger than a second distance between the third and the fourth channel zone. This difference may be optimized in function of the desired used. For example, for male persons the difference may be bigger.

In an embodiment which is preferred for a male person, the first and the second elongate channel zone may each have a front end adjacent to absorbent material and a rear end adjacent to absorbent material or on the transverse crotch line. And the third and the fourth elongate channel zone may each have a rear end adjacent to absorbent material and a front end adjacent to absorbent material or on the transverse crotch line (L). It is noted that the first channel zone may be connected to the third channel zone: in that case the rear end of the first channel zone and the front end of the third channel zone will be on the transverse crotch line. Similarly, the second channel zone may be connected to the fourth channel zone: in that case the rear end of the second channel zone and the front end of the fourth channel zone will be on the transverse crotch line.

In an embodiment which is preferred for a female person, the first and the second elongate channel zone may each have a rear end adjacent to absorbent material and a front end adjacent to absorbent material or on the transverse crotch line. And the third and the fourth elongate channel zone may each have a front end adjacent to absorbent material and a rear end adjacent to absorbent material or on the transverse crotch line (L). It is noted that the first channel zone may be connected to the third channel zone: in that case the front end of the first channel zone and the rear end of the third channel zone will be on the transverse crotch line. Similarly, the second channel zone may be connected to the fourth channel zone: in that case the front end of the second channel zone and the rear end of the fourth channel zone will be on the transverse crotch line.

For an embodiment with a central third channel zone (instead of a third and fourth channel zone) which is preferred for a male person, the first and the second elongate channel zone may each have a front end adjacent to absorbent material and a rear end adjacent to absorbent material or on the transverse crotch line. And the third elongate channel zone may have a rear end adjacent to absorbent material and a front end adjacent to absorbent material or on the transverse crotch line (L). It is noted that the first channel zone may be connected to the third channel zone: in that case the rear end of the first channel zone and the front end of the third channel zone will be on the transverse crotch line. Similarly, the second channel zone may be connected to the third channel zone: in that case the rear end of the second channel zone and the front end of the third channel zone will be on the transverse crotch line.

For an embodiment with a central third channel zone which is preferred for a female person, the first and the second elongate channel zone may each have a rear end adjacent to absorbent material and a front end adjacent to absorbent material or on the transverse crotch line. And the third elongate channel zone may have a front end adjacent to absorbent material and a rear end adjacent to absorbent material or on the transverse crotch line (L). It is noted that the first channel zone may be connected to the third channel zone: in that case the front end of the first channel zone and the rear end of the third channel zone will be on the transverse crotch line. Similarly, the second channel zone may be connected to the third channel zone: in that case the front end of the second channel zone and the rear end of the third channel zone will be on the transverse crotch line.

For an embodiment with a third and fourth channel zone, seen in a projection on the longitudinal direction of the absorbent core, the first and the second channel zone may extend over a length which is less than the length of the third and fourth channel zone. To fit better to the body the third and fourth channel zones which are closer to each other may be longer to extend over a longer part of the crotch region, for example the third and fourth channel zones may extend both in the first and the second portion of the absorbent core. Preferably, the first and the second channel zone extend over a length which is at least 5% less, more preferably at least 10% less than the length of the third and fourth channel zone. Preferably the first and the second channel zone extend over a length which is at least 25%, more preferably at least 35%, even more preferably at least 45% of the length of the third and fourth channel zone.

For an embodiment with a third channel zone, seen in a projection on the longitudinal direction of the absorbent core, the first and the second channel zone may extend over a length which is less than the length of the third channel zone. To fit better to the body the third channel zone may be longer to extend over a longer part of the crotch region, for example the third channel zone may extend both in the first and the second portion of the absorbent core. Preferably, the first and the second channel zone extend over a length which is at least 5% less, more preferably at least 10% less than the length of the third channel zone. Preferably the first and the second channel zone extend over a length which is at least 25%, more preferably at least 35%, even more preferably at least 45% of the length of the third channel zone.

In preferred embodiments, especially suitable for male persons, the first transverse edge may be a front edge intended to be positioned at a front side of a person, and the second transverse edge may be a rear edge intended to be positioned at a rear side of a person; wherein the first portion of the absorbent core is a front portion and the second portion is a rear portion.

In preferred embodiments, especially suitable for female persons, the first transverse edge may be a rear edge intended to be positioned at a rear side of a person, and the second transverse edge may be a front edge intended to be positioned at a front side of a person; wherein the first portion of the absorbent core is a rear portion and the second portion is a front portion.

The distance between the third and the fourth channel zone may be between 5 and 60% of the width of the absorbent core, more preferably between 10 and 40%. For example, the distance between the third and the fourth channel zone may be between 5 mm and 60 mm, more preferably between 10 mm and 50 mm, even more preferably between 15 mm and 40 mm.

The length of the third and/or the fourth channel zone may be larger than 5% of the length of the absorbent core; preferably larger than 10%, more preferably larger than 15%, e.g. larger than 20%.

The length of the third and the fourth channel zone may be larger than the length of the first and the second channel zone, preferably at least 10% larger, more preferably at least 20% larger.

In a possible embodiment, seen in a projection on a longitudinal direction of the absorbent article, a projection of the first and second channel zone does not overlap with a projection of the third and fourth channel zone. However, in other embodiments there may be a partial or even a full overlap. For example, the third and fourth channel zone may extend in between the first and second channel zone.

In a possible embodiment with a central third channel zone, seen in a projection on a longitudinal direction of the absorbent article, a projection of the first and second channel zone does not overlap with a projection of the third channel zone. However, in other embodiments there may be a partial or even a full overlap. For example, the third channel zone may extend in between the first and second channel zone.

In a possible embodiment the first channel zone may be separated from the third channel zone by absorbent material, and the second channel zone may be separated from the fourth channel zone by absorbent material. In that manner a capillary bridge is created between the first and second channel zones on the one hand and the third and fourth channel zones on the other hand.

In another possible embodiment the first channel zone may be connected to the third channel zone through a first semi-permanent channel zone, in particular a first semi-permanent attachment zone, and the second channel zone may be connected to the fourth channel zone through a second semi-permanent channel zone, in particular a second semi-permanent attachment zone. Such semi-permanent channel zones are configured to be dissolved or detached upon wetting, so that liquid can flow in a transverse direction through the absorbent material of the absorbent core.

Preferably, the first, second, third and fourth channel zones are permanent channel zones, in particular permanent attachment zones which remain attached upon wetting. Also, in an embodiment without the fourth channel zone, preferably the first, second, and third channel zones are permanent channel zones, in particular permanent attachment zones which remain attached upon wetting.

The length of the first and the second channel zone may be larger than 30 mm, preferably larger than 40 mm, more preferably larger than 50 mm. The length of the third and the fourth channel zone may be larger than 30 mm, preferably larger than 40 mm, more preferably larger than 50 mm.

The third channel zone and the fourth channel zone may be substantially parallel and extend in a longitudinal direction of the absorbent core; or an angle between the third channel zone and a longitudinal direction of the absorbent core and an angle between the fourth channel zone and the longitudinal direction of the absorbent core may be smaller than 5°.

Seen in a projection on a longitudinal direction of the absorbent core, the plurality of channel zones together may cover at least 30%, preferably at least 40% of a length of the absorbent core. In yet other embodiments which are suitable for both male and female persons (unisex), the difference between the first distance and the second distance may be less than 20% of the width of the absorbent article, preferably less than 10%, e.g. between 0 and 8% or between 1 and 5%, wherein the width is measured in the transverse direction of the absorbent core.

It is noted that in embodiments of the invention the top core wrap sheet and the bottom core wrap sheet may be formed as one integral sheet or may comprise separate portions around the absorbent material.

In an exemplary embodiment, seen in a longitudinal direction of the absorbent article, looking from the front edge to the rear edge, the absorbent core comprises subsequently a first, second, third, fourth and fifth zone. The absorbent core comprises a front portion extending between the front edge and a transverse crotch line of the absorbent core, and a rear portion extending between the rear edge and the transverse crotch line of the absorbent core. The first, second and third zone extend in the front portion of the absorbent core and the fourth and fifth zone extend in the rear portion.

Preferably, the at least one connecting channel zone connecting the first and second elongate channel zone extend in the second, third or fourth zone.

More preferably, the second and/or third zone comprises at least one front connecting channel zone connecting a first elongate channel zone and a second elongate channel zone; and/or the fourth zone comprises at least one rear connecting channel zone connecting a third elongate channel zone and a fourth elongate channel zone.

Preferably, in the first and fifth zone substantially no permanent channel zones, in particular attachment zones with a liquid guidance or distribution function are present. In other words, the first and fifth zones may comprise small local attachment points provided for other reasons than liquid distribution management.

Preferably, the second zone comprises at least a first elongate channel zone of the plurality of channel zones, said first channel zone extending from an edge of the first zone in the direction of the third zone.

Preferably, at least the fourth zone comprises at least a third elongate channel zone of the plurality of channel zones, said third channel zone extending from an edge of the fifth zone in the direction of the third zone.

Preferably at least one of said second, third and fourth zone comprises a bridge zone (B) allowing a liquid flow between the first and the second side edge by capillary action through the absorbent material and/or by mass flow. It is noted that the liquid path through the bridge zone may be any path going from an area near the first side edge to an area near the second edge.

It is noted that the third channel zone may extend in the third zone, i.e. in the front portion of the absorbent core.

It is noted that the first channel zone may extend in the third and/or the fourth zone, i.e. in the rear portion of the absorbent core.

By providing at least a first channel zone and at least a third channel zone as defined above channels are created when the absorbent core is wetted. By providing a bridge zone in at least one of the second, third and fourth zone, notwithstanding the creation of a channel, liquid taken up in absorbent material near the first side edge may migrate by capillary action and/or mass flow in the direction of the second side edge. In other words, the liquid is on the one hand distributed by the channels formed by the at least one front channel zone and at least one rear channel zone, and on the other hand allowed to be transported from one side edge to the other side edge by capillary action and/or by mass flow via the bridge zone. This is advantageous, especially when a person wearing the absorbent article is lying down on its side. Indeed, when lying down the liquid may flow towards one side edge by gravity. This will cause a swelling of the absorbent material near that side edge, and the bridge zone will allow the liquid to flow towards the other side edge against the gravity force by capillary action. On the other hand the channels will be able to provide for a fast liquid distribution through the second, third and fourth zone.

In an advantageous embodiment third elongate channel zone extends into the third zone. In that manner a continuous channel is formed between the front and the rear portion of the absorbent core.

Preferably, the first zone extends over a length corresponding with at least 5%, more preferably at least 10% of the length of the absorbent core seen in the longitudinal direction.

Preferably, the fifth zone extends over a length corresponding with at least 10% of the length of the absorbent core seen in the longitudinal direction, preferably at least 20%, more preferably at least 25%. In that manner the absorbent material in the first zone and the fifth zone will swell upon wetting and created bands at both sides of the crotch region. Such bands will create a barrier such that it is more difficult for any liquid in the crotch region to flow out of the absorbent core.

Preferably, the second, the third and/or the fourth zone each extends over a length corresponding with at least 10% of the length of the absorbent core, seen in the longitudinal direction, preferably at least 15%. More preferably the front and rear channel zone, when projected on the longitudinal direction extend over at least 70%, more preferably at least 80% of the total length of the second, the third and/or the fourth zone. In that manner a good channel creation with sufficient liquid distribution through the absorbent core is achieved.

In an exemplary embodiment the fourth zone comprises a fourth channel zone extending next to the third channel zone, seen in the longitudinal direction, said fourth channel zone extending preferably into the third zone.

Preferably, the bridge zone extends from a first portion of the absorbent core, preferably in the second or third zone, to a second portion of the absorbent core, preferably in the second or third zone, wherein the first portion is defined between the first side edge and a longitudinal center axis (CL) of the absorbent core and the second portion is defined between the second side edge and the longitudinal center axis (CL) of the absorbent core.

In an exemplary embodiment, the first and second channels zones are attachment zones, and the attachment between the top core wrap sheet and the back core wrap sheet in the first and the second attachment zone is a permanent attachment, and the absorbent core is configured such that, in a wetted state of the absorbent material, the absorbent material extends over the first and second attachment zone. In that matter, the absorbent material bulges over the first and second attachment zone, thereby causing a tension in the absorbent core which causes the absorbent core, which is in a substantially flat state when dry, to curl up to form a tub shaped and/or cup shaped absorbent core including the first and second channel.

According to a preferred embodiment, outside of the plurality of channel zones the absorbent core has a maximum thickness; wherein the first and second channel zone extend through at least 90% of the maximum thickness of the absorbent core, more preferably through 100% of the thickness of the absorbent core such that in the first and second channel zone substantially no absorbent material is present between the top core wrap sheet and the back core wrap sheet.

According to a preferred embodiment, the attachment between the top core wrap sheet and the back core wrap sheet is any one of the following or a combination thereof: pressure bonding, thermal bonding, sonic bonding, chemical bonding, adhesive.

According to an exemplary embodiment, the absorbent core has a front portion extending at one side of a transverse crotch line and a rear portion extending at the other side of the transverse crotch line. The first and second channel zone extend at least in the front portion of the absorbent core; and the third and fourth channel zone extend at least in the rear portion of the absorbent core. Preferably, the distance between the first and the second channel zone is smaller than the distance between the third and the fourth channel zone. The first channel zone may be connected to the third channel zone through a first transverse channel zone, and the second channel zone is connected to the fourth channel zone through a second transverse channel zone. In a preferred embodiment the distance between the first and the second attachment zone is between 10 mm and 50 mm, preferably between 15 mm and 30 mm. According to an exemplary embodiment, the length of the first and the second attachment zone is larger than 60 mm, preferably larger than 70 mm.

The absorbent core may be provided with a plurality of channel zones comprising at least a first and a second channel zone, said first and second attachment zone extending next to each other from a crotch region in the direction of the first and/or second transverse edge. A first binder is arranged in a first area between the top core wrap sheet and the back core wrap sheet at a distance from the first and second channel zone, and a second binder is arranged in a second area between the top core wrap sheet and the back core wrap sheet. Preferably, the first area is substantially complementary to the second area. Preferably, the second area includes the first and second channel zone. The first binder may be different from the second binder. According to another exemplary embodiment the first binder is the same as the second binder; and a transition zone is distinguishable between the first area and the second area.

According to an exemplary embodiment the first binder is arranged as a layer having a first thickness and the second binder is arranged as a layer having a second thickness which is different from the first thickness, preferably higher than the first thickness.

According to an exemplary embodiment the first area comprises a plurality of longitudinal stripes; and/or the second area comprises a plurality of longitudinal stripes.

According to an embodiment, a first binder is applied to at least one portion of the back core wrap sheet at a distance from the intended position of the first and/or second channel zones, in particular attachment zones, before the absorbent material is applied, and a second binder is applied to at least one portion of the top core wrap sheet before it is applied on top of the absorbent material on the back core wrap sheet.

According to an alternative embodiment, a first binder is applied to at least one portion of the top core wrap sheet at a distance from the intended position of the first and/or second channel zones, in particular attachment zones, before the absorbent material is applied, and a second binder is applied to at least one portion of the back core wrap sheet before it is applied on top of the absorbent material on the back core wrap sheet. Preferably, the at least one portion of the top core wrap sheet and the at least one portion of the back core wrap sheet are chosen such that in the application and attachment of the top core wrap sheet to the back core wrap sheet the plurality of portions are complementary, wherein preferably substantially the entire surface of the absorbent article is provided with binder on either the top core wrap sheet or the back core wrap sheet. According to an embodiment the first and second binder are the same binder. In alternative embodiments, the first and second binder are mutually different binders, such as different glues. It is clear to the skilled person that the first and second binder may be applied in either layers with the same thickness, or layers with a different thickness.

The skilled person understands that an absorbent article as described above, more in particular in view of the application of binder, can be distinguished from absorbent articles which are manufactured otherwise. More in particular, the above described application of binder, such as glue, is distinguishable in an absorbent article by examining the present bonds within the particular absorbent article by means of any one of the following: color analysis, UV analysis, chemical analysis, and the like. In other words, by examining the absorbent article, the skilled person can determine which type of binder has been used, where the particular binder has been applied, how many layers of binder have been applied, etc.

The skilled person will understand that the hereinabove described technical considerations and advantages for absorbent article embodiments also apply to the below described method embodiments, mutatis mutandis.

According to a further aspect, there is provided a method for manufacturing an absorbent article, said method comprising the steps of:

- guiding a first sheet material along a rotating member, wherein a surface of said rotating member is provided with a pattern with at least one suction zone and at least one non-suction zone; wherein said at least one non-suction zone comprise a first elongate zone, preferably extending in a circumferential direction of the rotating member; said first elongate zone having a first width (w1) at a first position and a second width (w2) at a second position, wherein the first width is larger than the second width;
- applying an absorbent material on said first sheet material on the rotating member such that the at least one suction zone is covered with absorbent material and substantially no absorbent material is present on the non-suction zones;
- applying a second sheet material on top of the absorbent material on the first sheet material; wherein one of said first and second sheet material is a top core wrap sheet material, and the other one is a back core wrap sheet material;
- attaching said first sheet material to said second sheet material at least in an area of the at least one non-suction zone, and such that a first elongate channel zone, in particular a first elongate attachment zone, is formed.

In a preferred embodiment, the attaching is done by applying pressure and heat on the top core wrap sheet material and/or the back core wrap sheet material in the area where substantially no absorbent material is present.

In a preferred embodiment, a binder is applied to at least one portion of the first sheet material at a distance from the intended position of the first attachment zone, before the absorbent material is applied on said first sheet material and a binder is applied to at least one portion of the second sheet material before it is applied on top of the absorbent material on the first sheet material. Preferably, the at least one portion of the first sheet material and the at least one portion of the second sheet material are chosen such that in the application and attachment of the first sheet material to the second sheet material the plurality of portions are complementary, wherein preferably substantially the entire surface of the absorbent article is provided with binder on either the first sheet material or the second sheet material.

According to a further embodiment, the attaching is done by a rotating member which is provided with at least a first seal rib dimensioned for applying pressure and heat on the top core wrap sheet material and/or the back core wrap sheet material in the areas where substantially no absorbent material is present in order to create the first channel zone, in particular the first attachment zone, respectively.

BRIEF DESCRIPTION OF FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

DESCRIPTION OF EMBODIMENTS

Figure 1A:
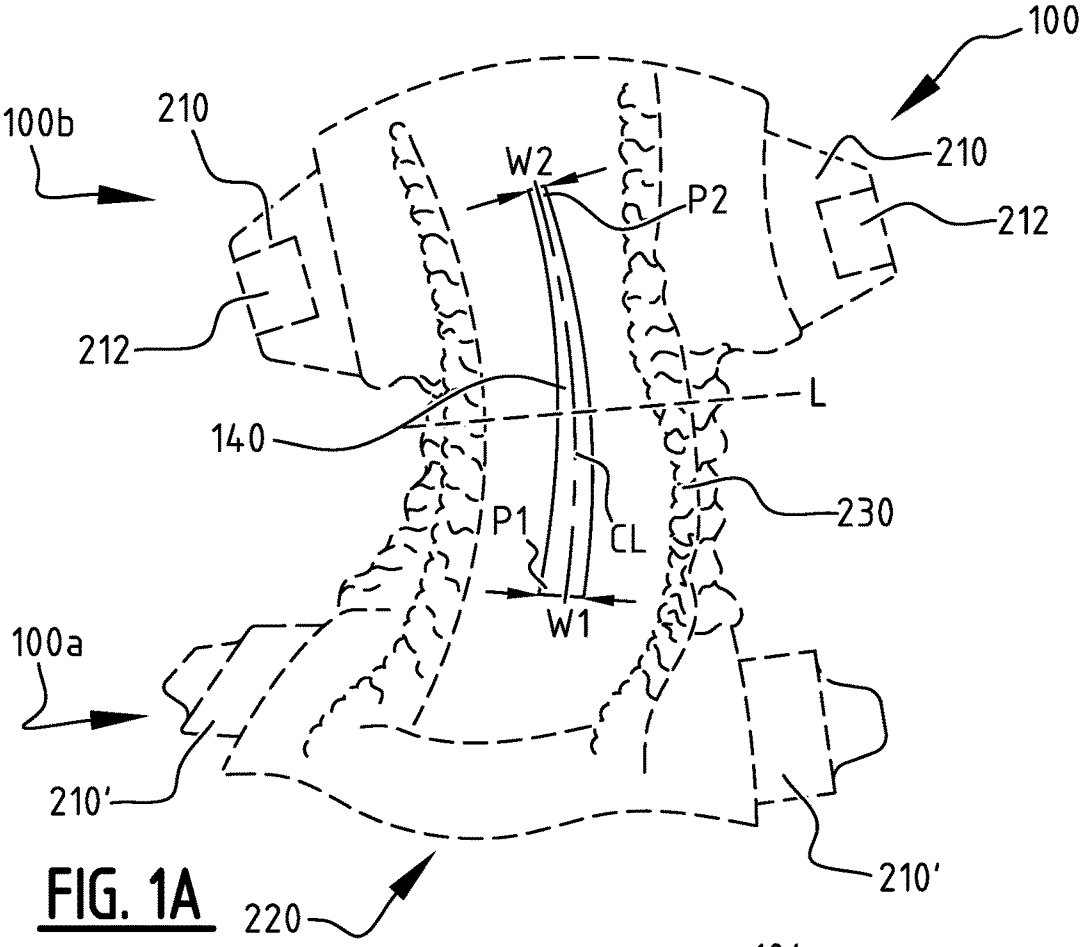
FIG. 1A is a perspective view of an exemplary embodiment of a diaper.

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates.

"Absorbent component" as used herein refers to a structural constituent of an absorbent article, e.g., a piece of an absorbent core, such as one of multiple pieces in a multi-piece absorbent core.

"Absorbent element" as used herein refers to a part of a functional constituent of an absorbent structure, e.g., a acquisition layer, a dispersion layer, core layer or a release structure formed of a material or materials having particular liquid handling characteristics suitable for the specific function.

"Absorbent fibrous polymer material" as used herein refers to an absorbent polymer material which is in thread-like from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer", "acquisition region", "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the caliper with appropriate unit conversions incorporated therein. Apparent density used herein has the unit $g/cm^3$.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garment s, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of a joint determined in dry state conditions, immediately after drying under specified conditions or after a period of conditioning in the standard laboratory atmosphere.

"Essentially cellulose free" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the f low of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The same or similar features and components are indicated with the same reference numerals throughout the figures.

Figure 1B:
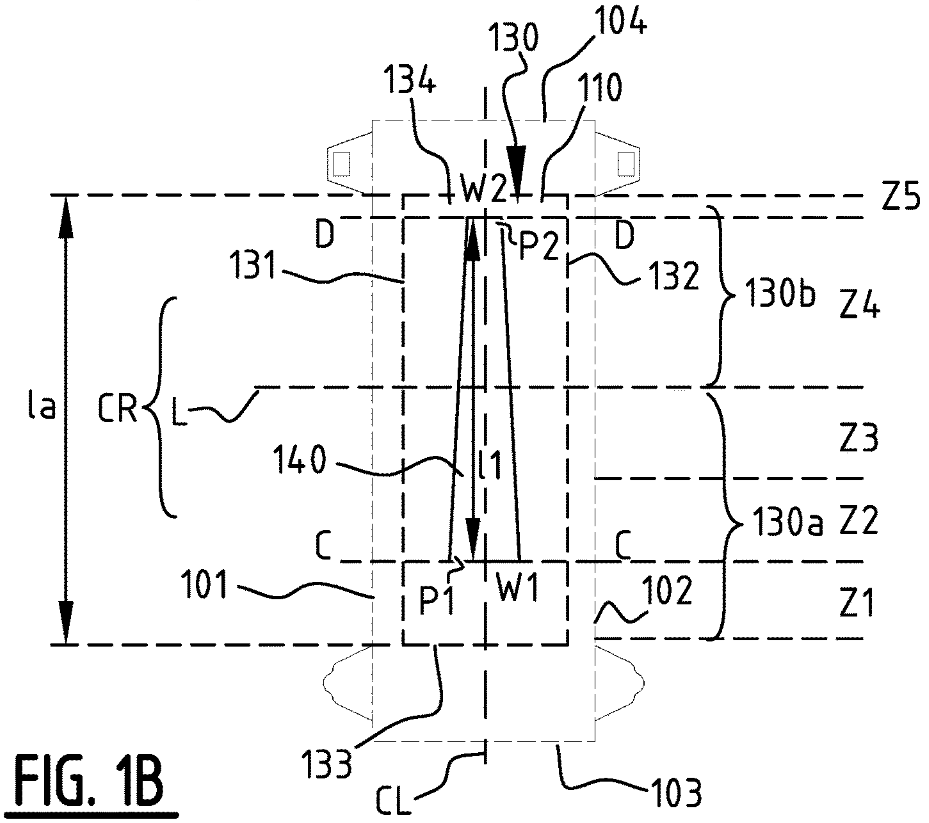
FIG. 1B is a top plan view of the diaper of FIG. 1A.

FIGS. 1A, 1B, 1C, 1D, 1E and 1F illustrate an exemplary embodiment of an absorbent article, here a diaper. FIG. 1B shows the absorbent article in its flat out, un-contracted state with the wearer side facing the viewer. The skilled person understands that the absorbent article may also be a pant or an adult incontinence garment or the like. The absorbent article 100 comprises a liquid pervious topsheet, a liquid impervious backsheet, and an absorbent core 130 positioned in between the topsheet and the backsheet. The absorbent core 130 comprises absorbent material 105 between a top core wrap sheet 110 and a back core wrap sheet 120. Absorbent core 130 has a first and second longitudinal edge 131, 132 and a first and second transverse edge 133, 134.

The absorbent core 130 is provided with at least a first elongated channel zone, in particular an attachment zone 145. The first attachment zone extends from the crotch region CR in the direction of the first and/or second transverse edge 133, 134. In the first attachment zone 145 the top core wrap sheet 110 may be attached to the back core wrap sheet 120. Alternatively, or in addition, in the first attachment zone 145 less absorbent material 105 is present as compared to other regions of the absorbent core 130. Upon wetting of the absorbent material, a first channel 140 is created at said first attachment zone 145 due to the top core wrap sheet 110 being attached to the back core wrap sheet 120 and/or due to less or substantially no absorbent material 105 being present in the first attachment zone 145. The first attachment zone has a first width (w1) at a first position (P1) and a second width (w2) at a second position (P2). The first width w1 is larger than the second width w2, and the width of the first attachment zone increases from the second position P2 to the first position P1. The width of the first attachment zone is measured perpendicularly to a center line (CL) of the first attachment zone. The center line is a line which is at the same distance of opposite edges of the first elongate attachment zone. Preferably the opposite edges extend in a length direction of the first elongate attachment zone. In this embodiment the center line of the first attachment zone is a straight line. In other embodiments, the center line of the first attachment zone may be a curve, or a polyline, etc.

The first width w1 is at least 2% larger than the second width w2, preferably 4% larger, more preferably 6% larger, even more preferably 8% larger, e.g. 10% larger or even 20% larger. The first width w1 may also be much larger than the second width w2, e.g. 50% larger, 60% larger, 70% larger, 100% larger (i.e. the double of the second width), 200% larger, etc. In some embodiments the second width w2 may be very small or zero, i.e. the elongate first attachment zone may e.g. end in a point.

The distance between the first position P1 and the second position P2 along the center line of the first attachment zone is larger than 4% of the length of the absorbent core la, preferably 8% larger, more preferably 12% larger, even more preferably 16% larger, most preferably 20% larger, e.g. 30% or 40% or 50% or 60% or 70% or even 100% of the length of the absorbent core. In the embodiment of FIG. 1A-1F the channel cover a length equal to l1+l3 which is more than 60% of the length la of absorbent core 130.

The first position P1 may be at a first end of the first attachment zone 145 and the second position P2 may be at a second end of the first attachment zone 145. The width of the attachment zone may then gradually vary between the first end and the second end. In some embodiments, the width of the attachment zone may also discontinuously vary between the first end and the second end. It is noted that between the first end and the second end the width may vary in any manner, and may e.g. increase first to decrease afterwards. This allows creating a width pattern creating an improved compromise between a good liquid distribution and a good anatomical fit, reducing leakage.

Because of the swelling of the core material of absorbent core upon wetting, the outer bands of absorbent core will rotate around channels inward, making the absorbent article the shape of a tub or cup, such that any liquid which would not yet be absorbed by the absorbent material is maintained in the tub shape. The varying width of the channel in combination with the tub or cup shape of the channel provides an absorbent article fitting perfectly to the body and a better protection against leakage. Hence the absorbent article creates more freedom of movement for the wearer of a wetted diaper.

The first channel 140 runs in the longitudinal direction of absorbent core 130. However, it is also possible for the first channel 140 to extend under a small angle with respect to the longitudinal direction of absorbent core 130, e.g. an angle between 5 and 10°. Preferably first channel 140 is arranged symmetrically with respect to a longitudinal center line CL of absorbent core 130.

Figure 1C:
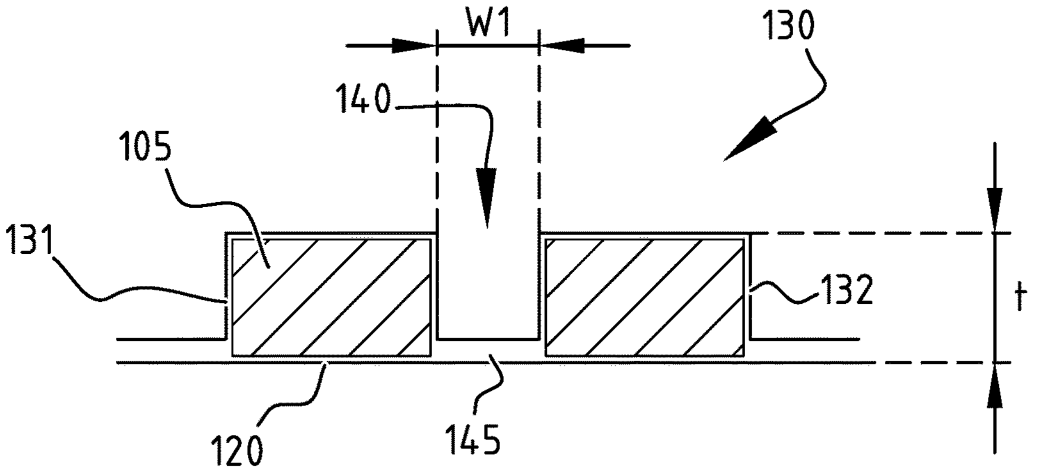
FIG. 1C is a schematic cross-section at the first position of the first channel zone, in particular the first attachment zone along line C-C of FIG. 1B, before a tube is formed on the absorbent core.
Figure 1D:
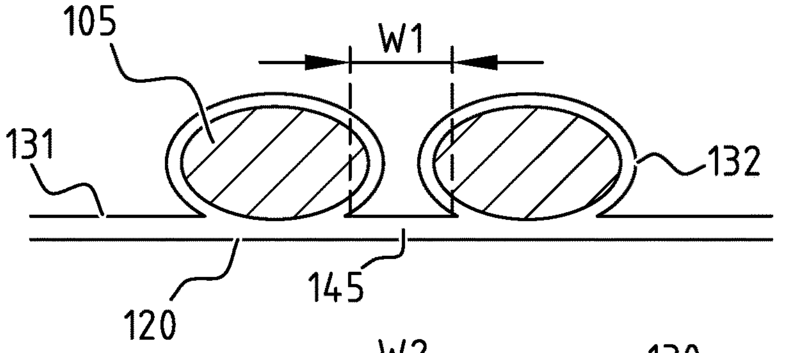
FIG. 1D is a schematic cross-section at the first position of the first channel zone, in particular the first attachment zone along line C-C of FIG. 1B, after a tube is formed on the absorbent core.
Figure 1E:
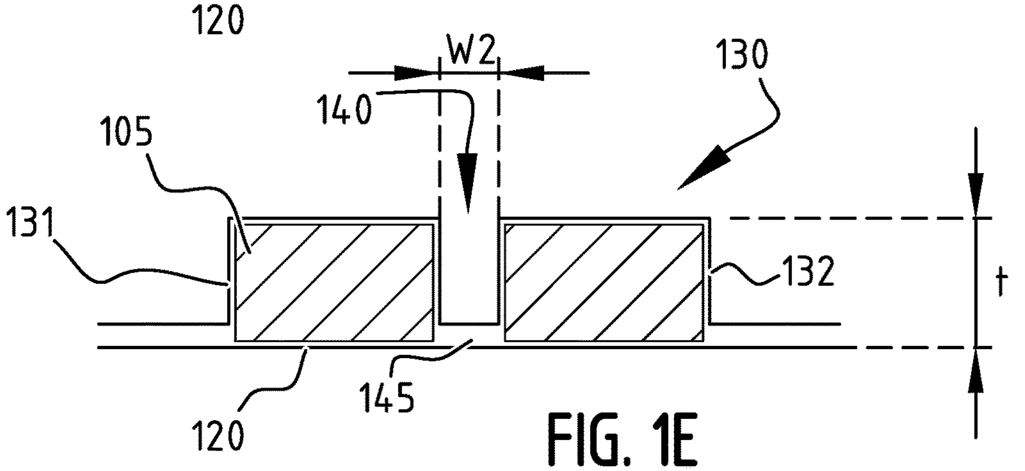
FIG. 1E is a schematic cross-section at the second position of the first channel zone, in particular the first attachment zone along line D-D of FIG. 1B, before a tube is formed on the absorbent core.
Figure 1F:
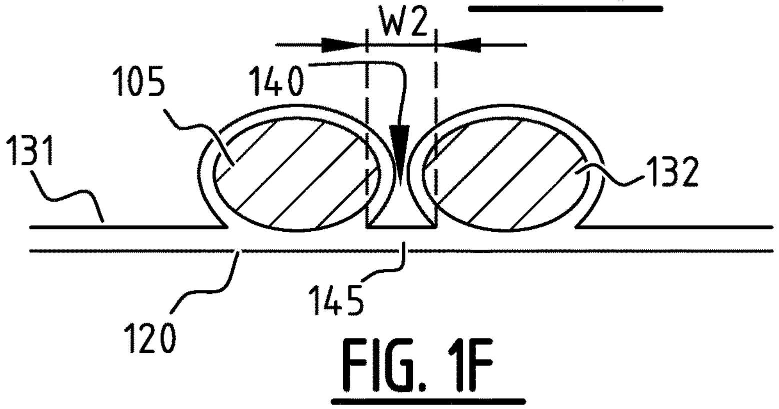
FIG. 1F is a schematic cross-section at the second position of the first channel zone, in particular the first attachment zone along line D-D of FIG. 1B, after a tube is formed on the absorbent core.

FIG. 1C illustrates a schematic cross-section at the first position P1 of the first attachment zone 145 along line C-C of FIG. 1B, before a tube is formed on the absorbent core 130 due to wetting. FIG. 1D illustrates a schematic cross-section at the first position P1 of the first attachment zone along line C-C of FIG. 1B, after the tube is formed on the absorbent core. FIG. 1E illustrates a schematic cross-section at the second position P2 of the first attachment zone along line D-D of FIG. 1B, before a tube is formed on the absorbent core. FIG. 1F illustrates a schematic cross-section at the second position P2 of the first attachment zone along line D-D of FIG. 1B, after the tube is formed on the absorbent core. The first channel 140 has a bottom which forms the attachment zone 145, see FIG. 1C, FIG. 1D, FIG. 1E and FIG. 1F. The attachment in this embodiment is a continuous attachment. However in other embodiments, the attachment may be a discontinuous attachment in a plurality of locations at a distance of each other, seen in a transverse direction of absorbent core 130. Preferably the attachment at the bottom between the top core wrap sheet and the back core wrap sheet is realized by any one of the following or a combination thereof: pressure bonding, thermobonding, sonic bonding, chemical bonding, adhesive, mechanical bonding. At bottom 145 top core wrap sheet 110 is attached to back core wrap sheet 120.

The first attachment zone has a first width w1 at a first position (FIG. 1C, 1D) and a second width w2 at a second position (FIG. 1E, 1F), wherein the first width is larger than the second width. After wetting of the absorbent core, the width of the channel may be maintained. The first width is at least 2% larger than the second width, preferably 4% larger, more preferably 6% larger, even more preferably 8% larger, most preferably 10% larger. The first width is at least 3 mm, preferably at least 5 mm, more preferably at least 7 mm, even more preferably at least 9 mm, most preferably at least 11 mm; and/or the second width is preferably at least 2 mm, more preferably at least 4 mm, even more preferably at least 6 mm, most preferably at least 8 mm. After wetting of the absorbent core, an elongate channel is formed. Accordingly, the elongate channel is wider at the first position than at the second position. Thanks to the attachment zones and associated channels the liquid is evenly spread, resulting in the formation of tubes which provide a tub shape to the absorbent core. In prior art where the channel has a constant width, the formed tubes may close-up the channel, which may reduce the liquid holding and distribution capacities of the channel during further liquid insults, as a result the risk of liquid overflow and leakage is increased. On the other hand in the present invention, when the absorbent core is wetted and tubes are formed, the channel is wider at the first position than at the second position (FIGS. 1D and 1F). The location of the first position may be designated depending on the amount of liquid expected, i.e. depending on the gender of the wearer. In this embodiment, the first position of the first attachment zone positioned at a front portion of the absorbent core. This embodiment may be advantageous for male wearer as more liquid is expected at a front portion of the absorbent core during a liquid insult. Therefore, the tubes formed at the first position of the channel may not close-up the channel, even when large amount of liquid is absorbed and the tubes are heavily swelling. As a result, the liquid holding and distribution capacities of the channel during further liquid insults are improved, and the risks of liquid overflow and leakage are decreased.

Outside of the channel 140, absorbent core 130 has a maximum thickness t. Preferably, each channel 140 extends through at least 90% of the maximum thickness of absorbent core 130, more preferably through 100% of the thickness of absorbent core 130, such that, in the channel 140, substantially no absorbent material is present that between top core wrap sheet 110 and back core wrap sheet 120. It is noted that the channel 140 may be located below and/or above the attachment zone 145, as will be explained in more detail below with reference to FIG. 16.

In a possible embodiment the attachment 145 between top core wrap sheet 110 and back core wrap sheet 120, here at a bottom of each channel 140, is a semi-permanent attachment configured to release after having been in contact with urine for a predetermined period of time, wherein said predetermined period of time is preferably smaller than 30 s.

Figure 11A:
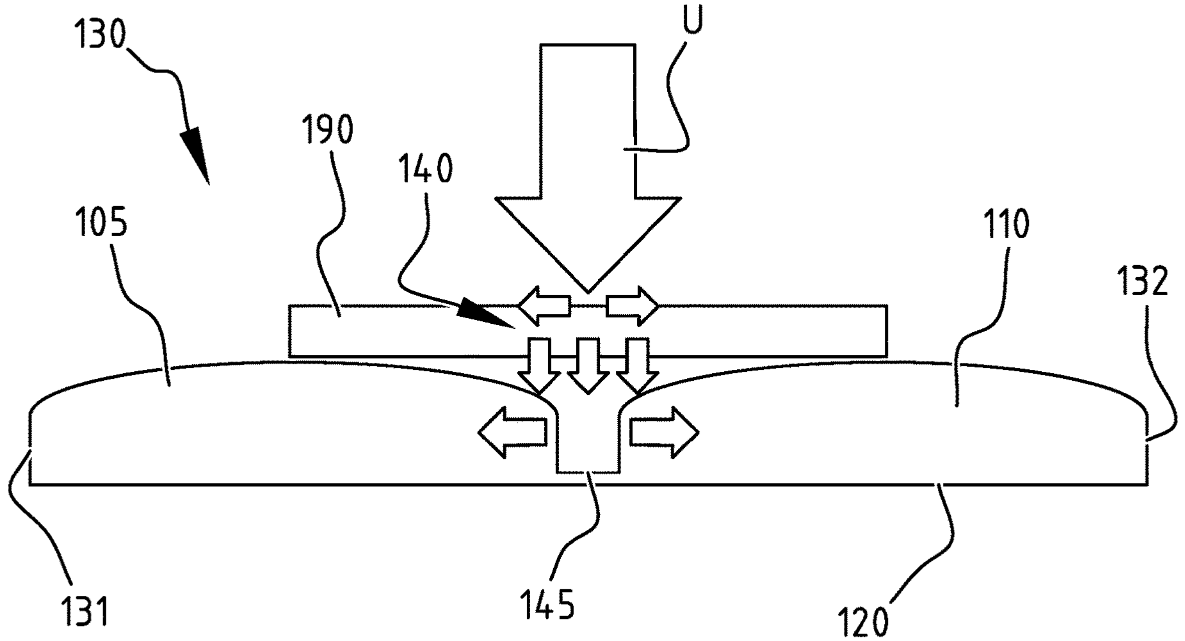
FIGS. 11A and 11B are cross-sectional views illustrating the effect of liquid being absorbed by the absorbent core of an exemplary embodiment of an absorbent article.
Figure 11B:
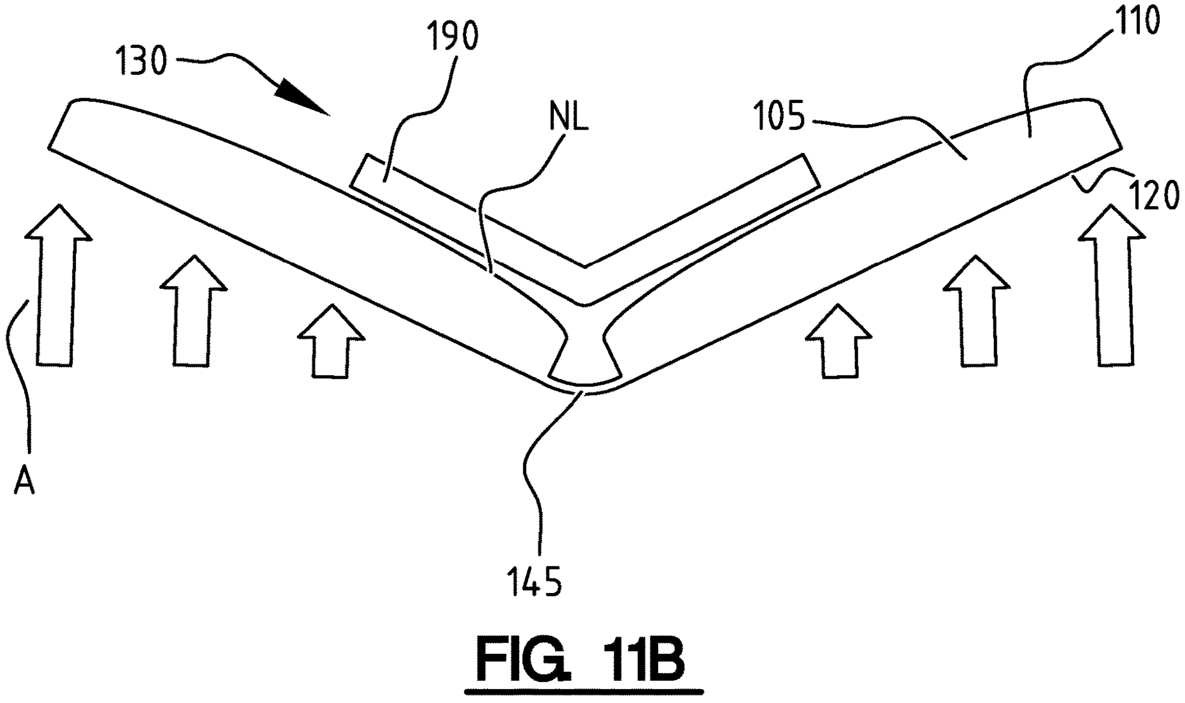

In another possible embodiment the attachment between top core wrap sheet 110 and back core wrap sheet 120, here at the bottom of the channel 140, is a permanent attachment; and absorbent core 130 is configured such that, in a wetted state of absorbent core 130, the absorbent material extends over bottom 145 of channel 140. This is illustrated in FIGS. 11A and 11B for the first channel 140. Channel 140 170 guides urine U or any other aqueous liquid through the side walls of channel 140 into absorbent core 130. Those side walls create an additional path along which the liquid can flow into absorbent core 130 and enhance the diffusion of the liquid into absorbent core 130. Also, because of the swelling of the core material of absorbent core 130, the outer bands of absorbent core 130 will rotate around channels 140 as indicated by arrows A in FIG. 11B. In that manner the diaper takes the shape of a tub or cup, such that any liquid NL which would not yet be absorbed by the absorbent material 105 is maintained in the tub shape. This results in a better protection against leakage and a diaper fitting perfectly to the body. Hence the diaper of FIGS. 1A-1E will create more freedom of movement for the wearer of a wetted diaper.

It is clear to the skilled person that the attachment zones may be provided by means of continuous attachments in the transversal direction of the absorbent core and/or continuous attachments in the longitudinal direction of the absorbent core and/or discontinuous attachments in the transversal direction of the absorbent core and/or discontinuous attachments in the longitudinal direction of the absorbent core.

Absorbent core 130 has a front portion 130*a* extending at one side of a transverse crotch line which corresponds in this embodiment with fold line L, and a rear portion 130*b* extending at the other side of the transverse crotch line L. The channel 140 covers at least 10% of the length of the absorbent core, preferably more than 20%, more preferably more than 30%, even more preferably more than 40%, most preferably more than 50%, e.g. 60% or 70% or even 100% of the length of the absorbent core, which allows a better liquid distribution over a large area of the absorbent core; indeed, in the embodiment of FIG. 1A-1F the channel cover a length equal to l1+l3 which is more than 60% of the length la of absorbent core 130.

The channel 140 may be indicated with a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. As the sheets may be partially transparent, the print may be arranged on a sheet in between the topsheet and the backsheet, as long as it is visible through the topsheet and/or the backsheet. Preferably the print is visible when looking at the topsheet of the diaper.

Preferably absorbent core 130 is provided with at least a first attachment zone 140 where the top core wrap sheet is attached to the back core wrap sheet, and where preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130*a* extending between the front edge 133 and a transverse crotch line L of the absorbent core, and a rear portion 130*b* extending between the rear edge 134 and the transverse crotch line L of the absorbent core 130. The first, second and third zone Z1, Z2, Z3 extend in the front portion 130*a* of the absorbent core and the fourth and fifth zone Z4, Z5 extend in the rear portion 130*b*. Preferably, in said first and fifth zone Z1, Z5 substantially no permanent attachment zones are present. However the first and/or fifth zone Z1, Z5 may comprise temporary secondary attachments that loosen upon wetting. The second zone Z2 comprises the front part of a first permanent elongate attachment zone 140, said front part of the first attachment zone 140 extending from an edge of the first zone Z1 in the direction of the third zone Z3.

The fourth zone Z4 comprises the rear part of a first elongate attachment zone 140, said rear part of the first attachment zone extending from an edge of the fifth zone Z5 in the direction of the third zone Z3.

The chassis of the diaper 100 in FIGS. 1A-1F comprises a liquid pervious topsheet (not shown in FIGS. 1C-1F, but the topsheet is a layer above top core wrap sheet 110) and liquid impervious backsheet (not shown in FIGS. 1C-1F, but the backsheet is a layer below back core wrap sheet 110). The topsheet may be attached to the top core wrap sheet 110, e.g. in the attachment zone 140. Also, the backsheet may be attached to the back core wrap sheet 120, e.g. in the attachment zone 140. Preferably the chassis further includes side panels or ears 210, elasticized leg cuffs 230 and elastic waist elements (not shown). A front end portion of diaper 100 is configured as a front waist region 100*a*. The opposite rear end portion is configured as a back waist region 100*b* of diaper 100. An intermediate portion of diaper 100 is configured as crotch region CR, which extends longitudinally between first and second waist regions 100*a* and 100*b*. Waist regions 100*a* and 100*b* may include elastic waist elements such that they gather about the waist of the wearer to provide improved fit and containment. Crotch region CR is that portion of diaper 100 which, when the diaper 100 is worn, is generally positioned between the wearer's legs. The periphery of diaper 100 is defined by the outer edges of the diaper 100 in which longitudinal edges 101, 102 run generally parallel to a longitudinal axis of diaper 100 and transverse end edges 103, 104 run between the longitudinal edges 101, 102 generally parallel to a transverse axis of diaper 100. The chassis also comprises a fastening system, which may include at least one fastening or securing member 212 and at least one landing zone 220. The various components within diaper 100 may be bound, joined or secured by any method known in the art, for example by adhesives in uniform continuous layers, patterned layers or arrays of separate lines, spirals or spots. Top core wrap sheet, topsheet, back core wrap sheet, backsheet, absorbent material and other components may be assembled in a variety of well-known configurations and are well known in the art.

Backsheet covers absorbent core 130 and preferably extends beyond the absorbent core 130 toward longitudinal edges 101, 102 and end edges 103, 104 of diaper 100 and may be joined with top sheet. Backsheet prevents bodily exudates absorbed by the absorbent core 130 and contained within diaper 100 from soiling other external articles that may contact the wearer, such as bed sheets and undergarments. In preferred embodiments, backsheet is substantially impervious to bodily exudates and comprises a laminate of a nonwoven and a thin plastic film such as a thermoplastic film. Backsheet may comprise breathable materials that permit vapor to escape from diaper 100 while still preventing bodily exudates from passing through backsheet. It may be semi-rigid, non-elastic and can be made fully or partially elasticized and include backing.

The top sheet which is located above the top core wrap sheet 110, is preferably soft, exhibits good strikethroughs and has a reduced tendency to rewet from the liquid absorbent material. Top sheet may be semi-rigid and non-elastic, or may be fully or partially elasticized. Topsheet is intended to be placed in close proximity to the skin of the wearer when diaper 100 is worn. Topsheet permits bodily exudates to rapidly penetrate it so as to flow more quickly toward absorbent core 130 via a top surface thereof and via the plurality of channels 140, preferably not allowing such bodily exudates to flow back through topsheet. Topsheet may be constructed from any one of a wide range of liquid and vapor permeable, preferably hydrophilic, materials. The upper and lower surface of topsheet may be treated differently. Topsheet may include e.g. a surfactant on the upper surface so as to facilitate liquid transfer there through, especially at a central zone or area of topsheet located over absorbent core 130, and/or a hydrophobic agent on the lower surface to minimize the liquid contained within absorbent core 130 from contact wetting topsheet thereby reducing rewet values. Topsheet may be coated with a substance having rash preventing or rash reducing properties. Preferably, topsheet covers substantially the entire wearer facing area of diaper 100, including substantially all of front waist region 100*a*, back waist region 100*b*, and crotch region CR. Optionally, side panels 210, 210' and/or waist feature layers of the inner region may be formed from the same single topsheet material. Alternatively, topsheet may be formed from multiple different materials which vary across of topsheet. Such a multiple piece design allows for creation of preferred properties and different zones of the topsheet.

Absorbent core 130 may comprise any absorbent material that is generally compressible, conformable, non-irritating to the wearer's skin, and capable of absorbing and retaining bodily exudates. Absorbent core 130 may comprise a wide variety of liquid absorbent materials commonly used in absorbent articles. Preferably, absorbent core 130 comprises fluff material, typically cellulosic fluff pulp. However, in other embodiments, absorbent core 130 may be substantially fluffless and comprise superabsorbent polymers. Also, absorbent core 130 may comprise a combination of cellulosic fluff pulp and superabsorbent polymers. Absorbent core 130 may be configured to extend substantially the full length and/or width of diaper 100. However, as in the embodiment of FIGS. 1A-1F, preferably absorbent structure 130 is not coextensive with the entire diaper 100 and is limited to certain regions of diaper 100 including crotch region CR. In various embodiments, the absorbent core 300 extends to the edges of diaper 100 but the absorbent material is concentrated in the crotch region CR or another target zone of the diaper 100. In FIGS. 1A-1F, absorbent core 130 is shown as having a substantially rectangular configuration, however, absorbent core 130 may be shaped differently, such as, elliptical, dogbane shaped, T-shaped or I-shaped. More in particular the width of the front portion 130*a* may be smaller than the width of the rear portion 130*b* of the absorbent core.

Examples of commonly occurring absorbent materials used for absorbent core 130 are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride.

Diaper 100 may also utilize a pair of containment walls or cuffs 230. Each cuff 230 is a longitudinally extending wall structure preferably positioned on each side of absorbent core 130 and spaced laterally from the center line CL. Preferably, cuffs 230 are attached, for example, by adhesive or sonic bonding to the lower structure. Preferably, cuffs 230 are equipped with elastic members. When released or otherwise allowed relaxing, the elastic members retract inwardly. When diaper 100 is worn, the elastic members function to contract cuffs 230 about the buttocks and the thighs of the wearer in a manner, which forms a seal between diaper 100, the buttocks and the thighs.

The waist regions 100*a* and 100*b* each comprise a central region and a pair of side panels or ears 210, 210' which typically comprise the outer lateral portions of the waist regions. These side panels 210, 210' may be unitary with the chassis or may be attached or joined thereto by any means know in the art. Preferably, the side panels 210 positioned in the back waist region 100*b* are flexible, extensible and/or elastic in at least the lateral direction. In another embodiment the side panels 210 are non-elastic, semi-rigid, rigid and/or stiff. In order to keep diaper 100 in place about the wearer, preferably at least a portion of the back waist region 100*b* is attached by fastening or securing members 212 to at least a portion of the front waist region 100*a*. The fastening or securing members 212 may be e.g. adhesive, mechanical fasteners, hook and loop features, conceivable strings and/or combinations thereof. The fastening or securing members 212 may also be co-adhesive such that they adhere to each other but not other materials. Preferably the materials making up the fastening or securing members 212 are flexible, extensible and/or elastic, allowing them to better conform to the shape and movements of the body and thus, to reduce the likelihood that the fastening system will irritate or injure the wearer's skin. Alternatively, the absorbent article may be pants and the like. In this configuration, the absorbent article may or may not have fastening members.

Diaper 100 may also employ additional layers, such as an acquisition layer and/or dispersion layer situated between topsheet and absorbent core 130, and/or coverstock layers, and/or other layers situated between absorbent core 130 and backsheet. An acquisition layer and/or dispersion layer serves to slow down the flow so that the liquid has adequate time to be absorbed by absorbent core 130. FIGS. 11A and 11B show an acquisition layer 190 above top core wrap layer 110.

Diaper 100 may also include such other features, components and elements as are known in the art including waistbands, waist cap features, elastics and the like to provide better fit, containment and aesthetic characteristics. These features may be assembled in a variety of well-known configurations and are well known in the art.

The absorbent article 100 comprises a liquid pervious topsheet, a liquid impervious backsheet, and an absorbent core 130 positioned in between the topsheet and the backsheet. The absorbent core 130 comprises absorbent material 105 between a top core wrap sheet 110 and a back core wrap sheet 120. Absorbent core 130 has a first and second longitudinal edge 131, 132 and a first and second transverse edge 133, 134.

Figure 3A:
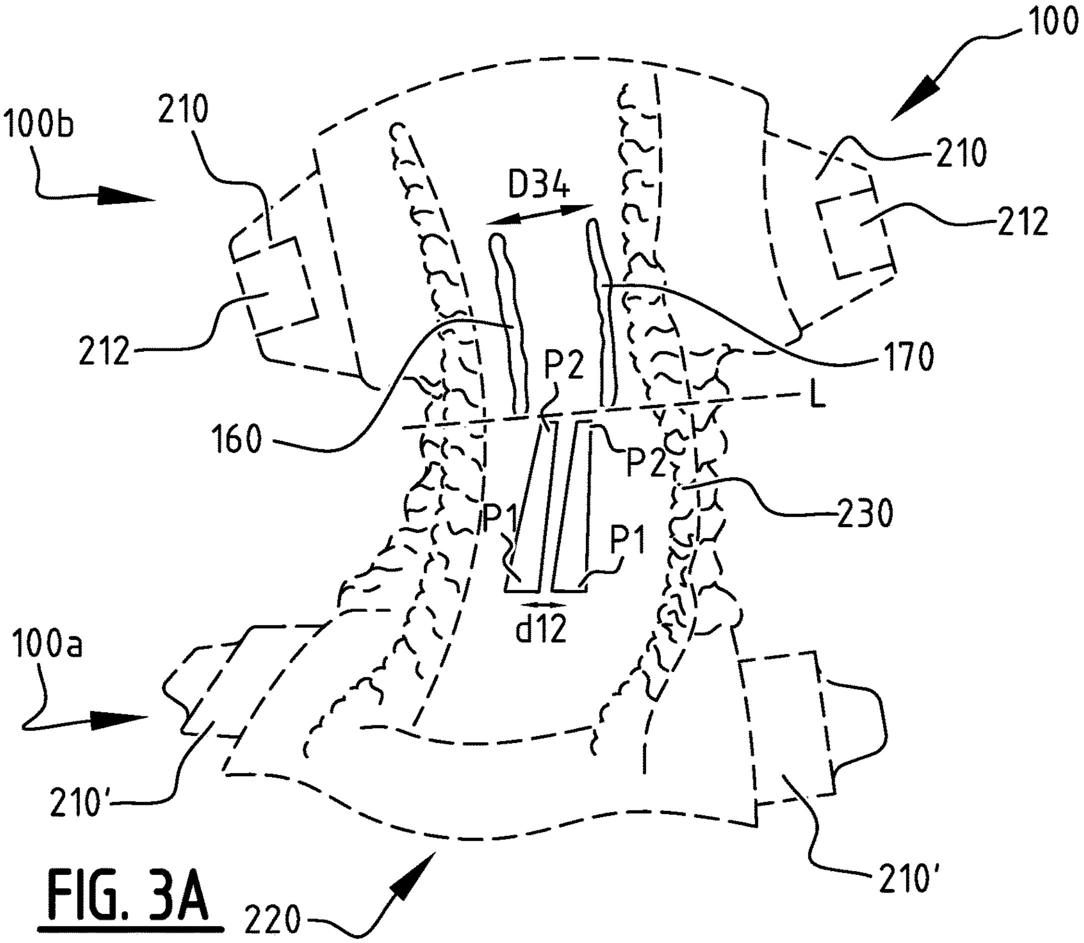
FIG. 3A is a perspective view of an exemplary embodiment of a diaper.
Figure 3B:
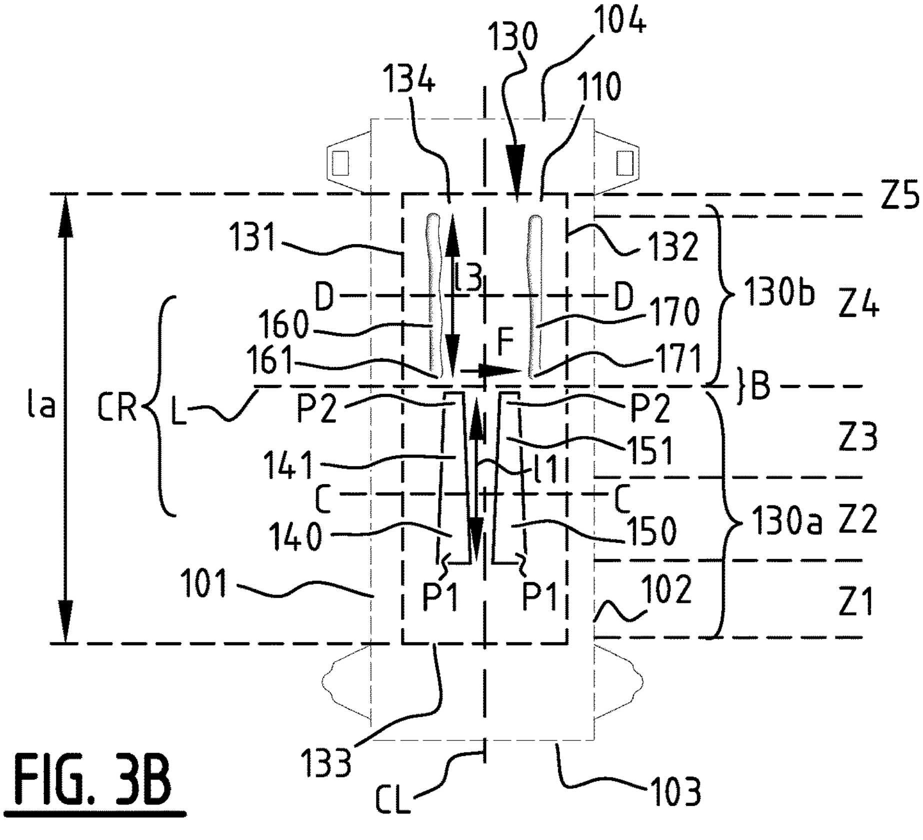
FIG. 3B is a top plan view of the diaper of FIG. 3A.

FIGS. 3A and 3B illustrate another exemplary embodiment of a diaper 100. Diaper 100 comprises a liquid pervious topsheet, a liquid impervious backsheet, and an absorbent core 130 positioned in between topsheet and backsheet. The absorbent core 130 is provided with a plurality of attachment zones 145, 155, 165, 175 comprising at least a first attachment zone 145 and a second attachment zone 155. The first and second attachment zones extend next to each other from the crotch region CR in the direction of the first and/or second transverse edge 133, 134. In first and second attachment zone 145, 155 the top core wrap sheet 110 is attached to the back core wrap sheet 120. Both the first and the second attachment zone have a first width w1 at a first position p1 and a second width w2 at a second position P2.

The first width w1 is larger than the second width w2, and the width of the first attachment zone gradually increases from the second position P2 to the first position P1.

In that manner, upon wetting of the absorbent material, a first and second channel 140, 150 are created at said first and second attachment zone 145, 155, respectively.

Absorbent article 100 is provided at said top core wrap sheet with at least a first and a second attachment zone 145, 155 located a distance d12 of each other. In that manner a first and second channel 140, 150 formed upon wetting, each extend from a crotch region CR in the direction of the first transverse edge 133. Preferably the distance d12 is between 10 mm and 50 mm, more preferably between 15 and 30 mm. Preferably, the length of the first and second channel is substantially the same, more preferably the length l1 of the first channel and the length l2 of the second channel is between 60 mm and 140 mm, more preferably between 75 mm and 125 mm. Preferably, the distance between the first attachment zone 145 and the first longitudinal side 131 is between 20 and 30 mm, and the distance between the second attachment zone 155 and the second longitudinal side 132 is between 20 and 30 mm. Preferably, the distance between the first/second attachment zone 145, 155 and the transverse edge 133 is between 50 and 125 mm, more preferably between 75 and 115 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second attachment zone 145, 155 (and hence first and second channel 140, 150) may be diverging slightly outwardly in the direction of first transverse edge 133. Preferably first channel 140 and second channel 150 are arranged symmetrically with respect to a longitudinal center line CL of absorbent core 130.

Absorbent article 100 is further provided with a third and a fourth channel 160, 170 located at a distance d34 of each other. Third and fourth channel 160, 170 each extend from crotch region CR in the direction of second transverse edge 134. The distance d12 between first and second channel 140, 150 is different from the distance d34 between third and fourth channel 160, 170. Preferably the distance d34 is between 25 mm and 80 mm, more preferably between 35 mm and 55 mm. Preferably, the length of the third and fourth channel 160, 170 is substantially the same, more preferably the length l3 of the third channel and the length l4 of the fourth channel is between 30 mm and 130 mm, more preferably between 30 mm and 70 mm. Preferably, the distance between the third attachment zone 165/third channel 160 and the first longitudinal side 131 is between 20 and 30 mm, and the distance between the fourth attachment zone 175 and the second longitudinal side 132 is between 20 and 30 mm. Preferably, the distance between the third/fourth attachment zone 165, 175 and the transverse edge 134 is between 30 mm and 100 mm, more preferably between 40 mm and 75 mm.

Third channel 160 and fourth channel 170 are substantially parallel and run in the longitudinal direction of absorbent core 130. However, it is also possible for third and fourth channel 160, 170 to extend under a small angle with respect to the longitudinal direction of absorbent core 130, e.g. an angle between 5 and 10°. For example, third and fourth channel 160, 170 may be diverging slightly outwardly in the direction of second transverse edge 134. Preferably third channel 160 and fourth channel 170 are arranged symmetrically with respect to a longitudinal center line CL of absorbent core 130.

Preferably, the distance between an end point 141 of first channel 140 and an end point 161 of third channel 160 is smaller than 25 mm, more preferably smaller than 20 mm. Similarly, preferably, the distance between an end point 151 of second channel 150 and an end point 171 of fourth channel 170 is smaller than 25 mm, more preferably smaller than 20 mm. More preferably, endpoints 141, 151, 161 and 171 are located on substantially the same transverse line L functioning as a fold line along which the diaper can be folded in two.

Absorbent core 130 has a front portion 130*a* extending at one side of a transverse crotch line which corresponds in this embodiment with fold line L, and a rear portion 130*b* extending at the other side of the transverse crotch line L. First and second channel 140, 150 extend at least in front portion 130*a* of absorbent core 130, and third and fourth channel 160, 170 extend at least in rear portion 130*b* of the absorbent core 130. Preferably the distance d12 between first and second channel 140, 150 in front portion 130*a* is smaller than the distance d34 between third and fourth channel 160, 170 in rear portion 130*b*.

The plurality of channels 140, 150, 160, 170 together cover at least 60%, preferably at least 70% of the length la of absorbent core 130; indeed, in the embodiment of FIG. 3A-3B the channels cover a length equal to l1+l3 which is more than 60% of the length la of absorbent core 130.

The plurality of channels 140, 150, 160, 170 may be indicated with a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. As the sheets may be partially transparent, the print may be arranged on a sheet in between the topsheet and the backsheet, as long as it is visible through the topsheet and/or the backsheet. Preferably the print is visible when looking at the topsheet of the diaper. For example, a topsheet area above first and second channels 140, 150 may be printed with an ink of a first color and a topsheet area above third and fourth channels 160, 170 may be printed with the same color or with a different color. In that manner a user will be able to easily recognize the front and rear portion of a diaper, and will recognize more easily how to put on the diaper.

Preferably absorbent core 130 is provided with a plurality of attachment zones 140, 150, 160, 170 where the top core wrap sheet is attached to the back core wrap sheet, and where preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130*a* extending between the front edge 133 and a transverse crotch line L of the absorbent core, and a rear portion 130*b* extending between the rear edge 134 and the transverse crotch line L of the absorbent core 130. The first, second and third zone Z1, Z2, Z3 extend in the front portion 130*a* of the absorbent core and the fourth and fifth zone Z4, Z5 extend in the rear portion 130*b*. Preferably, in said first and fifth zone Z1, Z5 substantially no permanent attachment zones are present. However the first and/or fifth zone Z1, Z5 may comprise temporary secondary attachments that loosen upon wetting. The second zone Z2 comprises a first and a second permanent elongate front attachment zone 130, 140, said first and second front attachment zones 130, 140 extending from an edge of the first zone Z1 in the direction of the third zone Z3.

The fourth zone Z4 comprises a first and second rear elongate attachment zone 160, 170, said first and second rear attachment zone extending from an edge of the fifth zone Z5 in the direction of the third zone Z3. At least one of said second, third and fourth zone comprises a capillary bridge zone B allowing a liquid flow F between the first and the second side edge 131, 132 by capillary action through the absorbent material. The capillary bridge zone B extends between the first front attachment zone 140 and the first rear attachment zone 160, such that upon wetting of the absorbent material, a front and rear channel are created at said first front and rear attachment zone 140, 160, respectively, wherein the capillary bridge zone B extends between said front and rear channel. Preferably a minimum distance x between the first front attachment zone 140 and the first rear attachment zone 160 is larger than 3 mm more preferably larger than 5 mm. The capillary bridge zone B further extends between the second front attachment zone 150 and the second rear attachment zone 170, such that upon wetting of the absorbent material, a front and rear channel are created at said second front and rear attachment zone 150, 170, respectively, wherein the capillary bridge zone B further extends between said front and rear channel. Preferably a minimum distance x between the second front attachment zone 150 and the second rear attachment zone 170 is larger than 3 mm more preferably larger than 5 mm.

Figure 4A:
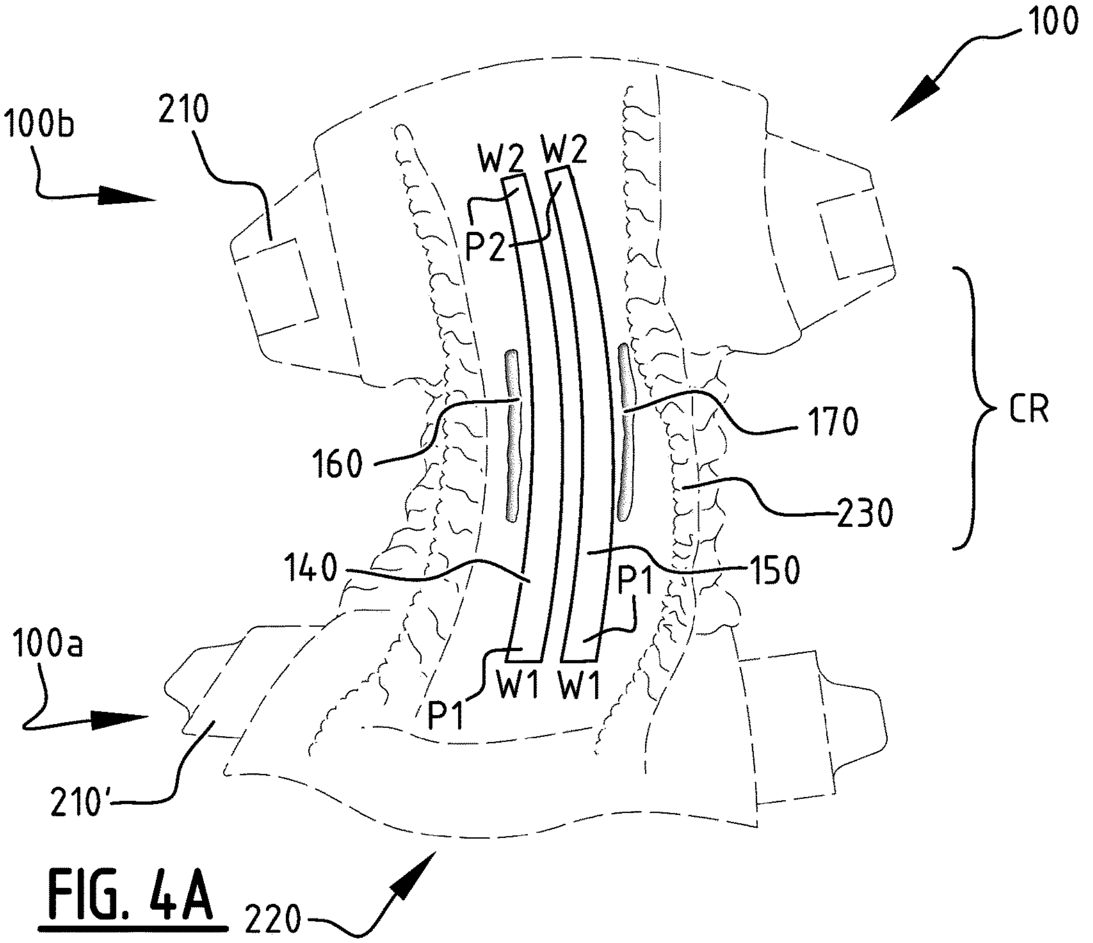
FIG. 4A is a perspective view of an exemplary embodiment of a diaper.
Figure 4B:
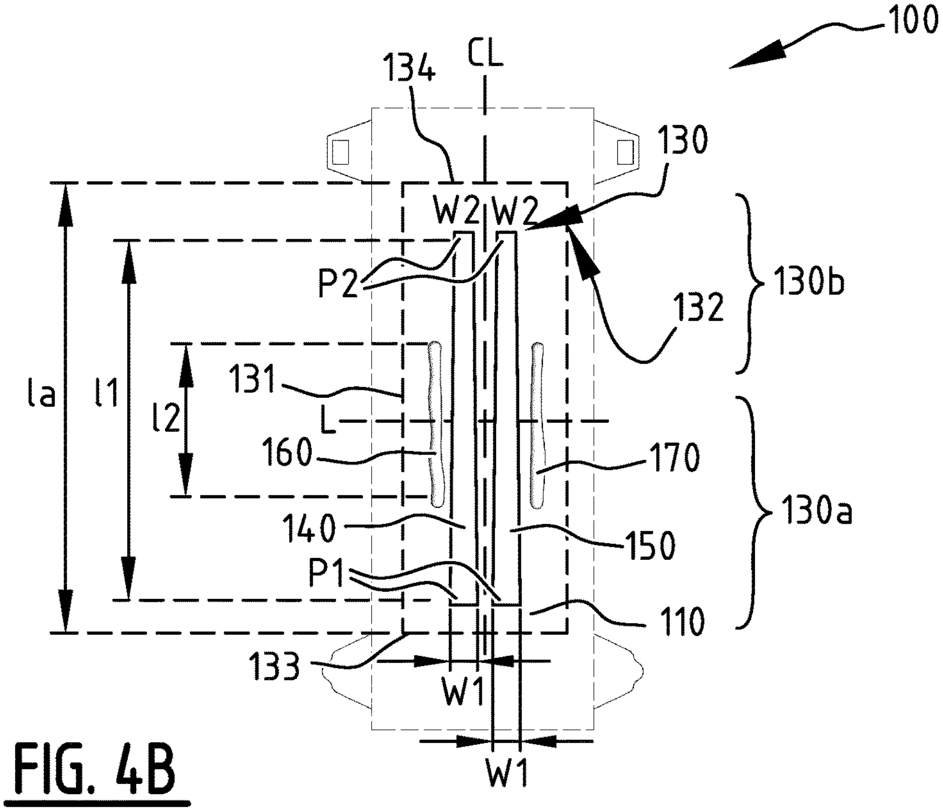
FIG. 4B is a top plan view of the diaper of FIG. 4A.

FIGS. 4A and 4B illustrate another exemplary embodiment of a diaper 100. Diaper 100 comprises a liquid pervious topsheet, a liquid impervious backsheet, and an absorbent core 130 positioned in between topsheet and backsheet. Absorbent core 130 has a first and second longitudinal edge 131, 132 and a first and second transverse edge 133, 134. Absorbent article 100 is provided at the top core wrap sheet 110 with a first and a second attachment zone 145, 155 for creating a first and second channel 140, 150 located a distance d12 of each other. Both the first and the second attachment zone have a first width w1 at a first position P1 and a second width w2 at a second position P2. The first width is larger than the second width, and the width of the first attachment zone gradually increases from the second position to the first position. First and second channel 140, 150 each extend from a crotch region CR in the direction of the first transverse edge 133 and the second transverse edge 134. In this embodiment, preferably, first and second channel extend over more than 80% of the length of absorbent core 130. Preferably the distance d12 is between 10 mm and 50 mm, more preferably between 15 and 30 mm. Preferably, the length of the first and second channel is substantially the same, more preferably the length l1 of the first channel and the length l2 of the second channel is between 100 mm and 300 mm, more preferably between 100 mm and 250 mm. Preferably, the distance between the first/second attachment zone 145, 155 and the transverse edge 133 is between 50 and 125 mm, more preferably between 75 and 115 mm, and the distance between the first/second attachment zone 145, 155 and the transverse edge 134 is between 50 and 125 mm, more preferably between 75 and 115 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second channel 140, 150 may be diverging slightly outwardly in the direction of first transverse edge 133 and may be diverging slightly outwardly in the direction of second transverse edge 134. Preferably first channel 140 and second channel 150 are arranged symmetrically with respect to a longitudinal center line CL of absorbent core 130.

Absorbent article 100 is further provided with a third and a fourth channel 160, 170 located a distance d34 of each other. Third and fourth channel 160, 170 may have a constant width. Third and fourth channel 160, 170 each extend from crotch region CR in the direction of first and second transverse edge 134. The distance d12 between first and second channel 140, 150 is different from the distance d34 between third and fourth channel 160, 170. Preferably the distance d34 is between 25 mm and 85 mm, more preferably between 35 mm and 55 mm. Preferably, the length of the third and fourth channel 160, 170 is substantially the same, more preferably the length l3 of the third channel and the length l4 of the fourth channel is between 50 mm and 150 mm, more preferably between 60 mm and 140 mm. Preferably, the distance between the third attachment zone 165 and the first longitudinal side 131 is between 10 and 30 mm, and the distance between the second attachment zone 175 and the second longitudinal side 132 is between 10 and 30 mm.

Third channel 160 and fourth channel 170 are substantially parallel and run in the longitudinal direction of absorbent core 130. However, it is also possible for third and fourth channel 160, 170 to extend under a small angle with respect to the longitudinal direction of absorbent core 130, e.g. an angle between 5 and 10°. For example, third and fourth channel 160, 170 may be diverging slightly outwardly in the direction of first transverse edge 133 and second transverse edge 134. Preferably third channel 160 and fourth channel 170 are arranged symmetrically with respect to a longitudinal center line CL of absorbent core 130.

In this embodiment, first, second, third and fourth channel 140, 150, 160, 170 each have a bottom 145, 155, 165, 175, similar to the bottom illustrated in FIG. 1C-FIG. 1F for the first embodiment of FIGS. 1A-1F. At bottom 145, 155, 165, 175 top core wrap sheet 110 is attached to back core wrap sheet 120 as described previously. Outside of the plurality of channels 140, 150, 160, 170, absorbent core 130 has a maximum thickness t. Preferably, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present that between top core wrap sheet 110 and back core wrap sheet 120.

Absorbent core 130 has a front portion 130*a* extending at one side of a transverse crotch line T, and a rear portion 130*b* extending at the other side of the transverse crotch line T. First, second, third and fourth channel 140, 150, 160, 170 each extend both in front portion 130*a* and rear portion 130*b* of absorbent core 130. Preferably the distance d12 between first and second channel 140, 150 is smaller than the distance d34 between third and fourth channel 160, 170, and the length l1 of first and second channel 140, 150 is bigger than the length l3 of third and fourth channel 160, 170. Such a channel pattern has the advantage that liquid can be distributed over substantially the entire absorbent core 130, and that any leakage risks in various positions of the wearer can be reduced.

The plurality of channels 140, 150, 160, 170 together cover at least 60%, preferably at least 70% of the length la of absorbent core 130; indeed, in the embodiment of FIGS. 1A-1F the channels cover a length equal to l1 which is more than 70% of the length la of absorbent core 130.

The plurality of channels 140, 150, 160, 170 may be indicated in a color and/or with a pattern which is different from the color and/or pattern of topsheet. More in particular the area of the channels may comprise a print allowing a user to visually distinguish the channels. For example, an area of the topsheet above front portions of channels 140, 150, 160, 170 may be printed with an ink of a first color and an area of the topsheet above rear portions the channels 140, 150, 160, 170 may be printed with a different color. In that manner a user will be able to easily recognize the front and rear portion of a diaper, and will recognize more easily how to put on the diaper.

Topsheet, backsheet and absorbent core 130 may have the same features as described above in connection with FIGS. 1A-1F.

Figure 5:
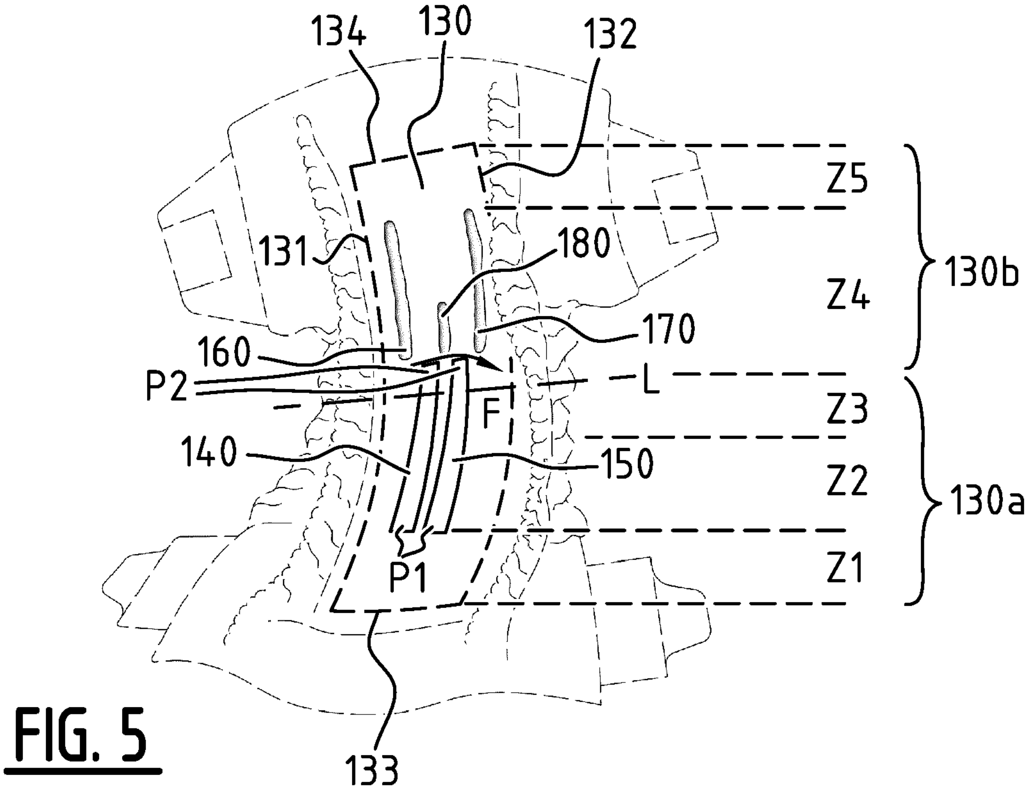
FIGS. 5-10 are perspective view of other exemplary embodiments of a diaper.

FIG. 5 illustrates a variant of diaper 100 of FIGS. 3A-3B. The features and characteristics are similar with this difference that a fifth channel 180 is provided in top core wrap sheet 110, in between third and fourth channel 160, 170 and extending along a longitudinal center line of diaper 100. Further, the first and second channels are slightly longer and extend over transverse fold line L in the direction of second transverse edge 134. The third and fourth channel are slightly shorter compared to the embodiment of FIGS. 3A-3B. By the additional channel 180 the distribution of the liquid can be further improved, especially for larger absorbent articles. Preferably, in the plurality of attachment zones 140, 150, 160, 170, 180 the top core wrap sheet is attached to the back core wrap sheet, and preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion **130*a* extending between the front edge 133 and a transverse crotch line L of the absorbent core, and a rear portion 130*b* extending between the rear edge 134 and the transverse crotch line L of the absorbent core 130. The first, second and third zone Z1, Z2, Z3 extend in the front portion 130*a* of the absorbent core and the fourth and fifth zone Z4, Z5 extend in the rear portion 130*b***. Preferably, in said first and fifth zone Z1, Z5 substantially no permanent attachment zones are present. However the first and/or fifth zone Z1, Z5 may comprise temporary secondary attachments that loosen upon wetting.

The second zone Z2 comprises a first and a second permanent elongate front attachment zone 130, 140, said first and second front attachment zones 130, 140 extending from an edge of the first zone Z1 in the direction of the third zone Z3, and here even into the fourth zone.

The fourth zone Z4 comprises a first, second and third rear elongate attachment zone 160, 170, 180 said first and second rear attachment zone extending from an edge of the fifth zone Z5 in the direction of the third zone Z3.

At least one of said second, third and fourth zone comprises a bridge zone B allowing a liquid flow F between the first and the second side edge 131, 132 by capillary action through the absorbent material. The bridge zone B extends between the first front attachment zone 140 and the first rear attachment zone 160, such that upon wetting of the absorbent material, a front and rear channel are created at said first front and rear attachment zone 140, 160, respectively, wherein the bridge zone B extends between said front and rear channel. Preferably a minimum distance x between the first front attachment zone 140 and the first rear attachment zone 160 is larger than 3 mm more preferably larger than 5 mm. The bridge zone B further extends between the second front attachment zone 150 and the second rear attachment zone 170, such that upon wetting of the absorbent material, a front and rear channel are created at said second front and rear attachment zone 150, 170, respectively, wherein the bridge zone B further extends between said front and rear channel. Preferably a minimum distance x between the second front attachment zone 150 and the second rear attachment zone 170 is larger than 3 mm more preferably larger than 5 mm.

Figure 6:
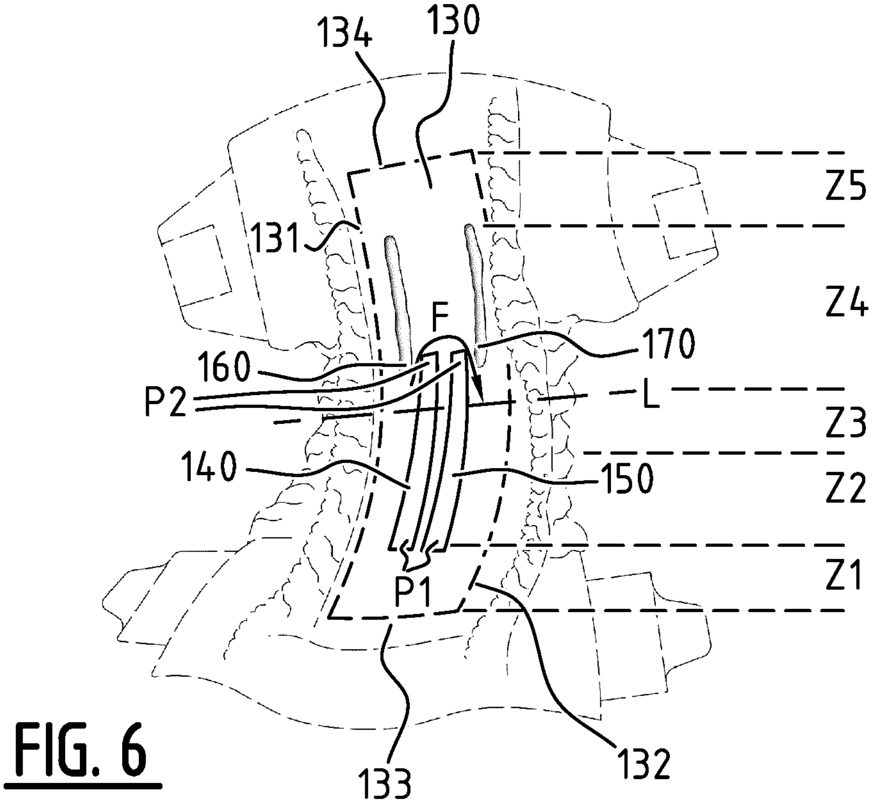

FIG. 6 illustrates a further variant of diaper 100 of FIGS. 3A-3B. The features and characteristics are similar with this difference that the first and second channels are slightly longer and extend over transverse fold line L in the direction of second transverse edge 134, in between third and fourth channel 160, 170. Depending on the shape and size of the absorbent article, the distribution of the liquid and the creation of the cup/tub shape can be further improved by this additional length. Also in FIG. 6 five zones Z1, Z2, Z3, Z4, Z5 can be distinguished with similar properties as those described above for FIG. 5.

Figure 7:
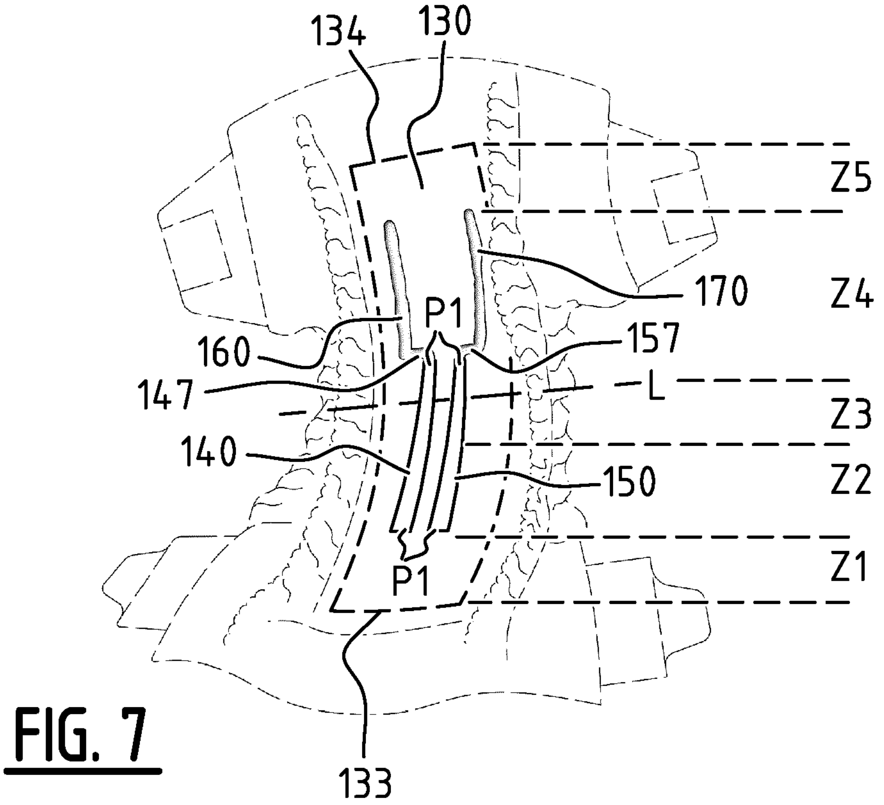

FIG. 7 illustrates a variant of diaper 100 of FIG. 6. The features and characteristics are similar with this difference that first channel 140 is connected to third channel 160 through a first transverse channel portion 147 and that second channel 150 is connected to fourth channel 170 through a second transverse channel portion 157. In that manner any liquid can flow from the first channel 140 to the third channel 160 and vice versa, and liquid can flow from the second channel 150 to the fourth channel 170 and vice versa, resulting in an even better distribution of the liquid. Also, channel portions 147, 157 may help in creating the tub shape upon wetting of the absorbent core 130. Preferably first and second channel 140, 150 extend in a longitudinal direction of absorbent core 130 over a length which is longer than the length of third and fourth channel 160, 170, wherein third and fourth channel extend between crotch region CR and second transverse edge 134 and first and second channel extend between crotch region CR and first transverse edge 133. Also in FIG. 7 five zones Z1, Z2, Z3, Z4, Z5 can be distinguished with similar properties as those described above for FIG. 5. It is noted that in the embodiment of FIG. 7 e.g. the channel portions 147, 157 could be provided in the form of temporary attachment portions which gradually loosen upon wetting in order to created a bridge zone for a liquid flow from one side edge 131 to the other side edge 132 and vice versa.

Figure 8:
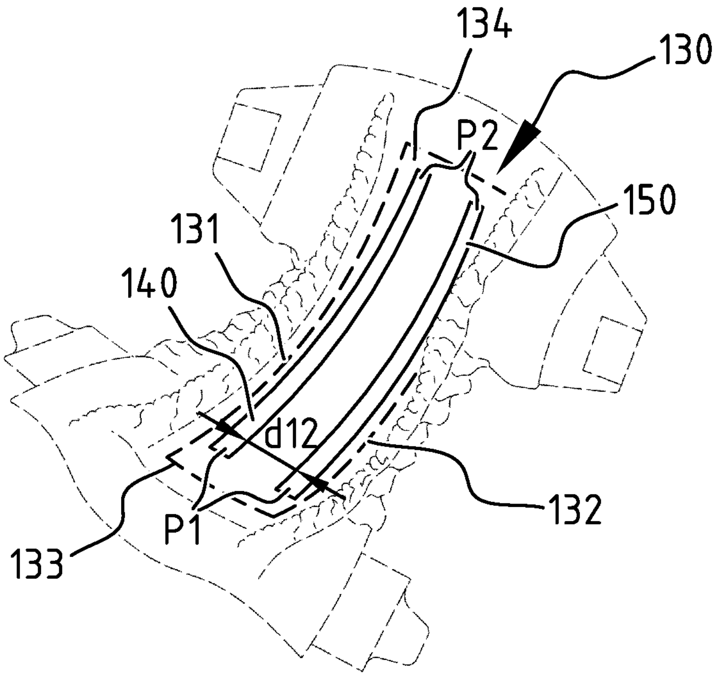

FIG. 8 illustrates another more basic exemplary embodiment of a diaper 100 according to the invention. Diaper 100 comprises a liquid pervious topsheet, a liquid impervious backsheet, and an absorbent core 130 positioned in between topsheet and backsheet. Absorbent core 130 has a first and second longitudinal edge 131, 132 and a first and second transverse edge 133, 134. Absorbent article 100 is provided with a first and a second attachment zone for creating a first and a second channel 140, 150 located a distance d12 of each other, upon wetting of the diaper 100. The first attachment zone has a first width w1 at a first position P1 and a second width w2 at a second position P2. The first width is larger than the second width, and the width of the first attachment zone increases from the second position to the first position. First and second channel 140, 150 each extend from a crotch region CR in the direction of the first transverse edge 133 and the se cond transverse edge 134. In this embodiment, preferably, first and second channel extend over more than 80% of the length of absorbent core 130. Preferably the distance d12 is between 10 mm and 90 mm, more preferably between 20 mm and 80 mm, even more preferably between 30 mm and 50 mm. Preferably, the length of the first and second channel is substantially the same, more preferably the length l1 of the first channel and the length l2 of the second channel is between 100 mm and 350 mm, more preferably between 150 mm and 300 mm. Preferably, the distance between the first channel 140 and the first longitudinal side 131 is between 10 mm and 30 mm, and the distance between the second channel 150 and the second longitudinal side 132 is between 10 mm and 30 mm. Preferably, the distance between the first/second channel 140, 150 and the transverse edges 133, 134 is between 20 mm and 100 mm, more preferably between 30 mm and 75 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second channel 140, 150 may be diverging slightly outwardly in the direction of first transverse edge 133 and may be diverging slightly outwardly in the direction of second transverse edge 134. Preferably first channel 140 and second channel 150 are arranged symmetrically with respect to a longitudinal center line CL of absorbent core 130.

First and second channel 140, 150 may each have a bottom 145, 155, similar to the bottom illustrated in FIGS. 1C-1F for the first embodiment fig. However, it is noted that the channel 140 may be located below and/or above the attachment zone 145, as will be explained in more detail below with reference to FIG. 16.

At the attachment zones 145, 155 top core wrap sheet 110 is attached to back core wrap sheet 120 as described previously. Outside of the plurality of channels 140, 150 absorbent core 130 has a maximum thickness t. Preferably, in the unwetted state, each channel 140, 150, extends through at least 90% of the maximum thickness of absorbent core 130, more preferably through 100% of the thickness of absorbent core 130, such that, in the channel 140, 150, substantially no absorbent material is present between top core wrap sheet 110 and back core wrap sheet 120.

The areas of the channels 140 and/or 150 may be indicated in a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. Preferably the print is visible when looking at the topsheet of the diaper.

For example, a front portion of the channel 140 and/or 150 may be indicated with an ink of a first color and a rear portion the channels 140 and/or 150 may be indicated with a different color. In that manner a user will be able to easily recognize the front and rear portion of a diaper. Indeed, the user will know that the first color has to be on the left and the second color on the right. Hence he will recognize more easily how to put on the diaper.

Topsheet, backsheet and absorbent core 130 may have the same features as described above in connection with FIGS. 1A-1F.

Figure 9:
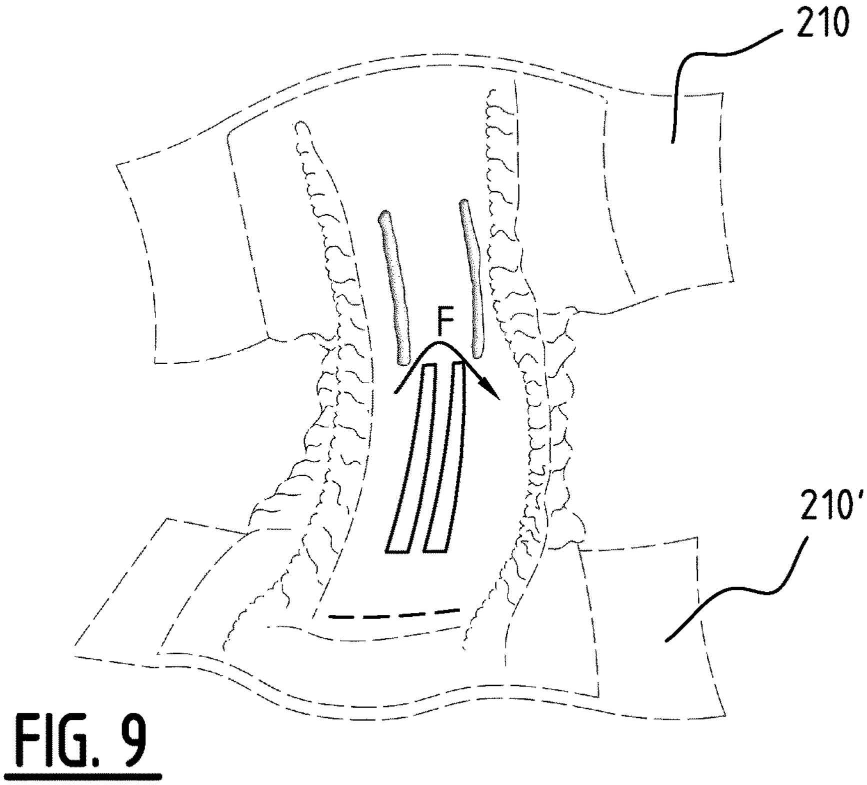
Figure 10:
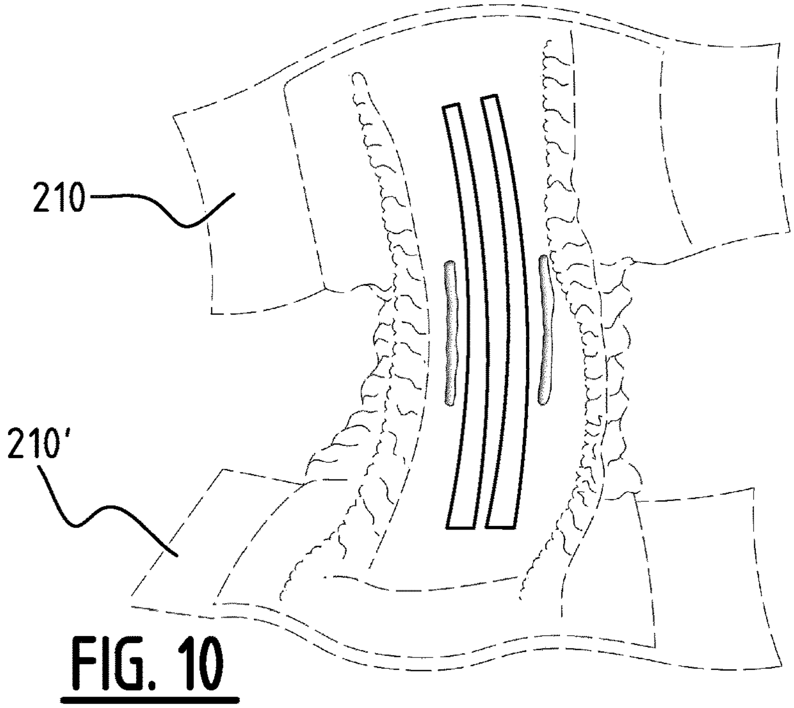

FIGS. 9 and 10 illustrate baby pants variants of the baby diaper embodiments of FIGS. 3A and 4A. In the embodiments of FIGS. 9 and 10 the side panels 210, 210' are larger compared to the embodiments of FIGS. 3A and 4A. It is clear to the skilled person that any embodiment described in view of baby diapers, is applicable in a similar manner to baby pants, mutatis mutandis.

Figure 12:
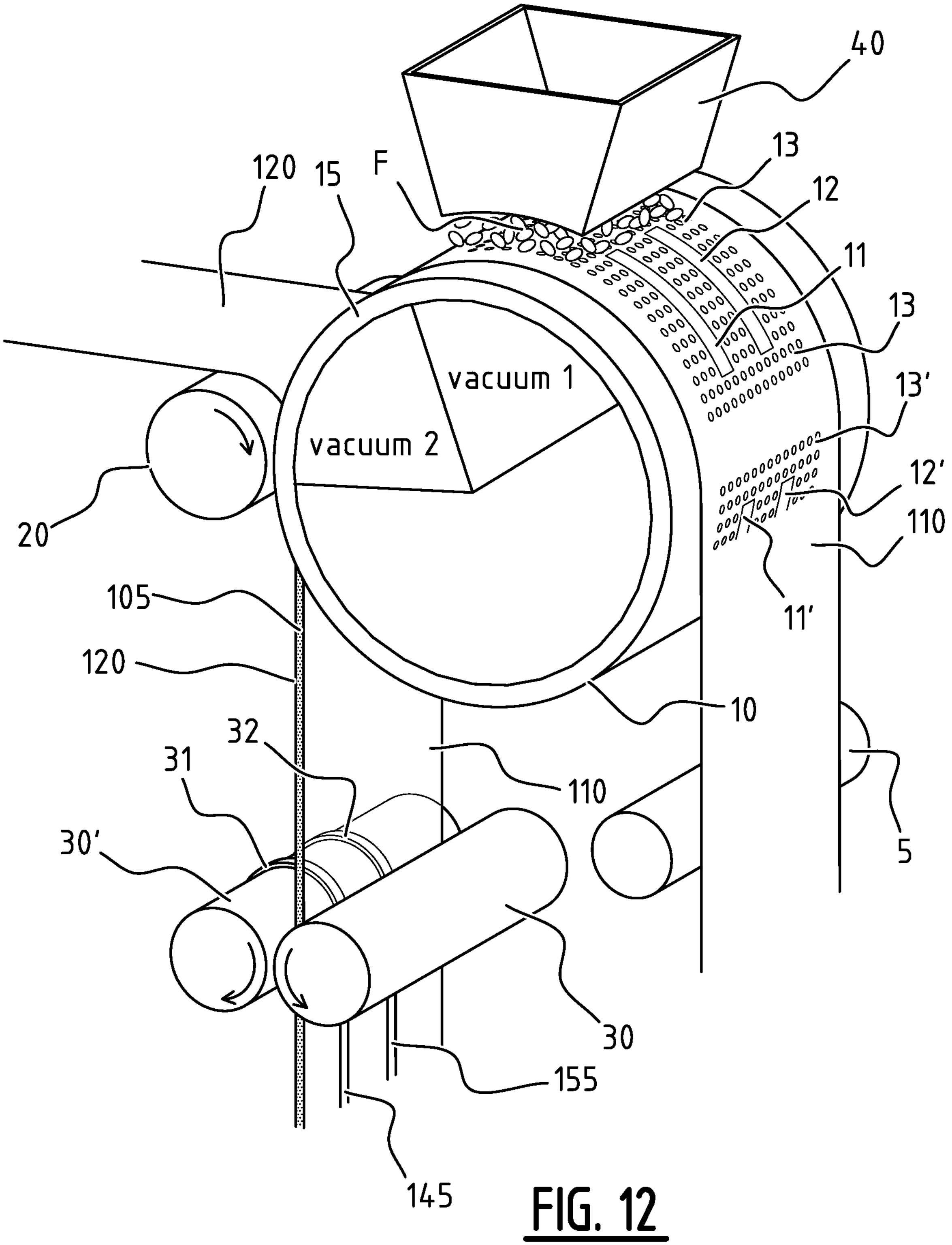
FIG. 12 illustrates schematically an exemplary embodiment of a method and apparatus for manufacturing an absorbent article.
Figure 12A:
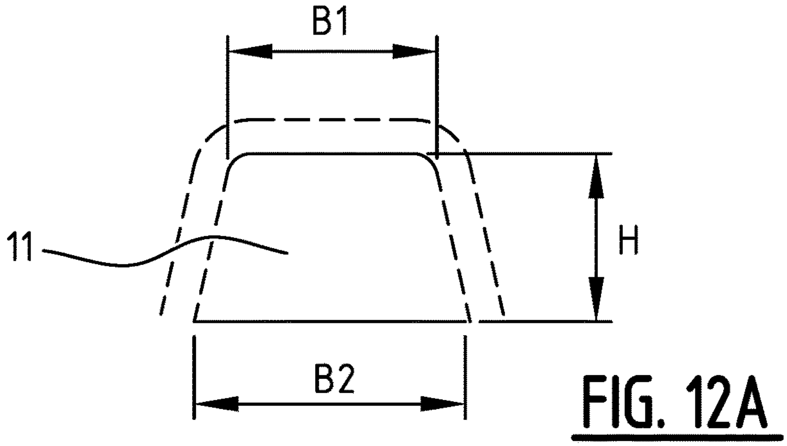
FIG. 12A shows a cross section of an insert placed at a non-suction zone of the exemplary embodiment of FIG. 12.
Figure 12B:
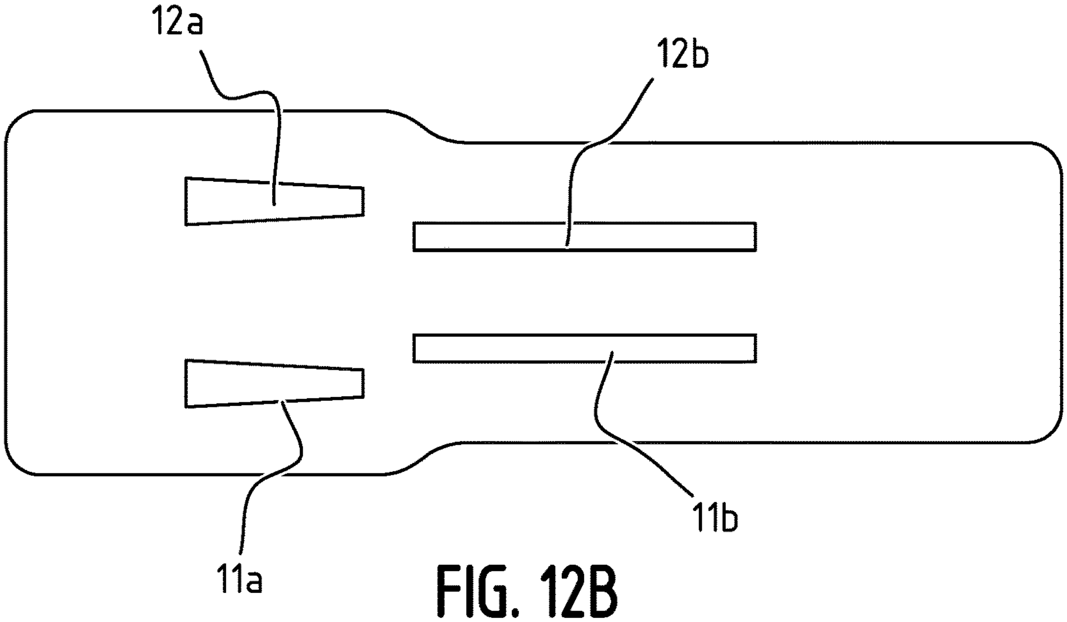
FIG. 12B shows a top view indicating how inserts may be positioned in order to create non-suction zones for the exemplary embodiment of FIG. 12.
Figure 12C:
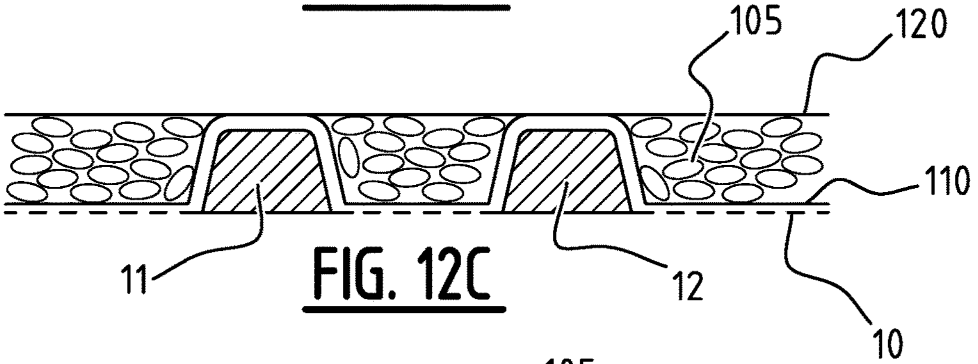
FIG. 12C shows a cross section of the absorbent core when the second sheet 120 is being applied.
Figure 12D:
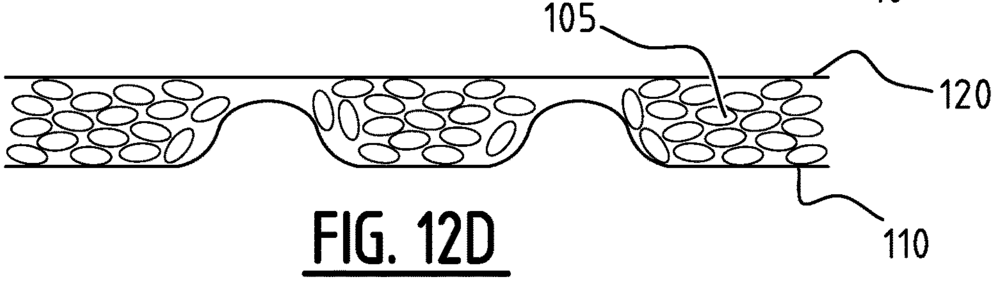
FIG. 12D shows a cross section of the absorbent core before attaching the first sheet 110 to the second sheet 120.
Figure 12E:
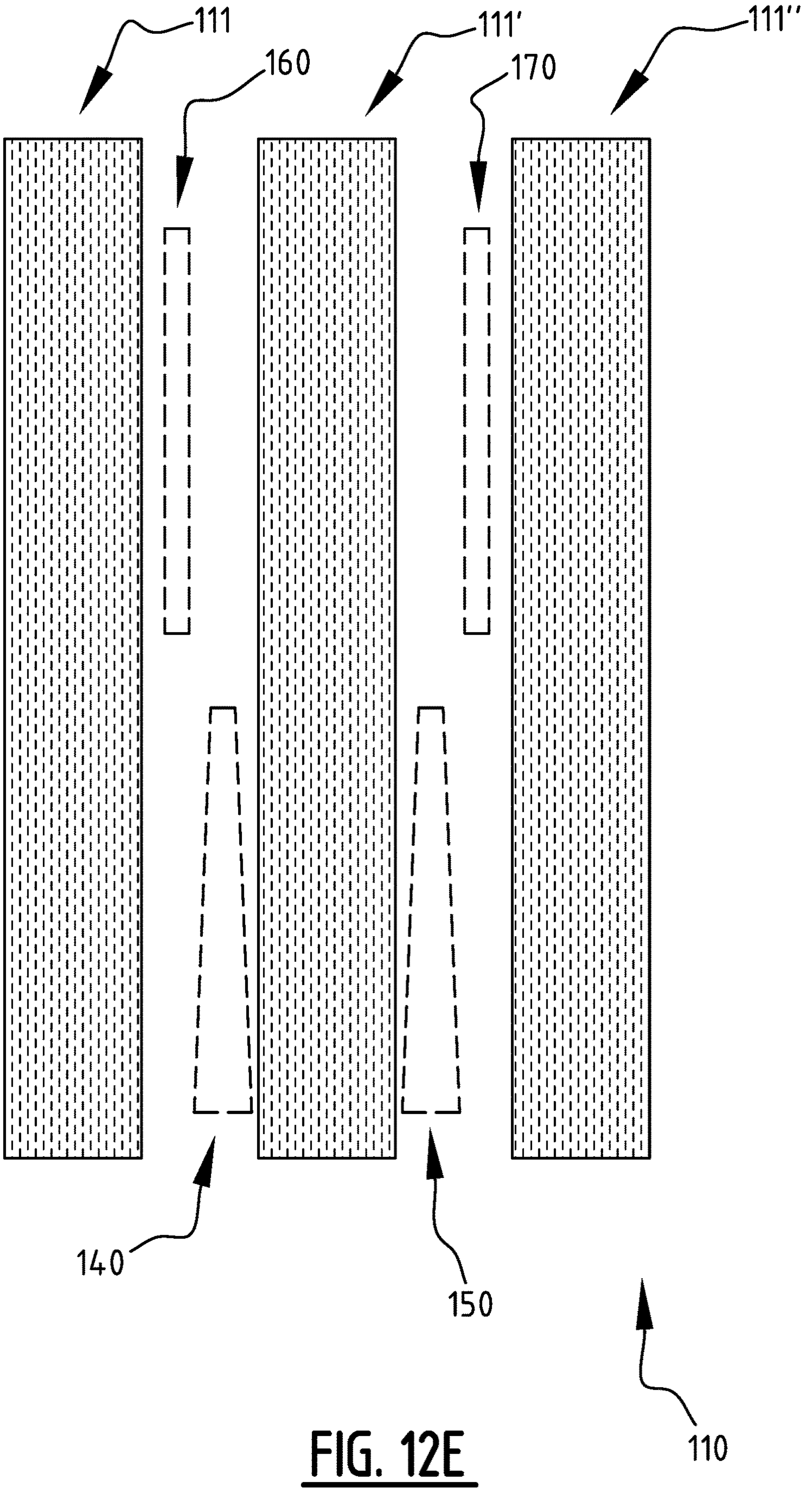
FIGS. 12E-12H illustrate an alternate method for manufacturing an absorbent article, wherein 12E shows glue application to the bottom core wrap, 12F shows glue application to the top core wrap, 12G shows the combined bottom and top core wraps, and 12F shows the absorbent article after the manufacturing steps.

FIG. 12 illustrates an embodiment of a method for manufacturing an absorbent article according to the invention. The method comprises in a first step guiding a first sheet material 110 along an optional guide roller 5, and further along a rotating member 10, wherein a surface 15 of said rotating member 10 is provided with a pattern with suction zones 13, 13' and non-suction zones 11, 12; 11', 12'. The first sheet material 110 is shown in a transparent manner to reveal the suction and non-suction zones of the rotating member 10. The suction zones 13, 13' may be provided with holes, and the non-suction zones 11, 12; 11', 12' are formed of closed material. For example, the non-suction zones 11, 12; 11', 12' may be provided with inserts as shown in FIG. 12A. As shown in FIG. 12A, the inserts 11, 12; 11', 12', may have a trapezoidal cross section. The inserts may have a top width B1 and a bottom width B2. The top width B1 and/or the bottom width B2 of at least one of the inserts may differ along a length direction of the insert according to the width of the attachment zone intended to be manufactured. FIG. 12B shows an insert pattern with four non-suction zones 11*a*, 11*b*, 12*a*, 12*b* per absorbent core. The inserts may be fixed e.g. with screws on the rotating member 10. At an inner area of the rotating member 10 a vacuum is applied, see VACUUM 1. The non-suction zones 11, 12; 11', 12' comprise at least a first elongate zone 11, 11' and a second elongate zone 12, 12' extending in a circumferential direction of the rotating member 10. In a second step an absorbent material F is applied via a hopper 40 on said first sheet material 110 on the rotating member 10 such that the suction zones 13, 13' are covered with absorbent material and substantially no absorbent material is present on the non-suction zones 11, 12; 11', 12'. In a third step a second sheet material 120 is applied on top of the absorbent material on the first sheet material 110, e.g. using a further rotating member 20. This is shown also in FIG. 12C where a cross section through the absorbent core is shown during the application of the second sheet material 120. FIG. 12D shows the cross section of the absorbent core downstream of rotating member 10. One of said first and second sheet material is a top core wrap sheet material, and the other one is a back core wrap sheet material. In the illustrated embodiment it is assumed that the first sheet material 110 is the top core wrap sheet material. Preferably, in a fourth step the first sheet material 110 is attached to the second sheet material 120 at least in the areas where substantially no absorbent material is present, and such that at least a first and a second channel 140, 150 are formed in said top core wrap sheet material 110. The attaching may be done by applying pressure and heat on the top core wrap sheet material 110 and/or on the back core wrap sheet material 120 in the areas where substantially no absorbent material is present, e.g. by a rotating member 30 and/or opposite rotating member 30' which is provided with at least a first and a second seal rib 31, 32 dimensioned for applying pressure and heat on the top core wrap sheet material 110 in the areas where substantially no absorbent material is present in order to create the first and second channel 140, 150, respectively.

While the above-described method of manufacturing absorbent articles has good results, the top core wrap sheet and the back core wrap sheet may not be sufficiently strongly attached to one another, especially in cases where a significant amount of liquid is absorbed. Therefore, it may be desirable to additionally use a binder, such as glue, to strengthen the bond between the top and back core wrap sheets.

It is however inadvisable to apply this binder to the entire surface area of the wrap sheet being guided over rotating member 10, since this may lead to the absorbent material and/or binder contaminating the attachments zones 140, 150, 160, 170, and therefore hindering the formation of channels.

Therefore it is advantageous to use a specific method to apply the glue to the back and/or top wrap sheets. In FIGS. 12E-12H, a manufacturing method including application of a binder is demonstrated which does not have this drawback.

In particular, taking as an example the possible manufacturing process for the embodiment of FIGS. 3A and 3B, while the first sheet material 110 is being guided along an optional guide roller and further along a rotating member a binder, such as glue, may first be applied to the first sheet material, but only in substantially parallel stripes which do not overlap with the intended locations of the attachment zones 140, 150, 160, 170. Note that in this embodiment, the first sheet material forms the bottom core wrap, but in other embodiments this can also be the top core wrap. The skilled person will be aware of various method of binder/glue application, such as spraying, contact application and so on.

Figure 13A:
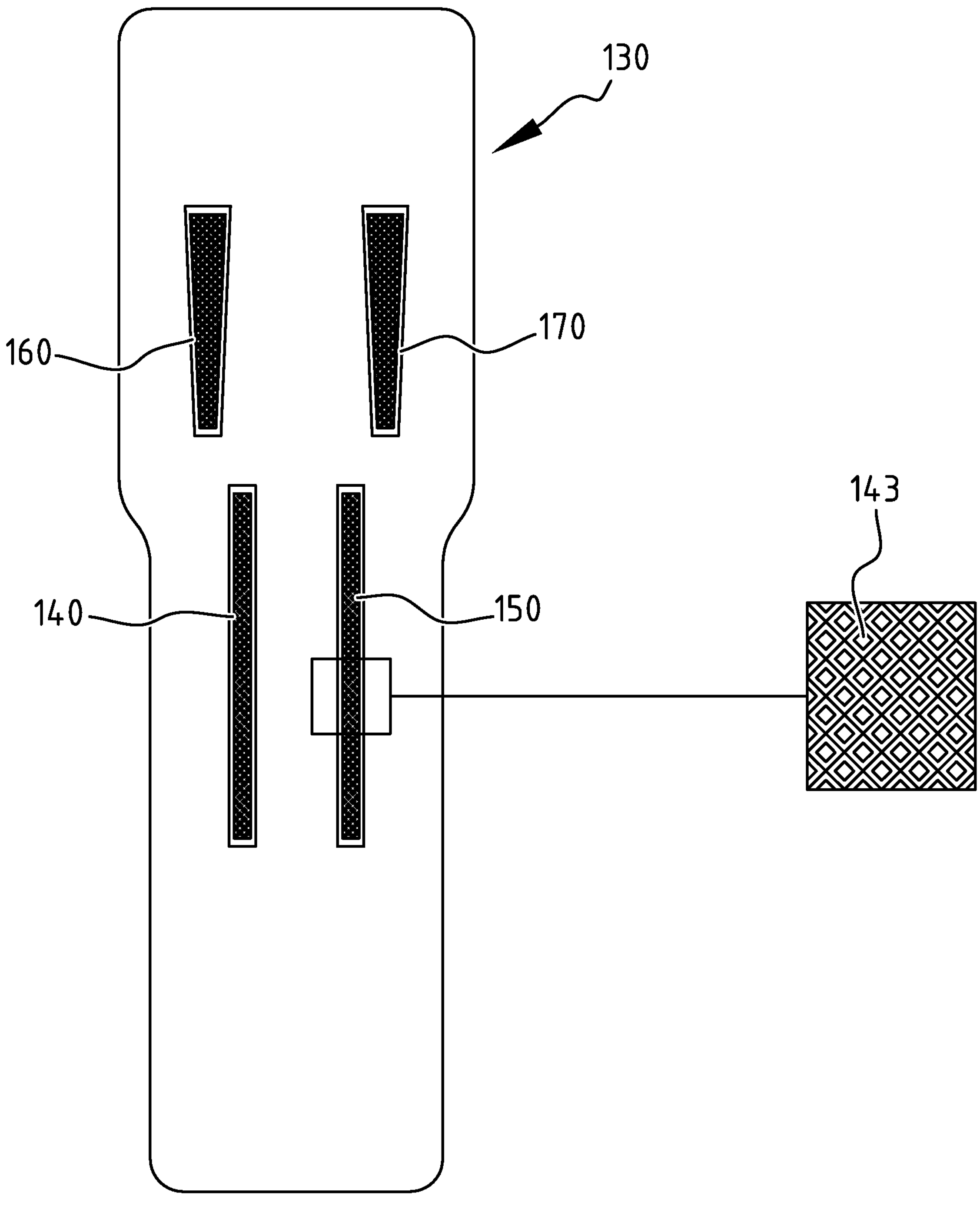
FIG. 13A shows a top view of an exemplary embodiment of an absorbent core with four channel zones, in particular four attachment zones using a first exemplary embodiment of a sealing pattern.
Figure 13B:
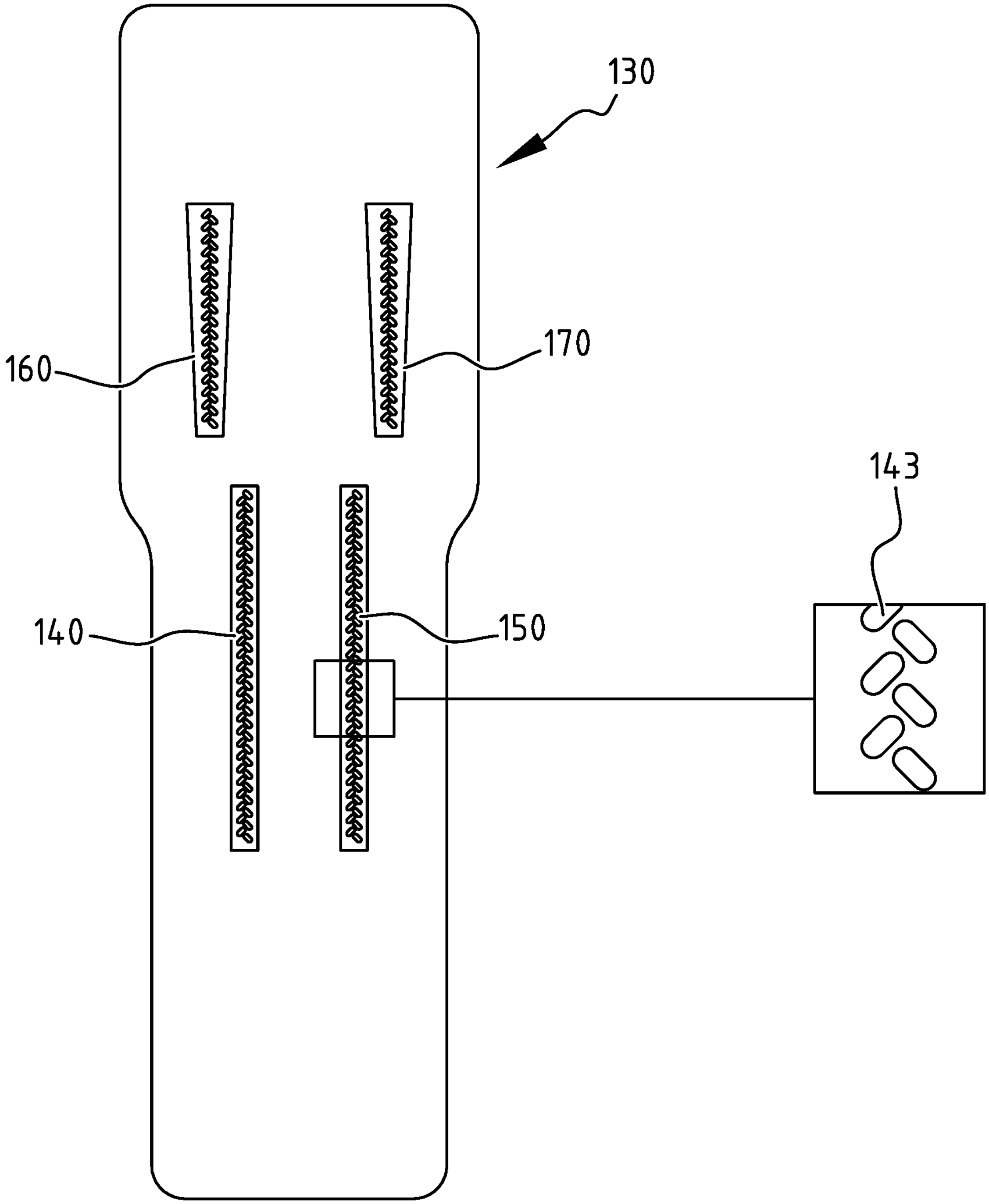
FIG. 13B shows a top view of an exemplary embodiment of an absorbent core with four channel zones, in particular four attachment zones using a second exemplary embodiment of a sealing pattern.
Figure 13C:
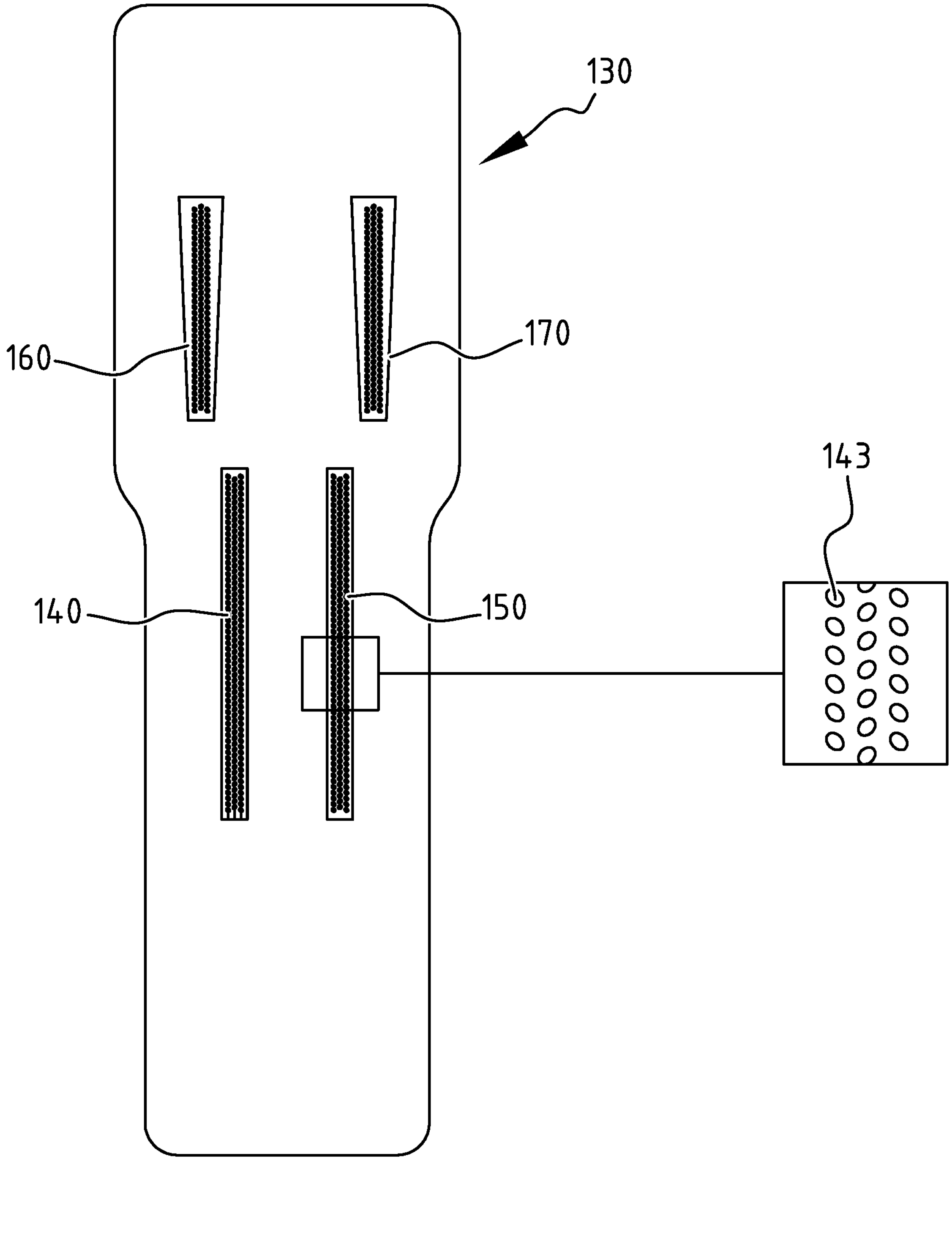
FIG. 13C shows a top view of an exemplary embodiment of an absorbent core with four channel zones, in particular four attachment zones using a third exemplary embodiment of a sealing pattern.
Figure 13D:
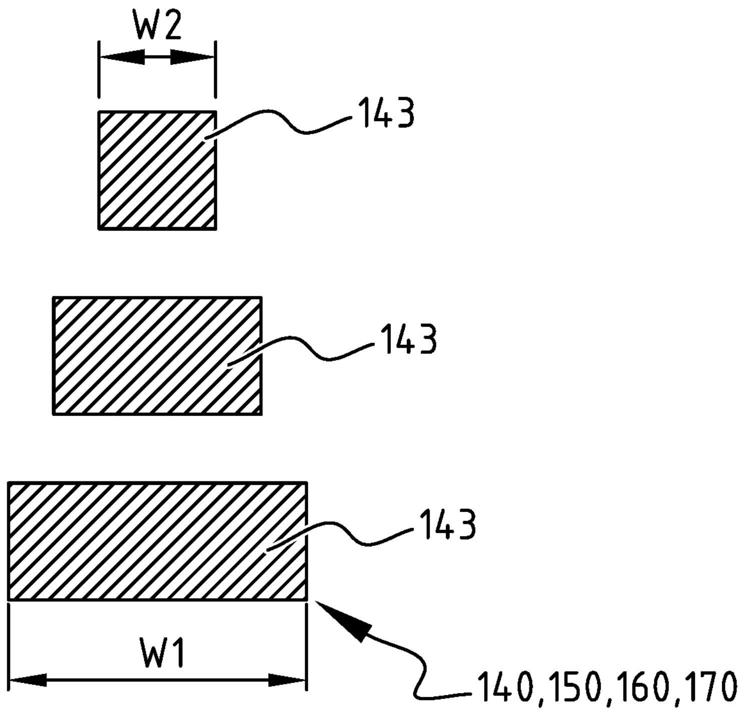
FIG. 13D illustrates a fifth exemplary embodiment of a possible sealing pattern.

FIG. 13D shows a possible pattern for the application of glue to the first sheet material, which will be the back core wrap. In particular, in this example there are three stripes 111, 111', 111'', but a different number of substantially parallel stripes, either continuous, intermittent and/or discontinuous in the longitudinal direction, may also be chosen depending on the shape and locations of the attachment zones 140, 150, 160, 170, which preferably cover a substantial portion of the surface of the bottom core wrap while not overlapping with the intended location of the attachment zones, and preferably while keeping some distance from the intended location of the attachment zones. Although, FIG. 13D illustrates an application pattern of stripes, it is clear to the skilled person that the application pattern can be adapted and tuned depending on the intended shape, configuration and location of the one or more attachment zones. Moreover, the skilled person will know how to best adapt the binder application zones on the first and second sheet materials 110, 120 for other configurations of attachments zones, such as the ones described in the present application. Preferably, the application of the glue to the bottom core wrap takes place while the bottom core wrap is moved towards the rotating number, and before the absorbent material is added to it. In such a way, the sheet material on the rotating member is already provided with binder, and may subsequently have absorbent material attached thereto via the hopper.

Please note that the dotted line indicating the intended location of the attachment zones is there for illustrative purposes only: it does not correspond to anything on the first sheet material 110.

Figure 12F:
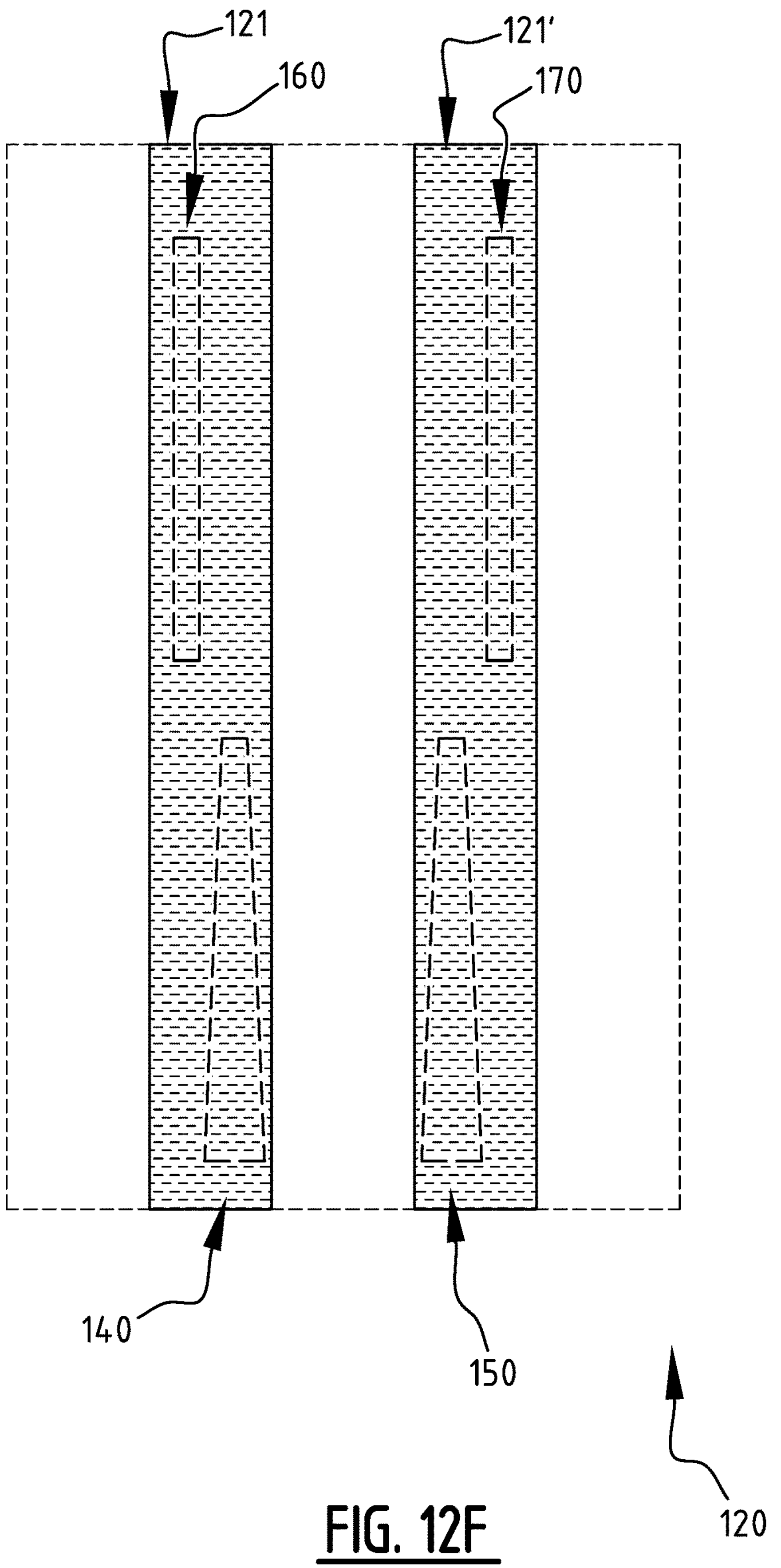

FIG. 12F shows application of glue to the second sheet material 120, which in this case will become the top core wrap. In this case too the application of the binder preferably happens along substantially parallel stripes 121, 121', which preferably are complementary to the stripes on the first sheet material 110. Preferably, the application of glue to the top core wrap sheet happens at a distance from hopper 40, to minimize the chance of contamination, i.e. absorbent material sticking to the areas that are to become attachment zones 140, 150, 160, 170. For instance, the binder may be applied before or while the sheet material is guided along further rotating member 20. Note that here, too, the dotted lines merely indicate the intended position of the attachment zones 140, 150, 160, 170; they do not indicate any interruption or change in the binder application. As before, the skilled person will be aware of various method of binder/glue application, such as spraying, contact application and so on.

Figure 12G:
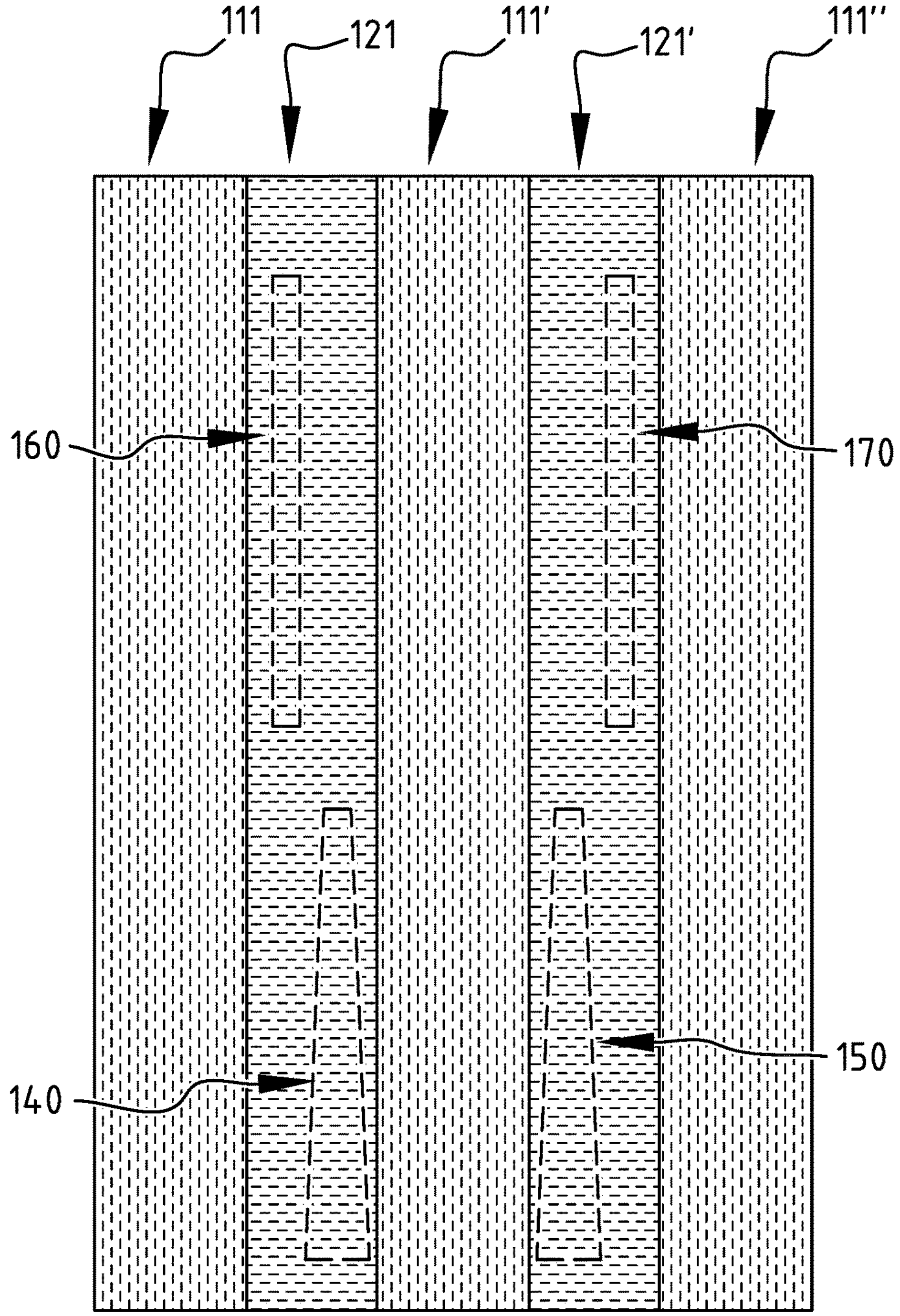

FIG. 12G shows the result after the third step described above has taken place, i.e. after the second sheet material 120, which here is the top core wrap sheet, is applied on top of the absorbent material on the first sheet material 110, e.g. using a further rotating member 20. Note that the pattern fill indicates the presence of binder, and not the presence of absorbent material, since the absorbent material will not be present in the areas indicated by the dotted lines. These areas will be bonded together in a fourth step such as described above, such that channels 140, 150, 160 and 170 are formed in said back core wrap sheet materials 110 and/or 120, for instance by applying pressure and heat on the back core wrap sheet material 110 and/or on the top core wrap sheet material 120 in the areas where substantially no absorbent material is present, e.g. by a rotating member 30 and/or opposite rotating member 30' which is provided with at least a first and a second seal rib 31, 32 dimensioned for applying pressure and heat in between the core wrap sheet materials 110 and 120 in the areas where substantially no absorbent material is present in order to create the channels 140, 150, 160 and 170.

Figure 12H:
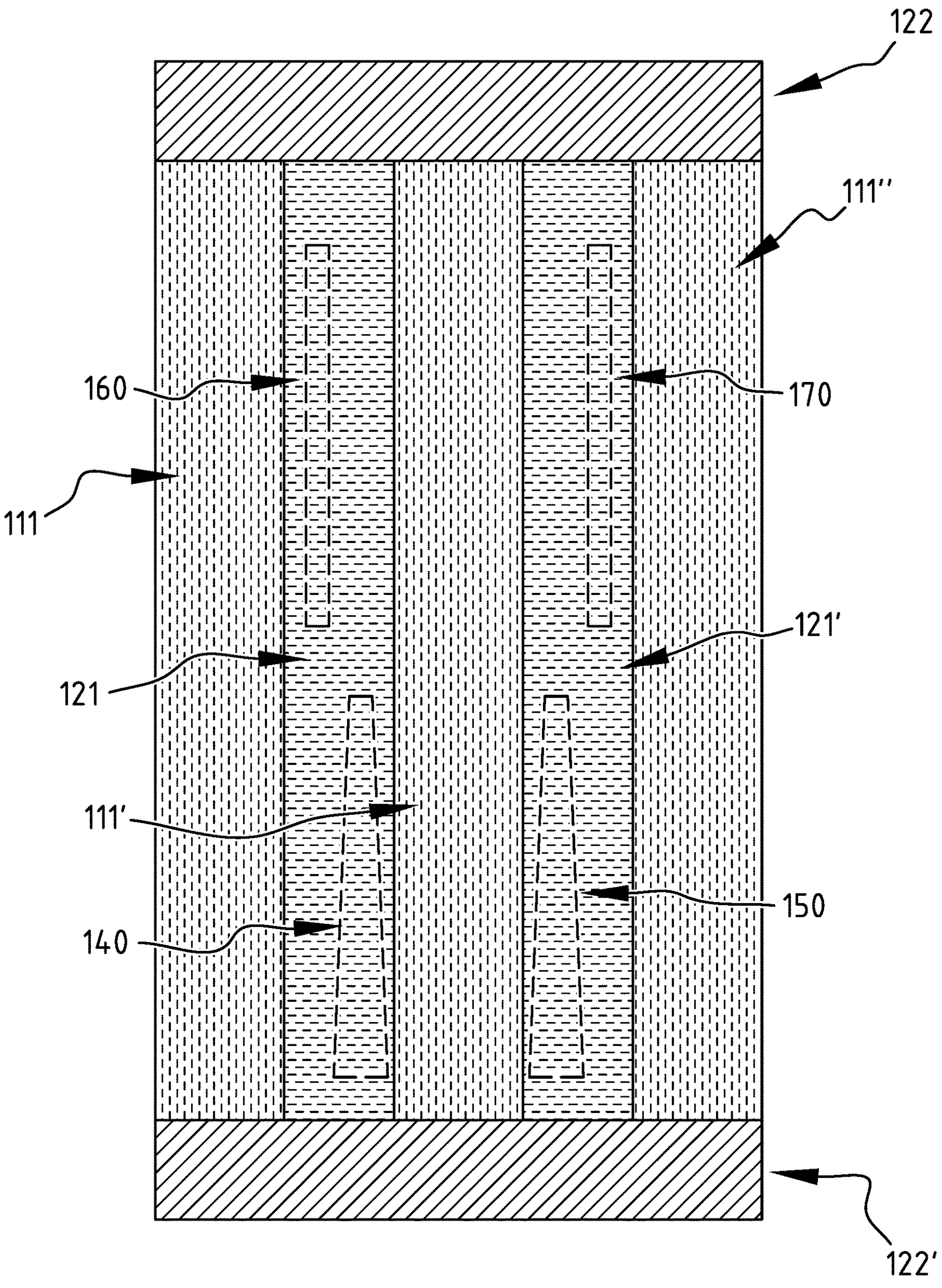

Finally, FIG. 12H shows the absorbent article resulting from the above-described method, in which a further step has taken place of traversal sealing in bands 122, 122' by chemical, thermal or physical binding such as for in stance glue, heat and/or pressure, which prevents the core from opening up and the front and the back. Note that this step of transversal sealing may also take place prior to the fourth step.

The above-described method may yield an absorbent article with higher dry and especially wet integrity and which avoids unwanted migration of absorbent material, while avoiding the risk of contamination in the attachment zones 140, 150, 160 and 170 which may impede the formation of channels. The skilled person will understand that this method is not limited to this particular configuration of attachment zones and will know how to best adapt the binder application zones on the first and second sheet materials 110, 120 for other configurations, such as the ones described in the present application. More in particular the skilled person understands that the method is also useful for absorbent cores with only one attachment zone or with more than two attachment zones.

FIG. 13A illustrates an exemplary embodiment of an absorbent core 130 with four attachment zones creating channels 140, 150, 160, 170. In the embodiment of FIG. 13A, the attachment zones are formed by welding the top core wrap sheet 110 to the back core wrap sheet 112. This welding may be done according to a predetermined sealing pattern. In the embodiment of FIG. 13A, the pattern consists of a plurality of discrete shapes 143, here a plurality of squares. Preferably, the discrete shapes 143 have dimensions smaller than 2 mm. Preferably, the distance between adjacent discrete shapes is between 0.5 and 3 mm.

FIG. 13B illustrates another exemplary embodiment of a sealing pattern that may be used in an embodiment of the invention. Here the pattern consists of a plurality of discrete shapes in the form of rounded elements 143. The rounded elements may have a length dimension between 0.5 mm and 5 mm, and a width dimension between 0.5 mm and 5 mm. Preferably, the discrete shapes are equally distributed in the attachment zones.

FIG. 13C illustrates yet another embodiment where the sealing pattern consists of discrete shapes which are rounded. In this embodiment, three columns of rounded discrete elements 143 are used for each attachment zone 140, 150, 160, 170.

In the exemplary embodiment of FIG. 13D, the attachment zones creating channels 140, 150, 160, 170 may be formed of a plurality of discrete elements 143. The discrete element at the first position of the attachment zone may have a width w1, and the discrete element at the second position of the attachment zone may have a width w2, wherein w1 is larger than w2.

Figure 14:
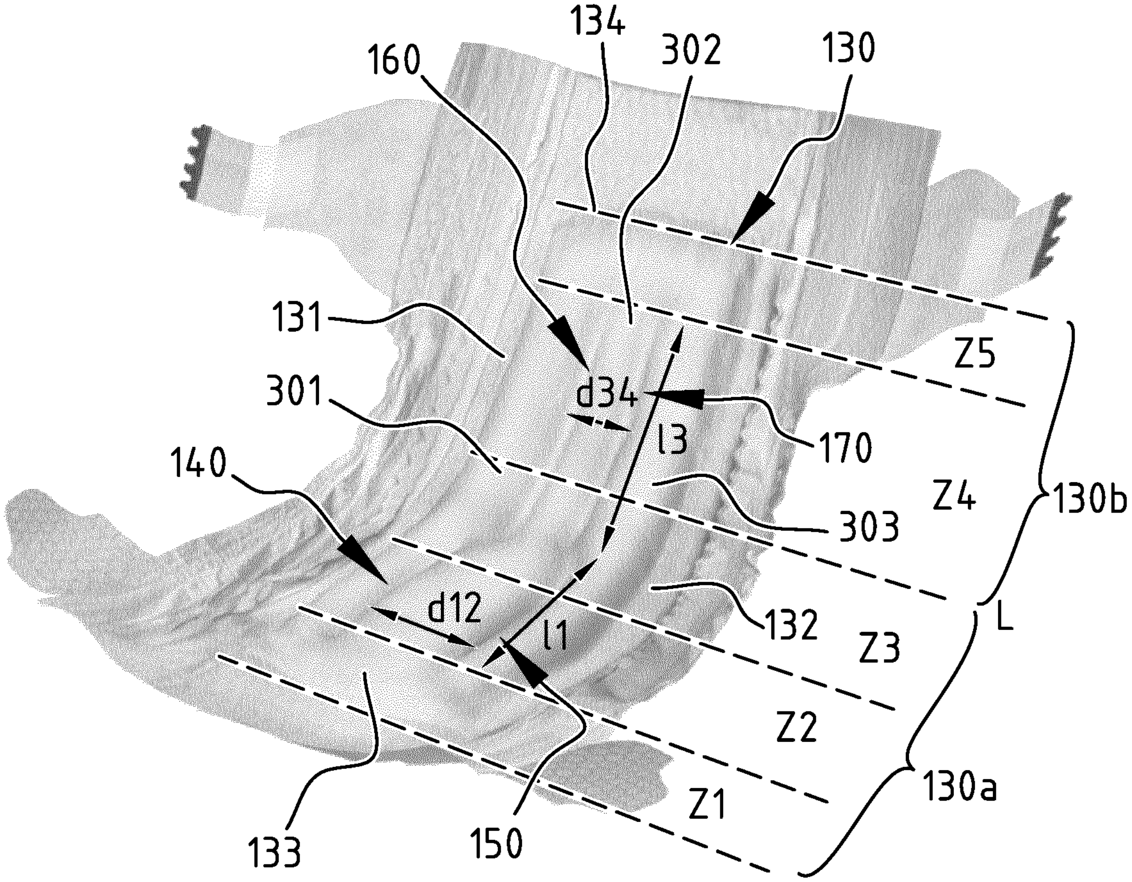
FIG. 14 is a perspective view of an exemplary embodiment of a diaper in a wetted state.
Figure 15A:
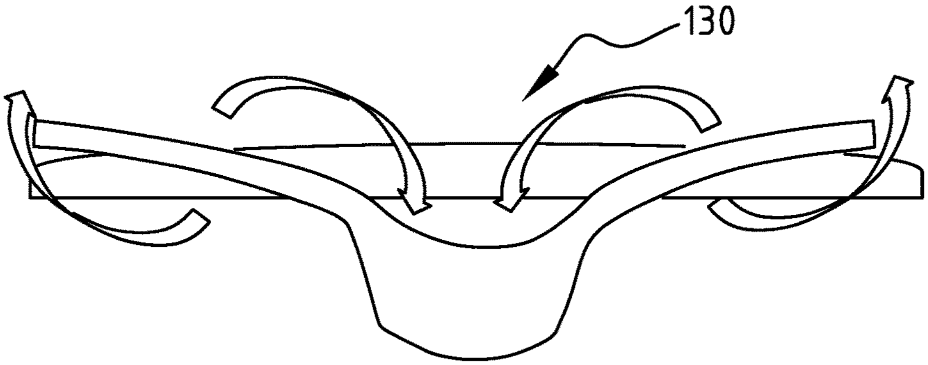
FIGS. 15A and 15B are cross-sectional views illustrating the effect of liquid being absorbed by a traditional absorbent core and liquid being absorbed by an absorbent core according to an exemplary embodiment of the invention, respectively.
Figure 15B:
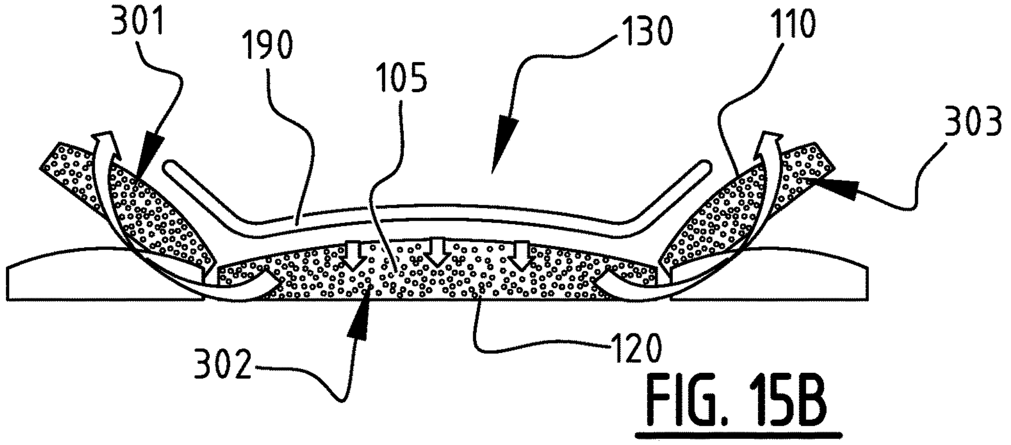

FIG. 15A illustrates an exemplary embodiment of a traditional absorbent core. When a traditional absorbent core absorbs liquid, the core becomes bulky such that the diaper is no longer well adapted to the body. The liquid does not spread evenly but remains in the center of the absorbent core. FIG. 15B illustrates an exemplary embodiment of an absorbent core of the invention. Thanks to the attachment zones and associated channels 140, 150, 160, 170, the liquid is evenly spread, resulting in the formation of tubes 301, 302, 303 which provide a tub shape to the absorbent core 130. Such a tub shape adapts perfectly to the body. Further, compared to prior art solutions, the liquid is kept in an improved manner absorbed in the absorbent core 130, and the risk on leakage is reduced. Also, because of the creation of the channels 140, 150, 160, 170, the liquid is absorbed faster. FIG. 14 shows a perspective view of a diaper in the wetted state. FIG. 14 clearly illustrates the formation of three tubes 301, 302, 303 giving the diaper a tub shape which is well adapted to the body. Preferably absorbent core 130 is provided with a plurality of attachment zones 140, 150, 160, 170 where the top core wrap sheet is attached to the back core wrap sheet, and where preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130*a* extending between the front edge 133 and a transverse crotch line L of the absorbent core, and a rear portion 130*b* extending between the rear edge 134 and the transverse crotch line L of the absorbent core 130. The first, second and third zone Z1, Z2, Z3 extend in the front portion 130*a* of the absorbent core and the fourth and fifth zone Z4, Z5 extend in the rear portion 130*b*. Preferably, in said first and fifth zone Z1, Z5 substantially no permanent attachment zones are present. However the first and/or fifth zone Z1, Z5 may comprise temporary secondary attachments that loosen upon wetting. The second zone Z2 comprises a first and a second permanent elongate front attachment zone 130, 140, said first and second front attachment zones 130, 140 extending from an edge of the first zone Z1 in the direction of the third zone Z3.

The fourth zone Z4 comprises a first and second rear elongate attachment zone 160, 170, said first and second rear attachment zone extending from an edge of the fifth zone Z5 in the direction of the third zone Z3.

The first and second rear elongate attachment zones 160, 170 extend from the fourth zone into the third zone Z3 so that an absorbent article is formed that fits well to the body of the wearer. Preferably a distance between the transverse crotch line L and a transverse center line T extending perpendicular on the longitudinal direction of the absorbent core, through the middle of the absorbent core, is smaller than 10%, more preferably smaller than 5% of the length of the absorbent core.

The first zone Z1 extends over a length corresponding with at least 5%, preferably at least 10% of the length la of the absorbent core seen in the longitudinal direction, e.g. between 10% and 20%. The fifth zone Z5 extends over a length corresponding with at least 10% of the length la of the absorbent core seen in the longitudinal direction, preferably at least 20%, more preferably at least 25%, e.g. between 20% and 40%.

Preferably the second, the third and/or the fourth zone Z1, Z2, Z3 each extends over a length corresponding with at least 10% of the length la of the absorbent core seen in the longitudinal direction, preferably at least 15%, e.g. between 10% and 20% of the length of the absorbent core.

Preferably the first front attachment zone 140 and the second front attachment zone 150 are arranged symmetrically with respect to a longitudinal center axis CL of the absorbent core 130. Preferably a minimum distance d12 between the first and the second front attachment zone is between 20 mm and 70 mm, more preferably between 30 mm and 60 mm, even more preferably between 40 mm and 55 mm. As explained in the summary, such a configuration is especially suitable for male persons.

Preferably the first rear attachment zone 160 and the second rear attachment zone 170 are arranged symmetrically with respect to the longitudinal center axis CL of the absorbent core. Preferably the distance d34 between the first and the second rear attachment zone 160, 170 is between 10 mm and 50 mm, more preferably between 15 mm and 40 mm, even more preferably between 20 mm and 30 mm.

A first smallest distance d12 between the first and the second front attachment zone 140, 150 is bigger than a second smallest distance d34 between the first and the second rear attachment zone 160, 170. The first and the second front attachment zone 140, 150 extend in a longitudinal direction of the absorbent core over a length l1 which is less than the length l3 of the first and second rear attachment zone. Preferably, the length l1 of the first and second front attachment zone 140, 150 is larger than 30 mm, more preferably larger than 40 mm, even more preferably larger than 50 mm.

The plurality of attachment zones 140, 150, 160, 170 may be permanent attachment zones which remain attached when wetted. The plurality of attachment zones may extend, seen in the transverse direction of the absorbent core, over the transverse distance which is at least 1 mm, preferably at least 3 mm, more preferably at least 4 mm, even more preferably at least 5 mm, most preferably at least 6 mm.

Figure 16:
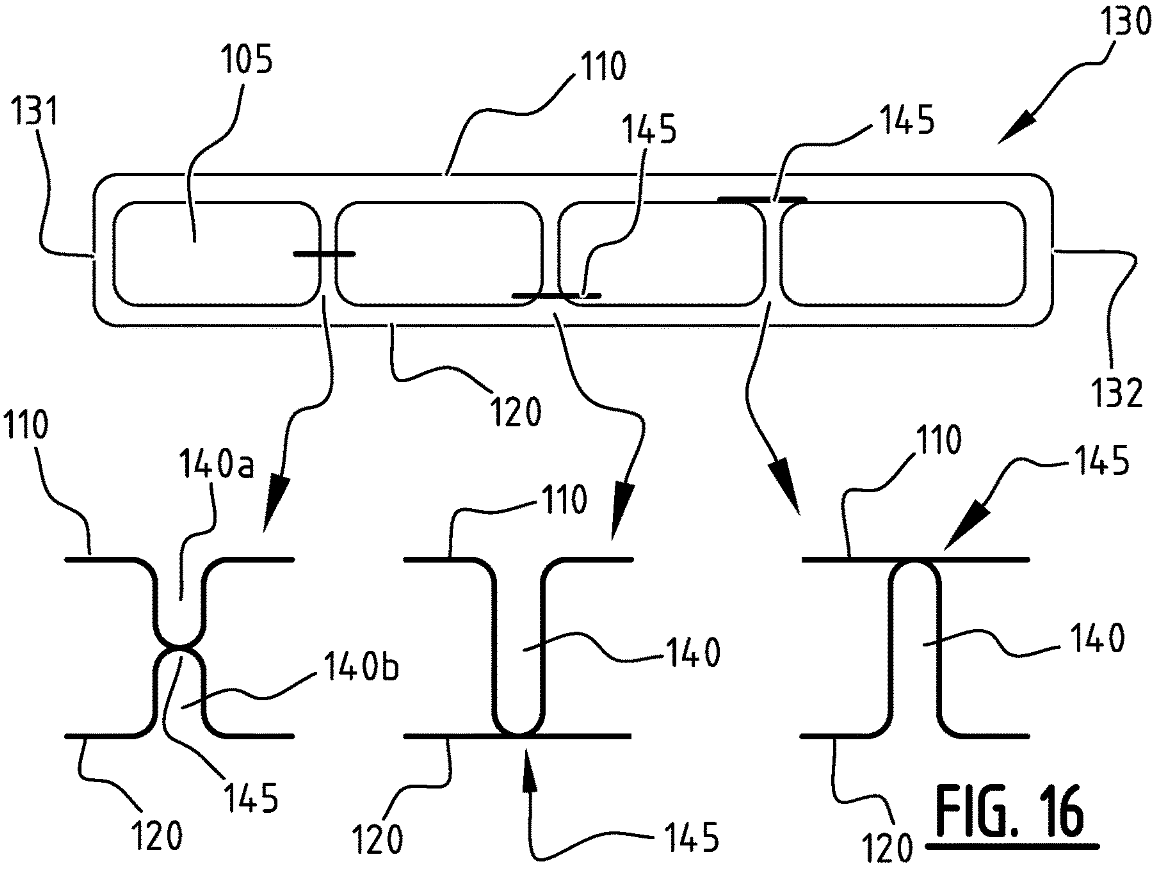
FIG. 16 illustrates a schematic cross-section of an absorbent core, wherein three possible locations are indicated for the channel zones.

FIG. 16 illustrates an absorbent core 130 comprising an absorbent material 105 between a top core wrap sheet 110 and a back core wrap sheet 120. The absorbent core has a first and second longitudinal edge 131, 132. The absorbent core 130 is provided with a plurality of attachment zones 145. FIG. 16 illustrates that the attachment zones 145 may be positioned at different locations. As illustrated on the left in FIG. 16, the attachment zone may be positioned more or less centrally such that an upper channel portion 140*a* and a lower channel portion 140*b* is formed. In an alternative embodiment, the attachment zone 145 may be positioned at the bottom such that an upper channel 140 is created, see the example in the middle of FIG. 16. According to yet another embodiment, the attachment zone 145 may be located at the top, such that the channel 140 is formed below top core wrap sheet 110. The skilled person understands that any variants thereof are also possible, as long as the attachment zones allow the formation of channels upon wetting of the absorbent core 130.

Although the method is illustrated for two channels, the skilled person understands that the method can be adapted for forming three, four or more channels, and in particular for manufacturing any one of the absorbent articles disclosed in the present application.

Figure 2A:
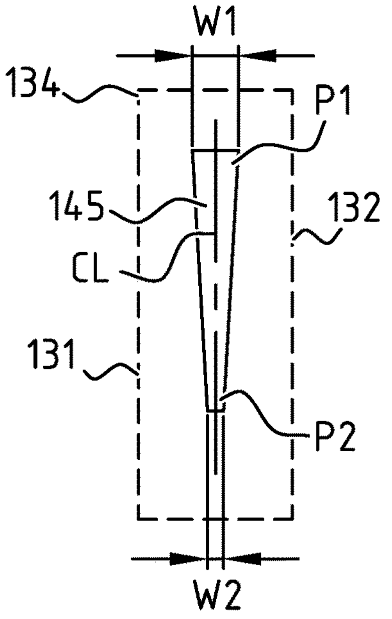
FIG. 2A-2U illustrate exemplary embodiments of an absorbent core comprising zones of different layouts.
Figure 2B:
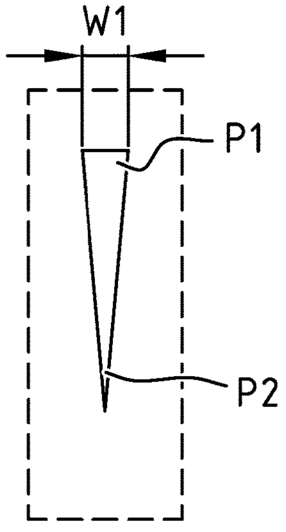
Figure 2C:
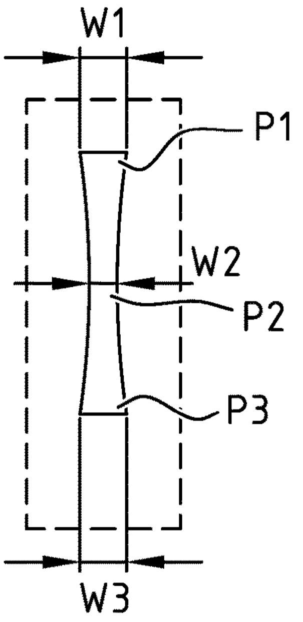
Figure 2D:
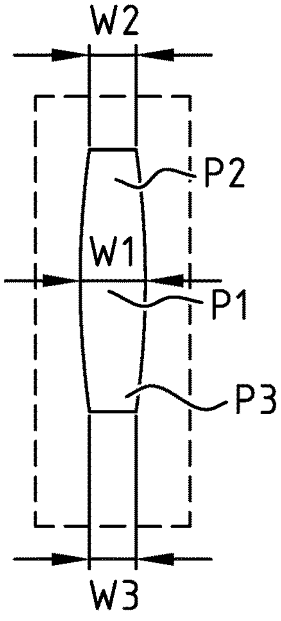
Figure 2E:
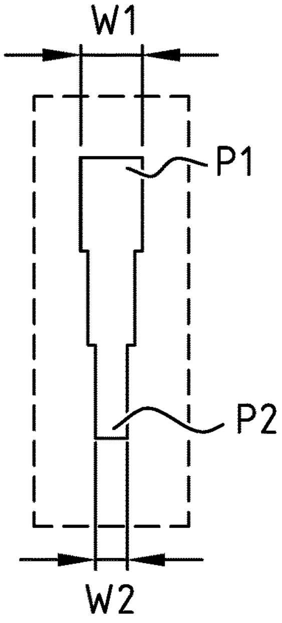
Figure 2F:
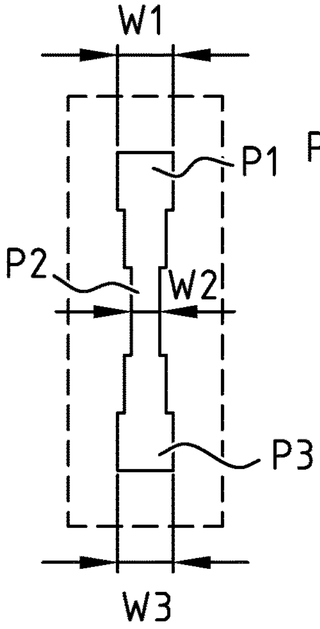
Figure 2G:
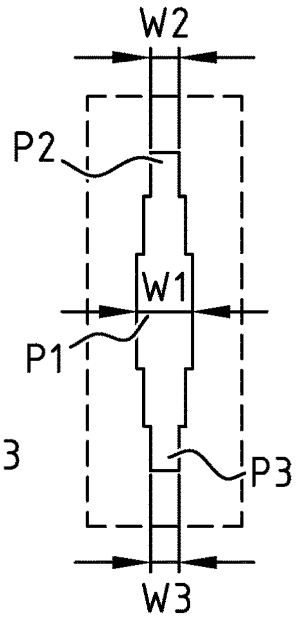
Figure 2H:
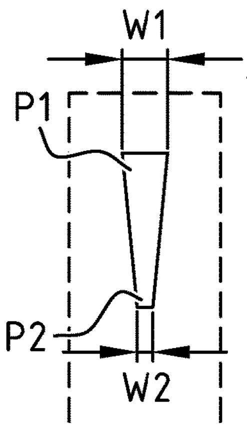
Figure 2I:
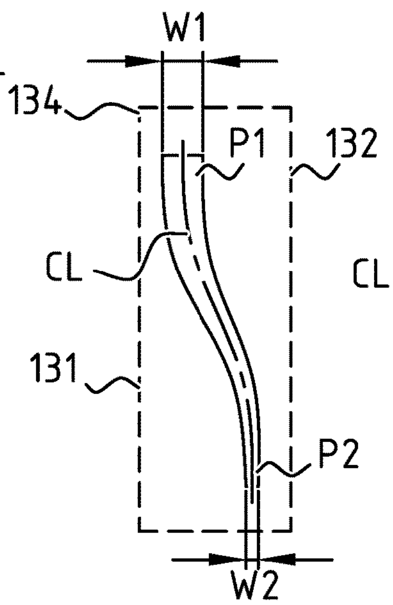
Figure 2J:
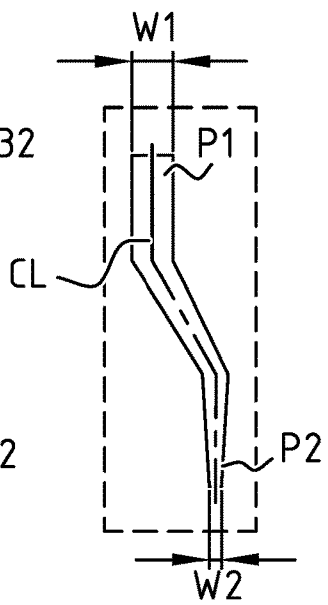
Figure 2K:
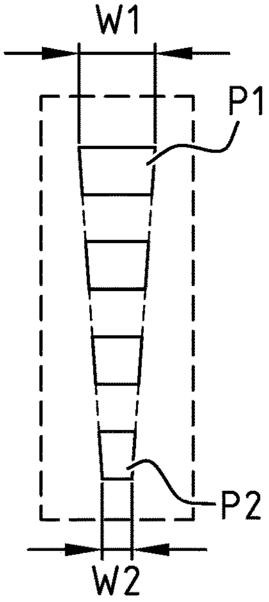
Figure 2L:
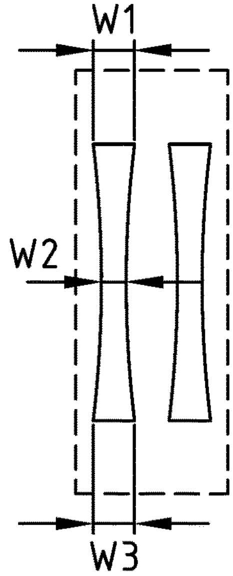
Figure 2M:
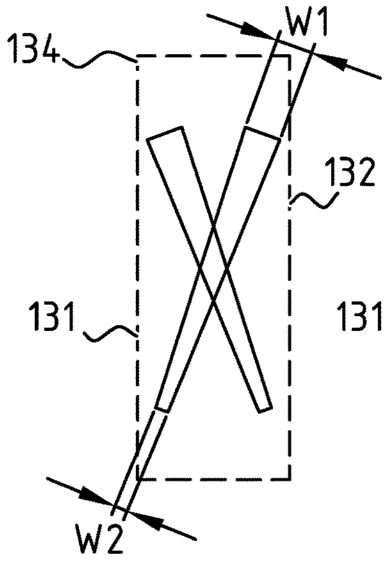
Figure 2N:
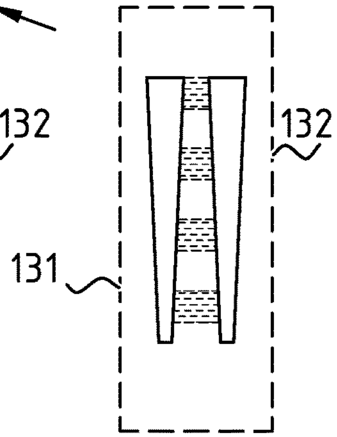
Figure 2O:
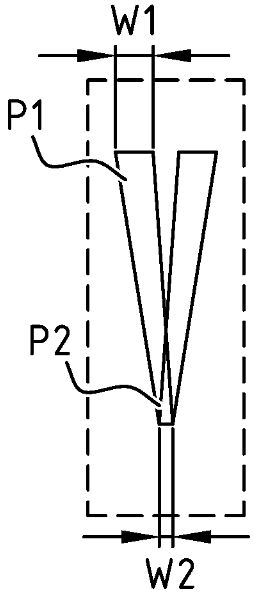
Figure 2P:
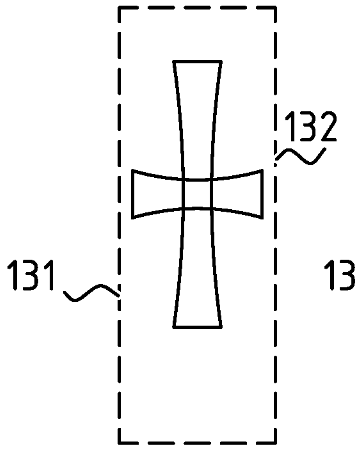
Figure 2Q:
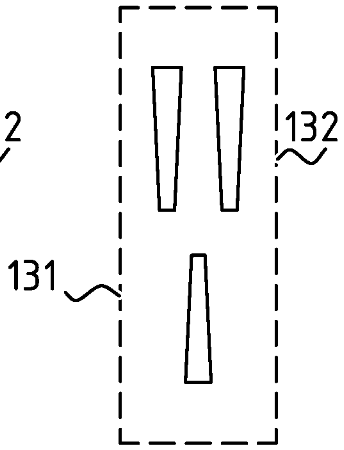
Figure 2R:
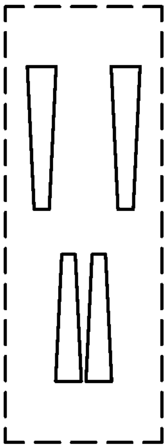
Figure 2S:
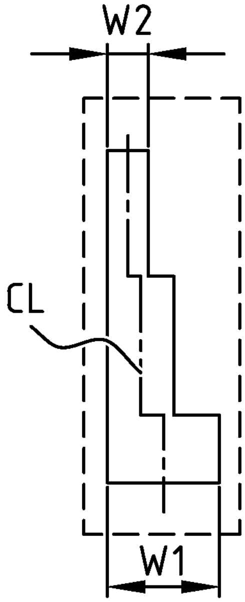
Figure 2T:
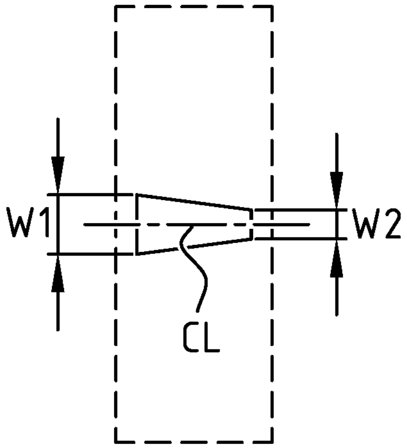
Figure 2U:
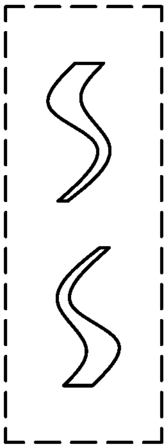

FIG. 2A-2U illustrate exemplary embodiments of an absorbent core comprising zones of different layouts. The principles about the zones set out thereafter for various embodiments may also be applied in other described embodiments.

FIG. 2A illustrates an exemplary embodiment of an absorbent core. The absorbent core comprises an absorbent material between a top core wrap sheet and a back core wrap sheet. The absorbent core has a first and second longitudinal edge 131, 132 and a first and second transverse edge 133, 134. The absorbent core is provided with at least a first elongated attachment zone 145 where the top core wrap sheet is attached to the back core wrap sheet. The first attachment zone has a first width w1 at a first position P1 and a second width w2 at a second position P2. The first position is at a first end of the first attachment zone and the second position is at a second end of the first attachment zone. In yet other embodiments, the first position and/or the second position can be located at positions other than the ends of the first attachment zone, i.e. the middle portion of the first attachment zone (e.g. FIG. 2C, 2D, 2F, 2G, 2L, 2P). The first width w1 is larger than the second width w2, and the width of the first attachment zone increases from the second position P2 to the first position P1, preferably the increase of width is continuous from the second position P2 to the first position P1.

The width of the first attachment zone is measured perpendicularly to a center line of the first attachment zone. In this embodiment the center line of the first attachment zone is a straight line. In yet other embodiments, the center line of the first attachment zone may be a non-straight line, i.e. a curve, or a polyline, or a plurality of intermittent lines, as illustrated in the embodiments of FIGS. 2I, 2J, and 2S. The first width is at least 2% larger than the second width, preferably 4% larger, more preferably 6% larger, even more preferably 8% larger, e.g. 10% larger or even 20% larger. The first width may also be much larger than the second width, e.g. 50% larger, 60% larger, 70% larger, 100% larger (i.e. the double of the second width), 200% larger, etc. Also, the second width may be very small or zero, i.e. the elongate first attachment zone may e.g. end in a point (FIG. 2B). The first width is at least 3 mm, preferably at least 5 mm, more preferably at least 7 mm, even more preferably at least 9 mm, most preferably at least 11 mm. The second width is preferably at least 2 mm, more preferably at least 4 mm, even more preferably at least 6 mm, most preferably at least 8 mm. In yet other embodiments, the second width may be less than 2 mm, i.e. substantially 0 mm as illustrated in the embodiment of FIG. 2B.

The distance between the first position and the second position along the center line of the first attachment zone is larger than 4% of the length of the absorbent core, preferably 8% larger, more preferably 12% larger, even more preferably 16% larger, most preferably 20% larger, e.g. 30% or 40% or 50% or 60% or 70% or even 100% of the length of the absorbent core.

The length of the first attachment zone is larger than 10% of the length of the absorbent core, preferably larger than 20%, more preferably larger than 30%, even more preferably larger than 40%, most preferably larger than 50%, which allows a better liquid distribution over a large area of the absorbent core.

The first attachment zone extends from a crotch region in the direction of the first and second transverse edge, allowing a better liquid distribution between the crotch region and the first and second transverse edge of the absorbent core. In yet other embodiments, the first attachment zone may extend from a crotch region in the direction of the first or second transverse edge, i.e. the embodiment of FIG. 2H. In yet other embodiments, the first attachment zone may extend substantially transversally between the first and second longitudinal edges, i.e. the embodiment of FIG. 2T.

In the first attachment zone substantially no absorbent material is present between the top core wrap sheet and the back core wrap sheet, preferably the first attachment zone is a continuous zone with substantially no absorbent material present between the top core wrap sheet and the back core wrap sheet. In yet other embodiments, the first attachment zone may comprise a plurality of sections which have substantially no absorbent material between the top core wrap sheet and the back core wrap sheet, and absorbent material may be present in area in-between adjacent said sections, between the top core wrap sheet and the back core wrap sheet, i.e. embodiment of FIG. 2K, which allows a better liquid flow and distribution between absorbent material on both sides of the first attachment zone.

Contour of the first attachment zone is adjacent to absorbent material, which comprises cellulosic fluff pulp and/or superabsorbent particles.

The first attachment zone is permanent attachment zones which remain attached when wetted, as a result, the channel remains after wetting of the absorbent core. It allows the channel to distribute liquid during further liquid insults, eg. during a second liquid insult, a third liquid insult, a fourth liquid insult, etc.

The first transverse edge is a front edge intended to be positioned at a front side of a person, and the second transverse edge is a rear edge intended to be positioned at a rear side of a person; or the first transverse edge is a rear edge intended to be positioned at a rear side of a person, and the second transverse edge is a front edge intended to be positioned at a front side of a person. For male wearer, preferably the first position of the channel is located nearer the front edge of the absorbent core.

A similar embodiment is illustrated in FIG. 2B. The first position is at a first end of the first attachment zone and the second position is at a second end of the first attachment zone, and the second width is substantially 0 mm. As a result, the first attachment zone has a substantially triangular shape.

In the embodiment of FIG. 2C, the first attachment zone further has a third width (w3) at a third position, wherein the second position is located between the first position and the third position, the second position being in a crotch region of the absorbent core. In yet other embodiments, the second position may be in a front portion or a rear portion of the absorbent core. The third width is larger than the second width, and the width of the first attachment zone increases from the second position to the third position. Such embodiment is particularly advantageous for male wearer, due to the specific physiological structure of male at the genital region. As the majority of the liquid enters the front and/or rear portion of the absorbent core during a liquid insult of a male wearer, this embodiment allows a larger quantity of liquid to be temporarily held in the and/or rear region of the absorbent core and a subsequent efficient distribution of liquid over substantially the entire absorbent core. As a result, the chance of liquid overflow and leakage during the liquid insult is decreased. This embodiment further improves fitting of the absorbent article to the body of the wearer.

A similar embodiment as the embodiment of FIG. 2C is illustrated in FIG. 2D, where the first attachment zone further has a third width at a third position, wherein the first position is located between the second position and the third position, the first position being in a crotch region of the absorbent core. In yet other embodiments, the first position may be in a front portion or a rear portion of the absorbent core. The third width is smaller than the first width, and the width of the first attachment zone decreases from the first position to the third position. Such embodiment is particularly advantageous for female wearer, due to the specific physiological structure of female at the genital region. As the majority of the liquid enters the crotch region of the absorbent core during a liquid insult of a female wearer, this embodiment allows a larger quantity of liquid to be temporarily held in the crotch region of the absorbent core and a subsequent efficient distribution of liquid over substantially the entire absorbent core. As a result, the chance of liquid overflow and leakage during the liquid insult is decreased. This embodiment further improves fitting of the absorbent article to the body of the wearer.

FIGS. 2E, 2F and 2G illustrate different embodiments of a first attachment zone of an absorbent core. In these embodiments, the width of the first attachment zone intermittently increases from the second position to the first position, in contrast to a continuously change of width as illustrated in embodiments of FIGS. 2A to 2D. In the embodiment of FIG. 2F, the first attachment zone further has a third width (w3) at a third position, wherein the second position is located between the first position and the third position, the second position being in a crotch region of the absorbent core. The third width is larger than the second width, and the width of the first attachment zone also intermittently increases from the second position to the third position. In the embodiment of FIG. 2G, the first attachment zone also has a third width at a third position, wherein the first position is located between the second position and the third position, the first position being in a crotch region of the absorbent core. The third width is smaller than the first width, and the width of the first attachment zone intermittently decreases from the first position to the third position. The embodiments of FIGS. 2E and 2F are advantageous for male wearer, and the embodiment of FIG. 2G is advantageous for female wear, as the location of the liquid insult with the most liquid volume is different between male and female wearers.

In the embodiments of FIGS. 2L to 2R, and 2U, the absorbent core is provided with a plurality of attachment zones where the top core wrap sheet is attached to the back core wrap sheet, wherein the plurality of attachment zones comprises at least a first attachment zone and further a second attachment zone. Preferably, the plurality of attachment zones are arranged symmetrically with respect to the longitudinal center line of the absorbent core, i.e. embodiments of FIGS. 2L to 2R. Yet in other embodiments, the plurality of attachment zones may be arranged asymmetrically with respect to the longitudinal center line of the absorbent core, i.e. embodiment of FIG. 2U. Such embodiments further improve liquid distribution over the entire absorbent core and further prevent liquid overflow and leakage.

In the embodiment of FIG. 2L, said first and second attachment zone extend substantially parallel and next to each other from the crotch region in the direction of the first and/or the second transverse edge.

Figure 19A:
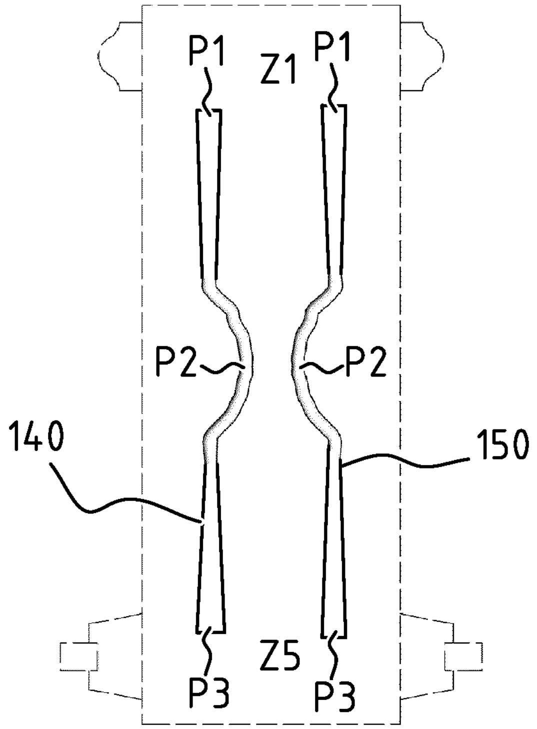
FIGS. 19A-19V illustrate yet other exemplary embodiments of an absorbent core according to the invention.
Figure 19B:
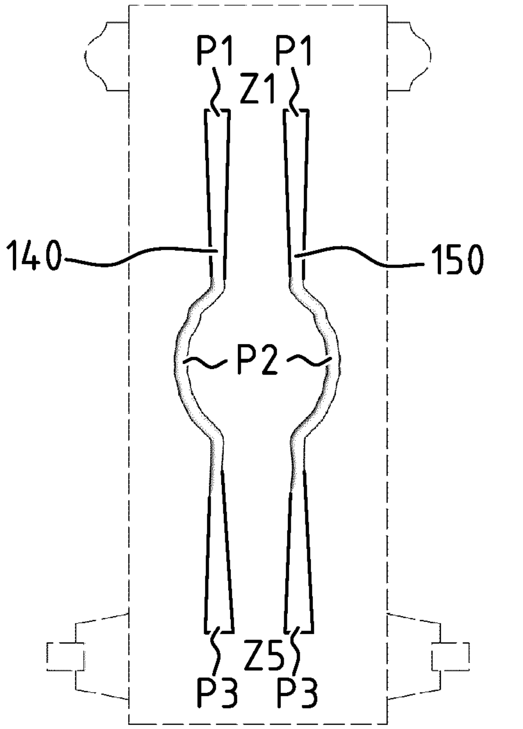
Figure 19C:
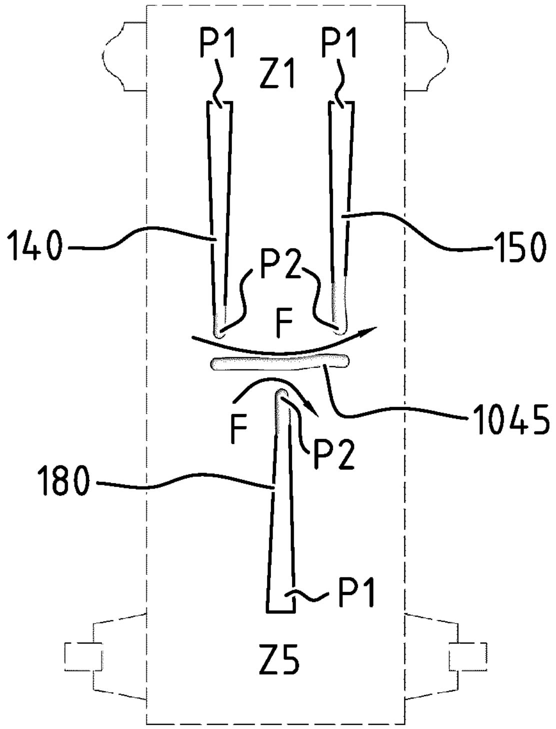
Figure 19D:
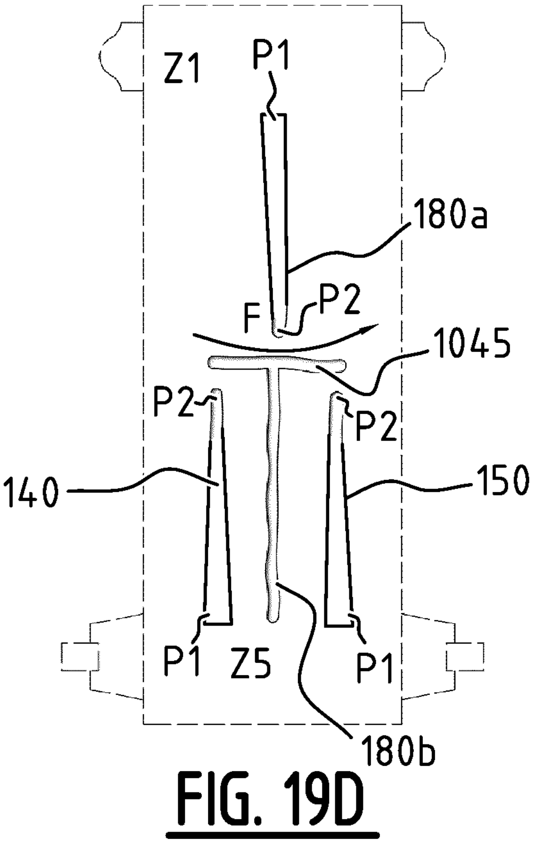
Figure 19E:
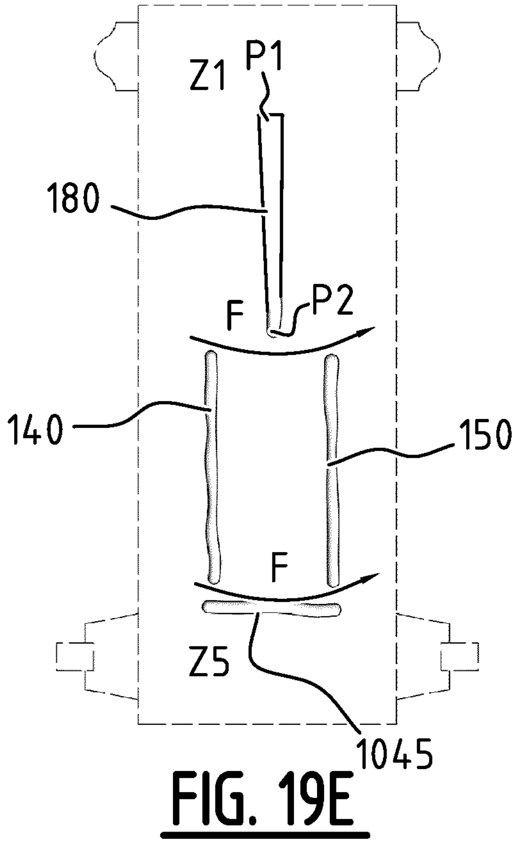
Figure 19F:
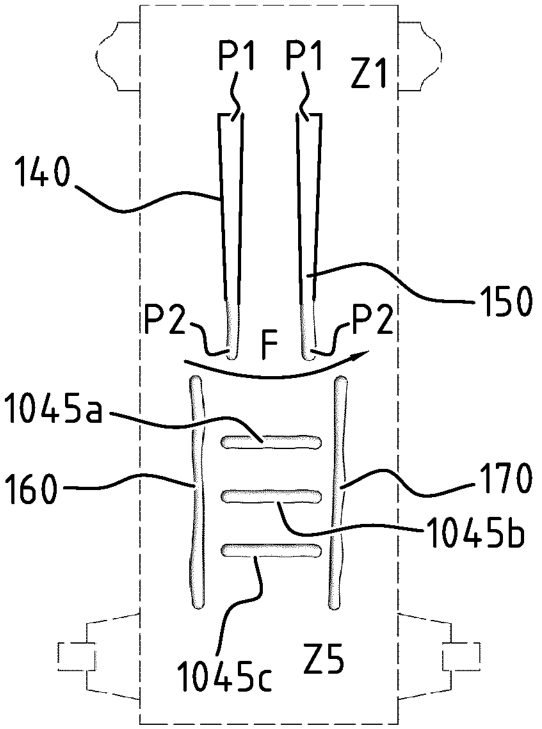
Figure 19G:
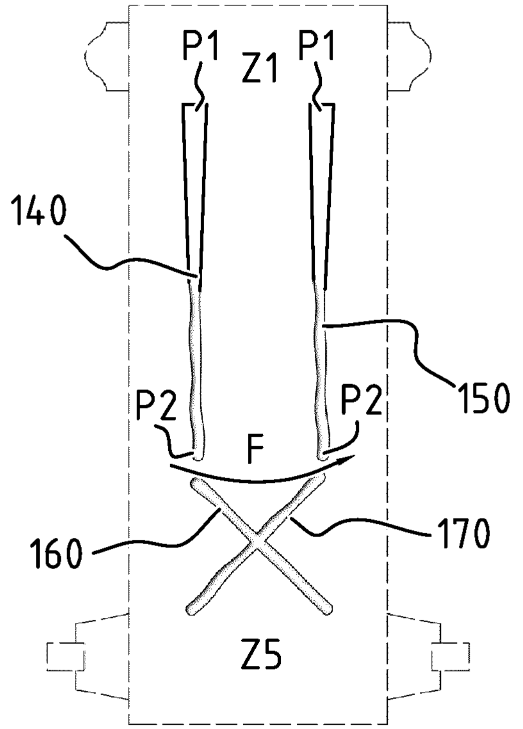

In the embodiment of FIG. 2M, the first attachment zone crosses the second attachment zone at a crossing point. The first and second attachment zones together form a substantially X-shaped zone. Preferably the crossing point is on a longitudinal center line of the absorbent core extending between the first and second transverse edge. Preferably the crossing point is in the crotch portion of the absorbent core. In other embodiments, an X-shaped zone may be combined with differently shaped zones, see e.g. FIG. 19G. Also, the X-shaped zone may comprise curved portions, see e.g. the embodiments of FIGS. 19H, 23N, 24P, 25U, 25V.

In the embodiment of FIG. 2N, the first attachment zone is connected to the second attachment zone through at least one semi-permanent attachment zone, preferably extending in a transverse direction. The at least one semi-permanent attachment zone is configured to release after having been in contact with liquid for a predetermined period of time, so that liquid can flow in a transverse direction through the absorbent material of the absorbent core, wherein said predetermined period of time is preferably smaller than 30 s.

In the embodiment of FIG. 2O, the first and second attachment zones together form a substantially V-shaped zone, wherein the V-shape is arranged such that it is symmetrical with respect to the longitudinal center line of the absorbent core. The first positions, or the second positions, or the third positions of the first and the second attachment zones join together respectively to form the V-shaped zone. Yet in other embodiments, the first and second attachment zones may together form a substantially U-shaped zone. A U-shape or V-shape provides for a good guidance of the liquid. With a V-shape, liquid may be guided from e.g. a left and right front portion to a center portion in the crotch region. Moreover, with a U-shaped attachment zone sharp angles may be avoided further improving a good liquid transport from a first attachment zone (one leg) of the U-shaped attachment zone to the second attachment zone (the other leg) of the U-shaped attachment zone.

In the embodiment of FIG. 2P, the second attachment zone extends in a substantially transverse direction between the first and second longitudinal edges of the absorbent core. The first attachment zone extends in a substantially longitudinal direction between the first and second transverse edges of the absorbent core, from the crotch region in the direction of the first and/or the second transverse edge. The first attachment zone crosses the second attachment zone at a crossing point. The first and second attachment zones together form a substantially cross-shaped zone. Preferably the crossing point is on a longitudinal center line of the absorbent core extending between the first and second transverse edge. Preferably the second attachment zone extends in the crotch region of the absorbent core, and the crossing point is in the crotch portion of the absorbent core. This embodiment provides for a good guidance of the liquid, e.g. from a left portion to a right portion in the crotch region of the absorbent core.

In the embodiments of FIG. 2Q, the plurality of attachment zones further comprises a third elongate attachment zone. In the embodiments of FIG. 20, the plurality of attachment zones further comprises a fourth elongate attachment zone. Both embodiments may comprise a bridge zone B allowing a liquid flow between the first and the second longitudinal edge by capillary action through the absorbent material and/or by mass flow, such that upon wetting of the absorbent material, front channels and rear channel(s) are created, wherein the bridge zone B extends between said front and rear channel(s); wherein a minimum distance between said front channels and rear channel(s) is preferably larger than 3 mm more preferably larger than 5 mm. The bridge zone B may extend from a first portion of the absorbent core to a second portion of the absorbent core, wherein the first portion is defined between the first longitudinal edge and the longitudinal center line of the absorbent core and the second portion is defined between the second longitudinal edge and the longitudinal center line of the absorbent core. The bridge zone B may comprise one or more temporary attachments between the top and back core wrap sheet which are configured to detach when wetted; and/or the bridge zone B may comprise at least one permanent attachment zone in a direction from the first to the second longitudinal edge; and/or the said bridge zone B may comprise absorbent material. Preferably, the absorbent material comprises cellulosic fluff pulp and/or superabsorbent particles.

FIGS. 17A-17X, 18A-18S, 19A-19V, 20A-20G, 21A-21D, 22A-22Z, 23A-23Z, 24A-24Z, 25A-25V, 26A-26C, 27A-27Z, 28A-28T illustrate exemplary embodiments of an absorbent core according to the invention. Preferably the absorbent core of those examples is provided with a plurality of attachment zones comprising at least a first attachment zone where the top core wrap sheet is attached to the back core wrap sheet, and where preferably substantially no absorbent material is present. The first attachment zone has a first width w1 at a first position P1 and a second width w2 at a second position P2. The first width is larger than the second width, and the width of the first attachment zone increases from the second position to the first position. In the embodiments of FIGS. 17L, 17M, 17N, 17S, 18Q, 18S, 19M, 19O, 19R, 20B, 20E, 21D, 24A, 24B, 24C, the first attachment zone may further comprise has a third width w3 at a third position P3 and the second position is located between the first position and the third position. The third width is larger than the second width, and the width of the first attachment zone increases from the second position to the third position. The second position is preferably in a crotch region of the absorbent core. In the embodiments of FIGS. 17J, 17O, 17P, 18H, 18P, 20C, 20G, 21A, 21B, 21C, 22M, 22N, 22O, 22P, 22U, 23C, 23D, 23E, 23Q, 23R, 24O, 24W, 24U, 25G, 25M, 25N, 25O, 25P, 25T, 27F, 27I, 27J, 27K, 28H, 28O, 28P, 28Q, 28R, the first attachment zone may further has a third width w3 at a third position P3, and the first position is located between the second position and the third position. The third width is smaller than the first width, and the width of the first attachment zone decreases from the first position to the third position. Preferably the first position is in a crotch region of the absorbent core.

FIGS. 17A-17X, 18A-18S, 19A-19V and 20A-F illustrate multiple advantageous positions for the attachment zones in an absorbent core according to the invention. Preferably the absorbent core of those examples is provided with a plurality of attachment zones comprising at least a first attachment zone where the top core wrap sheet is attached to the back core wrap sheet, and where preferably substantially no absorbent material is present. The first attachment zone has a first width w1 at a first position P1 and a second width w2 at a second position P2. The first width is larger than the second width, and the width of the first attachment zone increases from the second position to the first position. Seen in a longitudinal direction of the absorbent core, looking from the front edge to the rear edge, the absorbent core comprises subsequently a first, second, third, fourth and fifth zone Z1, Z2, Z3, Z4, Z5, as illustrated. The principles about the zones set out above for various embodiments may also be applied in the embodiments of FIGS. 17A-17X, 18A-18S, 19A-19V and 20A-F. In possible embodiments, although not illustrated, small portions of the attachment zones of FIGS. 17A-17X, 18A-18S, 19A-19V may be unattached to create one or more bridge zones. More generally, the bridge zone may comprise one or more temporary attachments between the top and back core wrap sheet which are configured to detach when wetted; and/or at one or more permanent attachment zones in a direction from the first to the second side edge; and/or absorbent material in order to make a transverse capillary flow and/or mass flow possible.

Figure 17A:
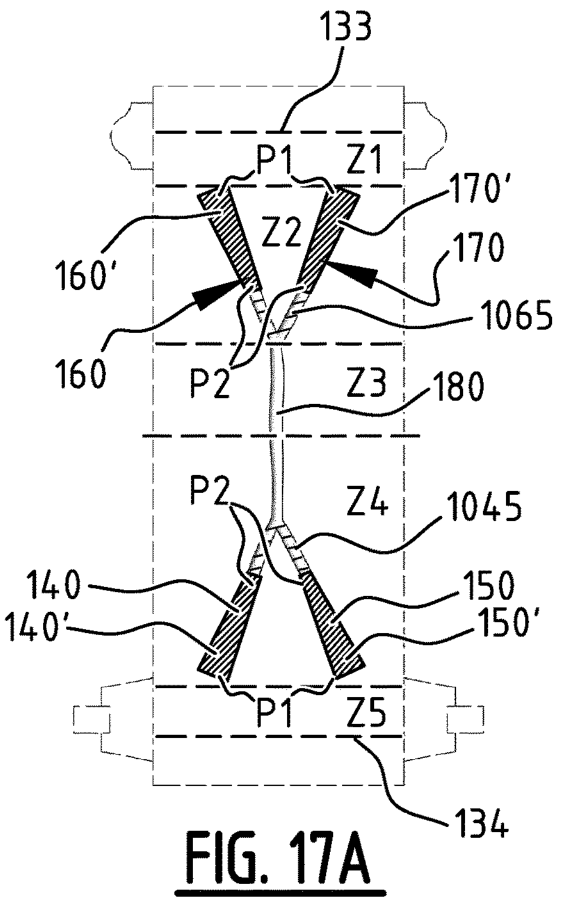
FIGS. 17A-17X illustrate exemplary embodiments of an absorbent core according to the invention.

According to the exemplary embodiment of FIG. 17A the plurality of attachment zones comprises a first attachment zone 140, a second attachment zone 150, a third attachment zone 160 and a fourth attachment zone 170, and a central attachment zone 180. The first and second attachment zones 140 diverge from the central attachment zone 180 in the crotch region in the direction of a rear transverse edge of absorbent core. The third and fourth attachment zone 160, 170 diverge from the central attachment zone 180 in the crotch region in the direction of a front transverse edge of absorbent core. Each of the first attachment zone 140, the second attachment zone 150, the third attachment zone 160 and the fourth attachment zone 170, has a first width w1 at a first position P1 and a second width w2 at a second position P2. The first width is larger than the second width, and the width of the first attachment zone increases from the second position to the first position.

The embodiment of FIG. 17A can be used for both male and female. In the embodiment of FIG. 17A the first attachment zone 140 and the second attachment zone 150 form together a substantially V-shaped zone. This substantially V-shaped zone comprises a first elongate attachment zone 140' (indicated as a solid fill area), a second elongate attachment zone 150' (indicated as a solid fill area), and a V-shaped connecting attachment zone 1045 (indicated as a hatched area). The first and second elongate attachment zone 140', 150' extend next to each other from the crotch region in the direction of the rear transverse edge 134. The connecting attachment zone 1045 connects said first elongate attachment zone 140' with said second attachment zone 150'. The connecting attachment zone 1045 is a front connecting attachment zone which connects a front end portion of the first attachment zone 140' to a corresponding front end portion of the second attachment zone 150'. Similarly, the third attachment zone 160 and the fourth attachment zone 170 form together a substantially V-shaped zone. This substantially V-shaped zone 160, 170 comprises a third elongate attachment zone 160', a fourth elongate attachment zone 170', and a V-shaped connecting attachment zone 1065. The third and fourth elongate attachment zone 160', 170' extend next to each other from the crotch region in the direction of the front transverse edge 133. The connecting attachment zone 1065 connects said third elongate attachment zone 160' with said fourth elongate attachment zone 170'. The connecting attachment zone 1065 is a rear connecting attachment zone which connects a rear end portion of the third attachment zone 160' to a corresponding rear end portion of the fourth attachment zone 170'. The V-shaped zone 160, 170 guides the liquid from left and right parts of the front portion. As illustrated the first interconnecting attachment zone 1045 may be arranged in the front portion, and more in particular in the second zone Z2, and the second interconnecting attachment zone 1065 may be arranged in the rear portion, and in particular in the fourth zone Z4. By connecting the first interconnecting attachment zone 1045 with the second interconnecting attachment zone 1065 in the crotch region with a central longitudinal attachment zone 180 a convenient liquid distribution channel network is created allowing the liquid to be distributed rapidly throughout the absorbent core.

Figure 17B:
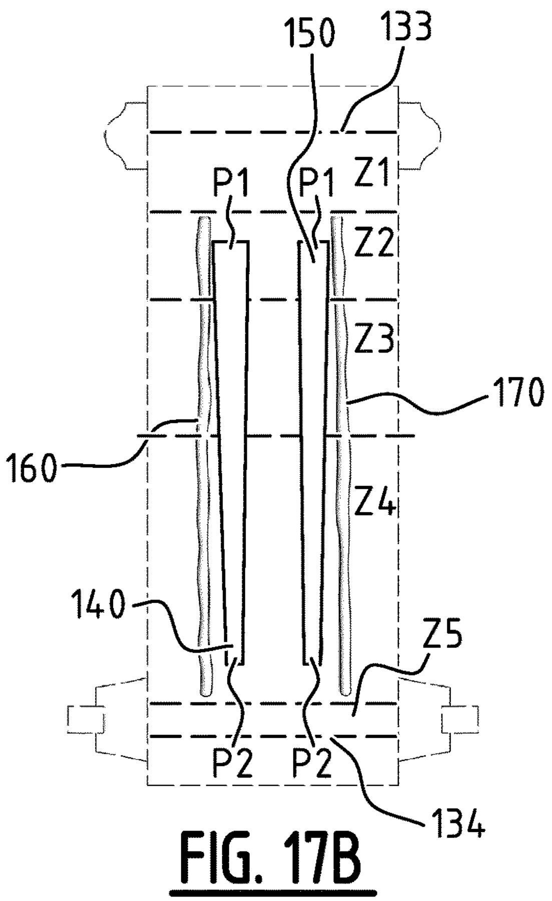

According to the exemplary embodiment of FIG. 17B the plurality of attachment zones comprises a first attachment zone 140, a second attachment zone 150, a third attachment zone 160 and a fourth attachment zone 170. The first attachment zone 140 and the second attachment zone 150 each have a first width w1 at a first position P1 and a second width w2 at a second position P2. The first width is larger than the second width, and the width of the first attachment zone increases from the second position to the first position. The third attachment zone 160 and the fourth attachment zone 170 each has a constant width. This embodiment is similar to the embodiment of FIG. 4A-4B, with this difference that the outer attachment zones 160, 170 are longer than the inner attachment zones 140, 150.

Figure 17C:
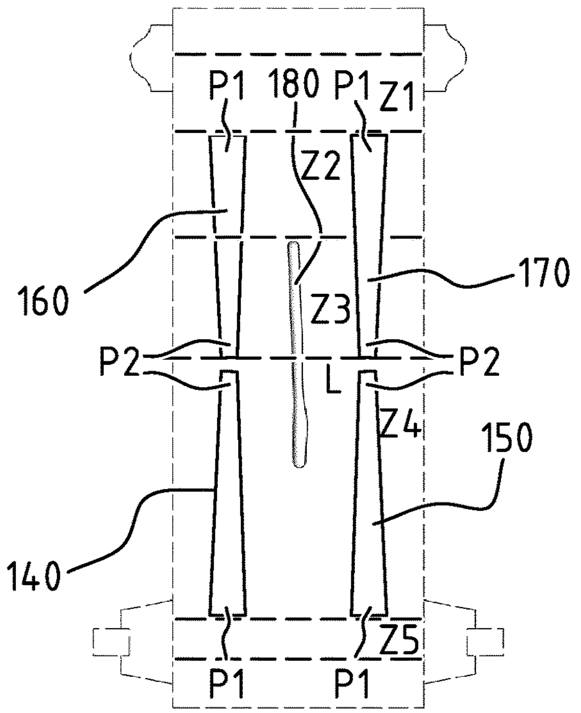

According to the exemplary embodiment of FIG. 17C the plurality of attachment zones comprises a first attachment zone 140, a second attachment zone 150, a third attachment zone 160 and a fourth attachment zone 170, and a central attachment zone 180. The first and third attachment zones 140, 160 are aligned in the longitudinal direction. Also, the second and fourth attachment zones 150, 170 are aligned and extend substantially parallel to the first and third attachment zones 140, 160. Each of the first attachment zone 140, the second attachment zone 150, the third attachment zone 160 and the fourth attachment zone 170, has a first width w1 at a first position P1 and a second width w2 at a second position P2. The first width is larger than the second width, and the width of the first attachment zone increases from the second position to the first position. The central attachment zone 180 has a constant width.

Figure 17D:
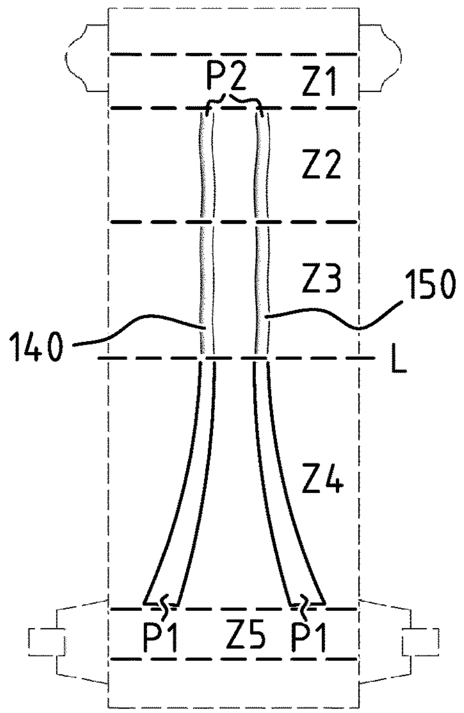

According to the exemplary embodiment of FIG. 17D the plurality of attachment zones comprises a first attachment zone 140 and a second attachment zone 150. The first and second attachment zones 140 are substantially parallel in the crotch region and diverge in the direction of a rear transverse edge of absorbent core. The first attachment zone 140 and the second attachment zone 150 each have a first width w1 at a first position P1 and a second width w2 at a second position P2. The first width is larger than the second width, and the width of the first attachment zone increases from the second position to the first position.

Figure 17E:
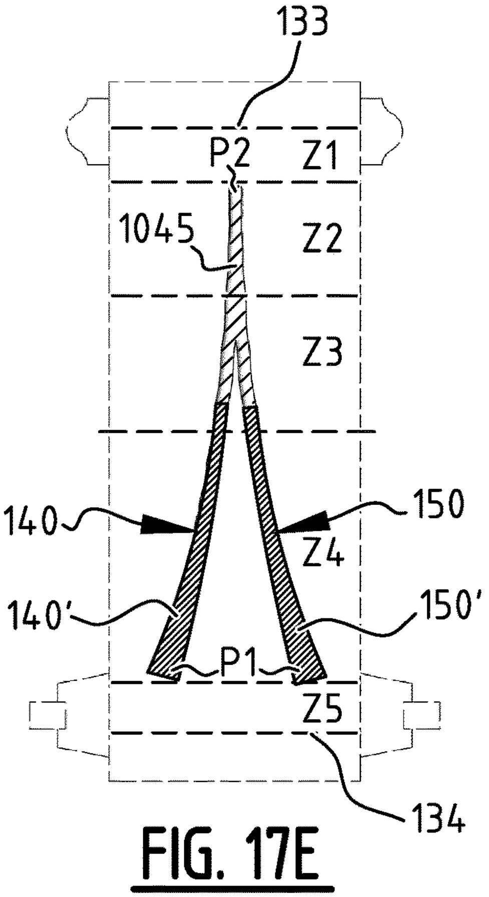

According to the exemplary embodiment of FIG. 17E the plurality of attachment zones comprises a first attachment zone 140 and a second attachment zone 150. The first and second attachment zones 140 partially overlap in the crotch region and diverge in the direction of a front transverse edge of absorbent core. The embodiment of FIG. 17E is preferable for a female.

In the embodiment of FIG. 17E the first attachment zone 140 and the second attachment zone 150 form together a substantially V-shaped zone. This substantially V-shaped zone comprises a first elongate attachment zone 140' (indicated as a solid fill area), a second elongate attachment zone 150' (indicated as a solid fill area), and a V-shaped connecting attachment zone 1045 (indicated as a hatched area). The first and second elongate attachment zone 140', 150' extend next to each other from the crotch region in the direction of the rear transverse edge 134, and more particularly in the fourth and third zone Z4 and Z3. The connecting attachment zone 1045 connects said first elongate attachment zone 140' with said second attachment zone 150'. The connecting attachment zone 1045 is a front connecting attachment zone which connects a front end portion of the first attachment zone 140' to a corresponding front end portion of the second attachment zone 150'. The V-shaped zone 140, 150 guides the liquid from the front portion to the left and right parts of the rear portion. As illustrated the first interconnecting attachment zone 1045 may be arranged in the front portion and more in particular in the second zone Z2. In that manner a convenient liquid distribution channel network is created allowing the liquid to be distributed rapidly throughout the absorbent core.

Figure 17F:
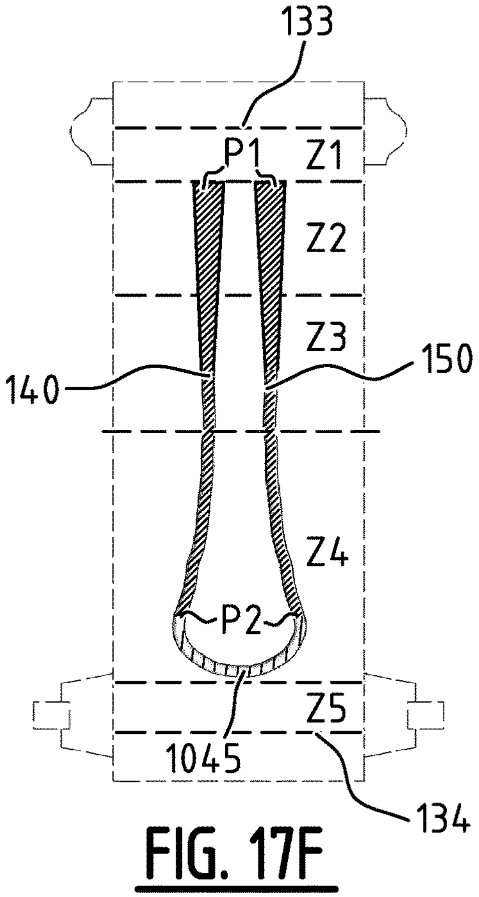

According to the exemplary embodiment of FIG. 17F the plurality of attachment zones comprises a first longitudinal attachment zone 140 and a second longitudinal attachment zone 150 which are interconnected by an attachment portion 1045 in a rear portion of the absorbent core. In that manner any leakage via the front portion can be reduced or avoided.

In the embodiment of FIG. 17F the first attachment zone 140, the second attachment zone 150 and the connecting attachment zone 1045 form together a substantially U-shaped zone. This substantially U-shaped zone comprises a first elongate attachment zone 140 (indicated as a solid fill area), a second elongate attachment zone 150 (indicated as a solid fill area), and a curved connecting attachment zone 1045 (indicated as a hatched area). The first and second elongate attachment zone 140, 150 extend next to each other from the crotch region in the direction of the front transverse edge 133 and in the direction of the rear transverse edge 134, and more particularly in the fourth, third and second zone Z4, Z3 and Z2. The connecting attachment zone 1045 connects said first elongate attachment zone 140 with said second attachment zone 150. The connecting attachment zone 1045 is a rear connecting attachment zone which connects a rear end portion of the first attachment zone 140 to a corresponding rear end portion of the second attachment zone 150. The U-shaped zone 140, 150, 1045 guides the liquid from the left and right parts of the front portion to the rear portion. As illustrated the first interconnecting attachment zone 1045 may be arranged in the rear portion and more in particular in the fourth zone Z4. In that manner a convenient liquid distribution channel network is created allowing the liquid to be distributed rapidly throughout the absorbent core.

Figure 17G:
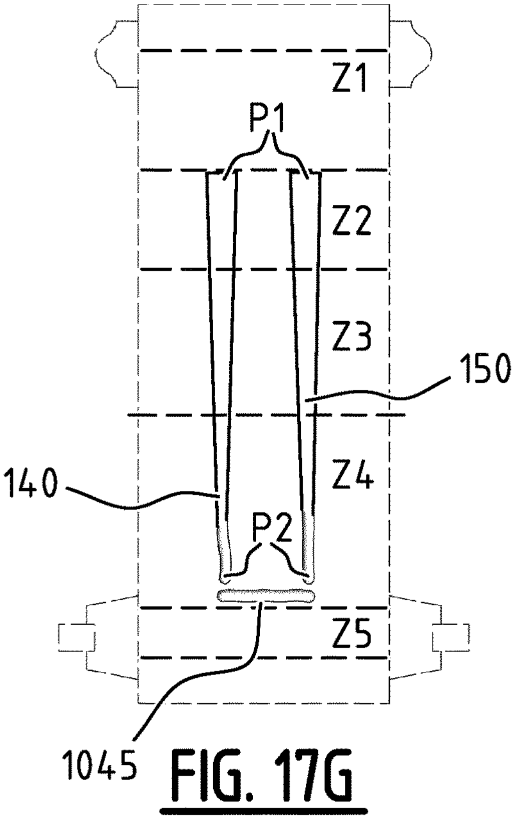

According to the exemplary embodiment of FIG. 17G the plurality of attachment zones comprises a first longitudinal attachment zone 140, a second longitudinal attachment zone 150, and a transverse attachment zone 1045 in a front portion of the absorbent core. The transverse attachment zone 1045 substantially connects a front end of first longitudinal attachment zone 140 and a front end of second longitudinal attachment zone 150. As illustrated the first interconnecting attachment zone 1045 may be arranged in the rear portion and more in particular in the fourth zone Z4.

Figure 17H:
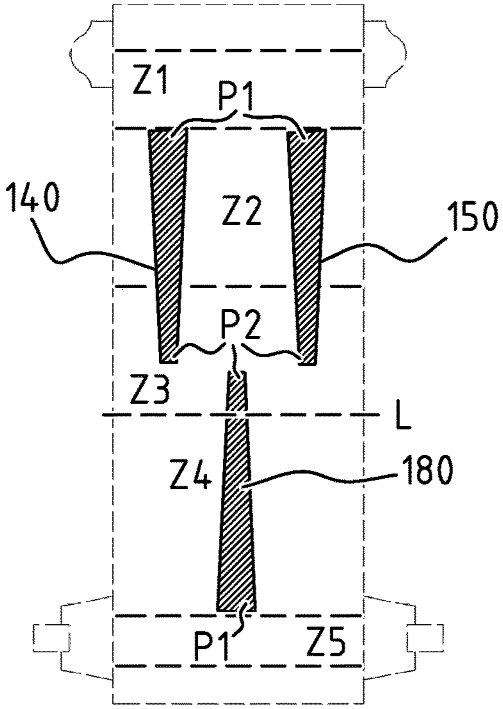

According to the exemplary embodiment of FIG. 17H the plurality of attachment zones comprises a first longitudinal attachment zone 140, a second longitudinal attachment zone 150, a central longitudinal attachment zone 180. The first and second longitudinal attachment zones 140, 150 extend adjacent to each other from the crotch region to a rear transverse edge of the absorbent core. The central longitudinal attachment zone 180 extends from the crotch region in the direction of the front transverse edge of the absorbent core.

Figure 17I:
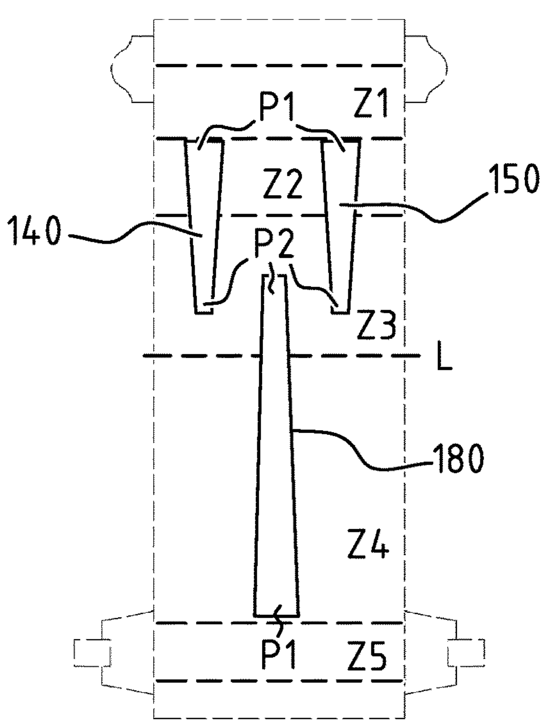

The exemplary embodiment of FIG. 17I is similar to the embodiment of FIG. 17H, with this difference that the central attachment zone 180 extends also from the crotch region in the direction of the rear transverse edge, partially in between the first and second attachment zone 140, 150.

Figure 17J:
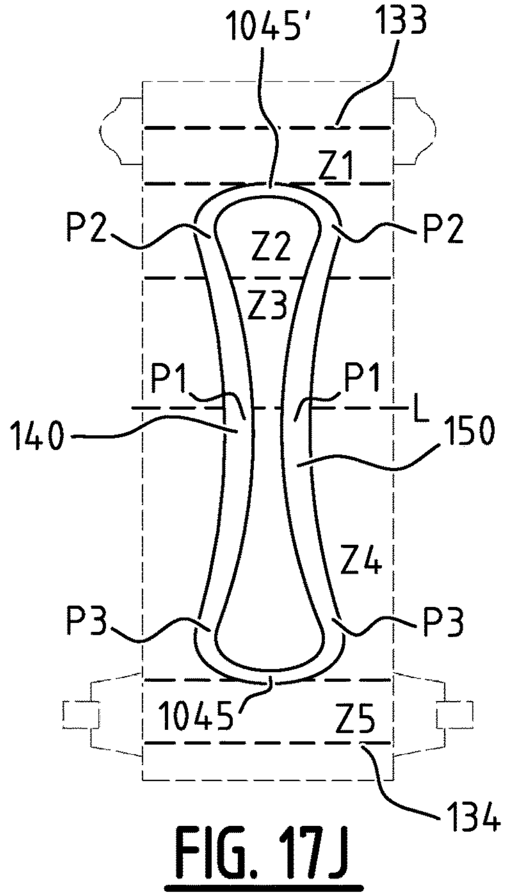

According to the exemplary embodiment of FIG. 17J the plurality of attachment zones comprises a first longitudinal attachment zone 140 and a second longitudinal attachment zone 150 which are interconnected by an attachment portion 1045 in a front portion of the absorbent core and an attachment portion 1045' in a rear portion of the absorbent core. In that manner any leakage via the front and rear portion can be reduced or avoided. In this embodiment the first longitudinal attachment zone 140 and the second longitudinal attachment zone 150 each has a third width w3 at a third position P3. The first position is located between the second position and the third position, and the third width is smaller than the first width, and the width of the first attachment zone decreases from the first position to the third position. The first position is in a crotch region of the absorbent core.

In the embodiment of FIG. 17J the first attachment zone 140, the second attachment zone 150 and two connecting attachment zones 1045, 1045' form together a substantially rectangular attachment zone. This substantially rectangular attachment zone comprises a first elongate attachment zone 140, a second elongate attachment zone 150, and two curved connecting attachment zones 1045, 1045'. The first and second elongate attachment zone 140, 150 extend next to each other from the crotch region in the direction of the front transverse edge 133 and in the direction of the rear transverse edge 134, and more particularly in the fourth, third and second zone Z4, Z3 and Z2. The connecting attachment zone 1045 is a rear connecting attachment zone which connects a rear end portion of the first attachment zone 140 to a corresponding rear end portion of the second attachment zone 150. The connecting attachment zone 1045 is located in the fourth zone Z4. The connecting attachment zone 1045' is a front connecting attachment zone which connects a front end portion of the first attachment zone 140 to a corresponding front end portion of the second attachment zone 150. The connecting attachment zone 1045' is located in the second zone Z2. In that manner a convenient liquid distribution channel network is created allowing the liquid to be distributed rapidly throughout the absorbent core.

Figure 17K:
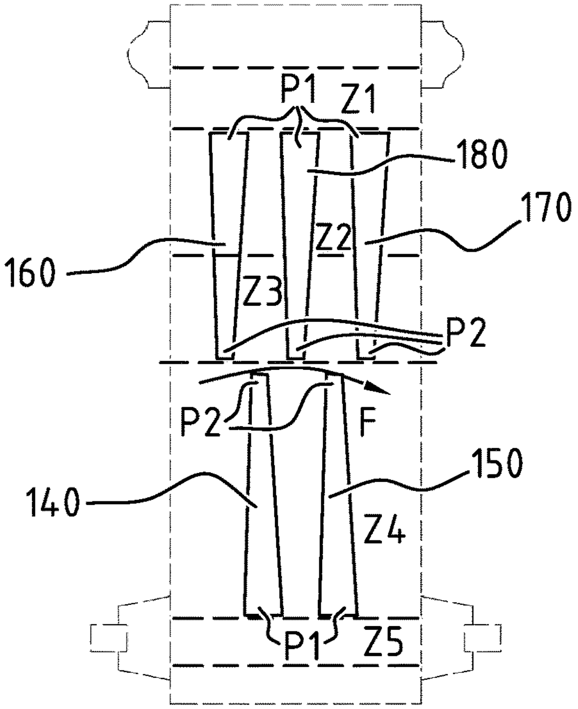

According to the exemplary embodiment of FIG. 17K the plurality of attachment zones comprises a first attachment zone 140, a second attachment zone 150, a third attachment zone 160 and a fourth attachment zone 170, and a central attachment zone 180. The first and second attachment zones 140, 150 extend adjacent to each other from a crotch region in the direction the front transverse edge. Also, the third and fourth attachment zones 160, 170, as well as the central attachment zone extend adjacent to each other from a crotch region in the direction the rear transverse edge. In that manner the distribution of liquid in the rear portion of the absorbent core can be further enhanced.

Figure 17L:
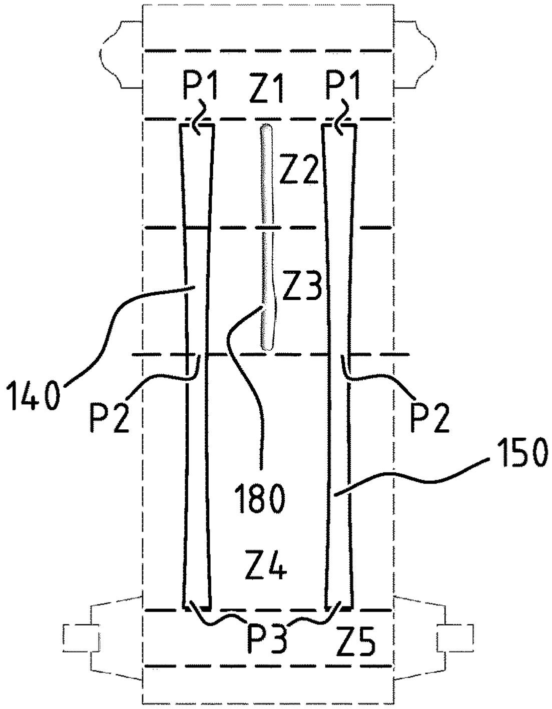

According to the exemplary embodiment of FIG. 17L the plurality of attachment zones comprises a first longitudinal attachment zone 140, a second longitudinal attachment zone 150, and a central longitudinal attachment zone 180. The first and second longitudinal attachment zones 140, 150 extend adjacent to each other over at least 60% of the length of the absorbent core. The central longitudinal attachment zone 180 extends between the first and second attachment zones 140, 150, from the crotch region in the direction of the rear transverse edge of the absorbent core. The first and second longitudinal attachment zones 140, 150 each has a third width w3 at a third position P3, wherein the second position is located between the first position and the third position. The third width is larger than the second width, and the width of the first attachment zone increases from the second position to the third position. The second position is in a crotch region of the absorbent core.

Figure 17M:
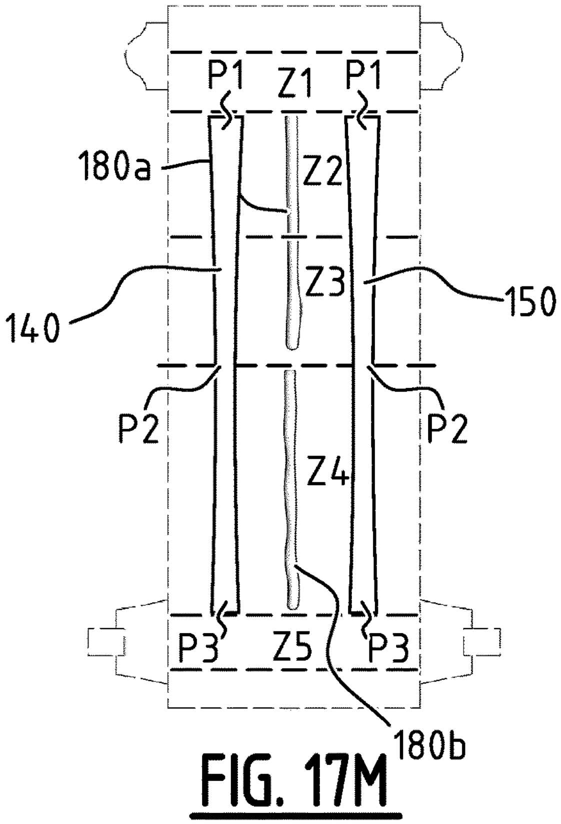

According to the exemplary embodiment of FIG. 17M the plurality of attachment zones comprises a first longitudinal attachment zone 140, a second longitudinal attachment zone 150, a central rear longitudinal attachment zone 180*a*, and a central front longitudinal attachment zone 180*b*. The first and second longitudinal attachment zones 140, 150 extend adjacent to each other over at least 60% of the length of the absorbent core. The central rear and front longitudinal attachment zones 180*a*, 180*b* extends between the first and second attachment zones 140, 150, in a rear and front portion of the absorbent core, respectively.

Figure 17N:
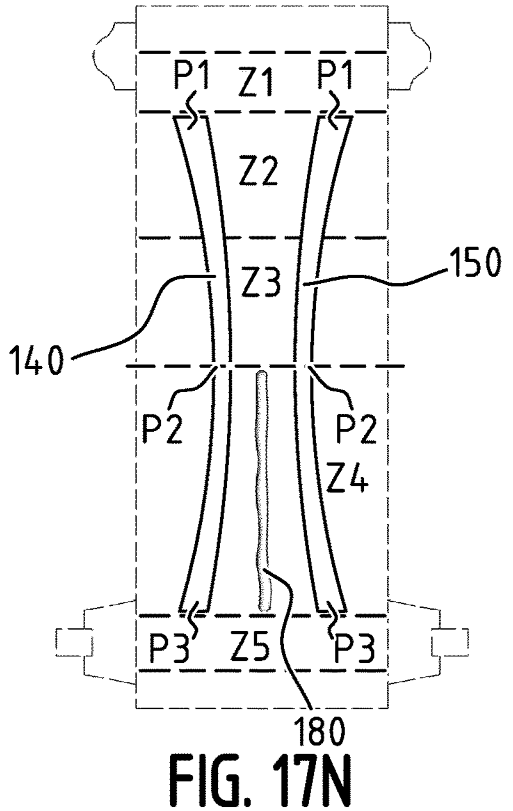

According to the exemplary embodiment of FIG. 17N the plurality of attachment zones comprises a first attachment zone 140, a second attachment zone 150, and a central attachment zone 180. The first and second attachment zones 140 diverge from the crotch region in the direction of a front and rear transverse edge of absorbent core. The central attachment zone is provided in between the first and second attachment zone 140, 150, mainly in a front portion of the absorbent core.

Figure 17O:
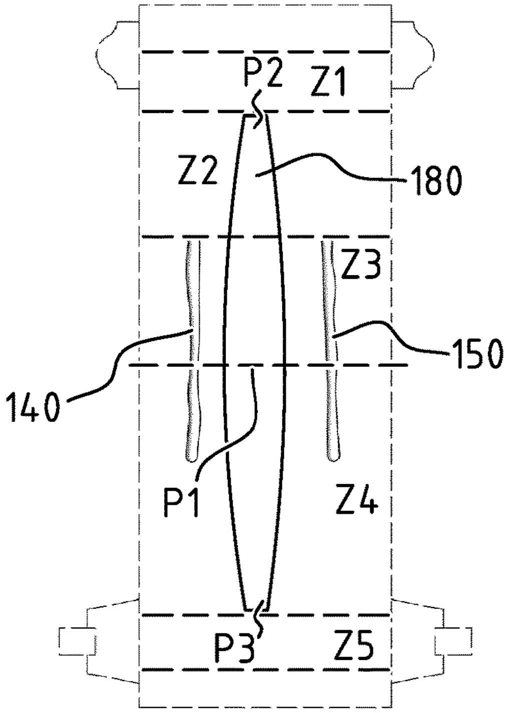

According to the exemplary embodiment of FIG. 17O the plurality of attachment zones comprises a first longitudinal attachment zone 140, a second longitudinal attachment zone 150, and a central longitudinal attachment zone 180. The first and second longitudinal attachment zones 140, 150 extend adjacent and parallel to each other in the crotch region. The central longitudinal attachment zone 180 extends between the first and second attachment zones 140, 150, over at least 60% of the length of the absorbent core.

Figure 17P:
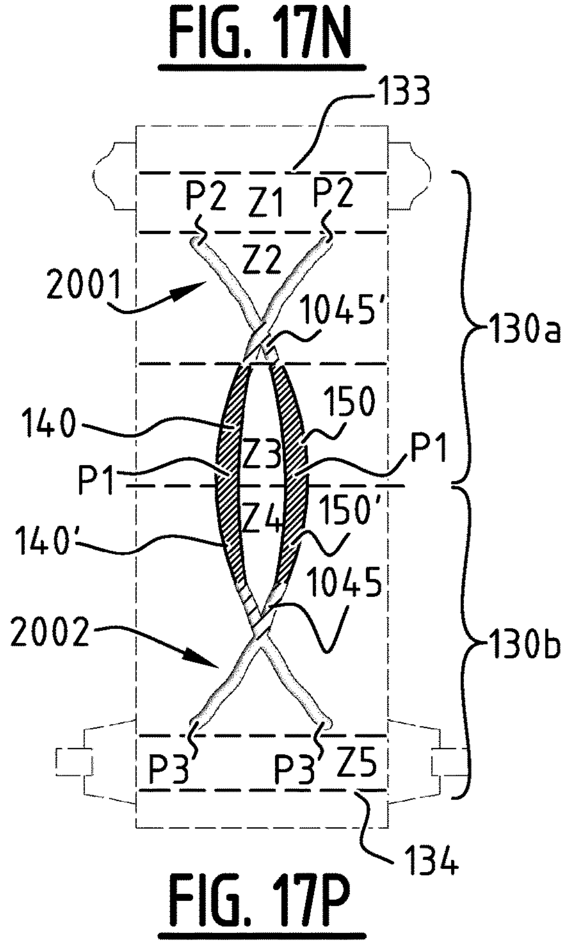

According to the exemplary embodiment of FIG. 17P the plurality of attachment zones comprises a first attachment zone 140 and a second attachment zone 150. The first and second attachment zones 140, 150 extend from the crotch region in the direction of a front and rear transverse edge of absorbent core, and are curved such that the first and second attachment zones 140, 150 cross each other at a first crossing point in a front portion of the absorbent core and in a second crossing point in the rear portion of the absorbent core.

In the embodiment of FIG. 17P a first elongate attachment zone 140', a second elongate attachment zone 150' and two connecting attachment zones 1045, 1045' form together a substantially O-shaped attachment zone. This substantially O-shaped attachment zone comprises the first elongate attachment zone 140', the second elongate attachment zone 150', and two V-shaped connecting attachment zones 1045, 1045'. The first and second elongate attachment zone 140', 150' extend next to each other from the crotch region in the direction of the front transverse edge 133 and in the direction of the rear transverse edge 134, and more particularly in the fourth, and third zone Z4, Z3. The connecting attachment zone 1045 is a rear connecting attachment zone which connects a rear end portion of the first attachment zone 140' to a corresponding rear end portion of the second attachment zone 150'. The connecting attachment zone 1045 is located in the fourth zone Z4. The connecting attachment zone 1045' is a front connecting attachment zone which connects a front end portion of the first attachment zone 140' to a corresponding front end portion of the second attachment zone 150'. The connecting attachment zone 1045' is located in the second zone Z2. Further a first and second V-shaped attachment zone 2001, 2002 may be provided at a rear side and front side of the substantially O-shaped attachment zone 140', 150', 1045, 1045'. In that manner a convenient liquid distribution channel network is created allowing the liquid to be distributed rapidly throughout the absorbent core.

Figure 17Q:
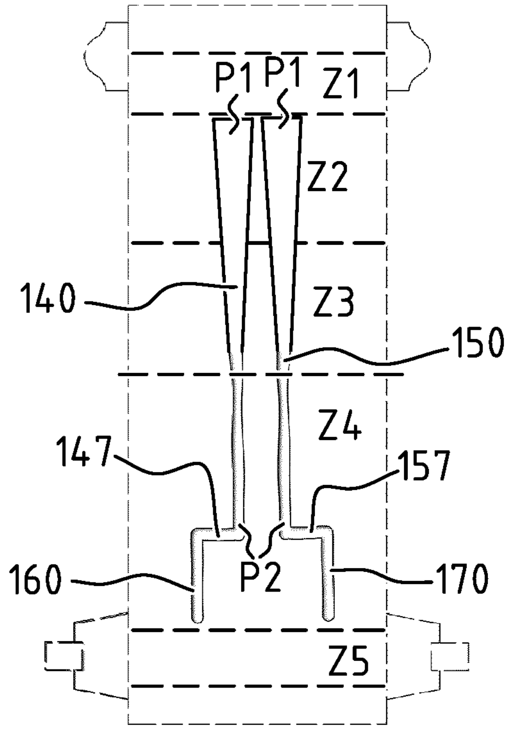

According to the exemplary embodiment of FIG. 17Q the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the rear transverse edge, and are interconnected via transverse attachment portions 147, 157 to third and fourth attachment zone 160, 170 extending from the crotch region to the front transverse edge, respectively.

Figure 17R:
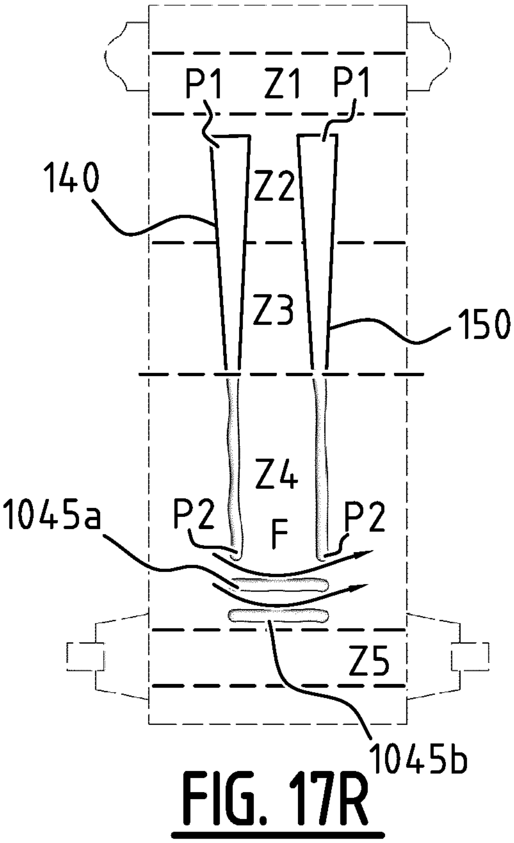

The exemplary embodiment of FIG. 17R is similar to the embodiment of FIG. 17G with this difference that two parallel transverse attachment zones 1045*a* and 1045*b* are provided in the front region of the absorbent core.

Figure 17S:
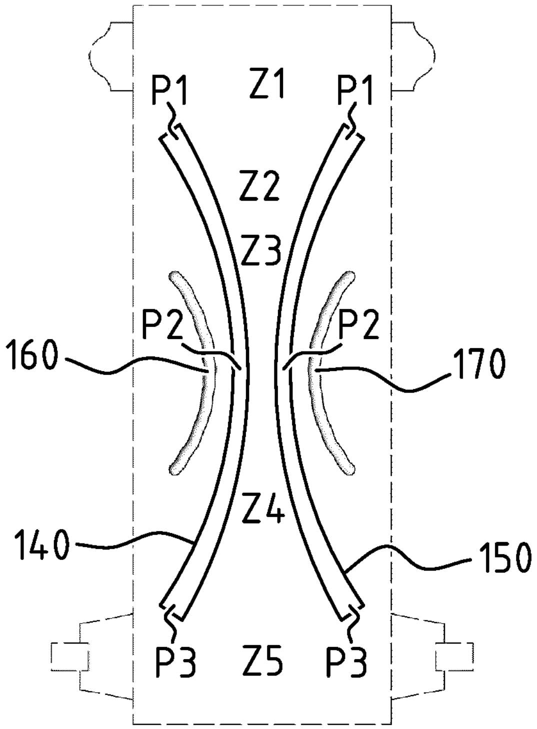

According to the exemplary embodiment of FIG. 17S the plurality of attachment zones comprises a first attachment zone 140, a second attachment zone 150, a third attachment zone 160 and a fourth attachment zone 170. The first and second attachment zones 140, 150 diverge from the crotch region in the direction of a front and rear transverse edge of absorbent core. The third and fourth attachment zones 160, 170 are located outwardly of the first and second attachment zones 140, 150, are shorter than the first and second attachment zones 140, 150, and also diverge from the crotch region in the direction of a front and rear transverse edge of absorbent core. In that manner, in the wetted state, a plurality of tubes is created, wherein the tubes are smaller in a center of the crotch region and gradually widen in the direction of the front and rear transverse edge of the absorbent core. In that manner the shape of the tub which is formed in the wetted state can be further improved to fit well to the body.

Figure 17T:
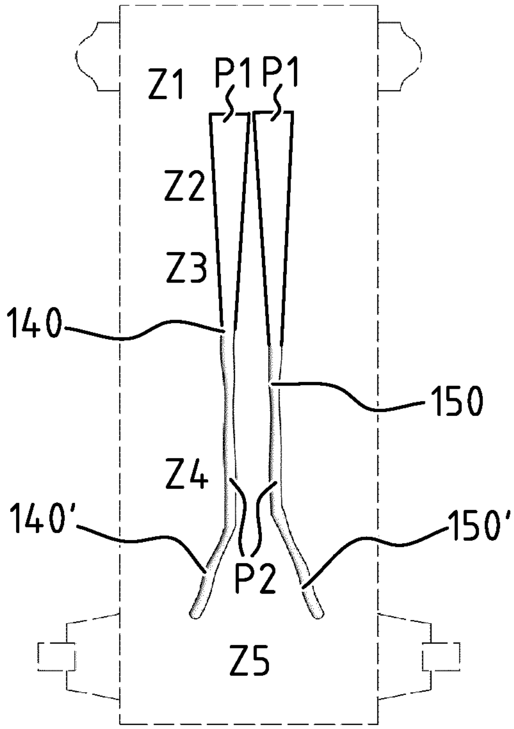

According to the exemplary embodiment of FIG. 17T the plurality of attachment zones comprises a first longitudinal attachment zone 140 and a second longitudinal attachment zone 150, wherein front end portions 140', 150' thereof diverge in the direction of the front transverse edge of the absorbent core.

Figure 17U:
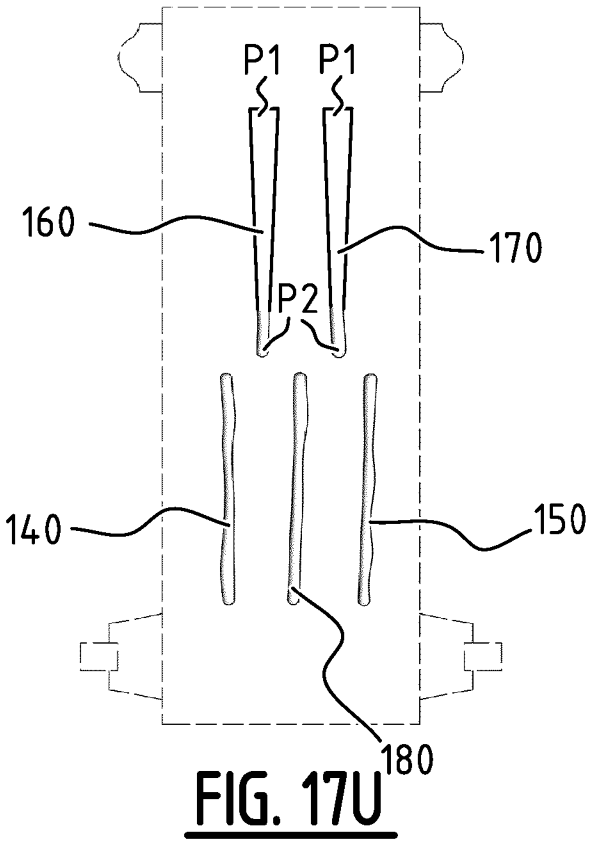

According to the exemplary embodiment of FIG. 17U the plurality of attachment zones comprises a first longitudinal attachment zone 140, a second longitudinal attachment zone 150, a third longitudinal attachment zone 160 and a fourth longitudinal attachment zone 170, and a central longitudinal attachment zone 180. The first and second attachment zones 140, 150, as well as the central attachment zone 180 extend adjacent to each other from a crotch region in the direction the front transverse edge. Also, the third and fourth attachment zones 160, 170 extend adjacent to each other from a crotch region in the direction the rear transverse edge. In that manner the distribution of liquid in the front portion of the absorbent core can be further enhanced.

Figure 17V:
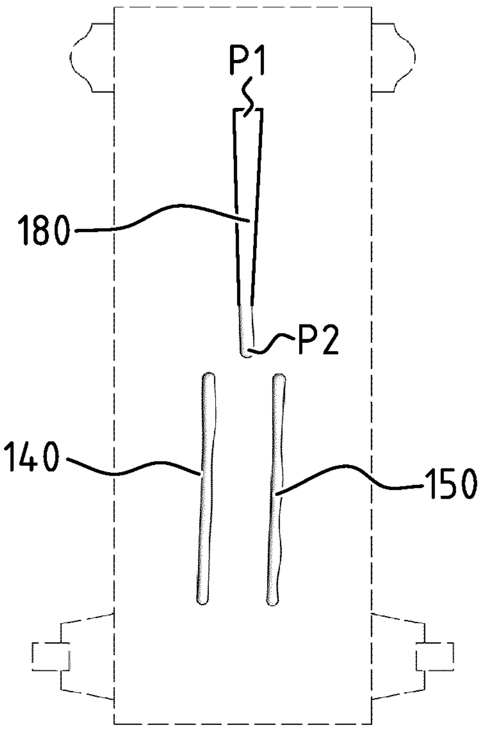

According to the exemplary embodiment of FIG. 17V the plurality of attachment zones comprises a first longitudinal attachment zone 140, a second longitudinal attachment zone 150, and a central longitudinal attachment zone 180. The first and second attachment zones 140, 150 extend adjacent to each other from a crotch region in the direction the front transverse edge. The central attachment zone 180 extends from a crotch region in the direction the rear transverse edge.

Figure 17W:
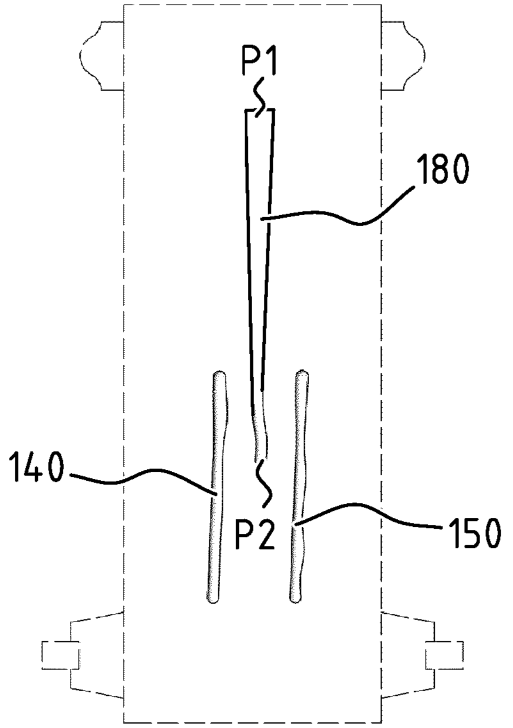

The exemplary embodiment of FIG. 17W is similar to the embodiment of FIG. 17V with this difference that the central attachment zone 180 extends partially in between the first and the second attachment zone 140, 150.

Figure 17X:
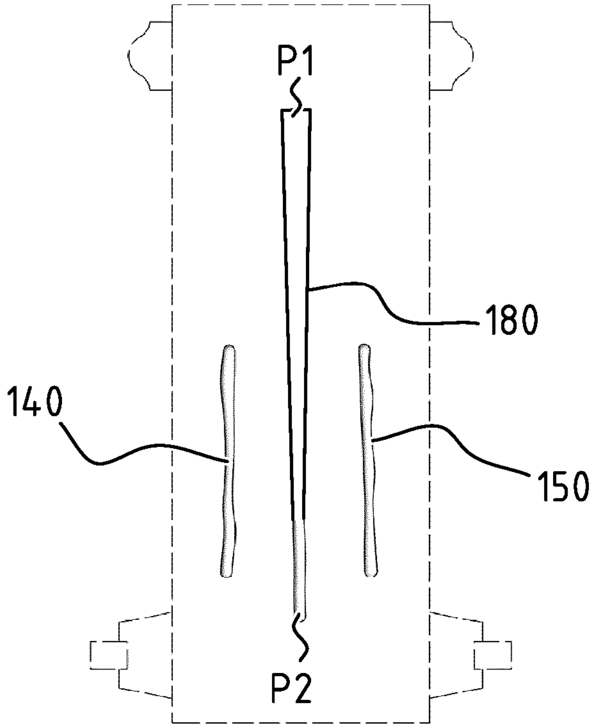

The exemplary embodiment of FIG. 17X is similar to the embodiment of FIG. 17V with this difference that the central attachment zone 180 extends all the way in between the first and the second attachment zone 140, 150 in the direction of the front transverse edge.

Figure 18A:
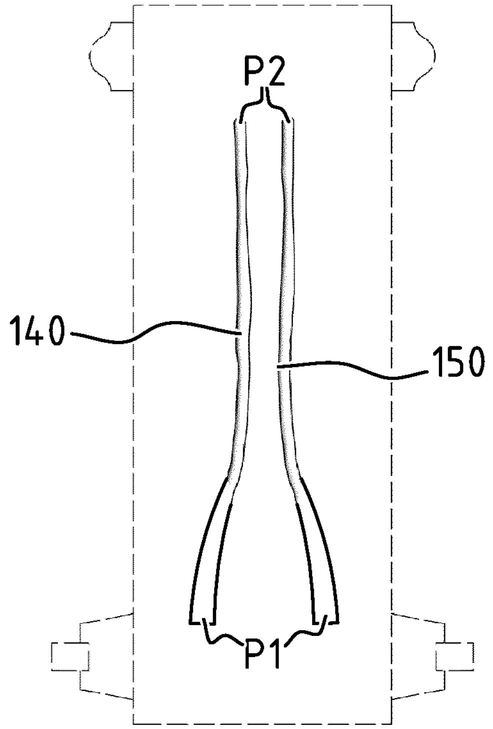
FIGS. 18A-18S illustrate other exemplary embodiments of an absorbent core according to the invention.

According to the exemplary embodiment of FIG. 18A the plurality of attachment zones comprises a first attachment zone 140 and a second attachment zone 150. The first and second attachment zones 140 are substantially parallel in a rear part of the crotch region, whilst the transverse distance between the first and second attachment zones gradually increases in the direction of a front transverse edge of absorbent core.

Figure 18B:
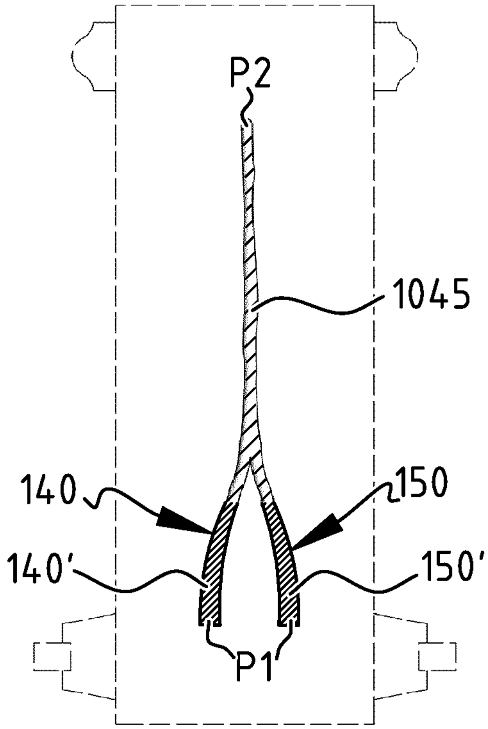

According to the exemplary embodiment of FIG. 18B the plurality of attachment zones comprises a first attachment zone 140 and a second attachment zone 150. The first and second attachment zones 140 partially overlap in a rear part of the crotch region, whilst the transverse distance between the first and second attachment zones gradually increases in the direction of a front transverse edge of absorbent core. The embodiment of FIG. 18B is preferable for female. FIG. 18B is similar to the embodiment of FIG. 17E with this difference that the elongate attachment zones 140', 150' are shorter and that the connecting zone 1045 comprises a longer longitudinal section extending from the second zone Z2 to the third zone Z3 into the fourth zone Z4 where the elongate attachment zones 140', 150' are located.

Figure 18C:
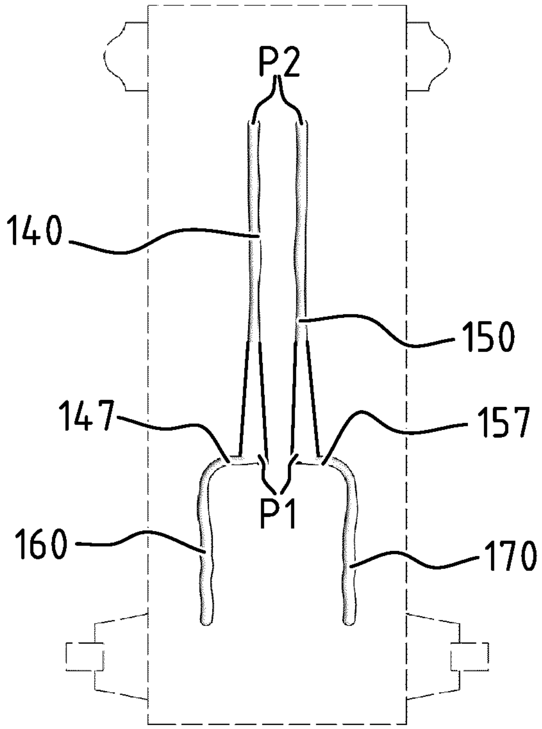
Figure 18D:
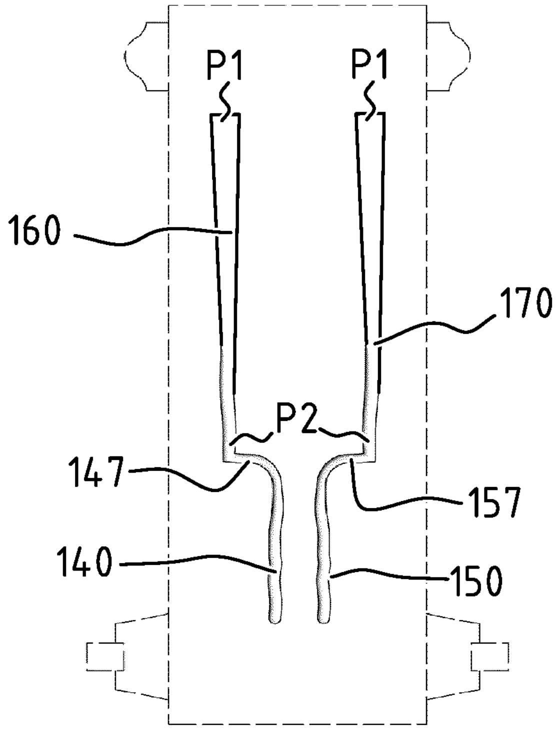
Figure 18E:
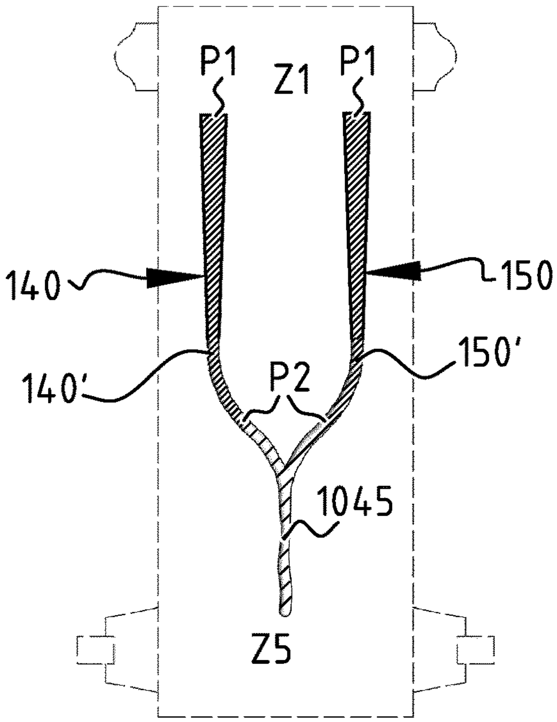

According to the exemplary embodiment of FIGS. 18C and 18D the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the rear transverse edge (FIG. 18D) or in the direction of the front transverse edge (FIG. 18C), and are interconnected via transverse attachment portions 147, 157 to third and fourth attachment zone 160, 170 extending from the crotch region to the front transverse edge (FIG. 18D) or in the direction of the rear transverse edge (FIG. 18C), respectively. In FIG. 18C the distance between the first and second attachment zones is smaller than the distance between the third and fourth attachment zones, whilst in FIG. 18D the distance between the first and second attachment zones is bigger than the distance between the third and fourth attachment zones. The embodiment of FIG. 18E is similar to the embodiment of FIG. 18D with this difference that the third and fourth attachment zones overlap in a front portion of the absorbent core. The embodiments of FIGS. 18C and 18E are preferable for female. The embodiment of FIG. 18D is preferable for male. The first and a second elongate attachment zone 140, 150 extend next to each other in the rear portion of the absorbent core in the direction of the rear transverse edge, and the third and fourth elongate attachment zone 160, 170 extend next to each other in the front portion of the absorbent core, in the direction of the front edge. Measured in a transverse direction, a first maximum distance between the first and the second attachment zone 140, 150 is smaller than a second maximum distance between the third and the fourth attachment zone 160, 170.

FIG. 18E is similar to the embodiment of FIG. 17E with this difference that the connecting zone 1045 is a rear connecting zone extending in the fourth zone Z4, whilst the elongate attachment zones 140', 150' are located mainly in the second and third zone Z2 and Z3, and that the first positions P1 of the first and second attachment zones are at a front portion of the absorbent core.

Figure 18F:
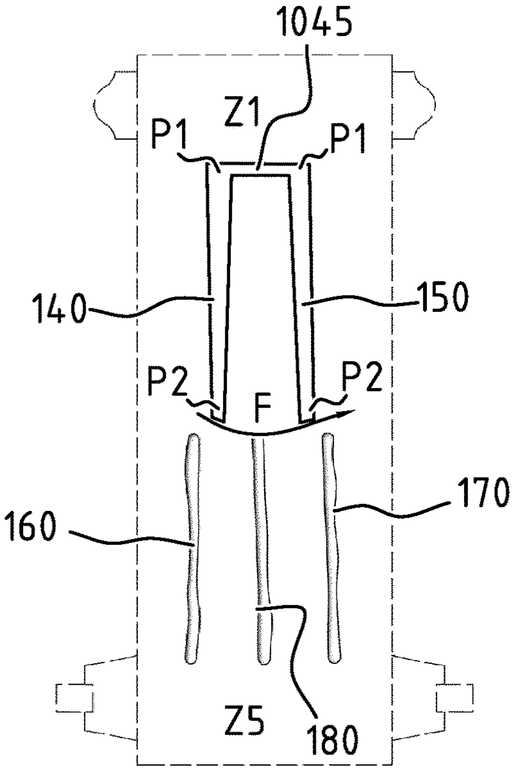

The embodiment of FIG. 18F is similar to the embodiment of FIG. 17U with this difference that the third and fourth longitudinal attachment zones 160, 170 are interconnected at their rear end by a transverse attachment zone 1045.

Figure 18G:
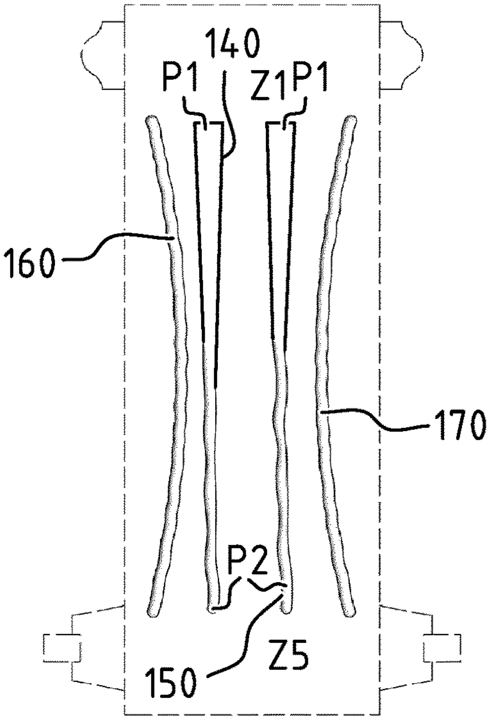

The embodiment of FIG. 18G is similar to the embodiment of FIG. 17B with this difference that the third and fourth longitudinal attachment zones 160, 170 have end portions which diverge outwardly in the direction of the front transverse edge and the rear transverse edge of the absorbent core.

Figure 18H:
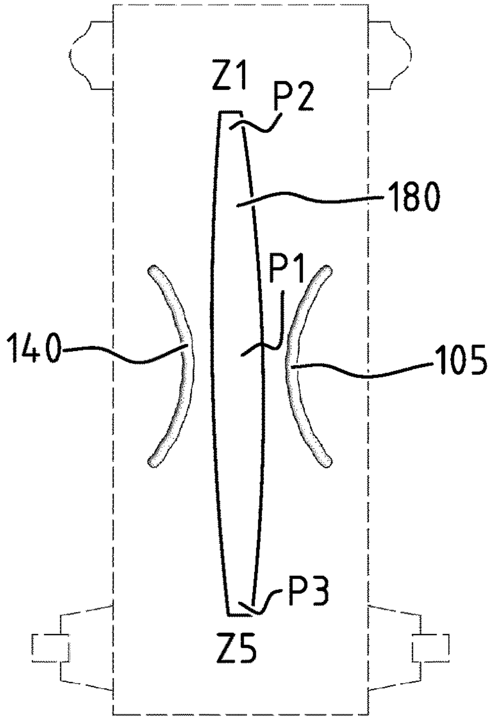

The embodiment of FIG. 18H is similar to the embodiment of FIG. 17O with this difference that the first and second attachment zones 140, 150 have end portions which diverge outwardly in the direction of the front transverse edge and the rear transverse edge of the absorbent core.

Figure 18I:
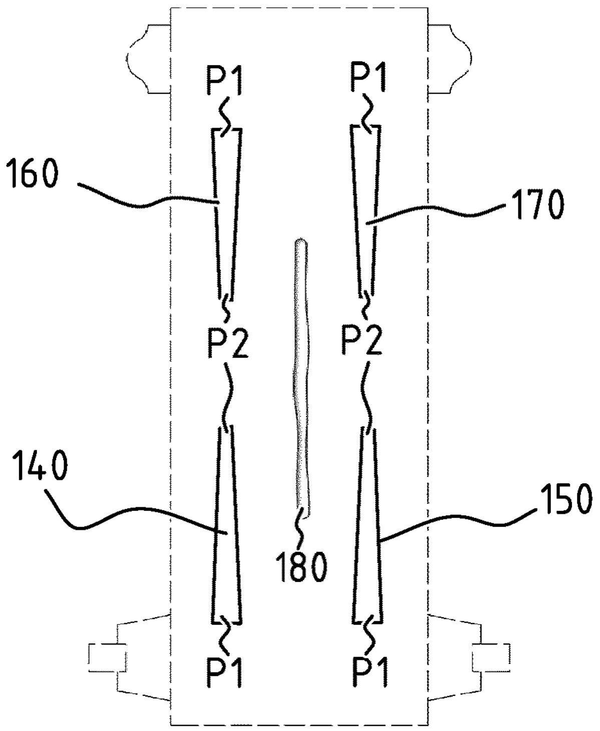

The embodiment of FIG. 18I is similar to the embodiment of FIG. 17C with this difference that the first, second, third and fourth attachment zones 140, 150, 160, 170 are shorter such that in a central part of the crotch region only central attachment zone 180 is present.

Figure 18J:
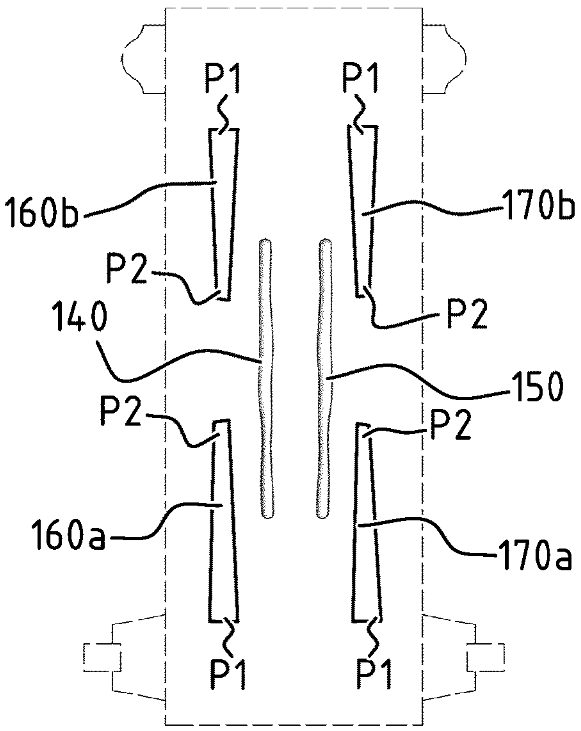

The embodiment of FIG. 18J is similar to the embodiment of FIG. 18I with this difference that the two central attachment zones 180 are provided between first and third attachment zones 140, 160 and second and fourth attachment zones 150, 170.

Figure 18K:
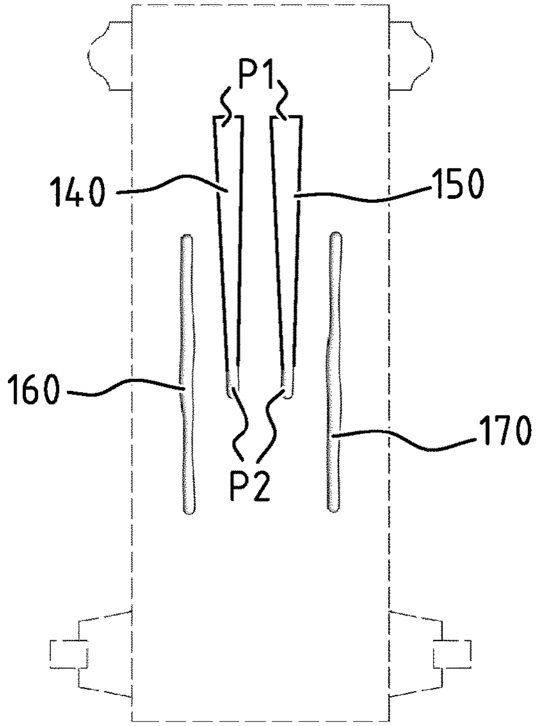
Figure 18L:
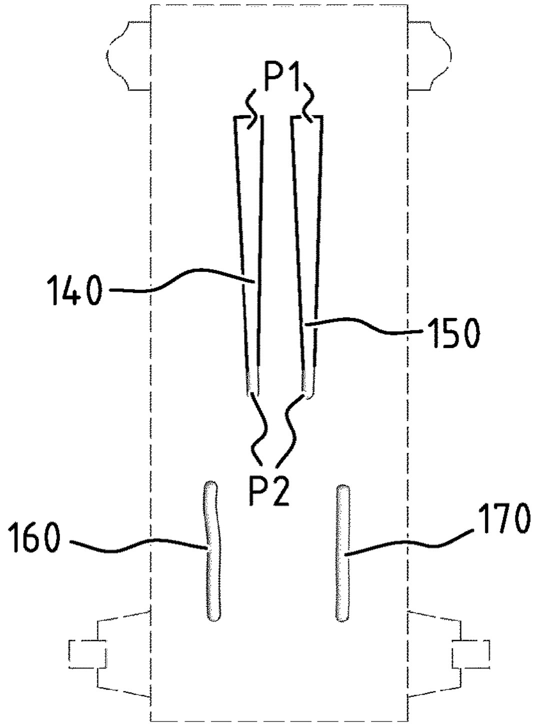

The embodiments of FIGS. 18K and 18L the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the front transverse edge. The third and fourth attachment zone 160, 170 extend from the crotch region to the rear transverse edge. The distance between the first and second attachment zones 140, 150 is bigger than the distance between the third and fourth attachment zones 160, 170. In FIG. 18K the third and fourth attachment zones 160, 170 extend partially between the first and second attachment zones 140, 150, whilst in FIG. 18L, seen in the longitudinal direction, the third and fourth attachment zones 160, 170 are at a distance of the first and second attachment zones 140, 150.

Figure 18M:
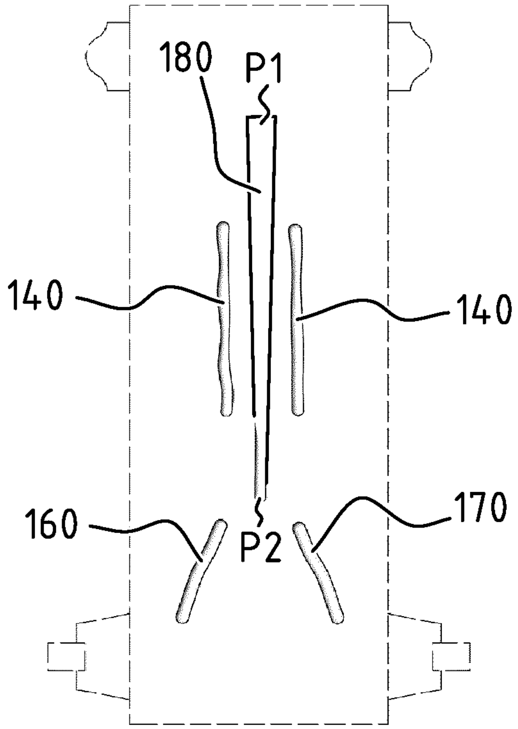
Figure 18N:
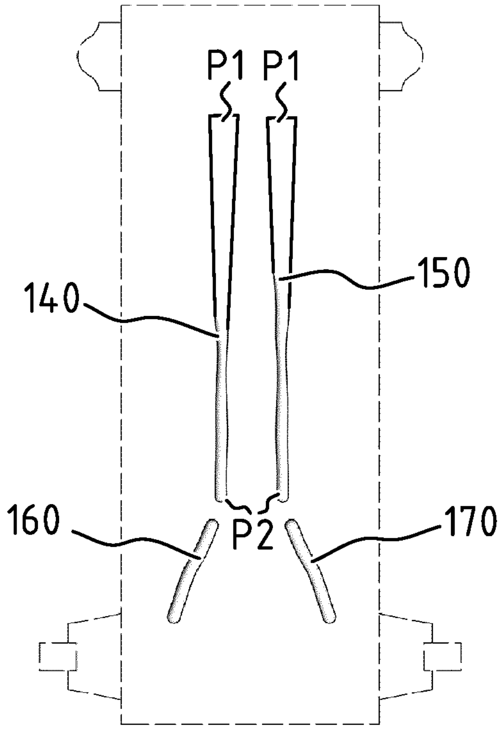
Figure 18O:
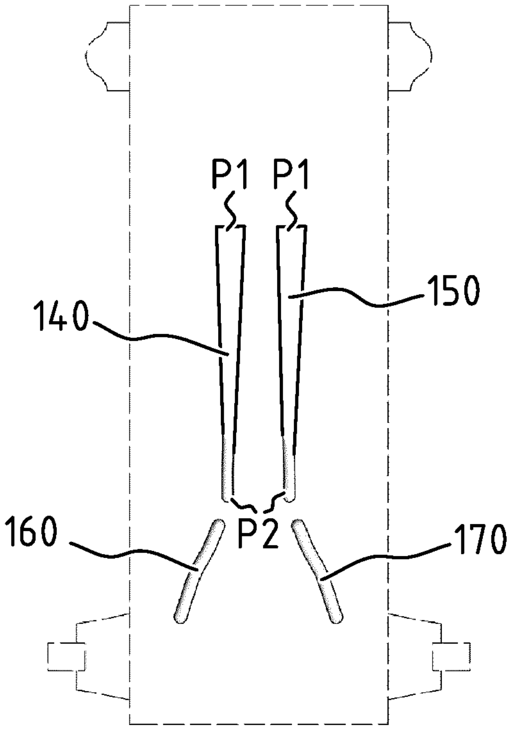

In the embodiments of FIGS. 18M, 18N and 18O the plurality of attachment zones comprises a first longitudinal attachment zone 140, a second longitudinal attachment zone 150, and outwardly diverging attachment zones 160, 170 in a front portion of the absorbent core. In FIG. 18M, additionally a central attachment zone 180 is provided between the first longitudinal attachment zone 140 and the second longitudinal attachment zone 150.

Figure 18P:
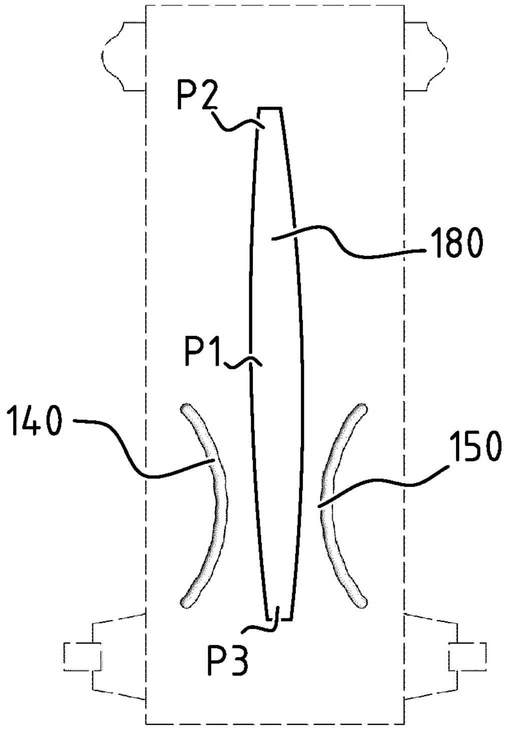

FIG. 18P is similar to the embodiment of FIG. 18H with this difference that first and second attachment zones are provided more to the front of absorbent core.

Figure 18Q:
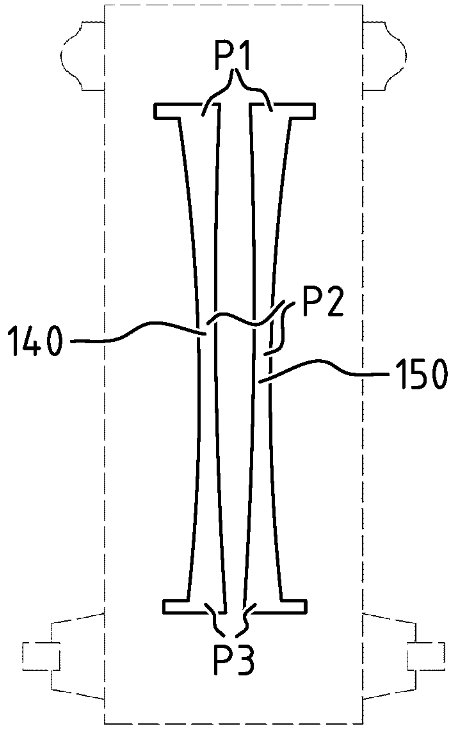

In the embodiment of FIG. 18Q the plurality of attachment zones comprises a first longitudinal attachment zone 140 and a second longitudinal attachment zone 150 which extend over at least 60% of the length of the absorbent core. The first longitudinal attachment zone 140 and the second longitudinal attachment zone 150 are each provided at a front end and at a rear end with an outwardly directed transverse portion. In that manner leakage risks at the front and rear portions of the absorbent core can be further reduced.

Figure 18R:
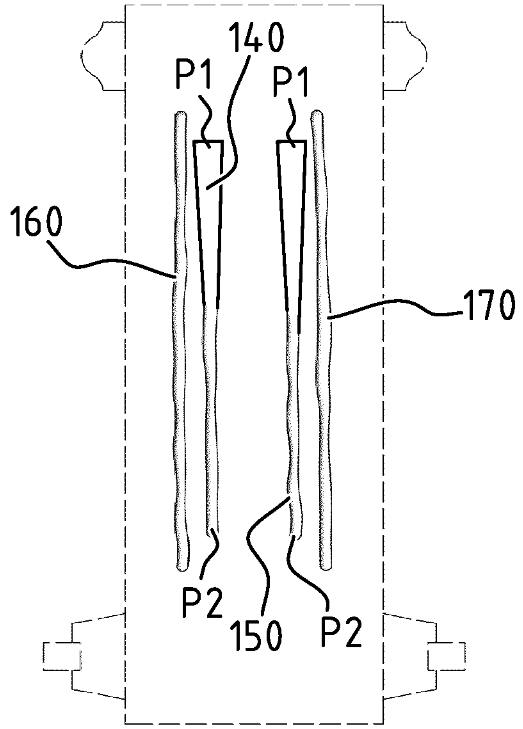

FIG. 18R is similar to the embodiment of FIG. 17B.

Figure 18S:
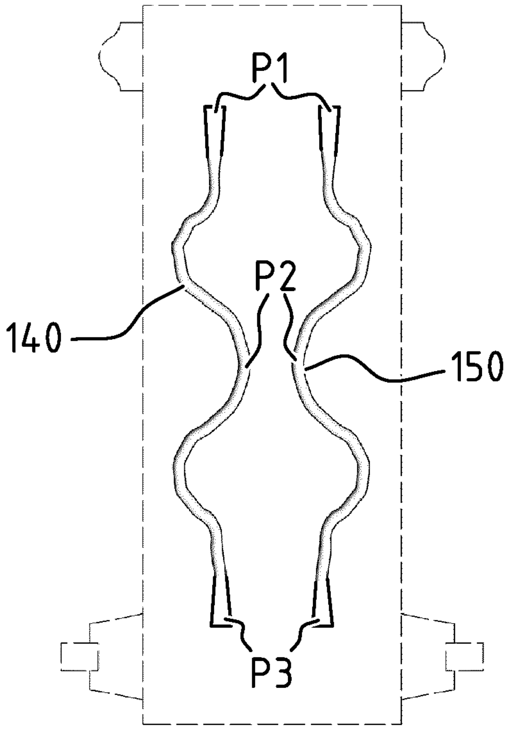

In the embodiment of FIG. 18S the plurality of attachment zones comprises a first undulated attachment zone 140 and a second undulated attachment zone 150 each extending over at least 60% of the length of the absorbent core. The undulations will increase the length of the channels 140, 150, further improving the liquid distribution in the absorbent core.

FIGS. 19A-19V and FIGS. 20A-20G illustrate yet other exemplary embodiments of an absorbent core according to the invention.

FIGS. 19A, 19B, 19H and 19K illustrate that the first and second attachment zones 140, 150 may comprise curved portions. FIGS. 19C, 19D, 19E, 19F, 19G, 19J, 19L, 19M, 19N, 19O, 19P, 19Q, 19R, 19S, 19T, 19U, 19V illustrate that various patterns are possible with one or more longitudinal sections 140, 150, 160, 170, 180, and/or one or more inclined sections 160, 170, 160*a*, 160*b*, 170*a*, 170*b* and/or one or more transverse sections 1045, 1045*a*, 1045*b*, 1045*c*. FIG. 19I illustrates that also curved transverse sections 1045*a*, 1045*b* may be used.

Figure 19H:
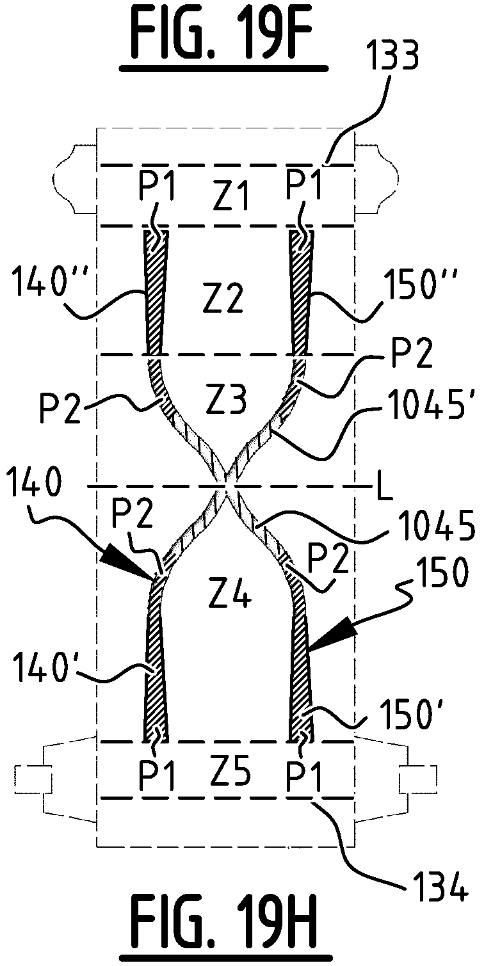
Figure 19I:
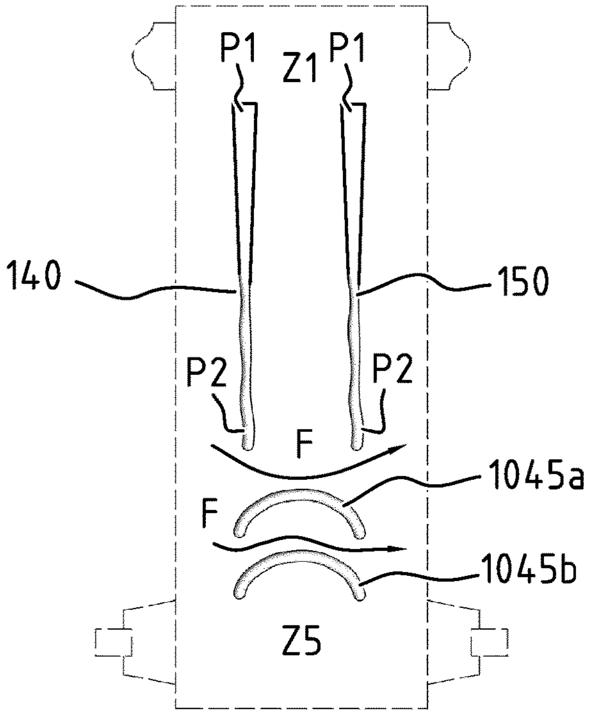
Figure 19J:
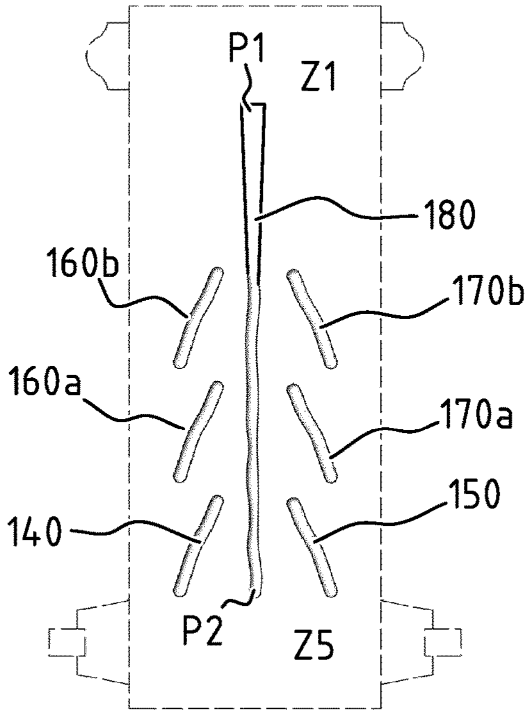

In the embodiment of FIG. 19H the first attachment zone 140 and the second attachment zone 150 form together two substantially V-shaped zones. A first substantially V-shaped zone is located in a rear portion (and in particular in the fourth zone Z4) and comprises a first elongate attachment zone 140' (indicated as a solid fill area), a second elongate attachment zone 150' (indicated as a solid fill area), and a V-shaped connecting attachment zone 1045 (indicated as a hatched area). The first and second elongate attachment zone 140', 150' extend next to each other from the crotch region in the direction of the rear transverse edge 134 and diverge in the direction of the rear transverse edge 134. The connecting attachment zone 1045 connects said first elongate attachment zone 140' with said second elongate attachment zone 150'. The connecting attachment zone 1045 is a front connecting attachment zone which connects a front end portion of the first attachment zone 140' to a corresponding front end portion of the second attachment zone 150'. Similarly, a third elongate attachment zone 140", a fourth elongate attachment zone 150" and a connecting attachment zone 1045' form together a second substantially V-shaped zone located in a front portion of the absorbent core and more in particular in the second and third zone Z2, Z3. This second substantially V-shaped zone 140", 150", 1045' may be joined to the first substantially V-shaped zone 104', 150', 1045. In the illustrated embodiment the connecting attachment zones 1045, 1045' are connected at or near the transverse crotch line L. The third and fourth elongate attachment zone 140", 150" extend next to each other from the crotch region in the direction of the front transverse edge 133 and diverge in this direction. The connecting attachment zone 1045' connects said third elongate attachment zone 140" with said fourth elongate attachment zone 150". The connecting attachment zone 1045' is a rear connecting attachment zone which connects a rear end portion of the third attachment zone 140" to a corresponding rear end portion of the fourth attachment zone 150". The first and second V-shaped zones guide the liquid from left and right parts of the front portion towards the rest of the absorbent core. As illustrated the first interconnecting attachment zone 1045' may be arranged in the front portion, and more in particular in the third zone Z3, and the second interconnecting attachment zone 1045 may be arranged in the rear portion, and in particular in the fourth zone Z4. By connecting the first interconnecting attachment zone 1045 with the second interconnecting attachment zone 1045' in the crotch region a convenient liquid distribution channel network is created allowing the liquid to be distributed rapidly throughout the absorbent core.

Figure 19K:
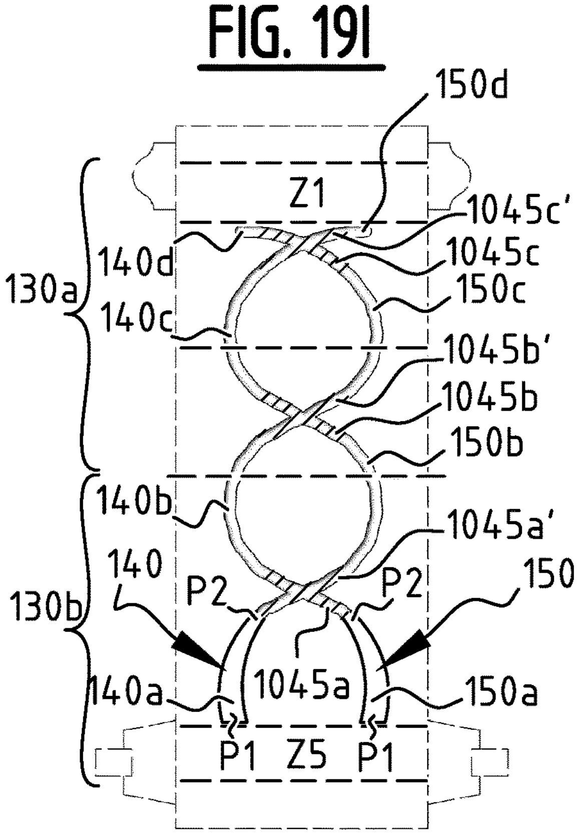
Figure 19L:
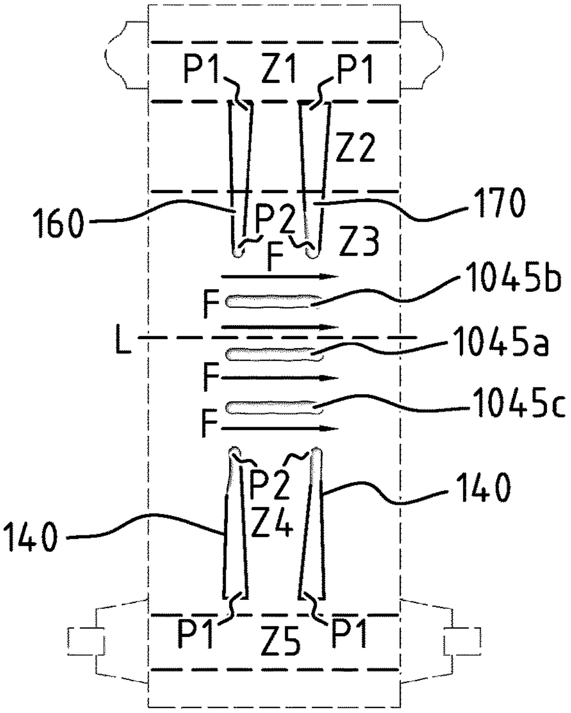
Figure 19M:
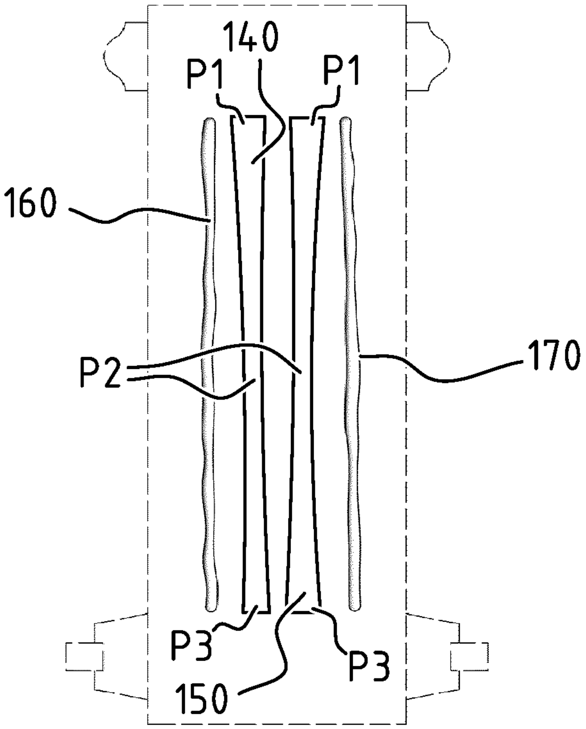
Figure 19N:
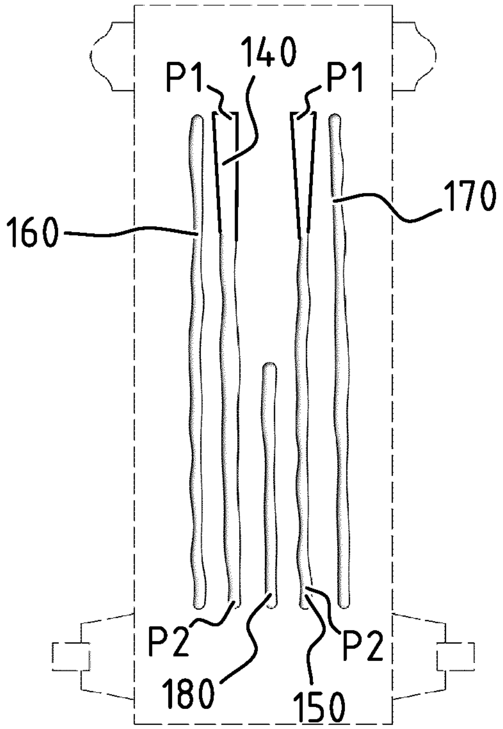
Figure 19O:
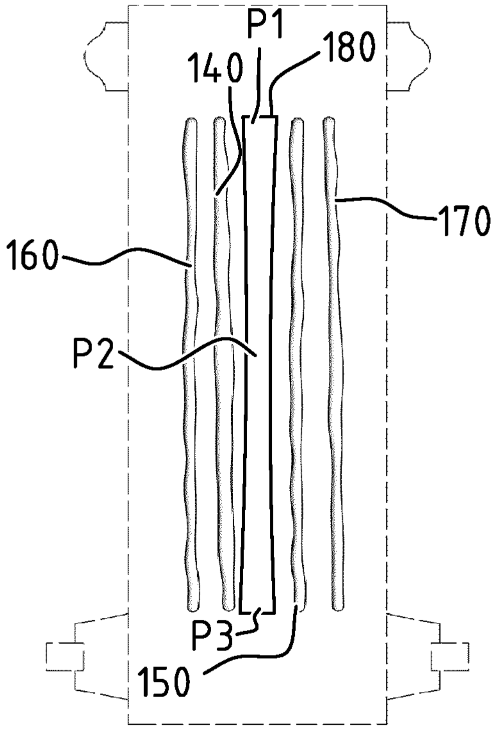
Figure 19P:
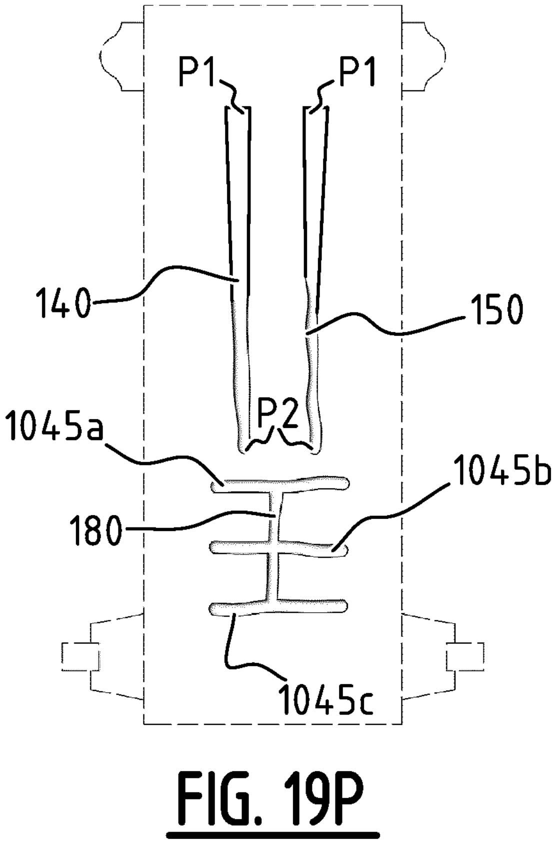
Figure 19Q:
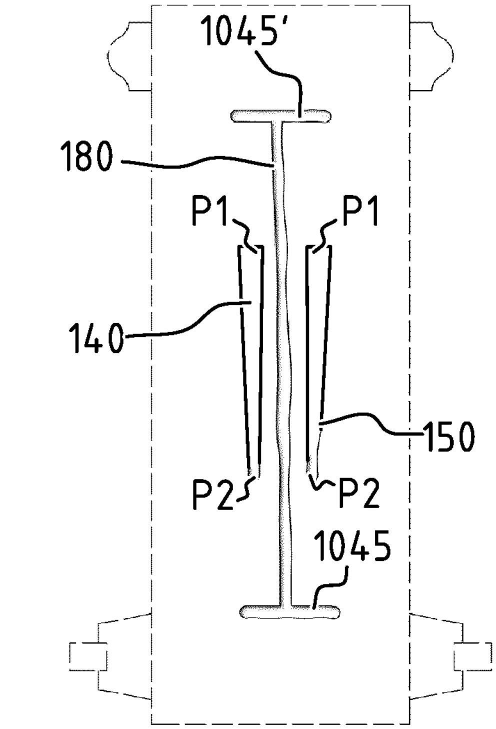
Figure 19R:
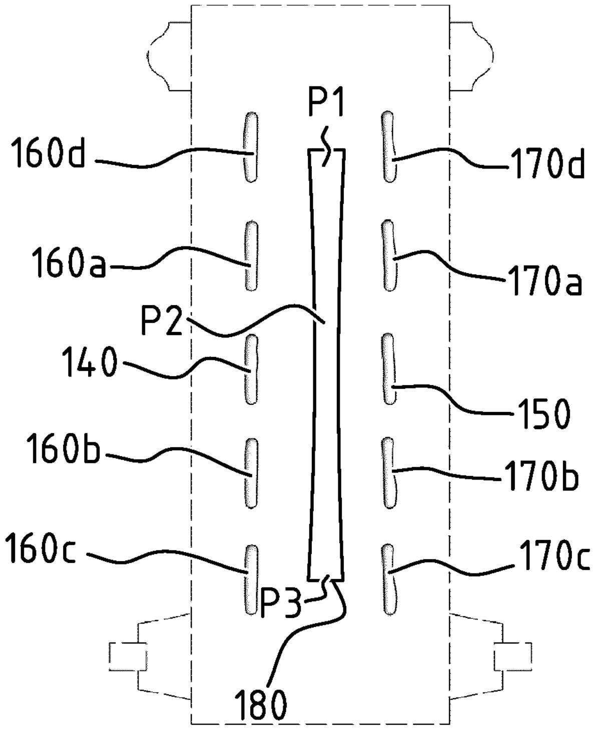
Figure 19S:
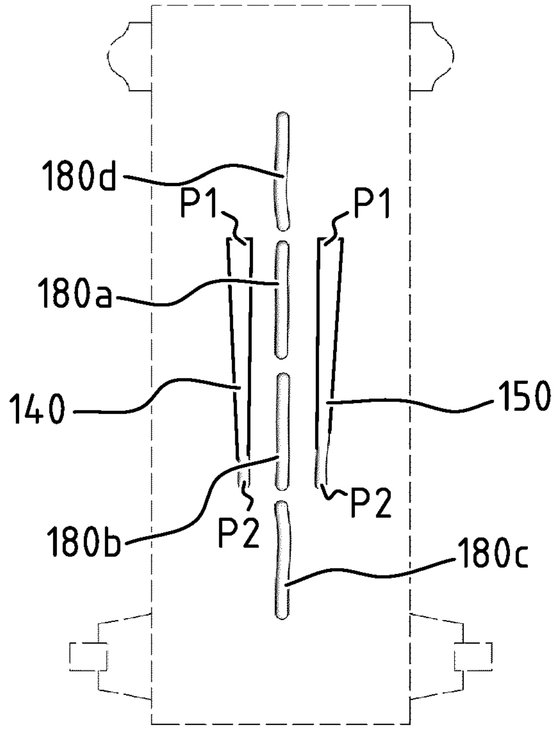
Figure 19T:
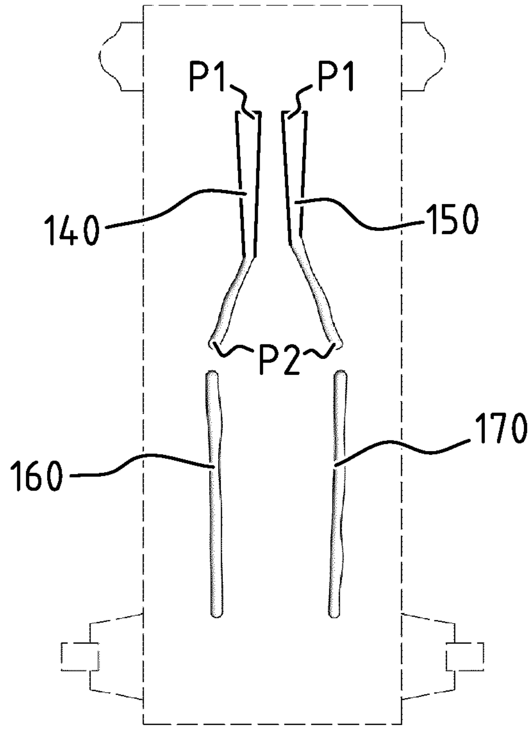
Figure 19U:
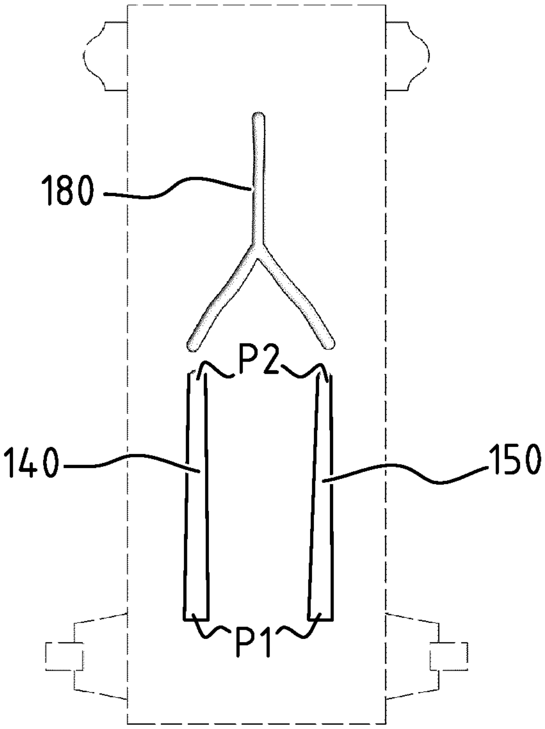
Figure 19V:
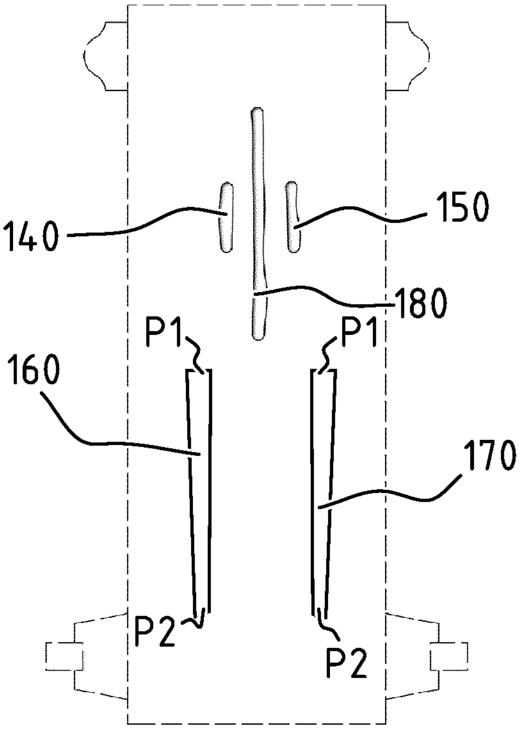

In the embodiment of FIG. 19K the first attachment zone 140 and the second attachment zone 150 form together two "O"-shaped zones between a first and a second substantially V-shaped zone. The first V-shaped zone comprises elongate attachment zones 140*a*, 150*a* interconnected by a connecting attachment zone 1045*a*. The first O-shaped zone comprises elongate attachment zones 140*b*, 150*b* interconnected by connecting attachment zones 1045*a*', 1045*b*. The second O-shaped zone comprises elongate attachment zones 140*c*, 150*c* interconnected by connecting attachment zones 1045*b*', 1045*c*. The second V-shaped zone comprises elongate attachment zones 140*d*, 150*d* interconnected by a connecting attachment zone 1045*c*'.

Figure 20A:
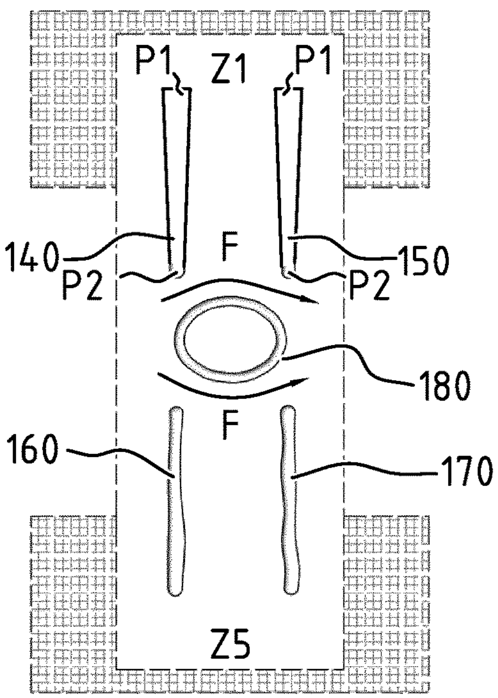
FIGS. 20A-20G illustrate yet other exemplary embodiments of an absorbent core according to the invention.
Figure 20B:
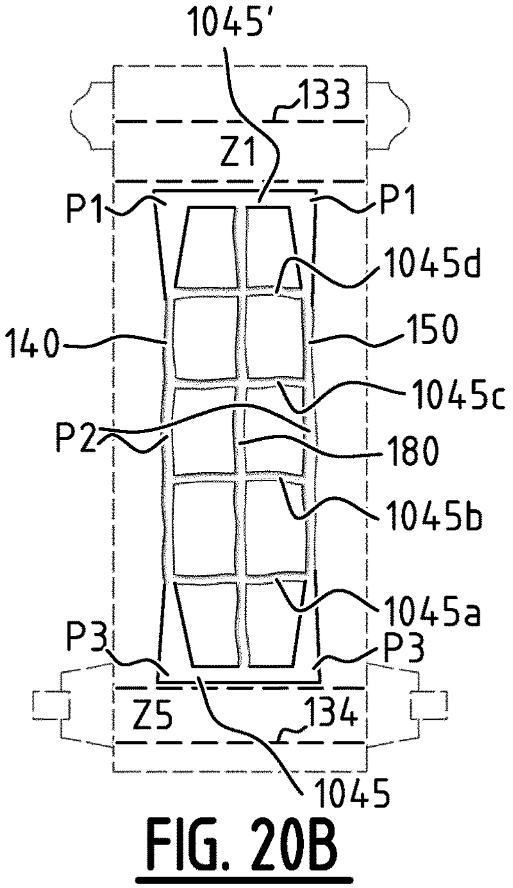
Figure 20C:
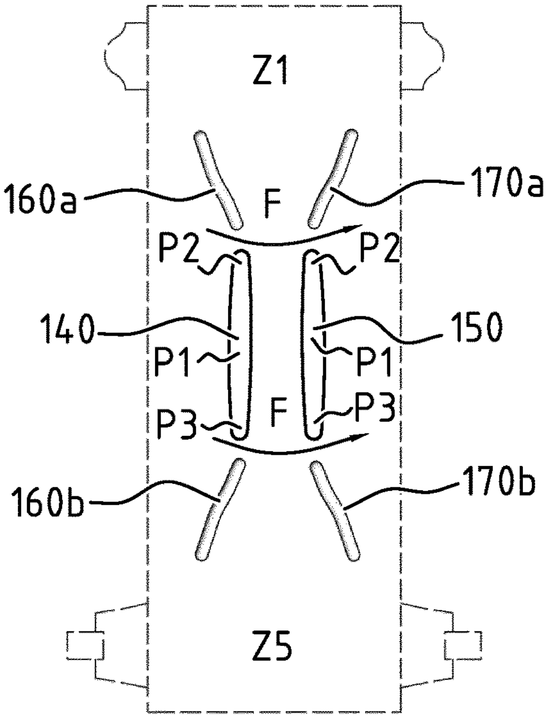
Figure 20D:
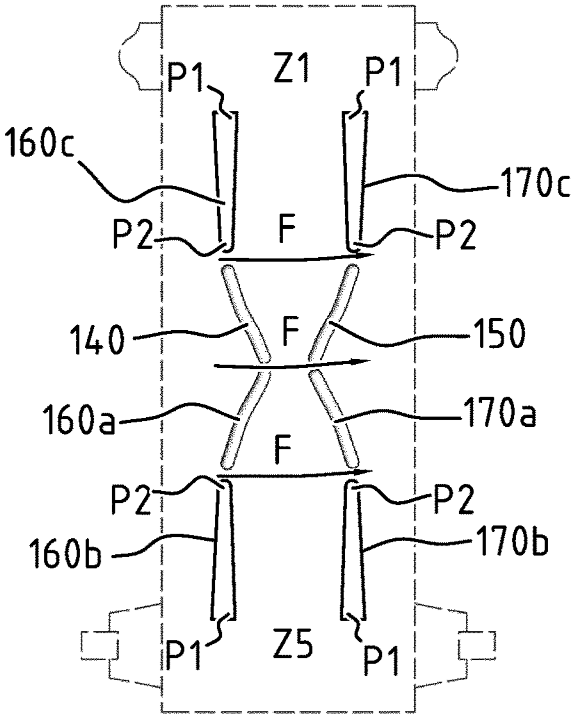
Figure 20E:
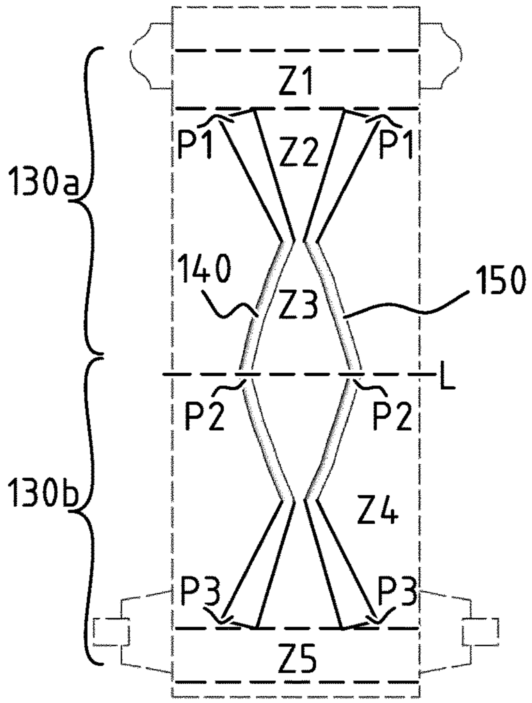
Figure 20F:
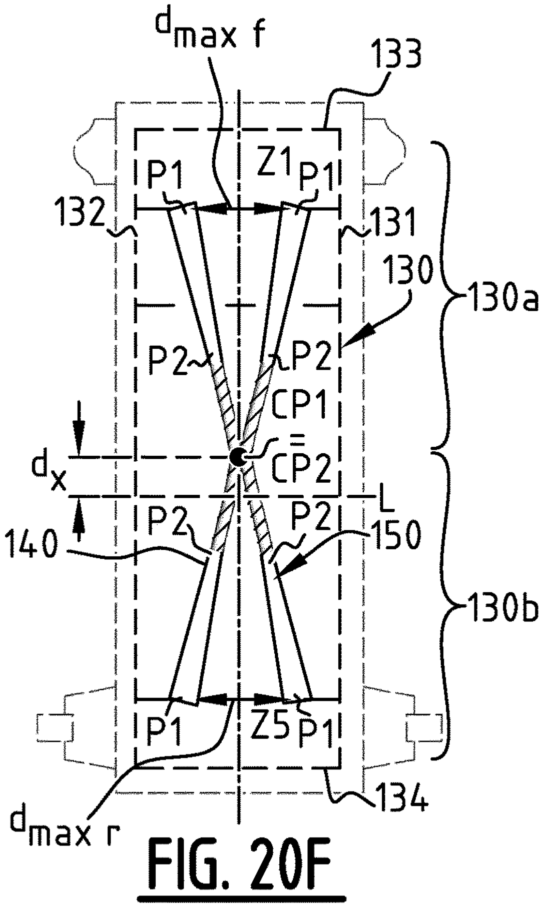
Figure 20G:
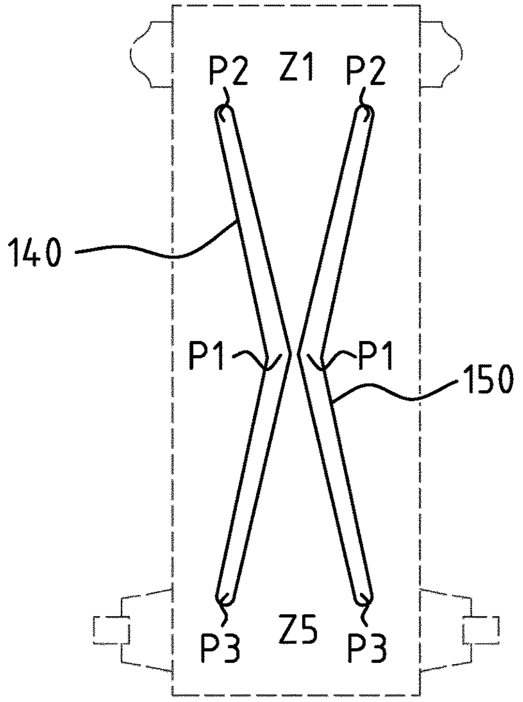

FIGS. 20A-20G illustrate further embodiments. In FIG. 20A the first to fourth attachment zones are similar to the first to fourth attachment zones of FIG. 18I, but instead of a central rectilinear attachment zone, there is provided an oval attachment zone 180 in the crotch region, between the first and second attachment zone 140, 150 and the third and fourth attachment zone 160, 170. FIGS. 20B, 20C, 20D illustrate that various patterns are possible with one or more longitudinal sections and/or one or more inclined sections and/or one or more transverse sections as described before. FIGS. 20E, 20F, 20G illustrate that the first and second attachment zones 140, 150 may comprise various rectilinear sections which are oriented at an angle with respect to the longitudinal direction of the absorbent core.

In the embodiment of FIG. 20B the first attachment zone 140 and the second attachment zone 150 are interconnected by a plurality of transverse connecting attachment zones comprising a front connecting attachment zone 1045', a rear connecting attachment zone 1045, and a plurality of intermediate connecting attachment zones 1045*a*, 1045*b*, 1045*c*, 1045*d*. The number of intermediate connecting attachment zones may be dependent on the size of the absorbent core. Preferably the first and second elongate attachment zone extend from the fourth to the second zone. Optionally one or more longitudinal intermediate attachment zones 180 may be provided.

In the embodiment of FIG. 20B the first attachment zone 140 and the second attachment zone 150 form two V-shaped attachment zones, similar to the embodiment of FIG. 19H but with straight zones 140, 150.

In the embodiment of FIG. 20F the absorbent core 130 comprises an absorbent material between a top core wrap sheet and a back core wrap sheet, said absorbent core 130 being positioned in between the topsheet and the backsheet of the absorbent article. The absorbent core 130 has a first and second longitudinal edge 131, 132 and a first and second transverse edge 133, 134. The absorbent core 130 has a longitudinal center line CL dividing the absorbent core 130 in a first longitudinal portion and a second longitudinal portion on either side of the longitudinal center line. The absorbent core 130 has a transverse crotch line L dividing the absorbent core 130 in a front portion 130*a* and a rear portion 130*b* on either side of the transverse crotch line L. The absorbent core 130 is provided with a plurality of attachment zones 140, 150 where the top core wrap sheet is attached to the back core wrap sheet, The plurality of attachment zones 140, 150 comprises a first elongate attachment zone 140 crossing the longitudinal center line CL in a first crossing point CP1, in said front portion 130*a* and/or in said rear portion 130*b*, from the first longitudinal portion to the second longitudinal portion. In the illustrated embodiment the first crossing point is located at a distance dx of the transverse crotch line L, here in the front portion 130*a*. However, in other embodiments the first crossing point CP1 may be located in the rear portion 130*b* of the absorbent core 130. In yet other embodiments, the first crossing point CP1 may also be located on the transverse crotch line L, i.e. at the border of the front portion 130*a* and the rear portion 130*b*. The plurality of attachment zones 140, 150 comprises a second elongate attachment zone 150 crossing said longitudinal center line CL in a second crossing point CP2, in said front portion 130*a* and/or in said rear portion 130*b*, from the second longitudinal portion to the first longitudinal portion. In the illustrated embodiment of FIG. 20F, the first and second crossing point CP1, CP2 are the same point. The position of the first and second crossing point CP1, CP2 (and in particular the distance dx) may be optimized in function of whether the absorbent article is intended for a male or female.

Preferably, the distance between the first and/or second crossing point CP1, CP2 and the transverse crotch line is larger than 1% of the length of the absorbent core, more preferably larger than 2%, even more preferably larger than 3%. Preferably, the distance between the first and/or second crossing point CP1, CP2 and the transverse crotch line is smaller than 20% of the length of the absorbent core, more preferably smaller than 10%.

A distance between the transverse crotch line L and a transverse center line T extending perpendicular on the longitudinal direction of the absorbent core, through the middle of the absorbent core, is smaller than 10%, more preferably smaller than 5% of the length of the absorbent core. The transverse center line T is not shown in FIG. 20F but is drawn in FIG. 29B.

Preferably, the first elongate attachment zone 140 extends both in the front portion 130*a* and in the rear portion 130*b* and the second elongate attachment zone 150 extends both in the front portion 130*a* and in the rear portion 130*b*. Preferably, the first elongate attachment zone 140 and the second elongate attachment zone 140 are arranged symmetrically with respect to the longitudinal center line CL of the absorbent core 130.

Preferably, a maximum distance dmaxf, dmaxr between the first and the second elongate attachment zone 140, 150 is between 15 and 70% of the width of the absorbent core, more preferably between 20 and 50%. A maximum distance dmaxf between the first and the second attachment zone 140, 150 in the front portion 130*a* may be different from a maximum distance dmaxr between the first and the second attachment zone 140, 150 in the rear portion 130*b*.

Preferably, the length of the first and second attachment zone is larger than 10% of the length of the absorbent core, more preferably larger than 30%, even more preferably larger than 50%. Preferably, the attachment zones 140, 150 are permanent attachment zones which remain attached when wetted. Preferably, said first and second attachment zone 140, 150 each extend, seen in the transverse direction of the absorbent core, over the transverse distance which is at least 1 mm, preferably at least 3 mm, more preferably at least 4 mm, even more preferably at least 5 mm, most preferably at least 6 mm.

A front end of the first attachment zone 140 is preferably located in the second zone Z2, and a rear end of the first attachment zone 140 is preferably located in the fourth zone Z4. Similarly, a front end of the second attachment zone 150 is preferably located in the second zone Z2 or in the third zone, and a rear end of the second attachment zone 150 is preferably located in the fourth zone Z4, wherein the zone may be defined as described in the summary.

Figure 28A:
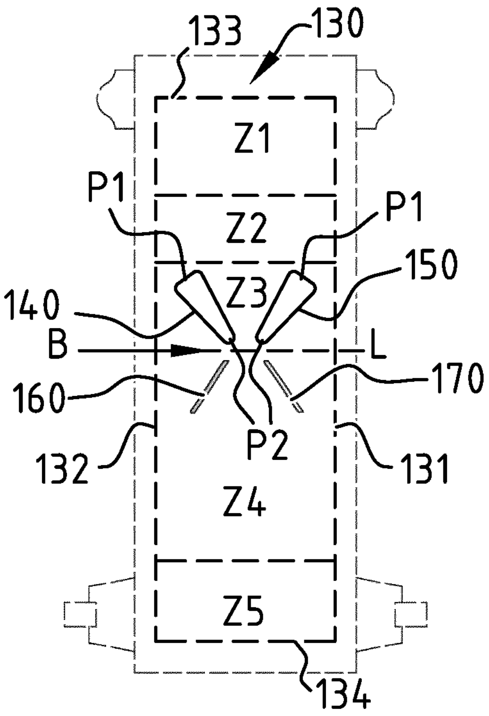
FIGS. 28A-28T illustrate yet other exemplary embodiments of an absorbent core according to the invention.
Figure 28B:
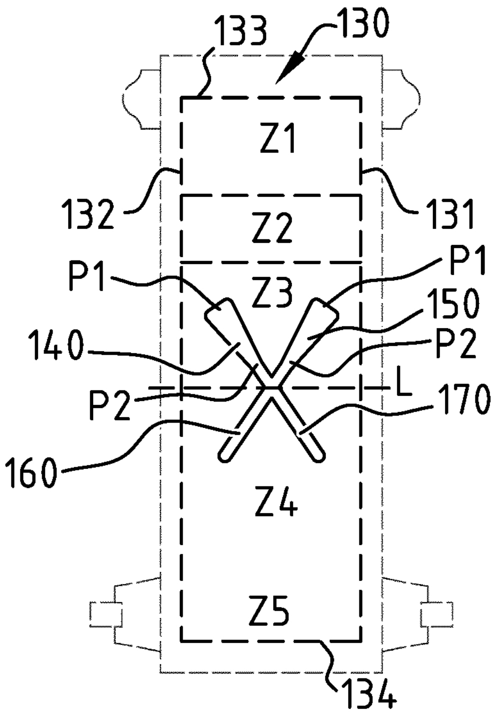
Figure 28C:
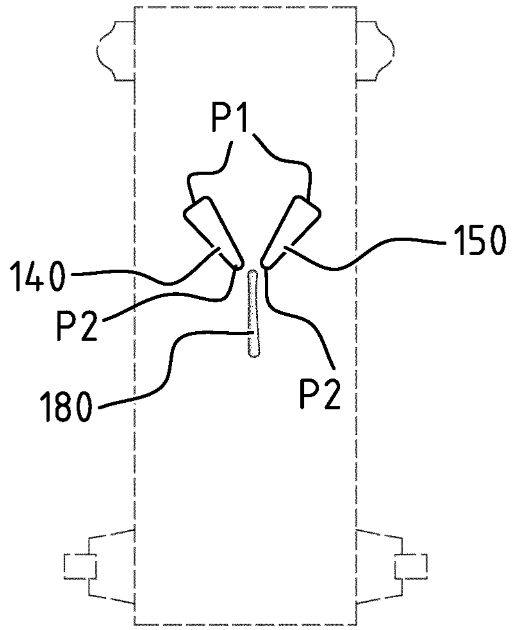
Figure 28D:
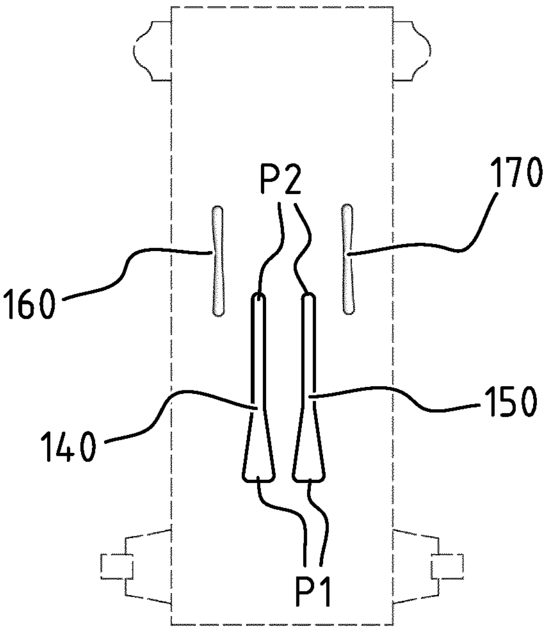
Figure 28E:
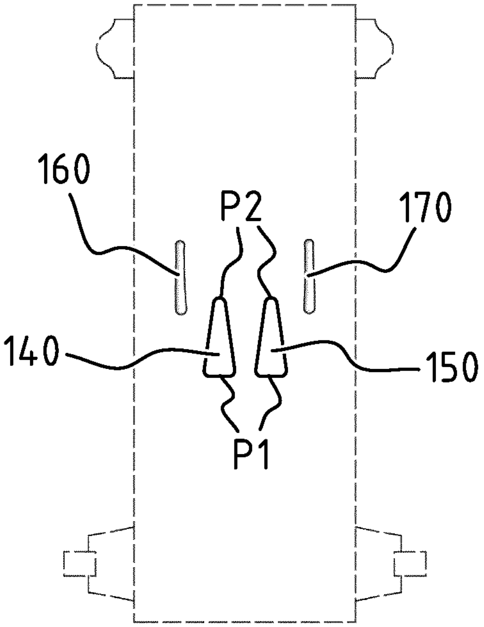
Figure 28F:
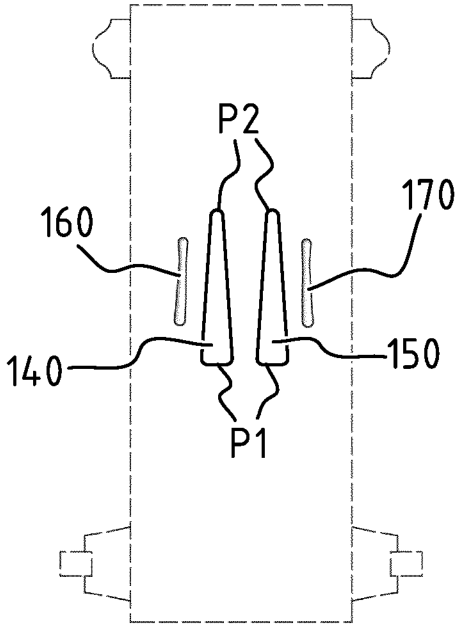

A similar embodiment is illustrated in FIG. 28B, where the first elongate attachment zone comprises portions 140, 160, and the second elongate attachment zone comprises portions 150, 170.

Figure 28G:
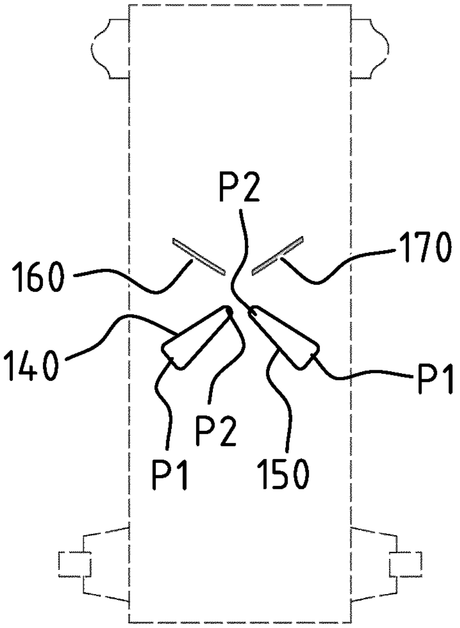
Figure 28H:
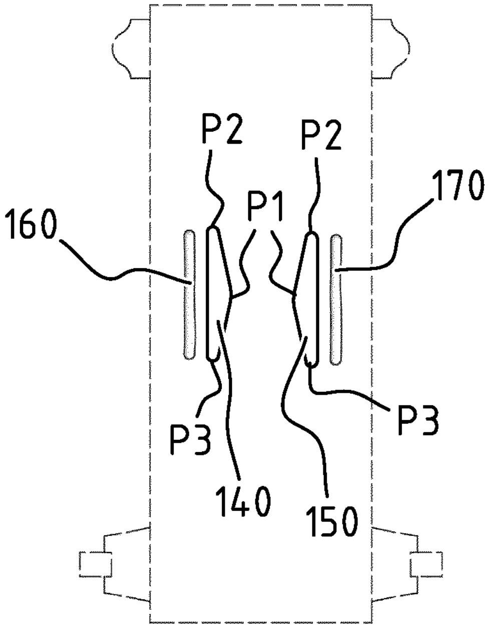
Figure 28I:
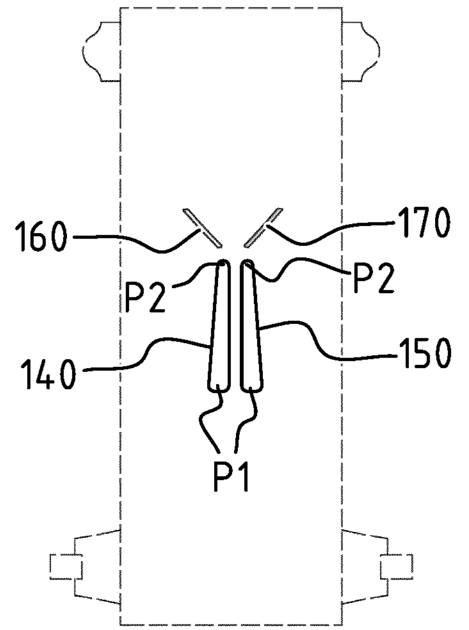
Figure 28J:
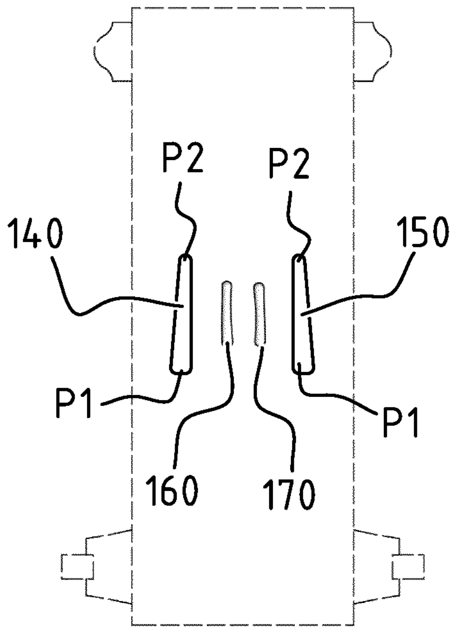
Figure 28K:
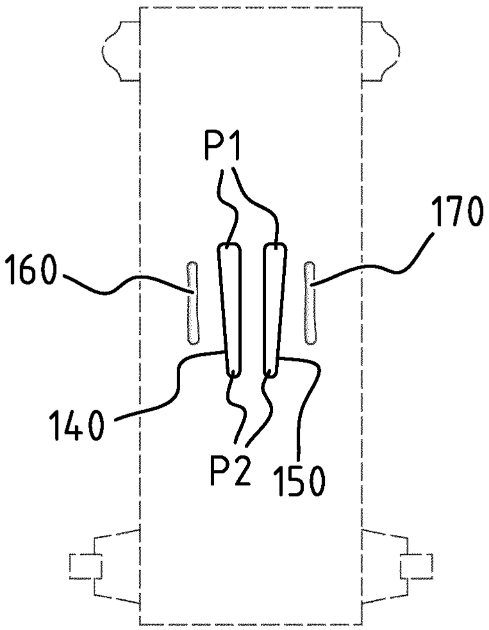
Figure 28L:
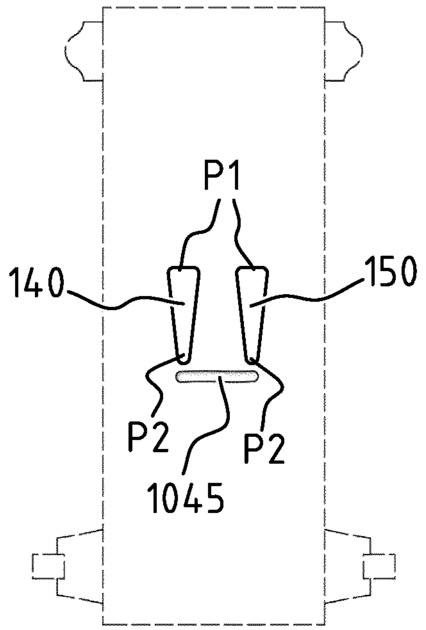
Figure 28M:
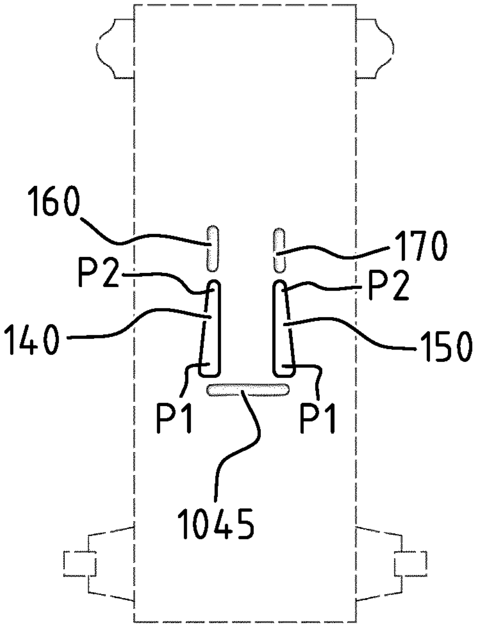
Figure 28N:
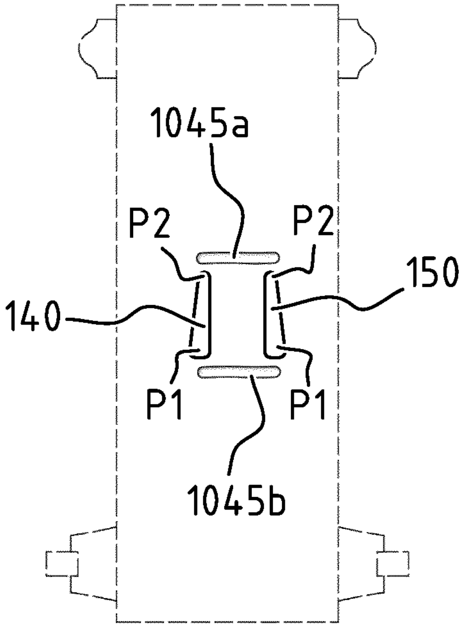
Figure 28O:
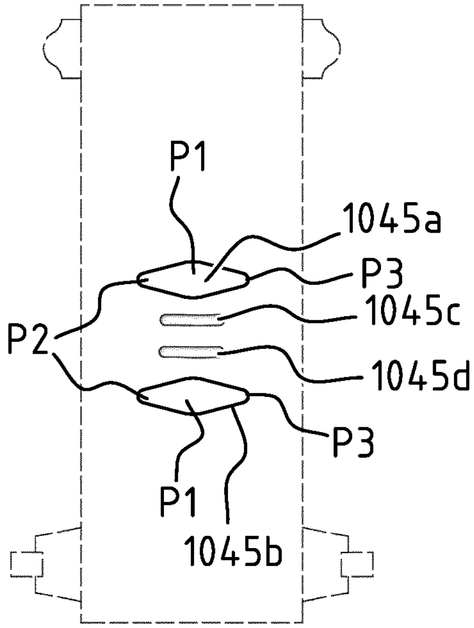
Figure 28P:
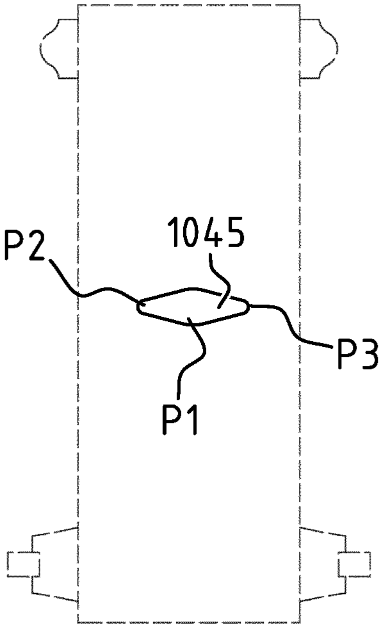
Figure 28Q:
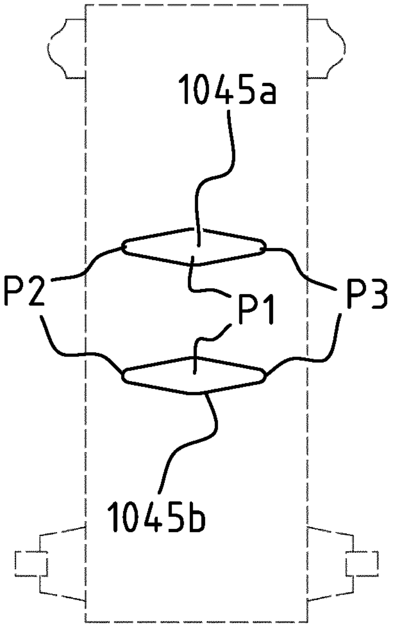
Figure 28R:
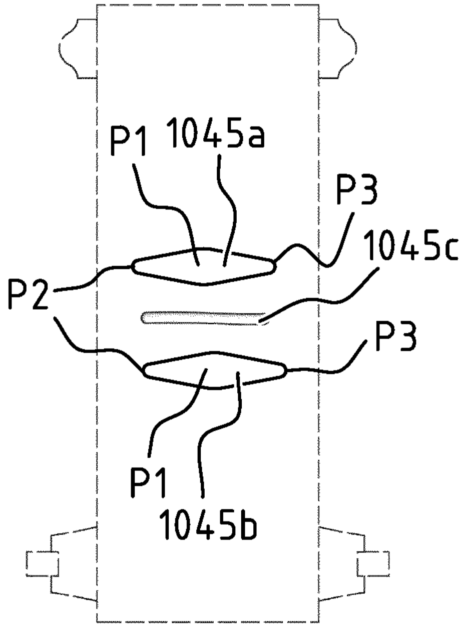
Figure 28S:
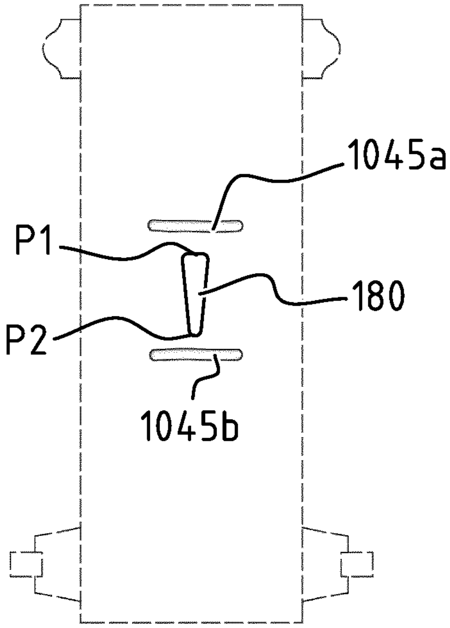
Figure 28T:
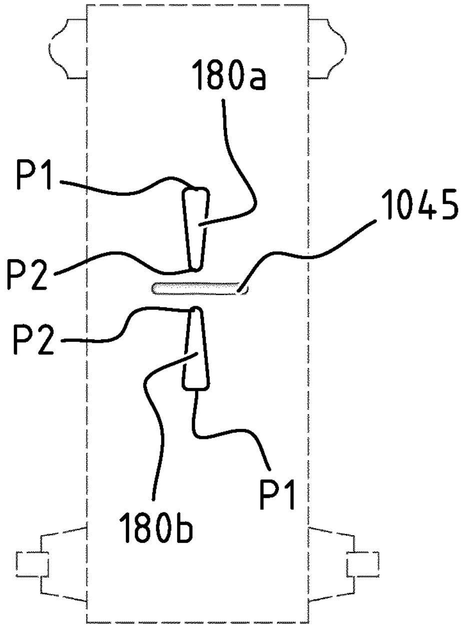

In the embodiments of FIGS. 28A and 28G, the first and second elongate attachment zone 140, 160; 150, 170 may comprise a bridge zone B allowing a liquid flow between the first and the second longitudinal edge 131, 132 by capillary action through the absorbent material and/or by mass flow, such that upon wetting of the absorbent material, front channels 140, 150 and rear channels 160, 170 are created, wherein the bridge zone B extends between said front and rear channels; wherein a minimum distance between said front and rear channel is preferably larger than 3 mm more preferably larger than 5 mm. The bridge zone B may extend from a first portion of the absorbent core to a second portion of the absorbent core, wherein the first portion is defined between the first longitudinal edge 131 and the longitudinal center axis CL of the absorbent core 130 and the second portion is defined between the second longitudinal edge 132 and the longitudinal center axis CL of the absorbent core. The bridge zone B may comprise one or more temporary attachments between the top and back core wrap sheet which are configured to detach when wetted; and/or the bridge zone B may comprise at least one permanent attachment zone in a direction from the first to the second longitudinal edge 131, 132; and/or the said bridge zone B may comprise absorbent material. Preferably, the absorbent material comprises cellulosic fluff pulp and/or superabsorbent particles.

In the embodiments of FIGS. 20F, 20G, 26A, 26B and 26 G, the first and second attachment zone together for a substantially X-shaped zone arranged symmetrically with respect to the longitudinal center line CL. In other embodiments, an X-shaped zone may be combined with differently shaped zones, see e.g. FIG. 19G. Also, the X-shaped zone may comprised curved portions, see e.g. the embodiments of FIGS. 19H, 23N, 24P, 25U, 25V.

In yet other embodiments, multiple X-shaped zones may be combined, see e.g. the embodiments of FIGS. 17P, 19K, 20E. In the embodiment of FIGS. 17P and 20E a first X-shaped attachment zone (including V-shaped portion 2001 and a front portion of 140', 150') is located in the front portion 130*a*, and a second X-shaped attachment zone (including V-shaped portion 2002 and a rear portion of 140', 150') is located in the rear portion 130*b*. The first X-shaped attachment zone is connected to the second X-shaped attachment zone at the transverse crotch line L. In the embodiment of FIG. 19K a first X-shaped attachment zone (including portion 1045*c*, 1045*c'*) is located in the second zone Z2 of the front portion 130*a*, a second X-shaped attachment zone (including portions 1045*b*, 1045*b'*) is located in the third zone Z3 of the front portion 130*a*, and a third X-shaped attachment zone (including portions 1045*a*, 1045*a'*) is located in the fourth zone Z4 of the rear portion 130*b*. The first X-shaped attachment zone is connected to the second X-shaped attachment zone, and the second X-shaped attachment zone is connected to the third X-shaped attachment zone.

FIGS. 21A-21D illustrate further embodiments wherein the absorbent core is provided with at least a first attachment zone 140, wherein in said first attachment zone 141 said top core wrap sheet is attached to said back core wrap sheet along an attachment which extends, seen in a transverse and/or longitudinal direction of the absorbent core, over a transverse and/or longitudinal distance which is at least 1 mm, preferably at least 2 mm, more preferably at least 3 mm, most preferably at least 4 mm; and/or said top core wrap sheet is attached to said back core wrap sheet along a discontinuous attachment at a plurality of locations at a distance of each other, seen in the transverse and/or longitudinal direction of the absorbent core; such that upon wetting of the absorbent material, a first channel is created at said first attachment zone 140. The first attachment zone has a first width w1 at a first position P1 and a second width w2 at a second position P2. The first width is larger than the second width, and the width of the first attachment zone increases from the second position to the first position.

Figure 21A:
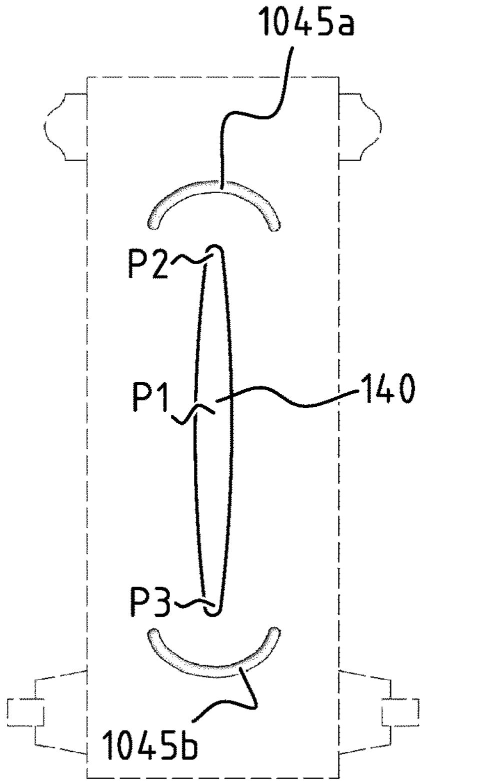
FIGS. 21A-21D illustrate yet other exemplary embodiments of an absorbent core according to the invention.
Figure 21B:
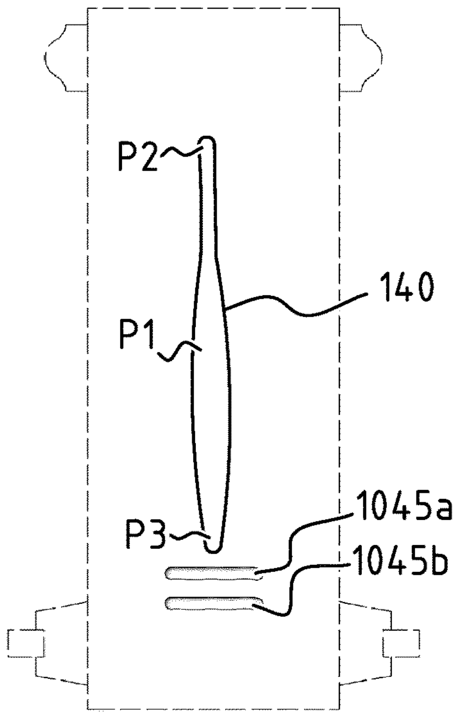
Figure 21C:
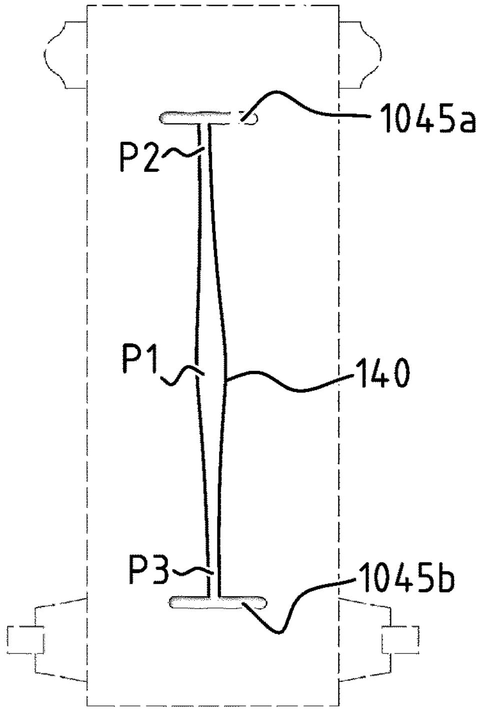
Figure 21D:
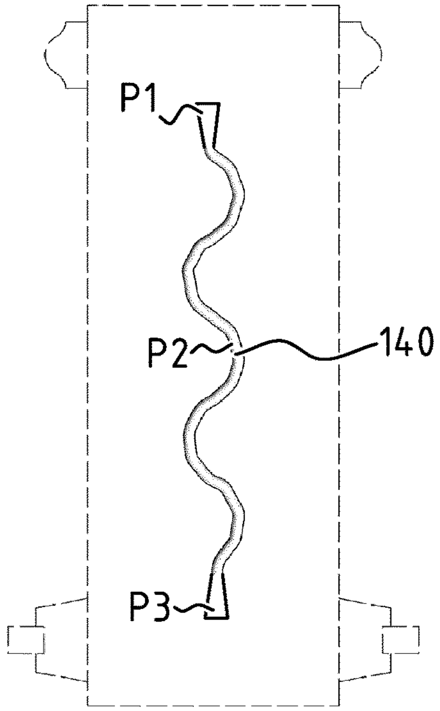

In the embodiment of FIG. 21A, a single longitudinal attachment zone 140 is illustrated, along with a first and second transversal attachment zone 1045*a*, 1045*b* which are positioned at either end of the longitudinal attachment zone 140. The first and second transversal attachment zone 1045*a*, 1045*b* are illustrated as curved zones, but it is clear to the skilled person that the first and/or second transversal attachment zone may also be provided as straight zones. In the embodiment of FIG. 21B, a single longitudinal attachment zone 140 is illustrated, along with a first and second transversal attachment zone 1045*a*, 1045*b* which are positioned between the attachment zone 140 and the first transversal edge of the absorbent core. In addition to, or alternative to the embodiment of FIG. 21B the first and second transversal attachment zones 1045*a*, 1045*b* may be positioned between the attachment zone 140 and the second transversal edge of the absorbent core. In other words, it is clear to the skilled person that e.g. a third and/or fourth transversal attachment zone may be added. In the embodiment of FIG. 21C, a single longitudinal attachment zone 140 is illustrated, along with a first and second transversal attachment zone 1045*a*, 1045*b* which are positioned at either side of the longitudinal attachment zone 140. Although the transversal attachment zones 1045*a*, 1045*b* are illustrated to be connected to the longitudinal attachment zone 140, it is clear to the skilled person that other embodiments exist wherein the transversal attachment zones 1045*a*, 1045*b* are not connected to the longitudinal attachment zone 140. In the embodiment of FIG. 21D, a single longitudinal attachment zone 140 is illustrated. The illustrated longitudinal attachment zone 140 comprises curved sections, however, in addition or alternatively the longitudinal attachment zone 140 may comprise straight sections. It is clear to the skilled person that any of the earlier described embodiments related to at least two longitudinal attachment zones, or any combination thereof may be applied to the embodiments wherein the absorbent core comprises a single longitudinal attachment zone.

Since liquid may in many cases not be distributed evenly or symmetrically, it may be advantageous to include at least one attachment zone through which liquid may go from the first and second channels 140, 150 and vice-versa. This will allow a good distribution over the entire absorbent core as well as an improved formation of the channels and the tub-shape upon swelling of the absorbent core.

In the embodiments of FIGS. 22A-22W, 22Z, 23G-23M, 23O-23T, 23V-23X, 23Z, 24D-24M, 24R-24Z, 25A-25L, this is achieved with a transversal attachment zone 1045 connecting the front ends of longitudinal attachment zones 140, 150. As will be clear from the figures, the presence of such a transversal attachment zone 1045 does not preclude the elements mentioned in conjunction with the previous figures, such as the presence of a central attachment zone 180 and/or variations of the length, position and/or shape of longitudinal attachment zones 140, 150. The figures furthermore show that the presence of such a transversal attachment also does not preclude the presence of third and fourth longitudinal attachment zones 160, 170, or of transversal attachment zones 147, 157 which connect the longitudinal attachment zones 140, 150 to the further longitudinal attachment zones 160, 170. Furthermore, the figures show that the transversal attachment zone 1045 need not be straight: it may be rounded as in for example FIGS. 22A-22D, rounded at the edges only as for example in FIGS. 22E-22H, or take another shape.

In the embodiments of FIGS. 22A-22Z, 23G-Z, 24D-24N, 24R-Z, 25A-25L, 25U-V the first attachment zone 140, 160 (where present; in some embodiments the zone is indicated with one reference number 140 and in other embodiments with two reference numbers 140, 160), the second attachment zone 150, 170 (where present) and the connecting attachment zone 1045 form together a substantially U-shaped zone. The substantially U-shaped zone may extend from the rear portion to the front portion (and in particular from the fourth zone Z4 to the second zone Z2). The first and second elongate attachment zone 140, 150, 160, 170 (where present) extend next to each other from the crotch region in the direction of the rear transverse edge 134 and/or the front transverse edge 133. Optionally the first and second elongate attachment zone 140, 150, 160, 170 (where present) may diverge in the direction of the front transverse edge 133. The connecting attachment zone 1045 connects said first elongate attachment zone 140, 160 (where present) with said second elongate attachment zone 150, 170 (where present). The connecting attachment zone 1045 may be a front connecting attachment zone which connects a front end portion of the first attachment zone to a corresponding front end portion of the second attachment zone (FIG. 22X-Y); or a rear connecting attachment zone which connects a rear end portion of the first attachment zone to a corresponding rear end portion of the second attachment zone (FIGS. 22A-W, and 22Z, 23G-23Z). It is noted that also two U-shaped attachment zones may be provided, see FIGS. 23N and 24N, 25U, 25V. The presence of a central attachment zone 180, especially in the front portion may further enhance the liquid distribution. The length of the central attachment zone 180 is preferably at least 20% of the length of the first and second elongate attachment zone 140, 150, and is preferably located at least partially between the first and second elongate attachment zone 140, 150.

Figure 22A:
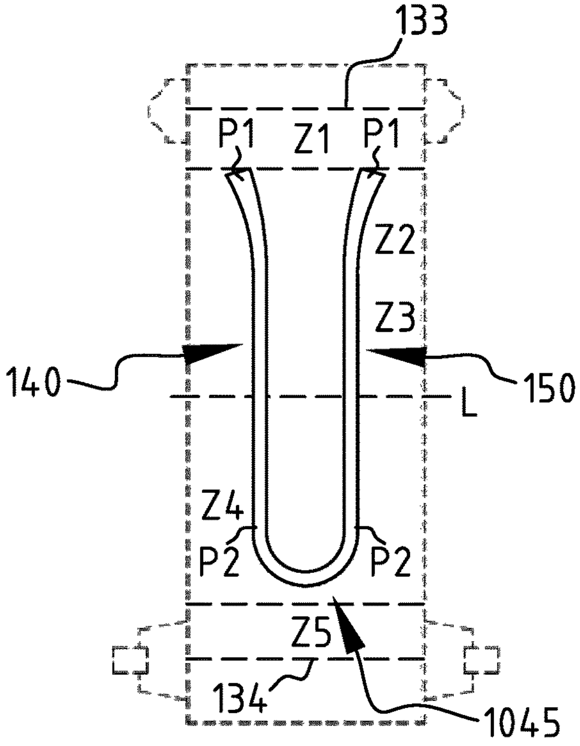
FIGS. 22A-22Z illustrate yet other exemplary embodiments of an absorbent core according to the invention.
Figure 22B:
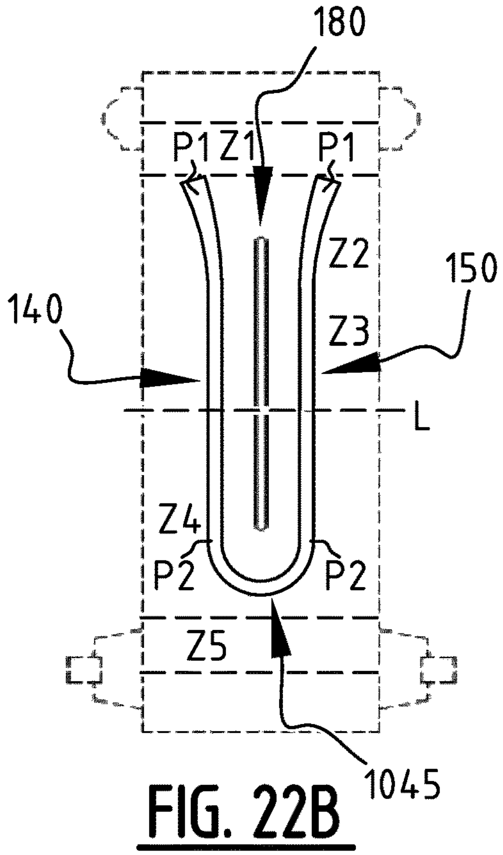
Figure 22C:
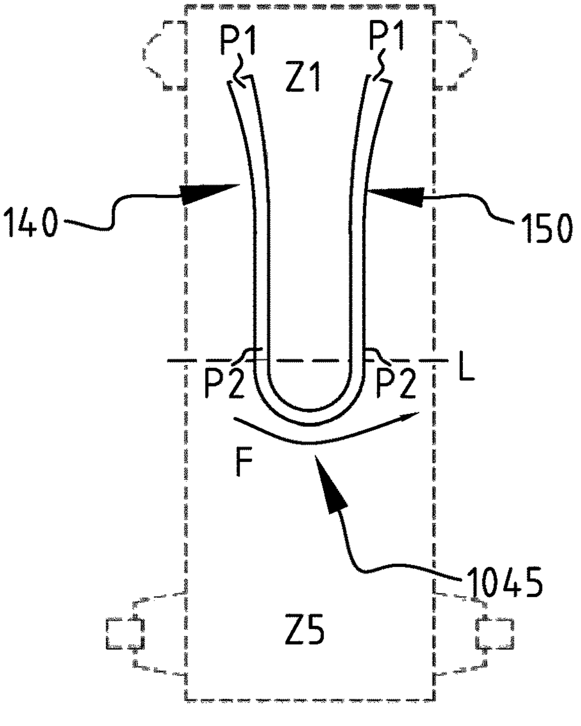
Figure 22D:
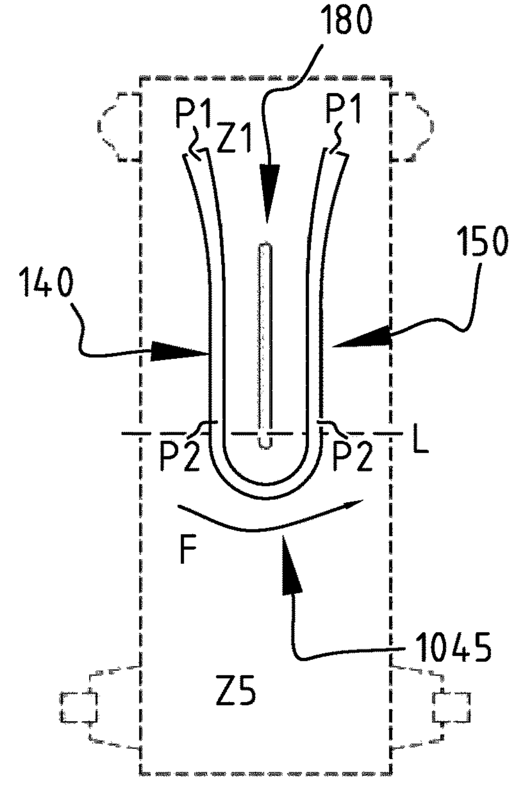
Figure 22E:
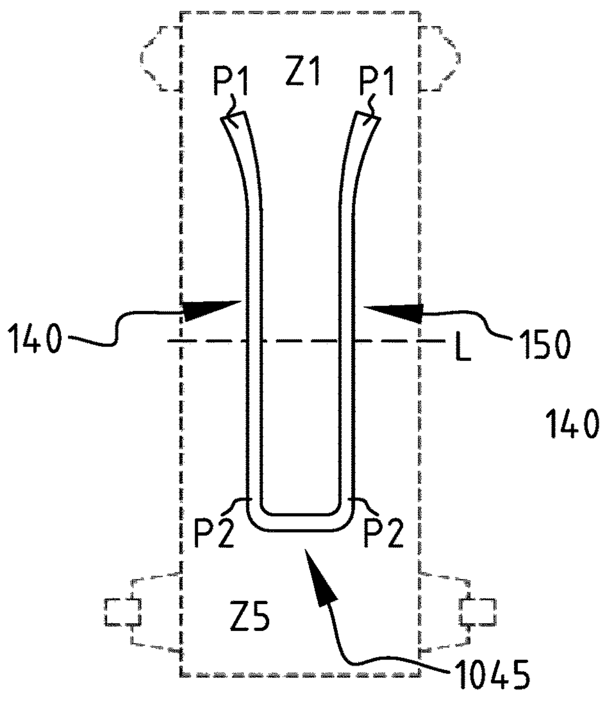
Figure 22F:
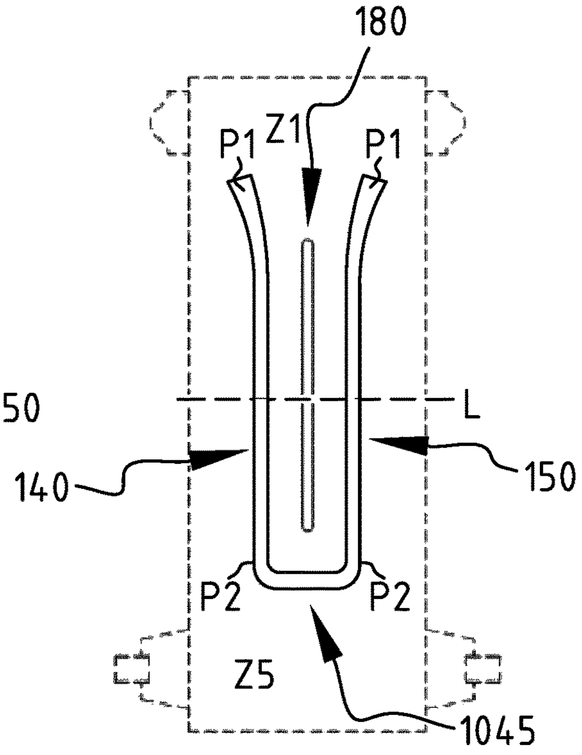
Figure 22G:
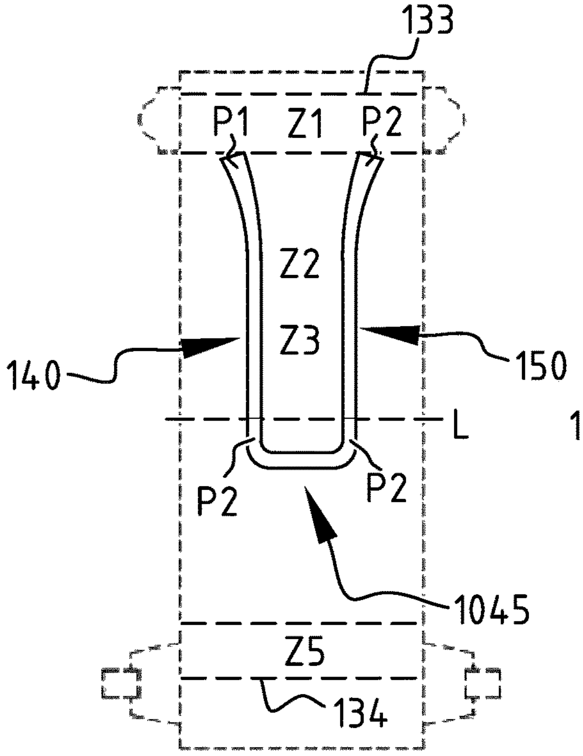
Figure 22H:
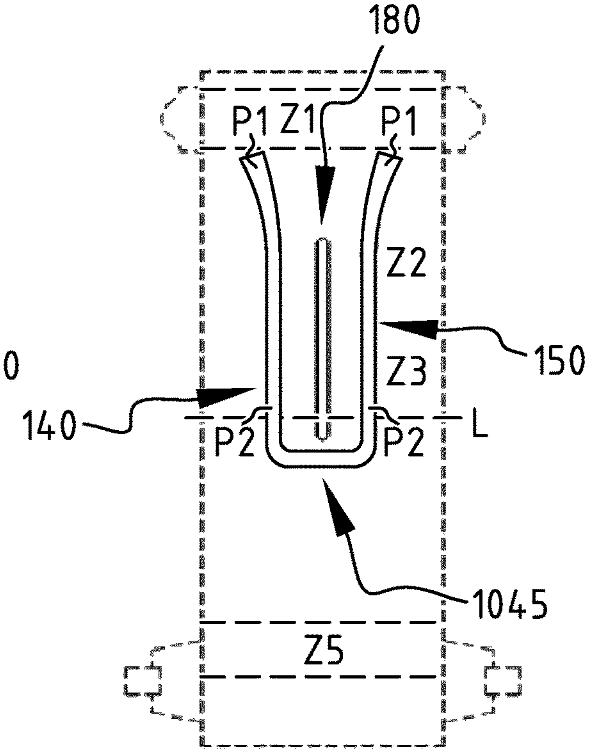
Figure 22I:
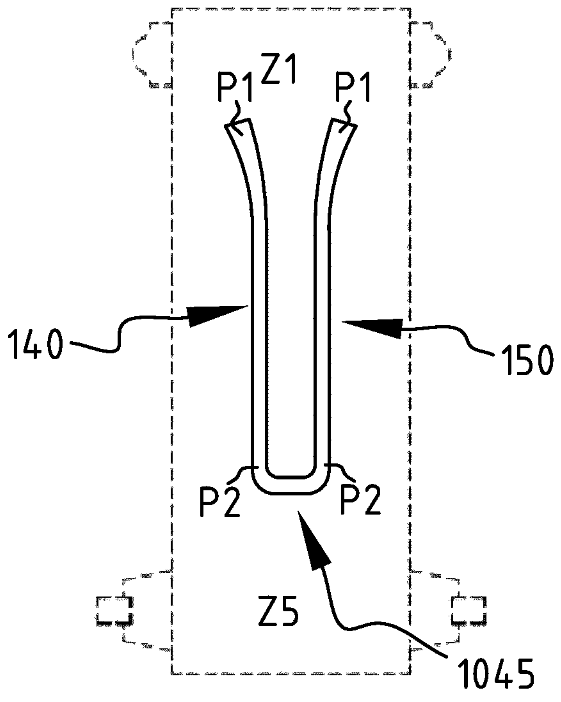
Figure 22J:
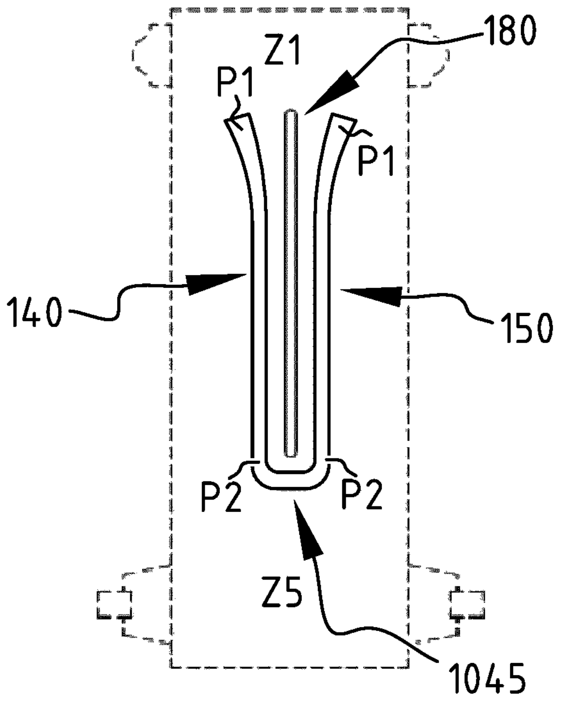
Figure 22K:
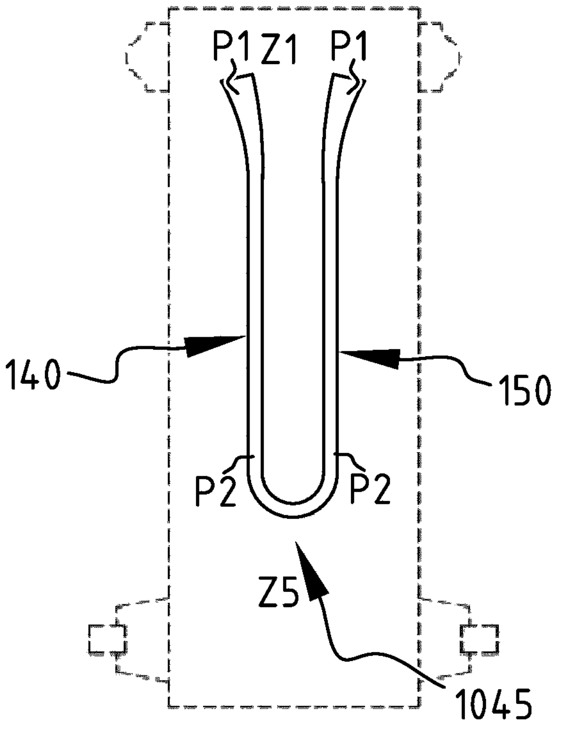
Figure 22L:
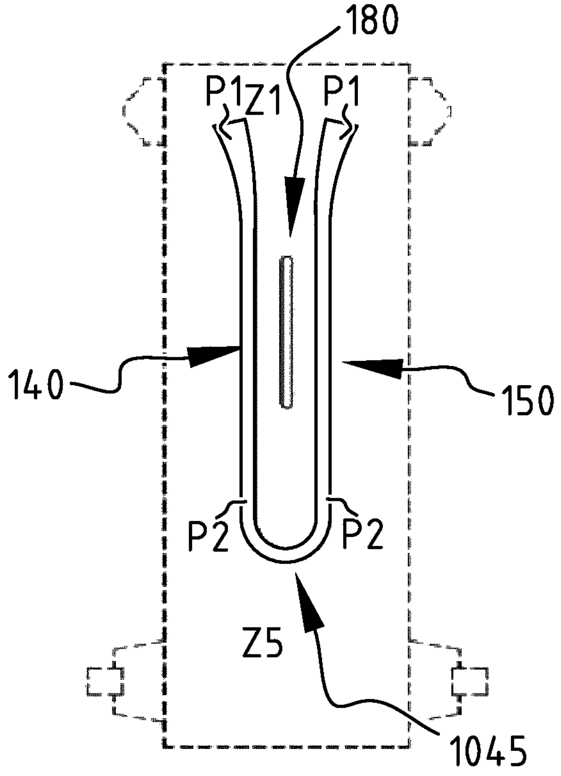
Figure 22M:
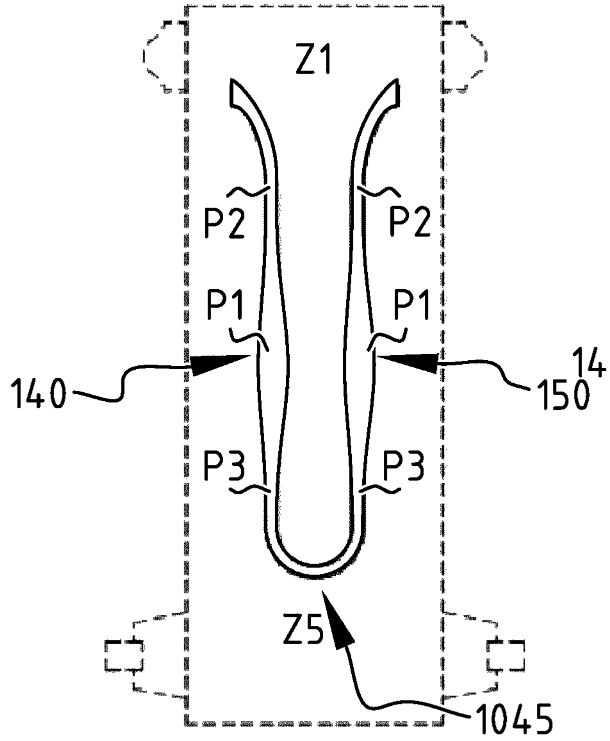
Figure 22N:
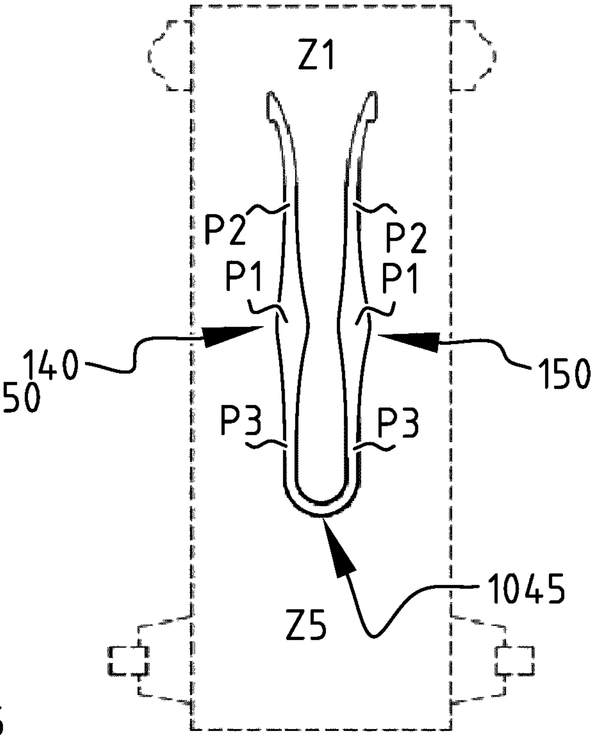
Figure 22O:
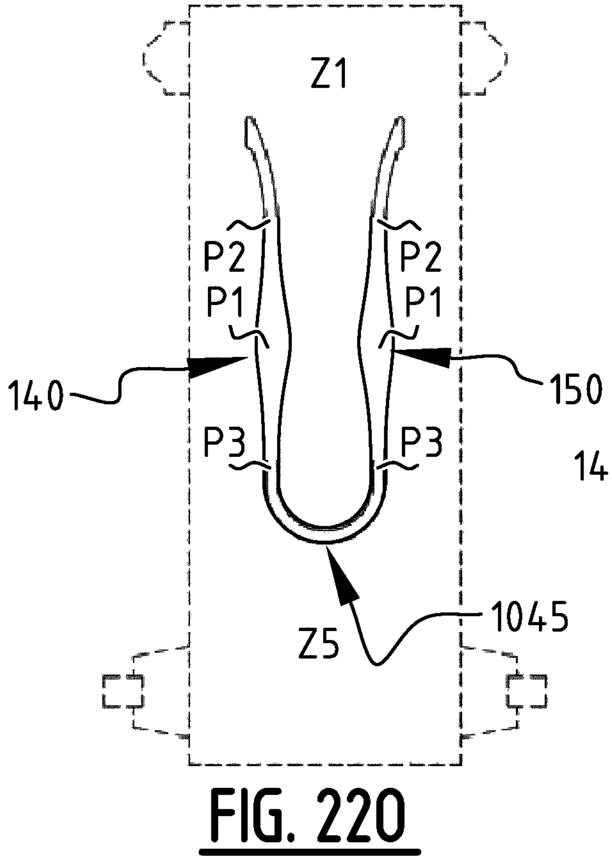
Figure 22P:
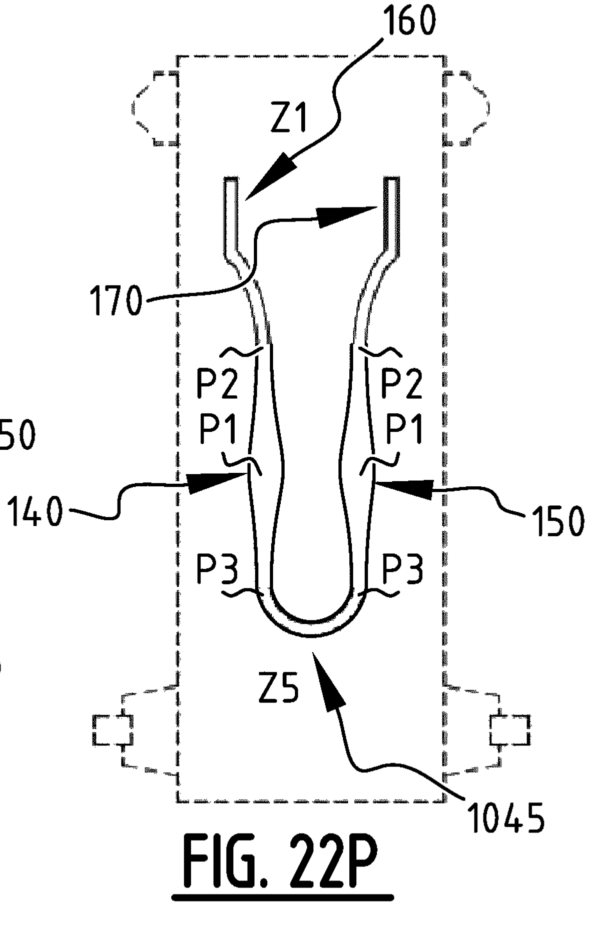
Figure 22Q:
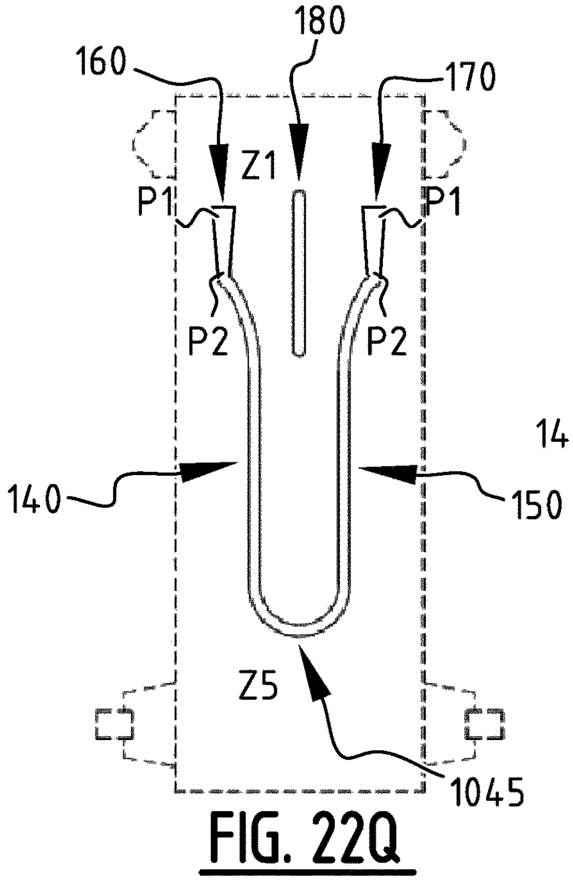
Figure 22R:
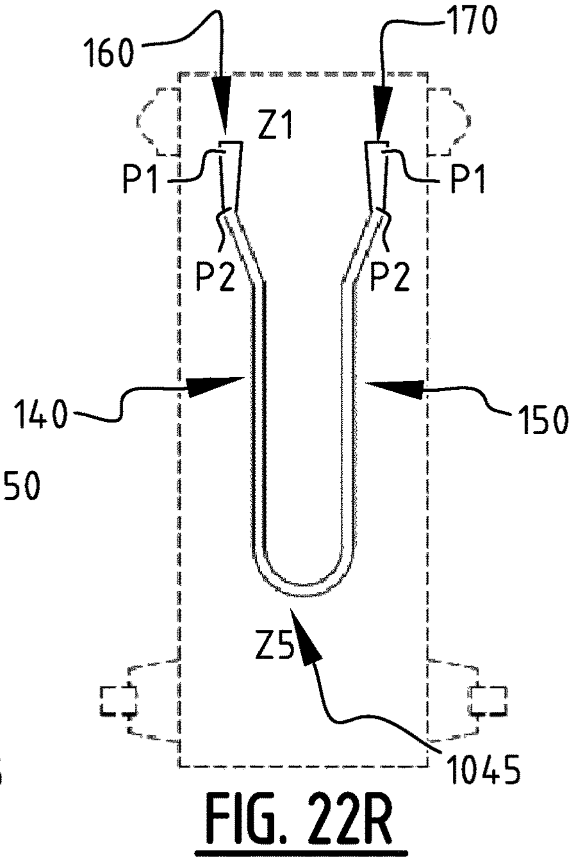
Figure 22S:
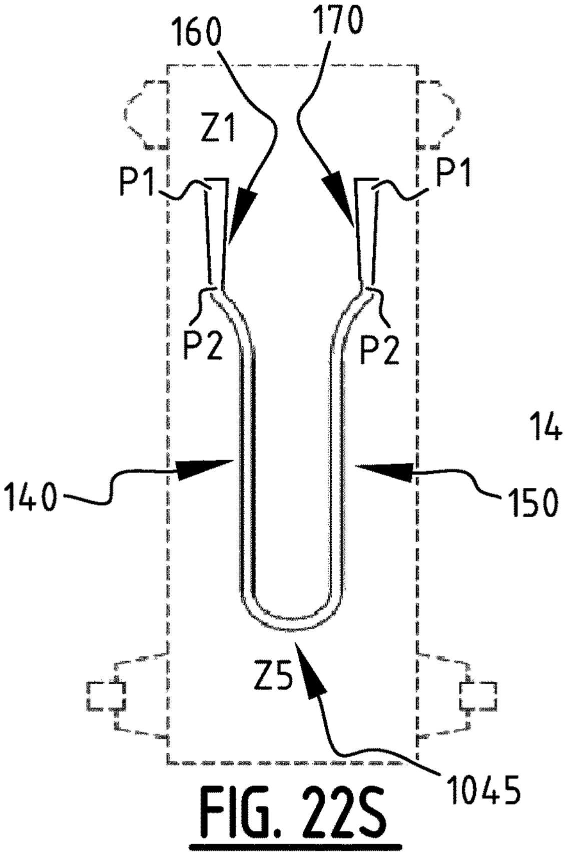
Figure 22T:
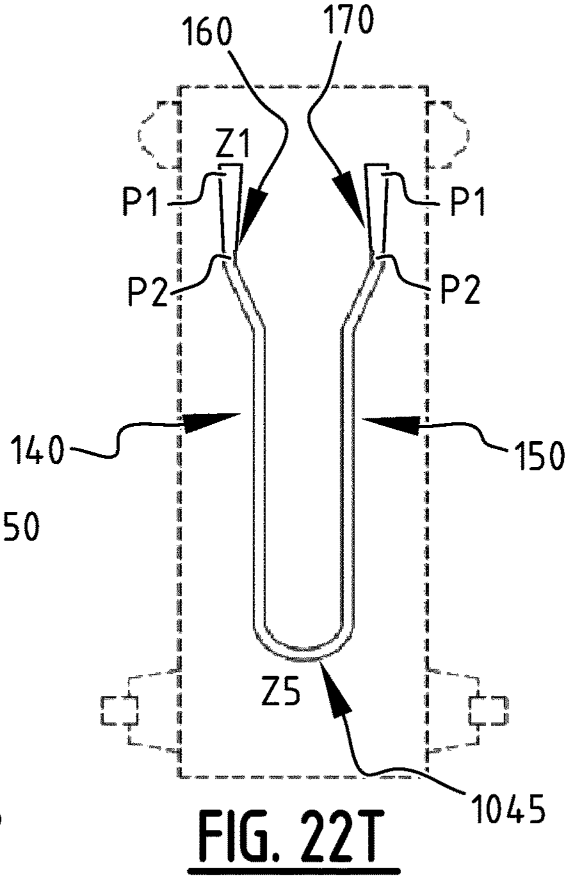
Figure 22U:
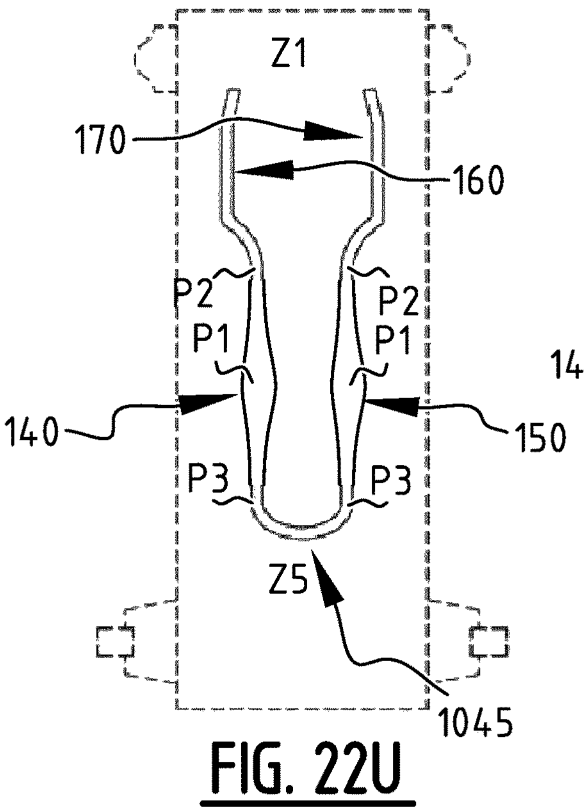
Figure 22V:
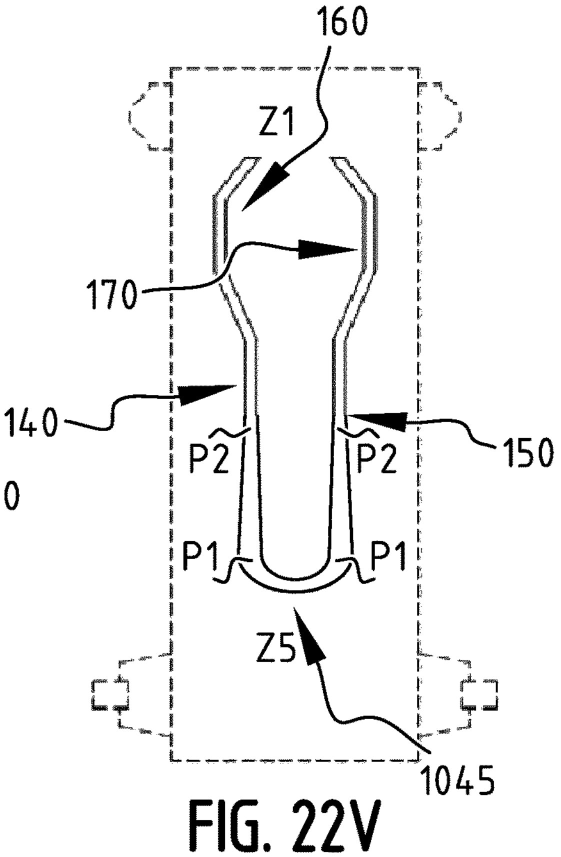
Figure 22W:
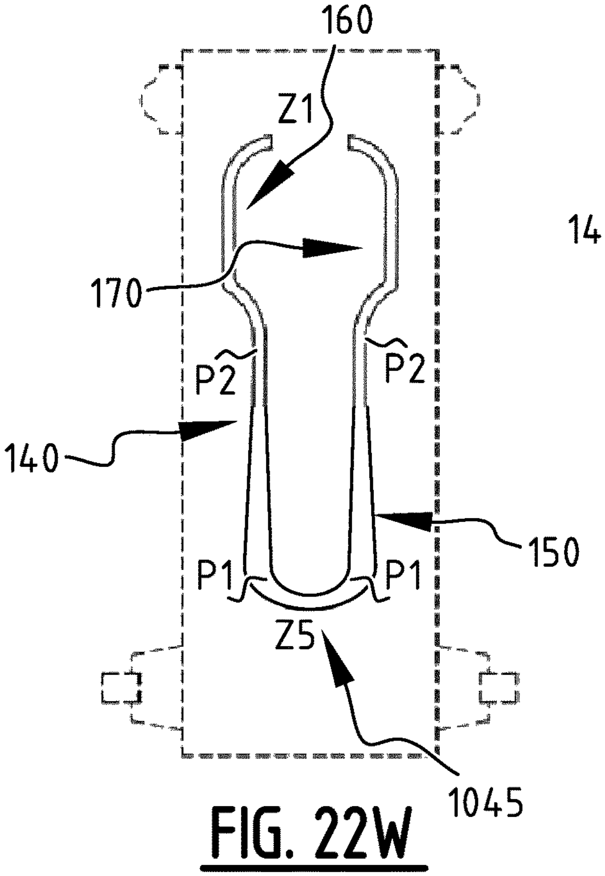
Figure 22X:
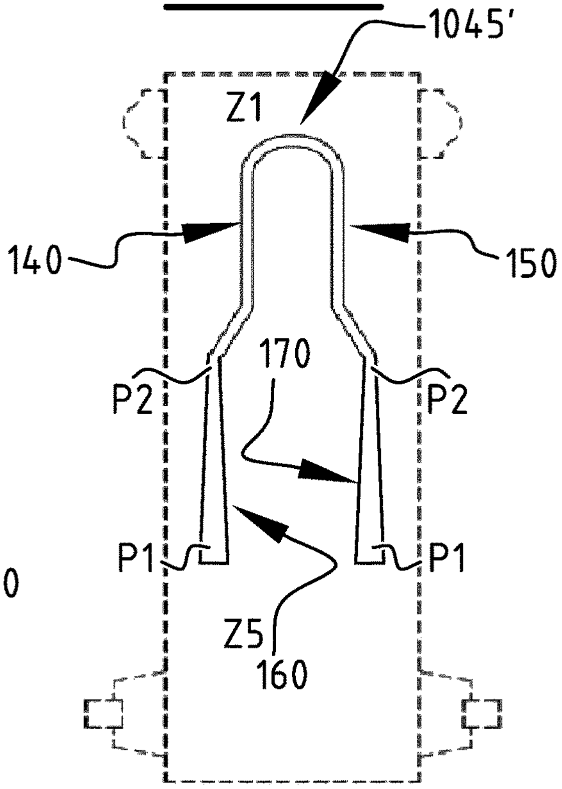
Figure 22Y:
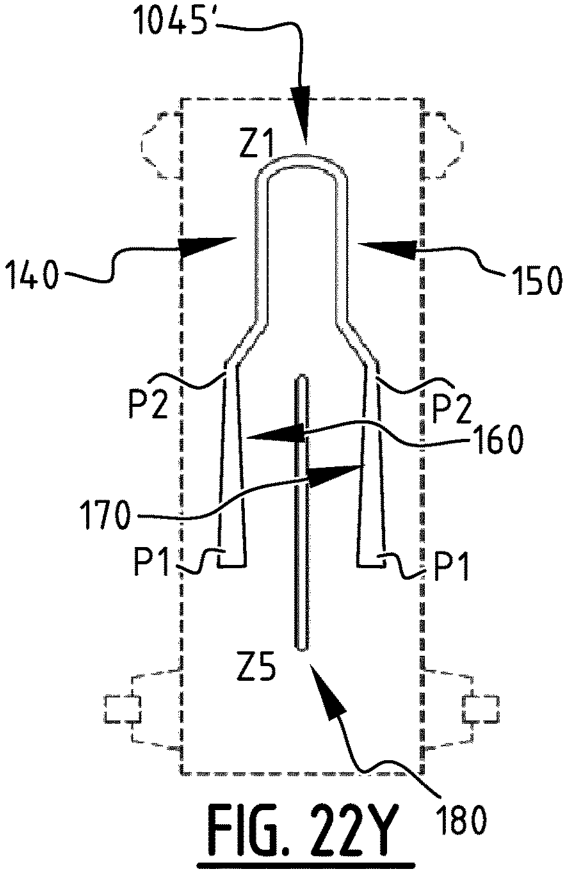
Figure 22Z:
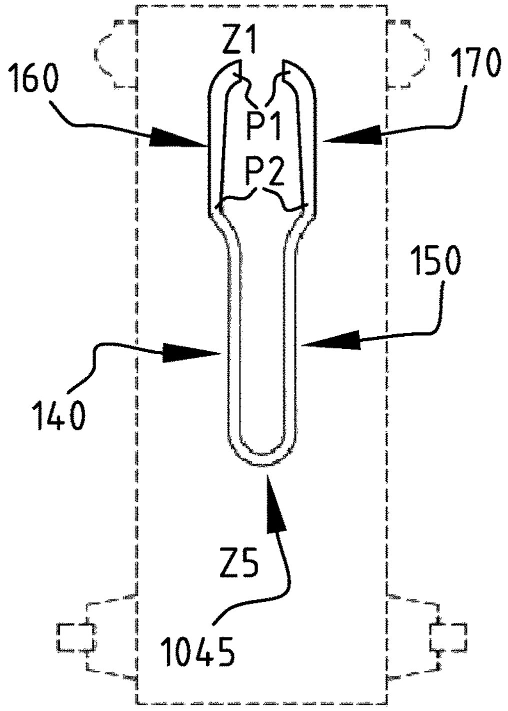
Figure 23A:
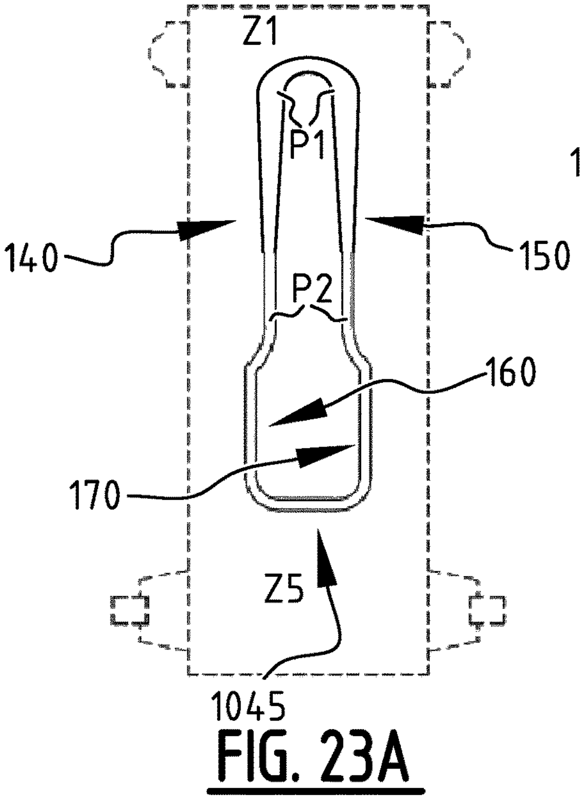
FIGS. 23A-23Z illustrate yet other exemplary embodiments of an absorbent core according to the invention.
Figure 23B:
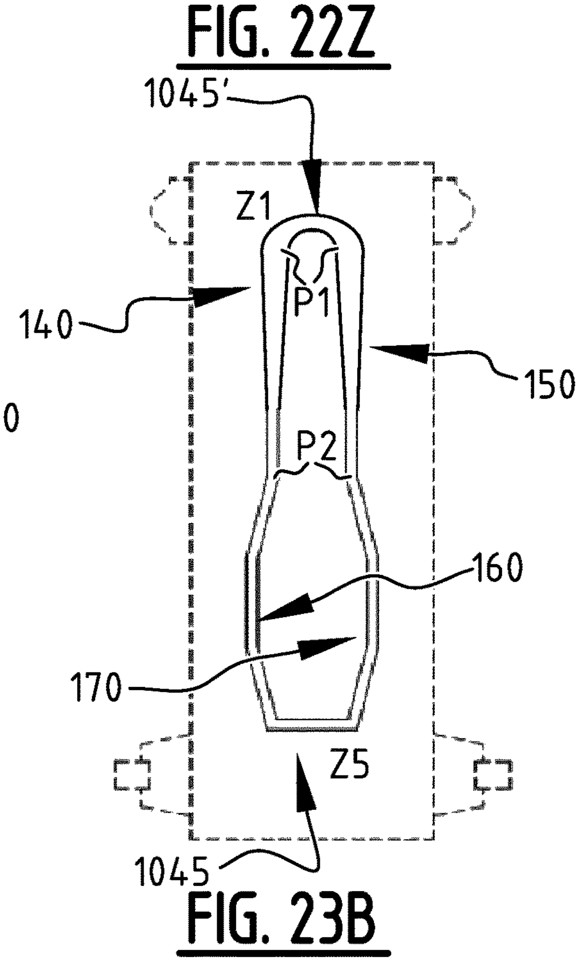
Figure 23C:
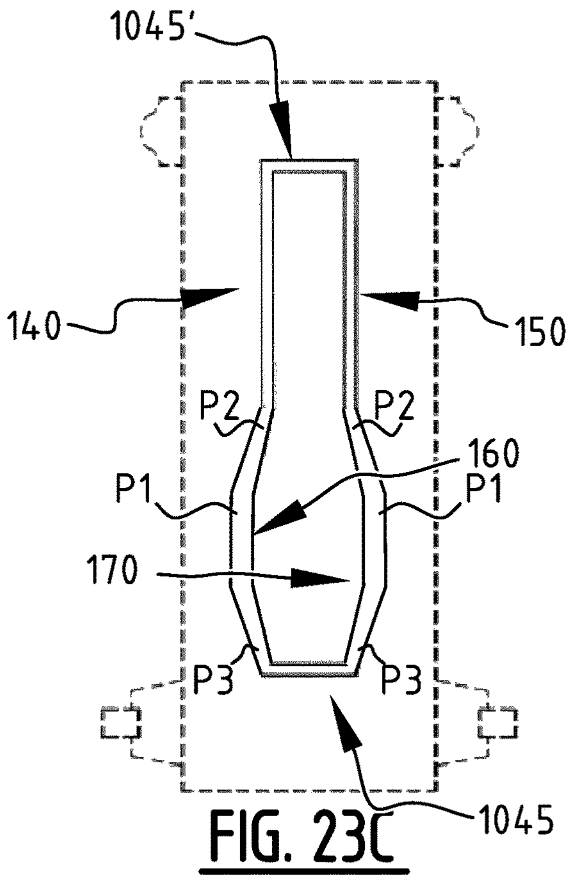
Figure 23D:
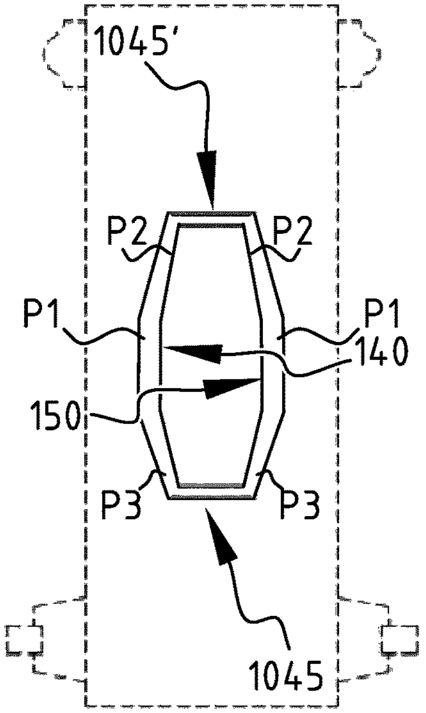
Figure 23E:
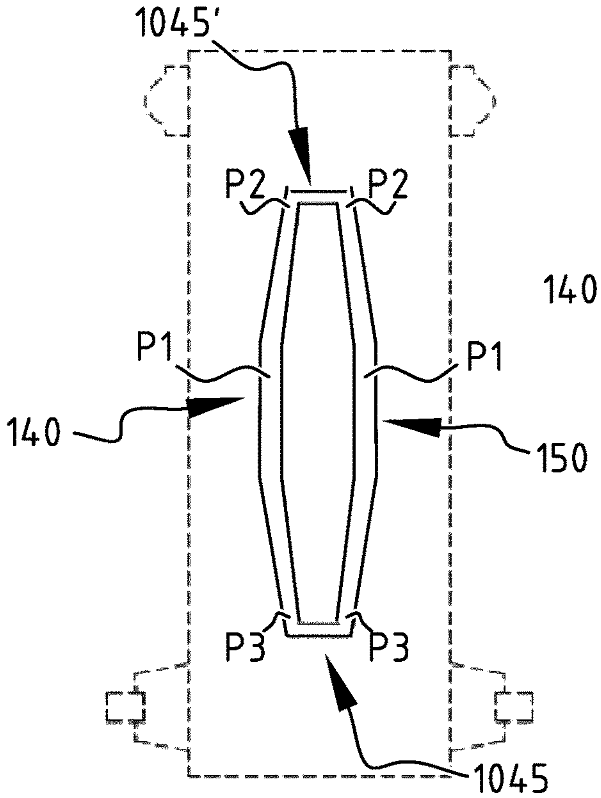
Figure 23F:
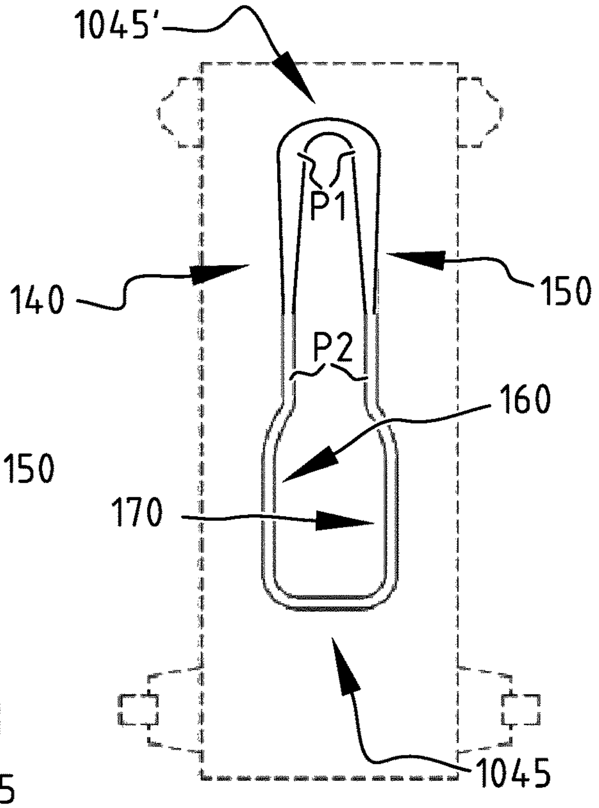
Figure 23G:
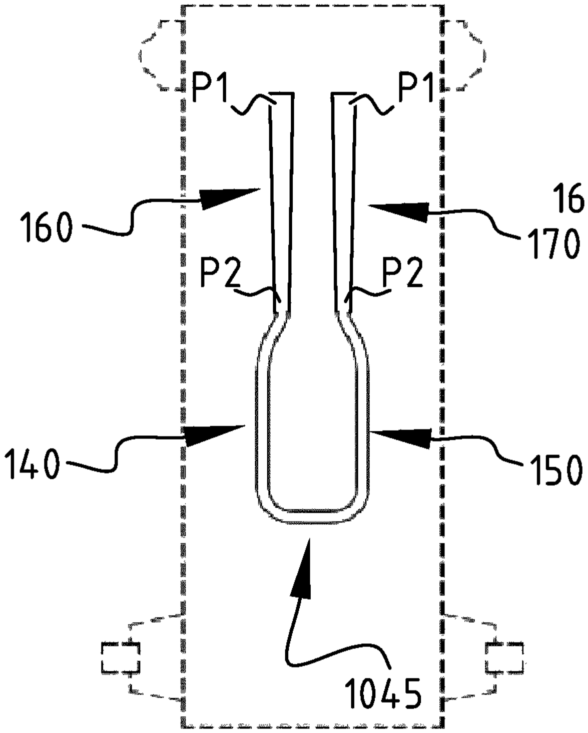
Figure 23H:
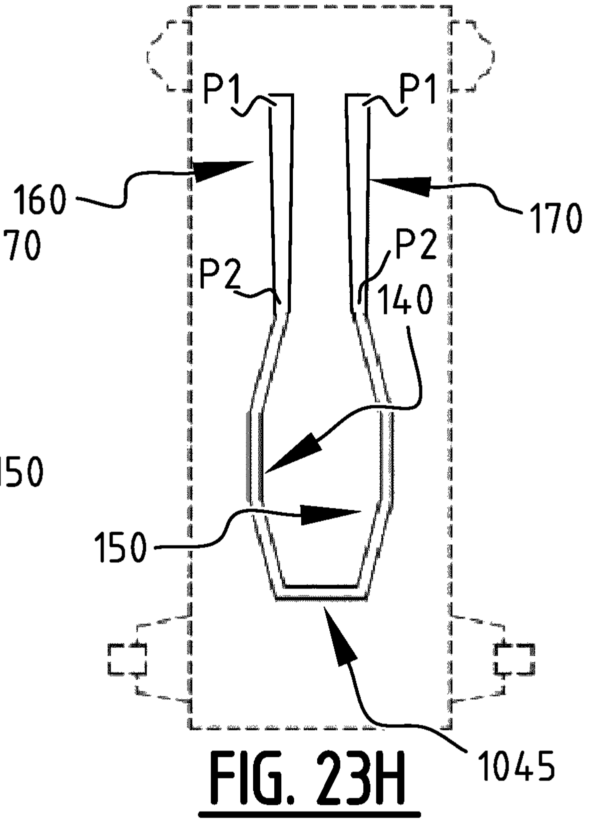
Figure 23I:
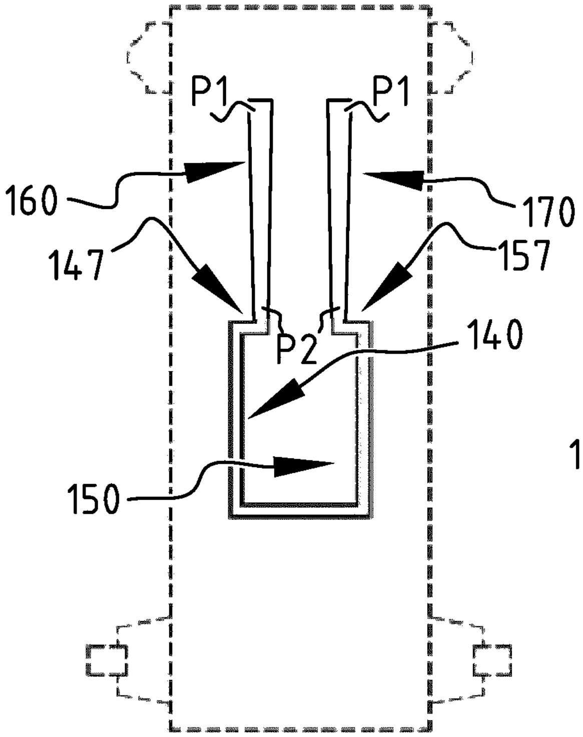
Figure 23J:
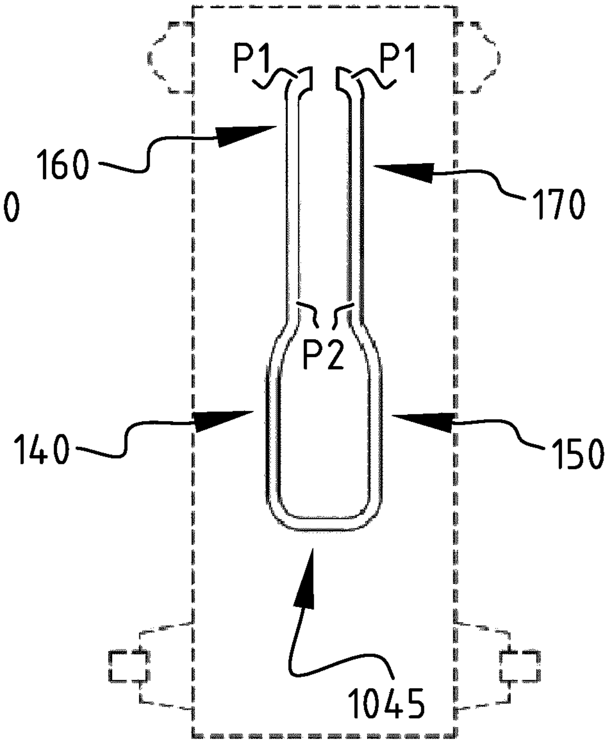
Figure 23K:
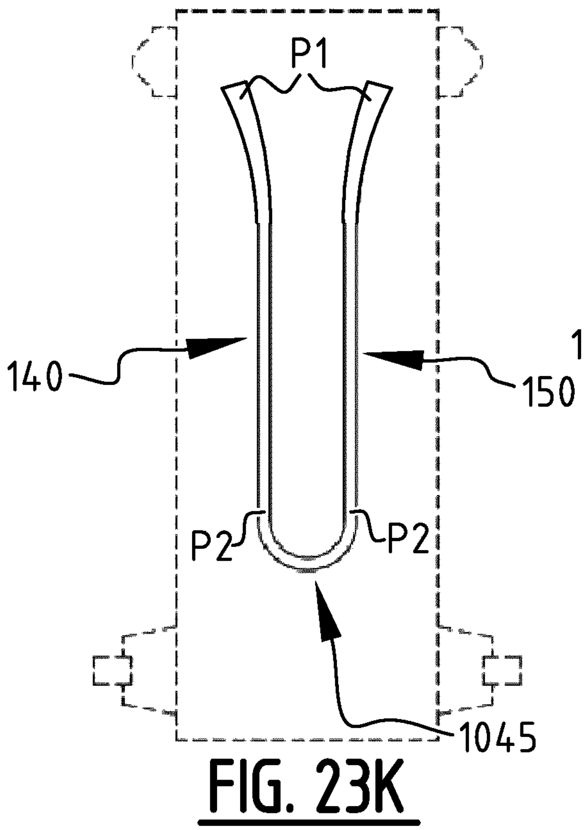
Figure 23L:
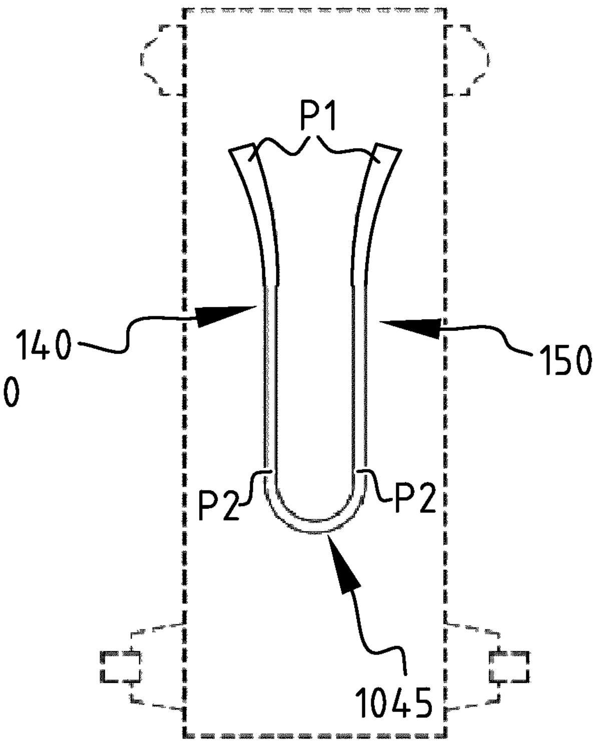
Figure 23M:
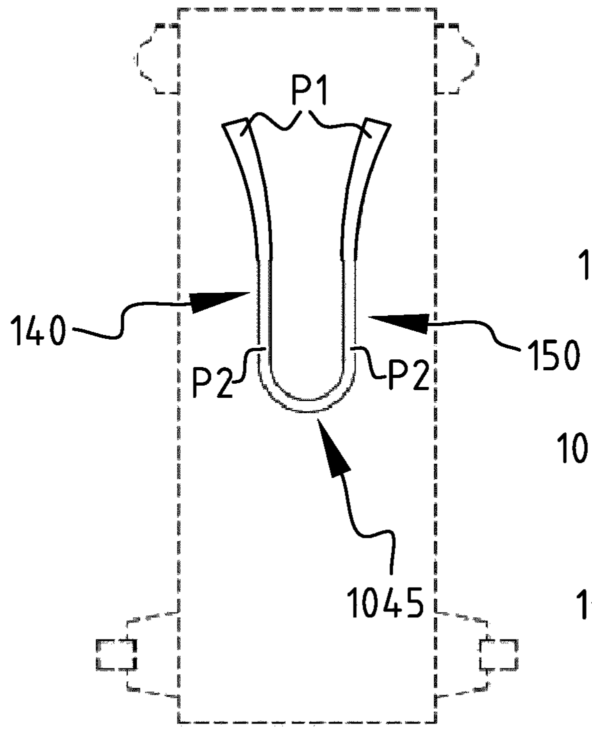
Figure 23N:
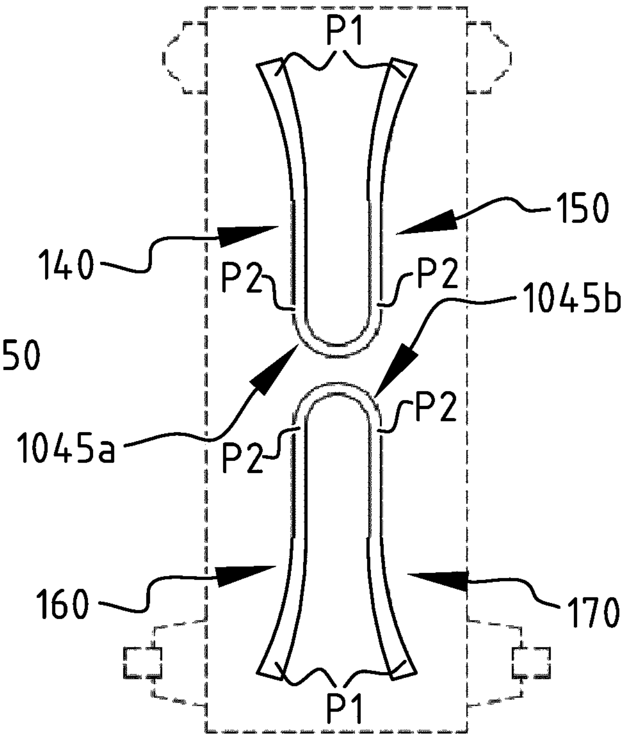
Figure 23O:
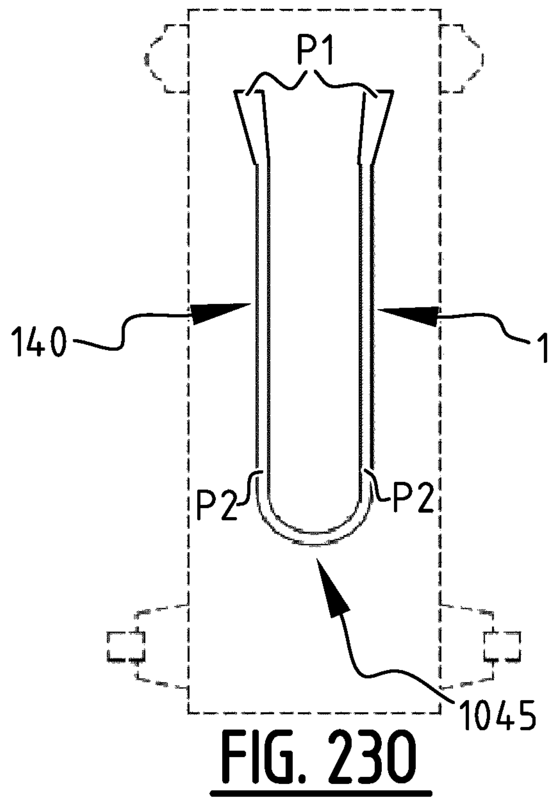
Figure 23P:
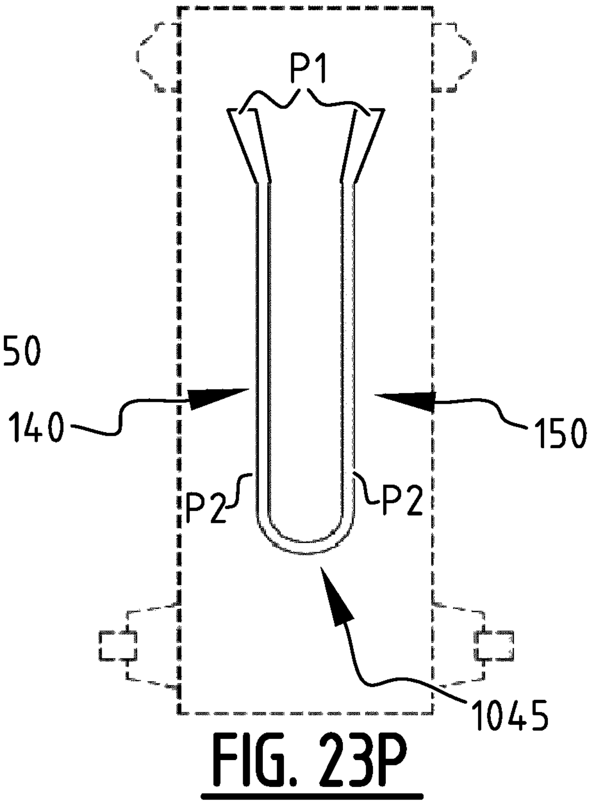
Figure 23Q:
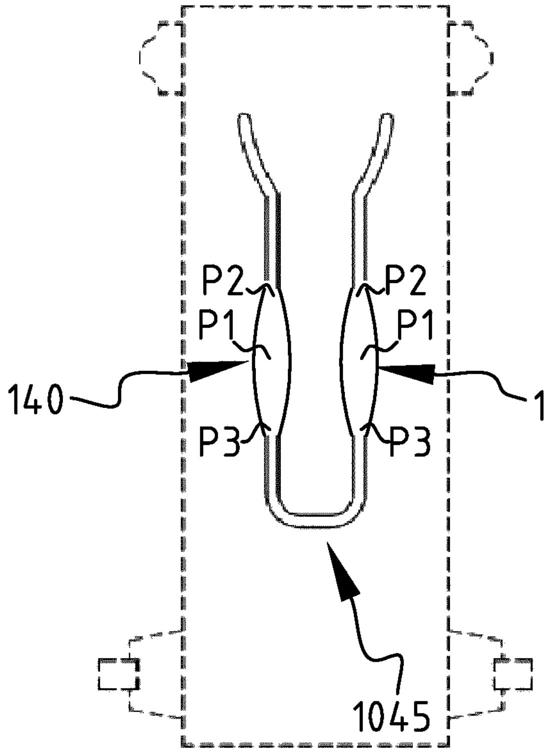
Figure 23R:
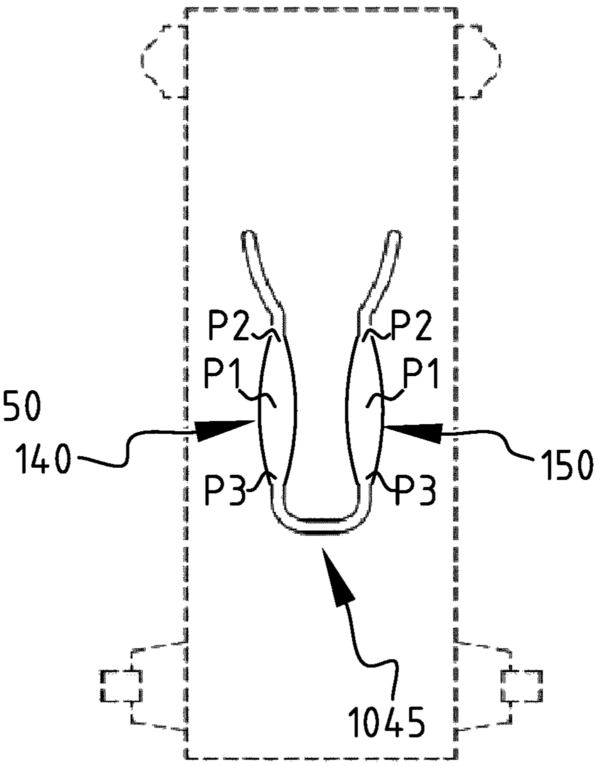
Figure 23S:
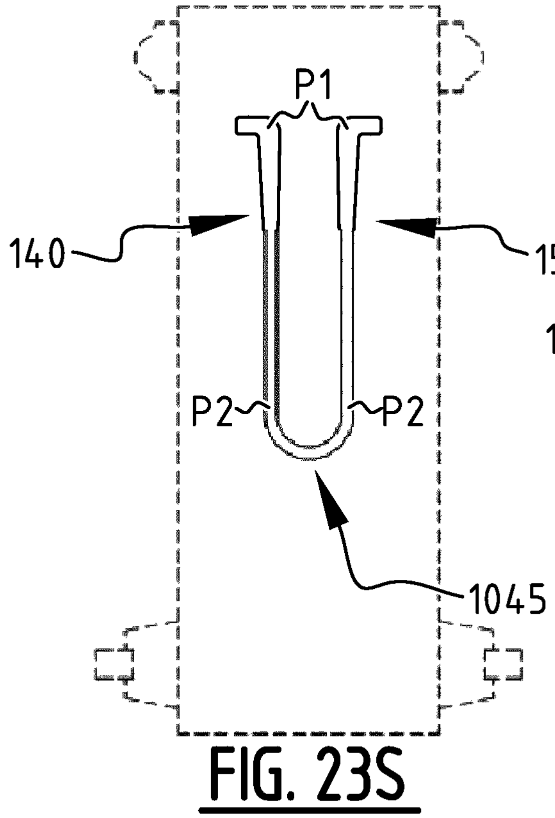
Figure 23T:
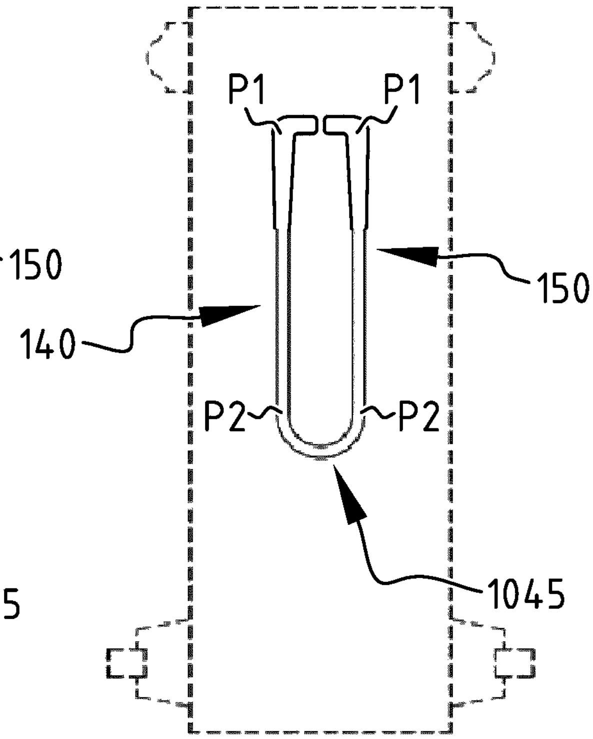
Figure 23U:
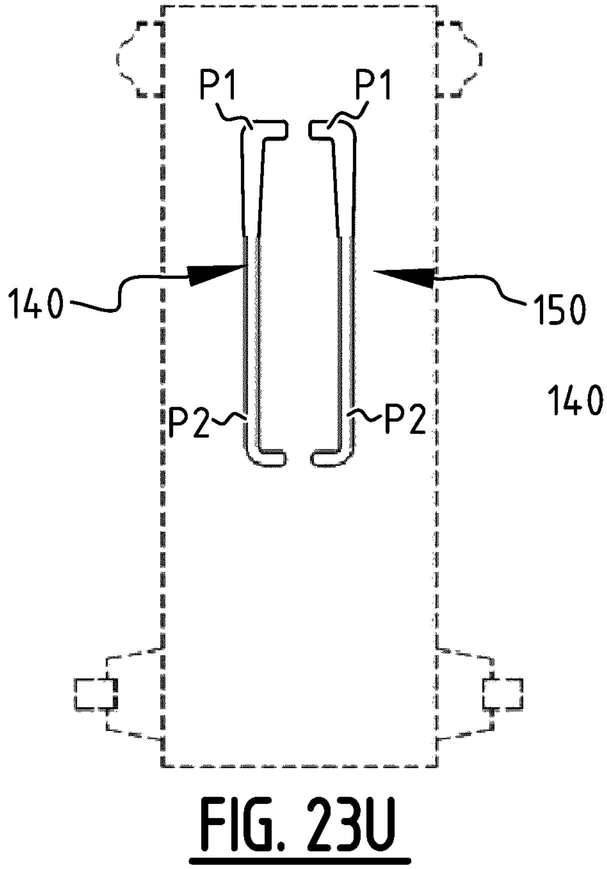
Figure 23V:
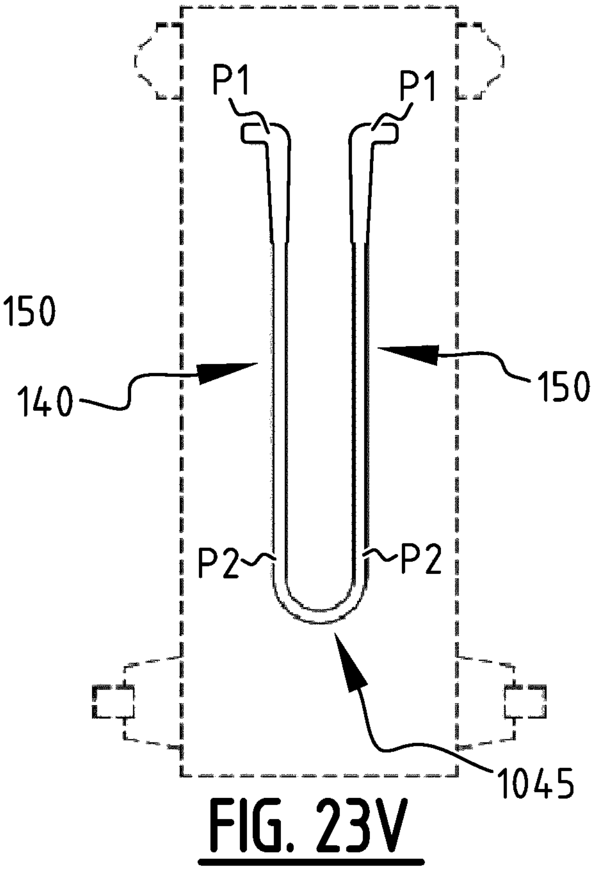
Figure 23W:
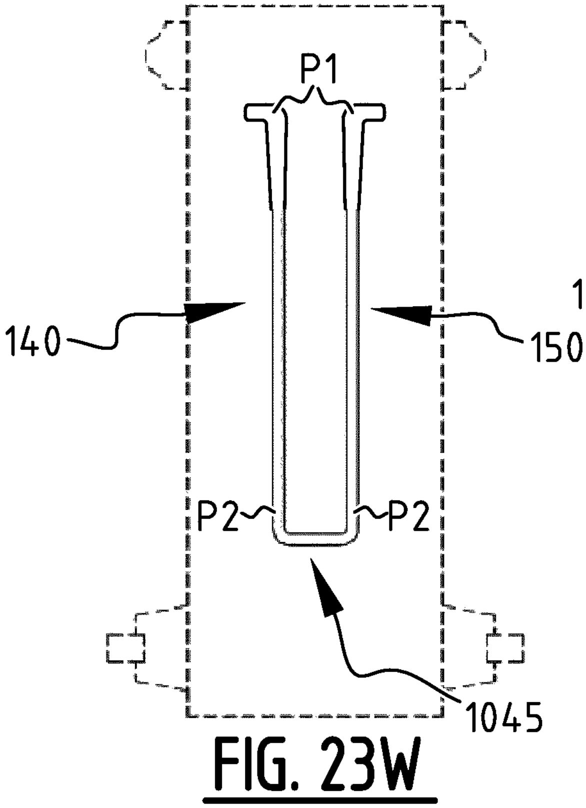
Figure 23X:
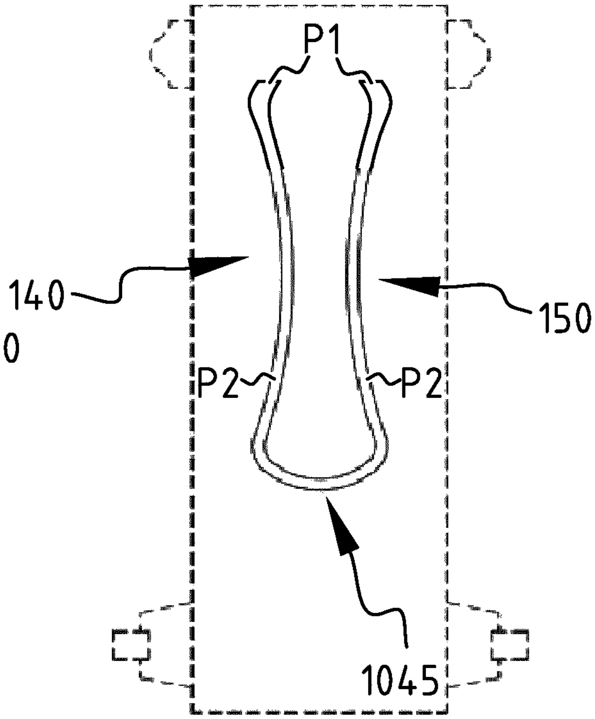
Figure 23Y:
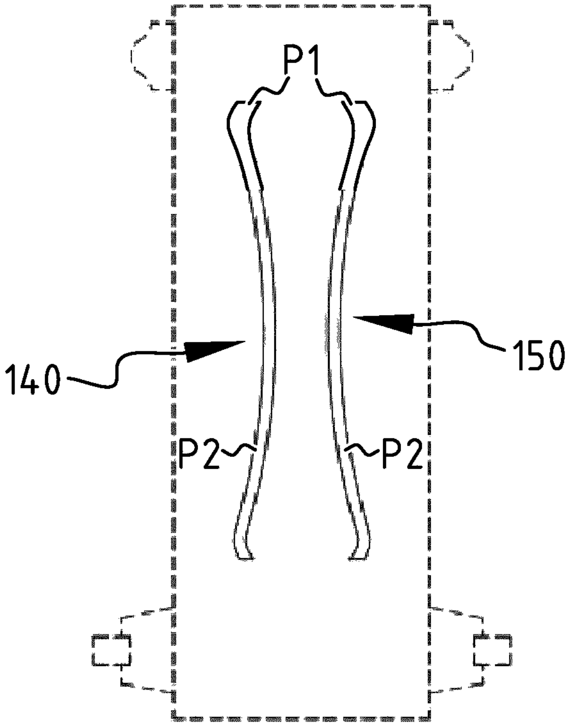
Figure 23Z:
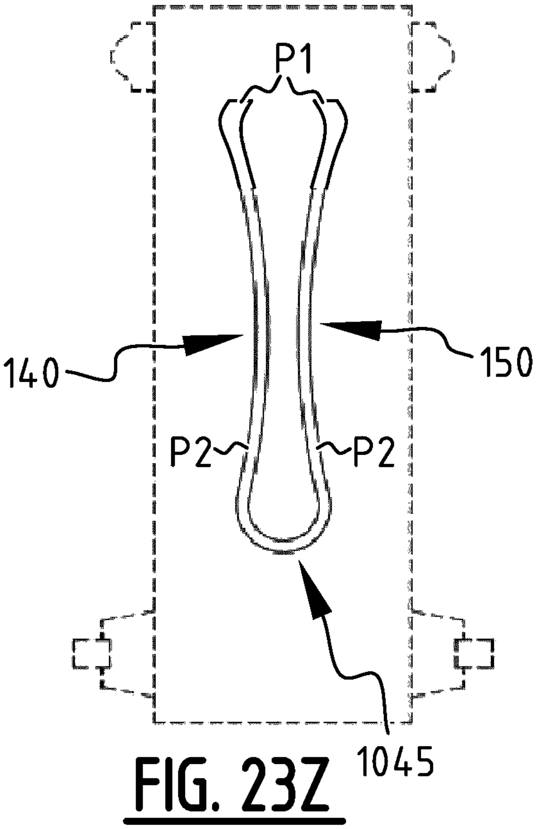
Figure 24A:
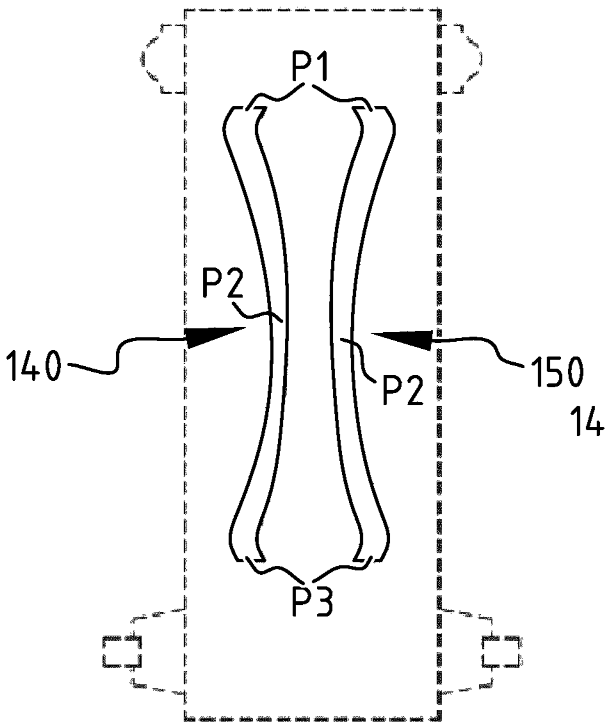
FIGS. 24A-24Z illustrate yet other exemplary embodiments of an absorbent core according to the invention.
Figure 24B:
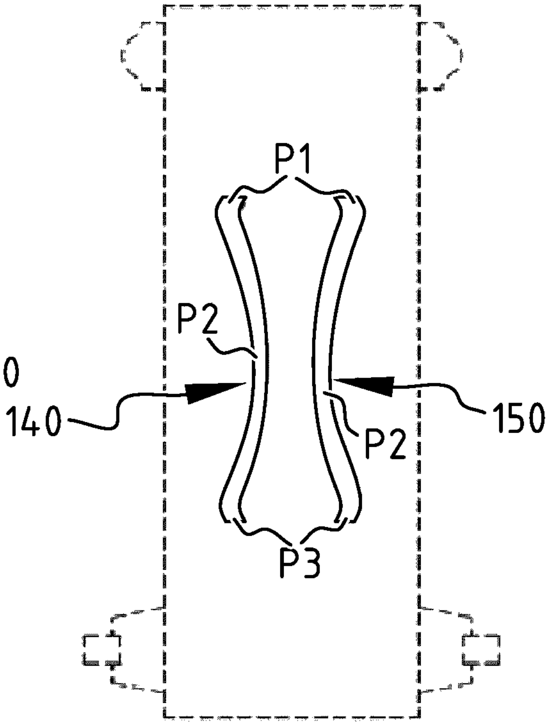
Figure 24C:
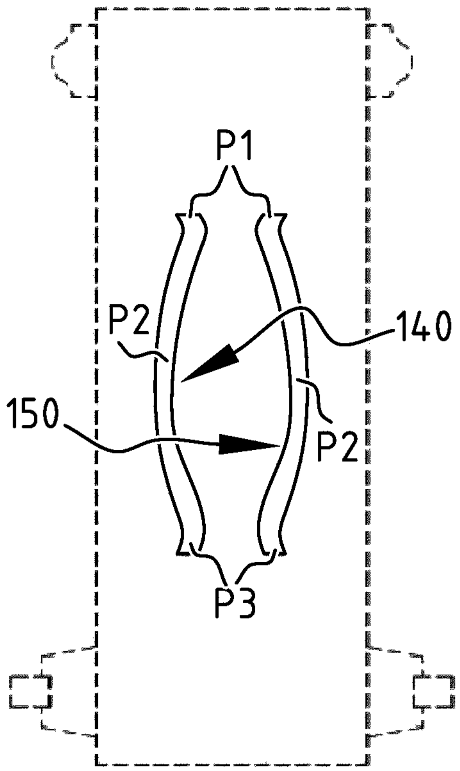
Figure 24D:
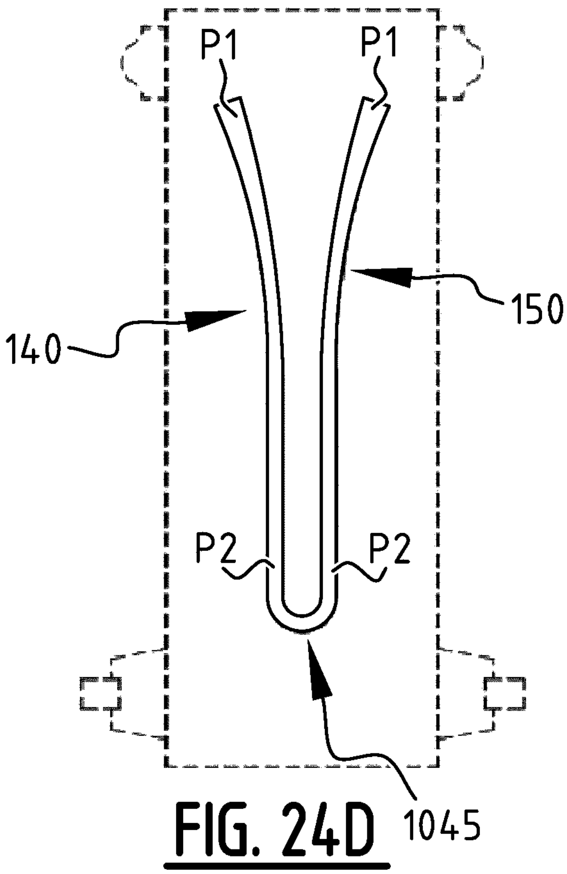
Figure 24E:
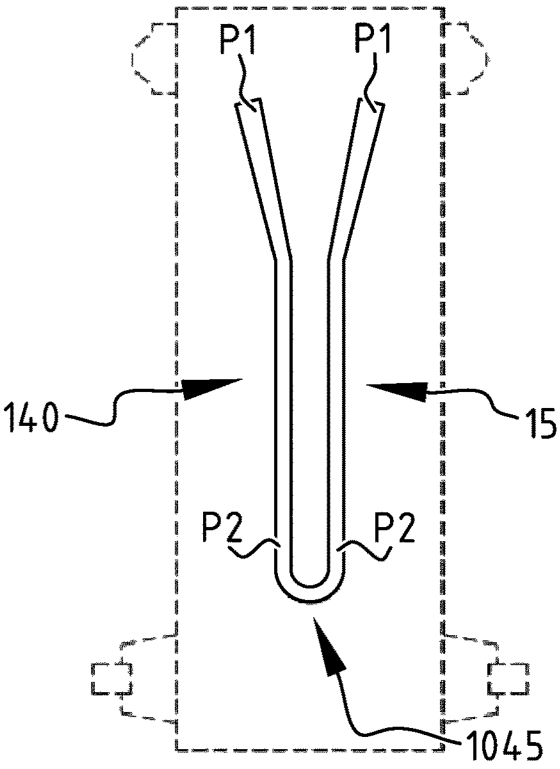
Figure 24F:
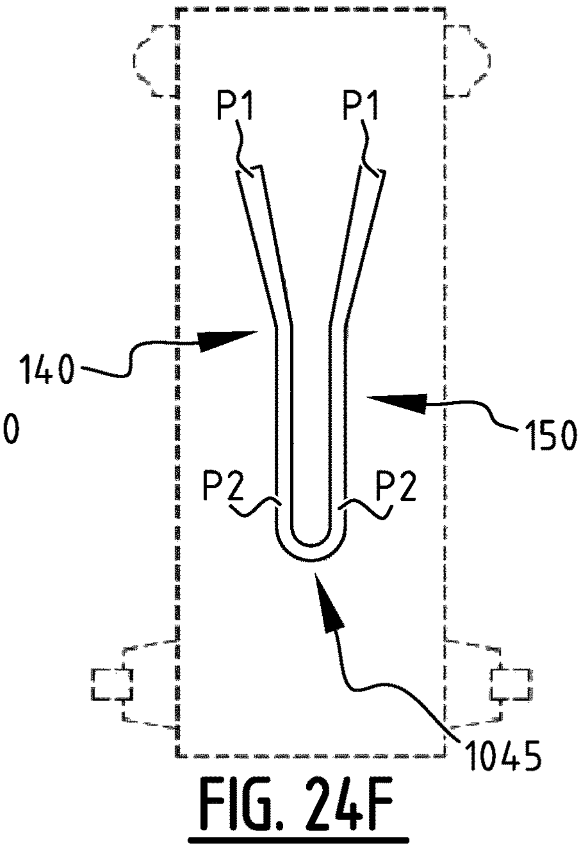
Figure 24G:
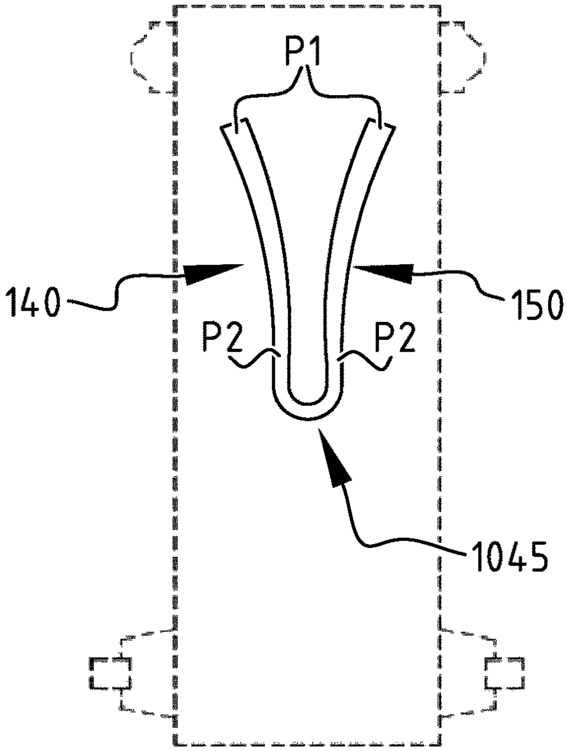
Figure 24H:
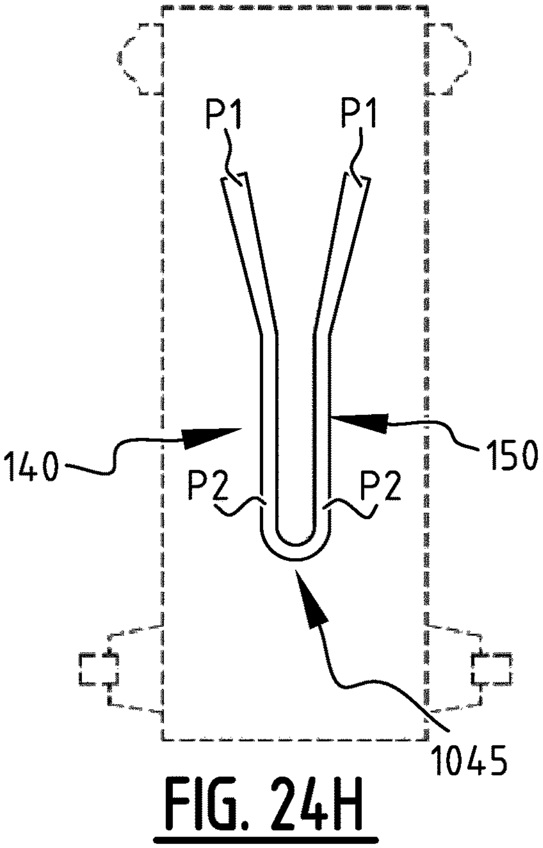
Figure 24I:
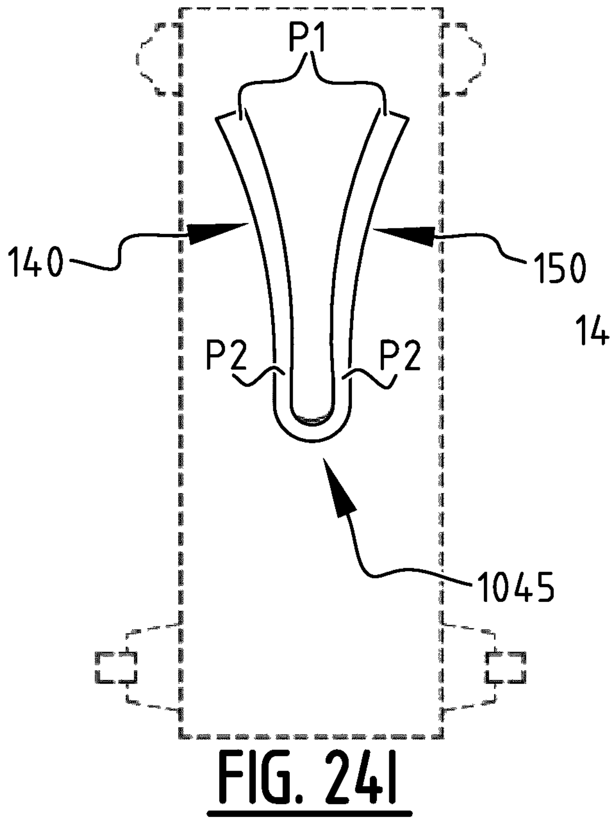
Figure 24J:
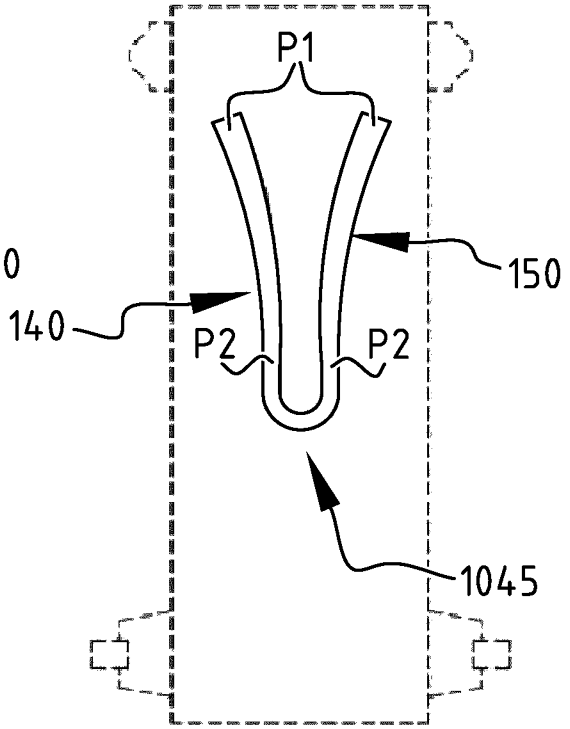
Figure 24K:
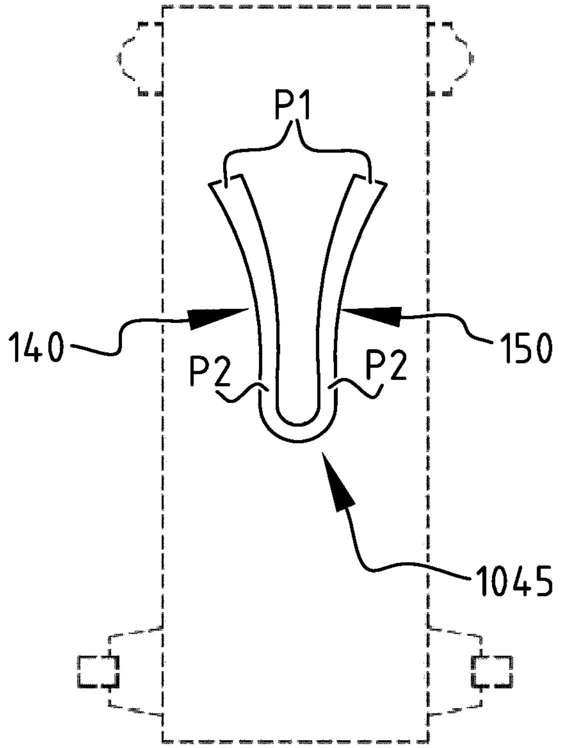
Figure 24L:
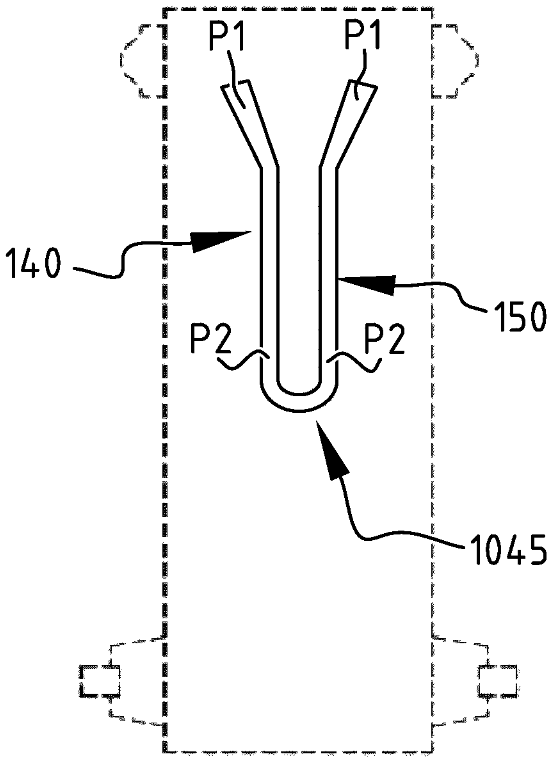
Figure 24M:
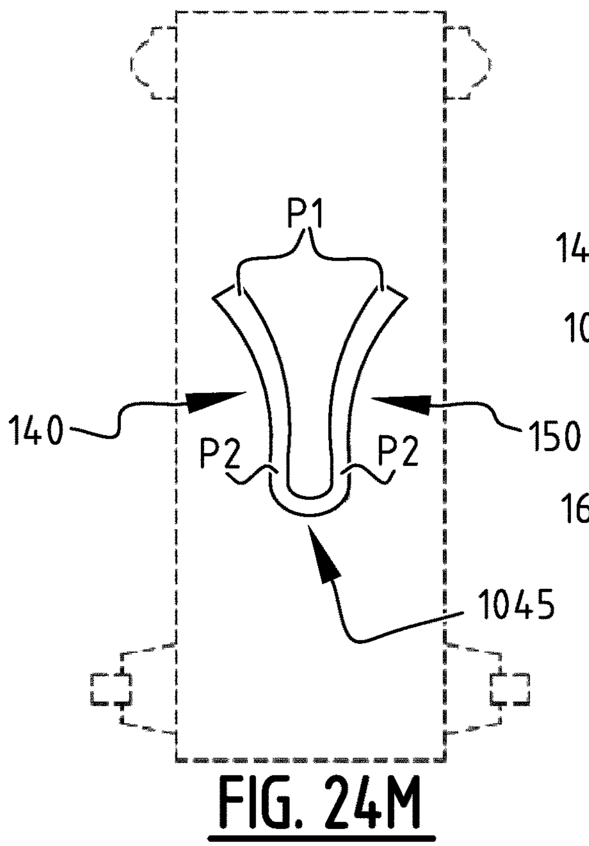
Figure 24N:
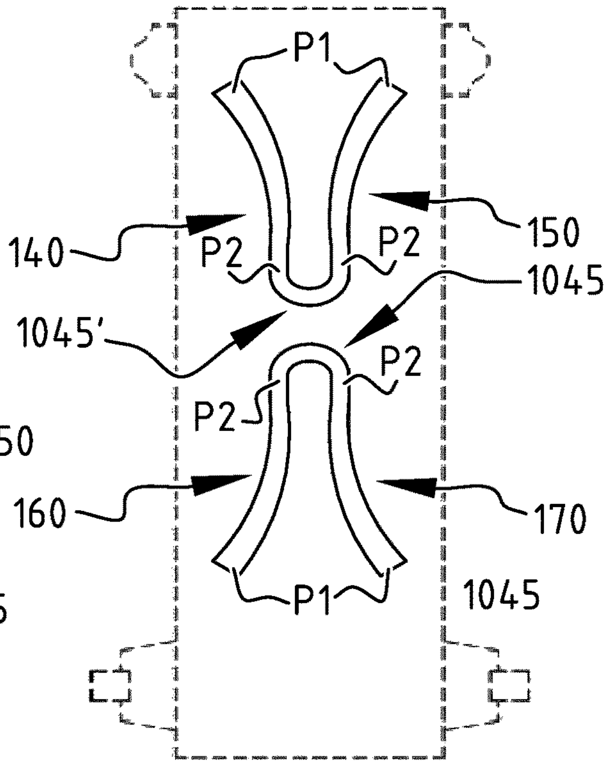
Figure 24O:
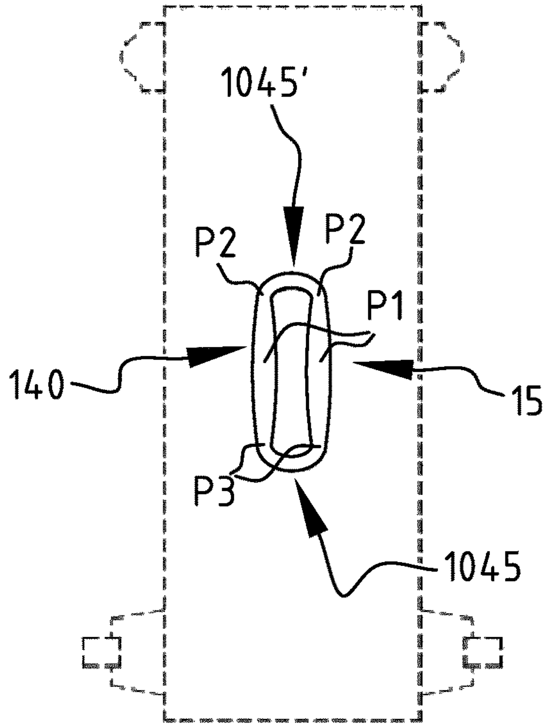
Figure 24P:
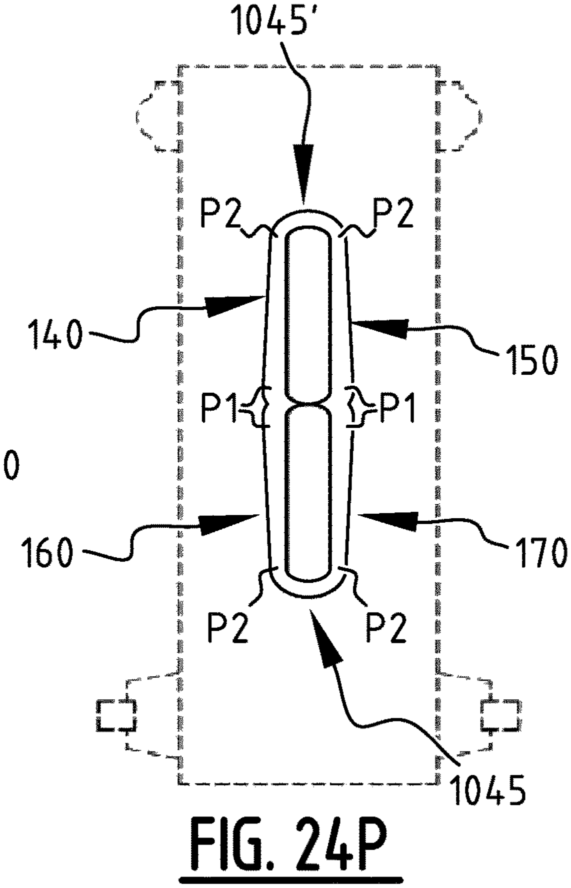
Figure 24Q:
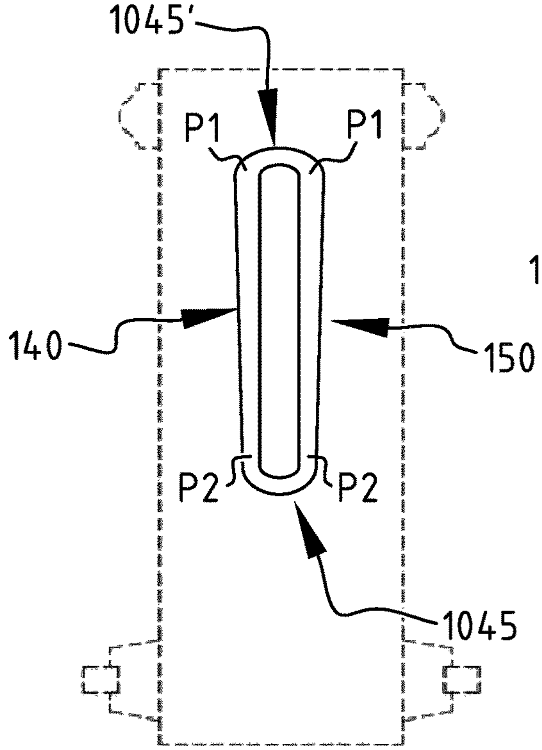
Figure 24R:
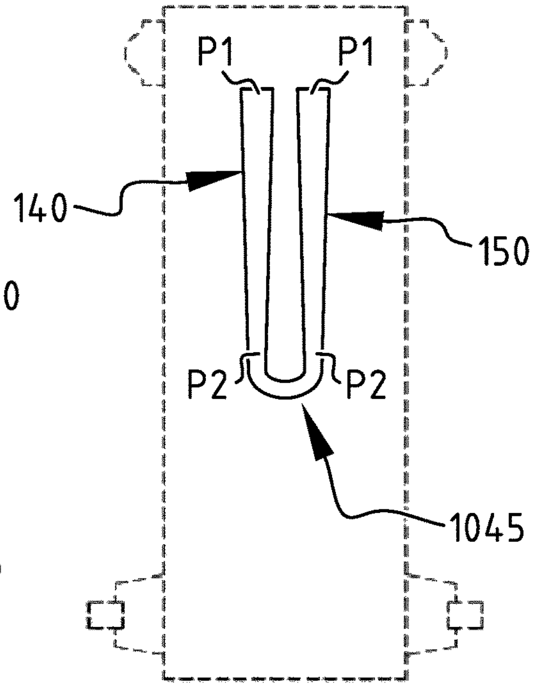
Figure 24S:
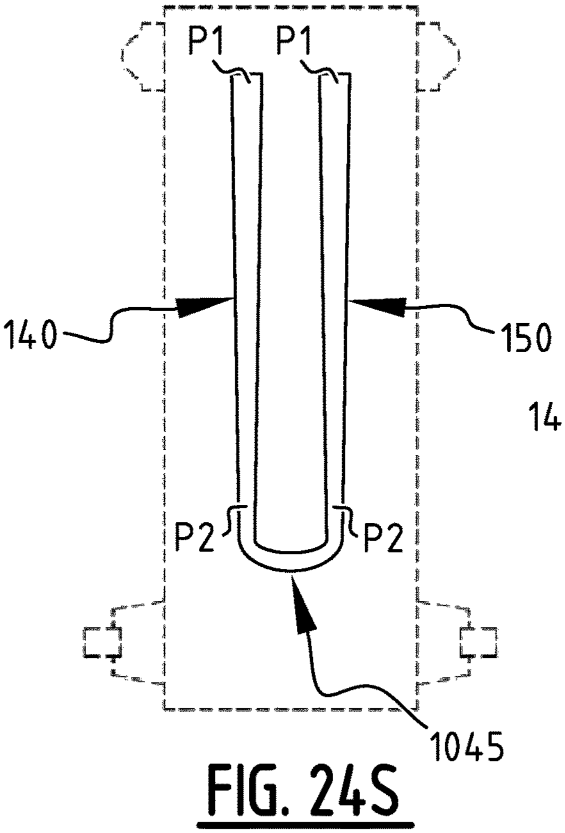
Figure 24T:
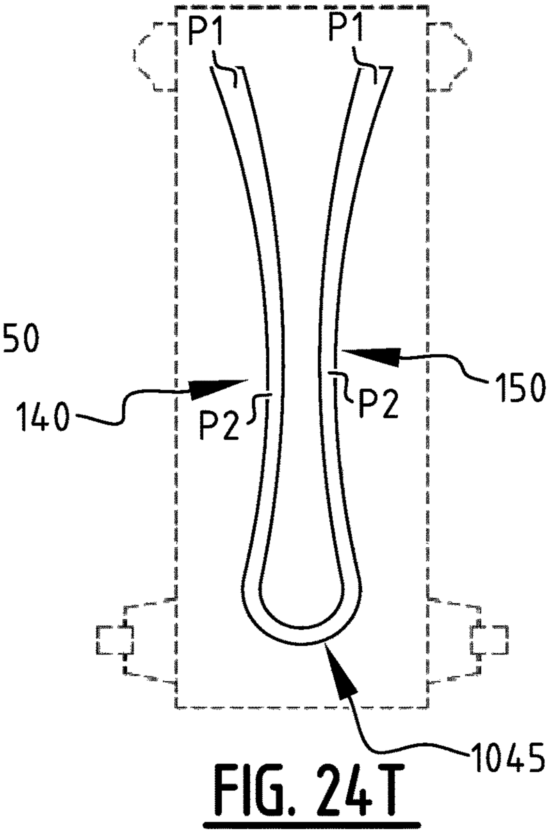
Figure 24U:
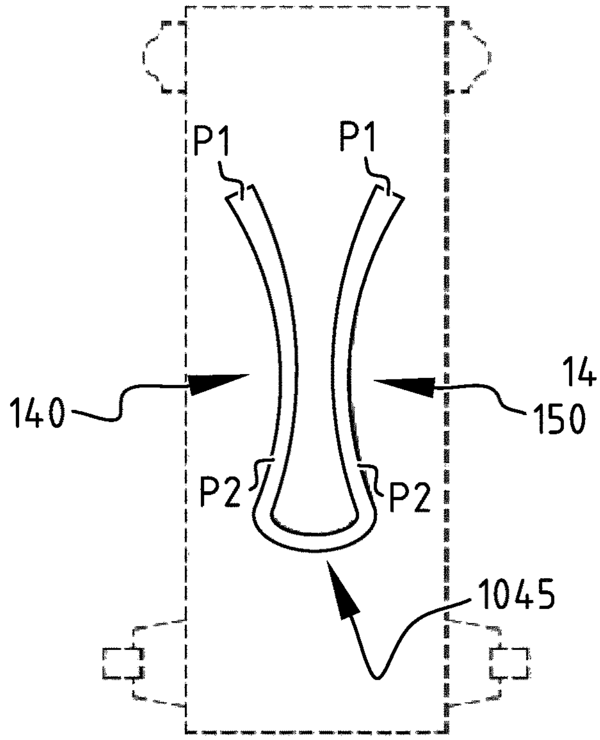
Figure 24W:
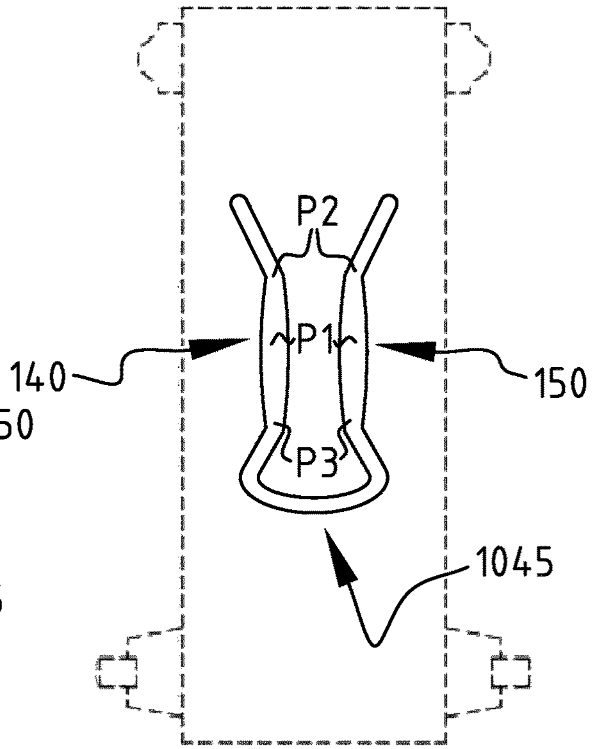
Figure 24V:
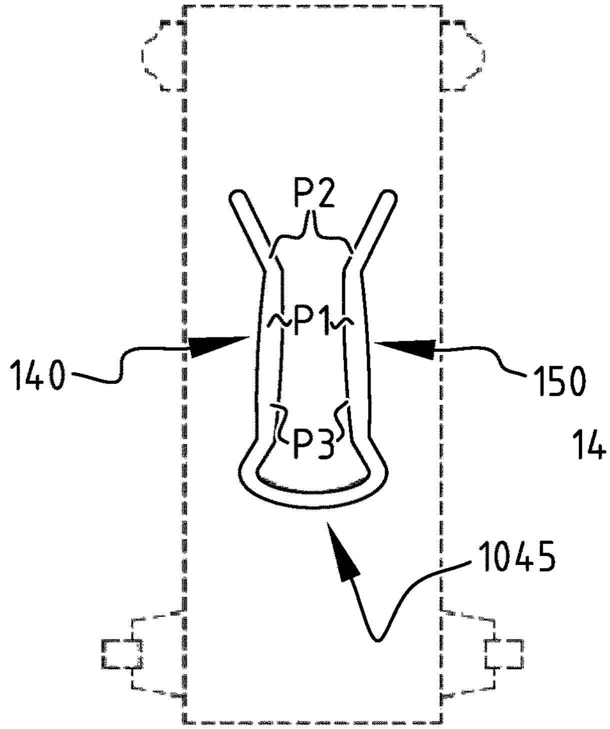
Figure 24X:
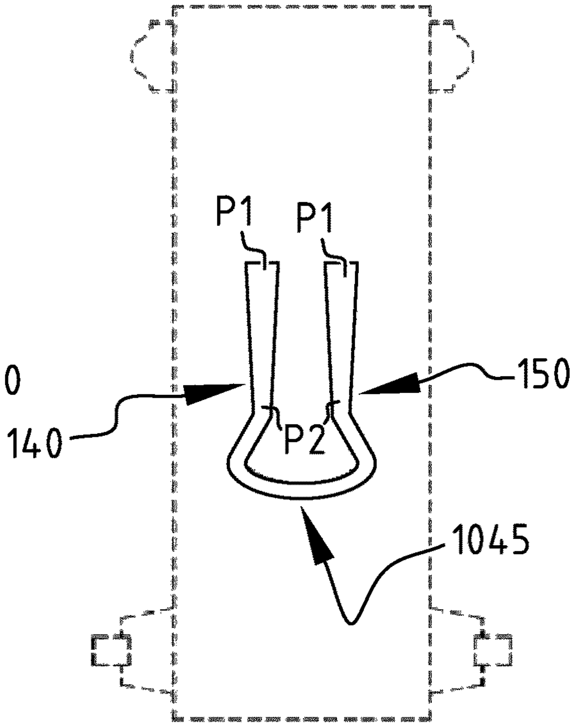
Figure 24Y:
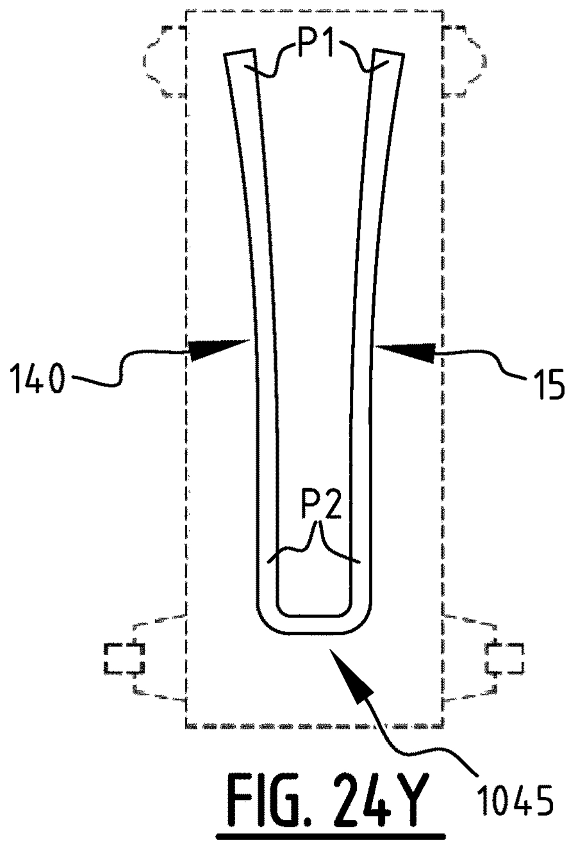
Figure 24Z:
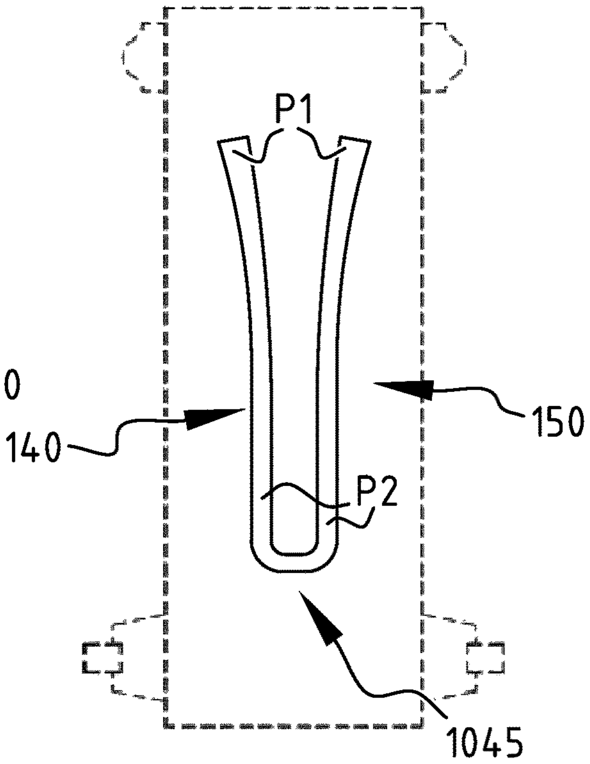

In the embodiments of FIGS. 22X-22Y, a transversal attachment zone 1045' connects the back ends of longitudinal attachment zones 140, 150. In the embodiments of FIGS. 23A-23F, 240-24Q, 25M-25P, there are two transversal attachment zones 1045 and 1045', respectively connecting the front and back ends of the longitudinal attachment zones 140, 150, 160, 170. In the embodiments of FIGS. 23N, 24N, 25U and 25V, there are two longitudinal attachment zones 140, 150 positioned toward the back side of the absorbent core which are connected by a transversal attachment zone 1045' at their front ends, as well as two longitudinal attachment zones 160, 170 positioned toward the front side of the absorbent core which are connected by a transversal attachment zone 1045 at their back ends.

In the embodiment of FIGS. 23A-23F, 24O-24Q, 25M-25P the first attachment zone 140, 160 (where present), the second attachment zone 150, 170 (where present) and two connecting attachment zones 1045, 1045' form together a substantially rectangular or O-shaped attachment zone. This substantially rectangular attachment zone comprises a first elongate attachment zone 140, 160 (where present), a second elongate attachment zone 150, 170 (where present), and two straight or curved connecting attachment zones 1045, 1045'. The first and second elongate attachment zone 140, 150, 160, 170 (where present) extend next to each other from the crotch region in the direction of the front transverse edge 133 and/or in the direction of the rear transverse edge 134, and more particularly in the fourth, third and second zone Z4, Z3 and Z2. The connecting attachment zone 1045 is a rear connecting attachment zone which connects a rear end portion of the first attachment zone 140, 160 (where present) to a corresponding rear end portion of the second attachment zone 150, 170 (where present). Preferably, the connecting attachment zone 1045 is located in the fourth zone Z4. The connecting attachment zone 1045' is a front connecting attachment zone which connects a front end portion of the first attachment zone 140 to a corresponding front end portion of the second attachment zone 150. Preferably, the connecting attachment zone 1045' is located in the second zone Z2. In that manner a convenient liquid distribution channel network is created allowing the liquid to be distributed rapidly throughout the absorbent core.

Figure 25A:
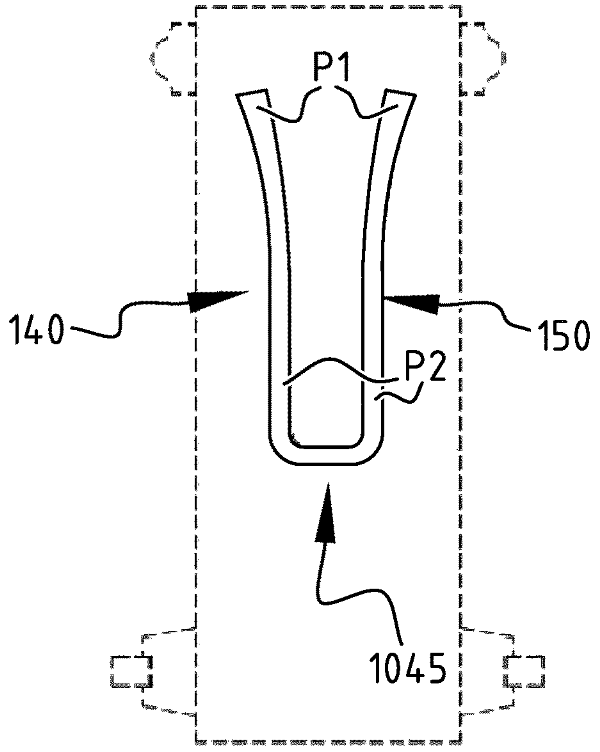
FIGS. 25A-25V illustrate yet other exemplary embodiments of an absorbent core according to the invention.
Figure 25B:
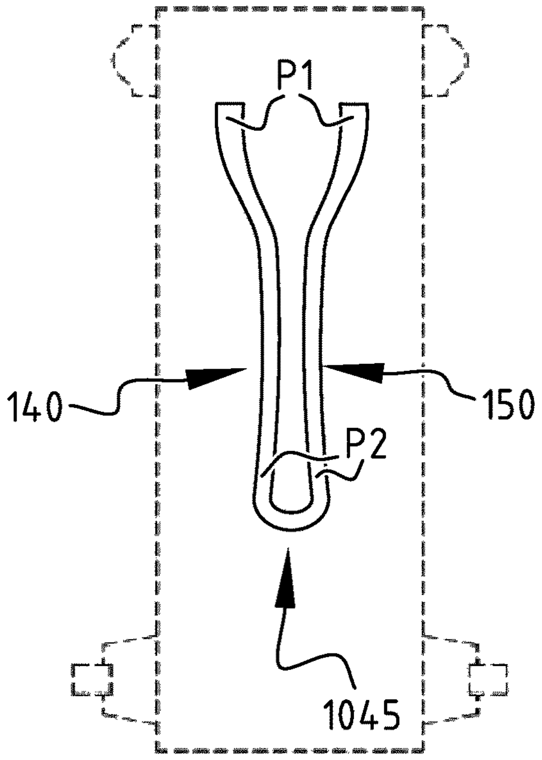
Figure 25C:
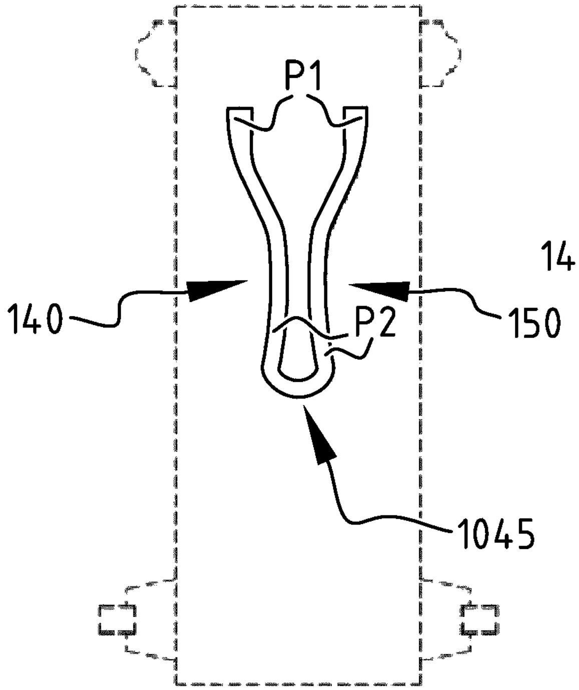
Figure 25D:
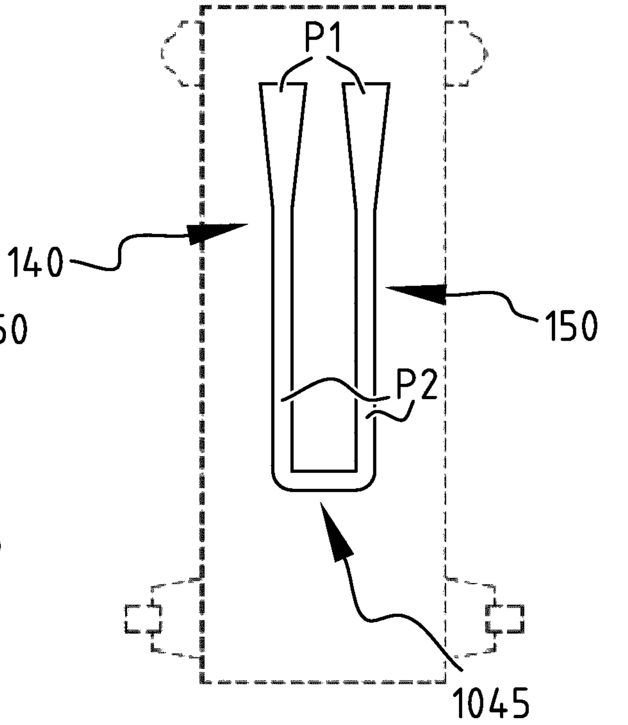
Figure 25E:
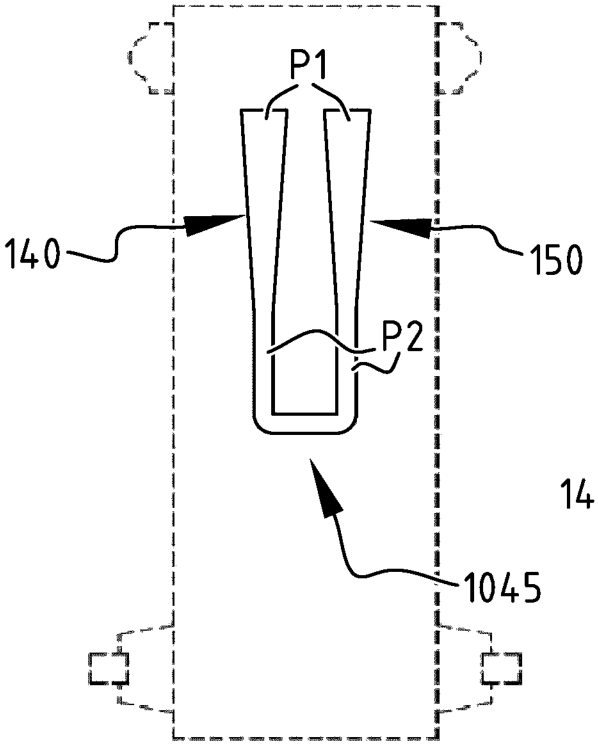
Figure 25F:
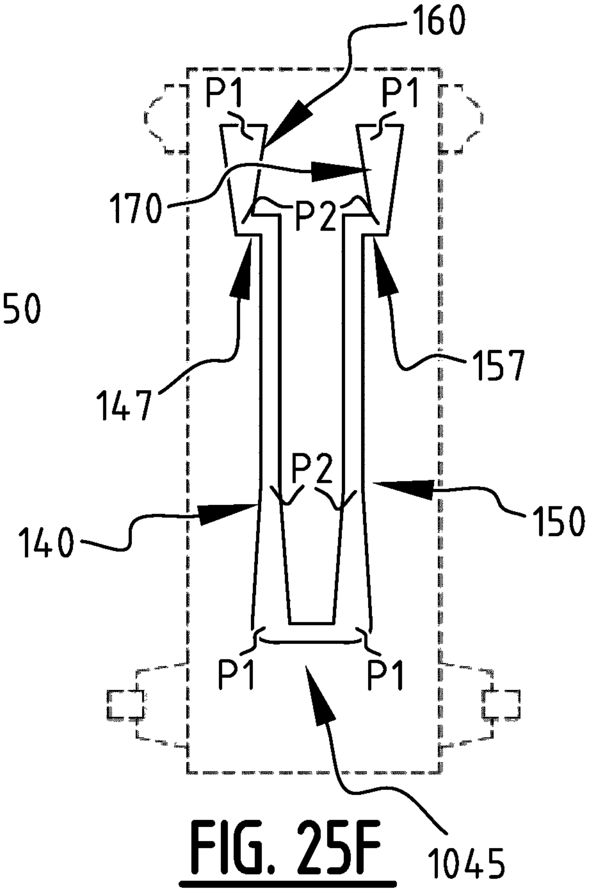
Figure 25G:
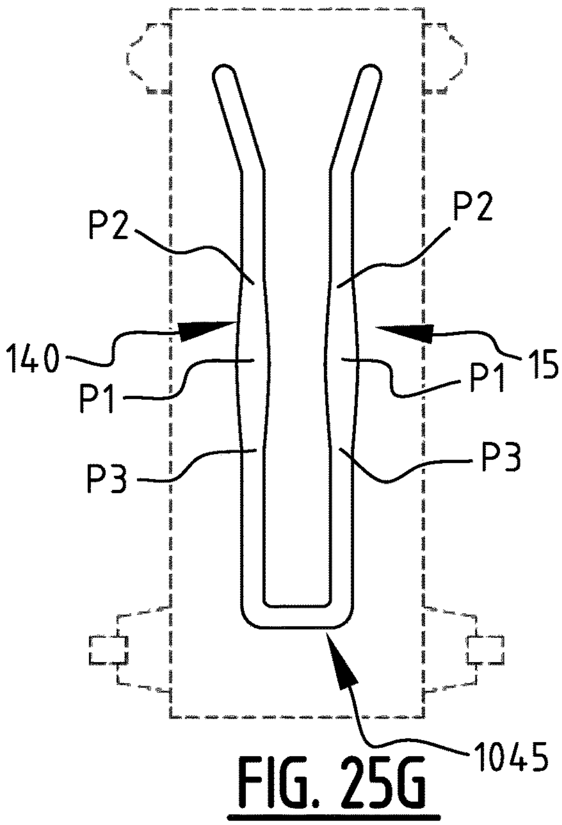
Figure 25H:
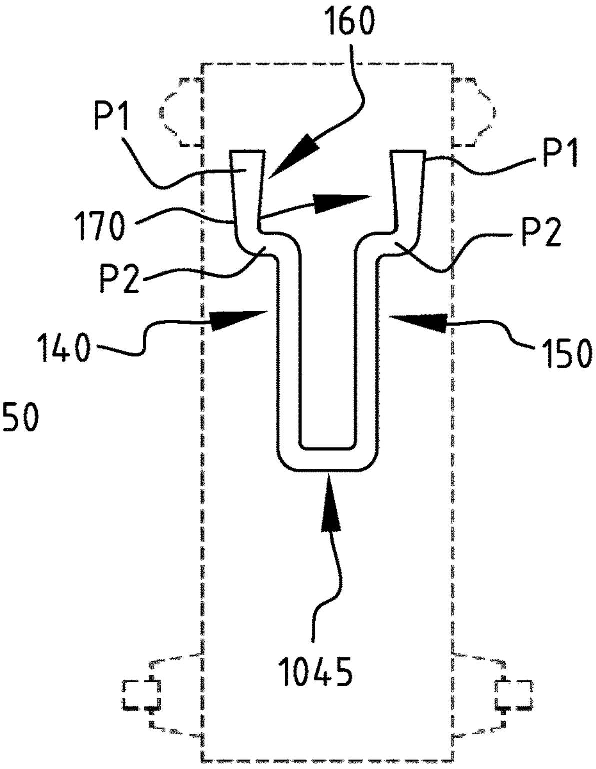
Figure 25I:
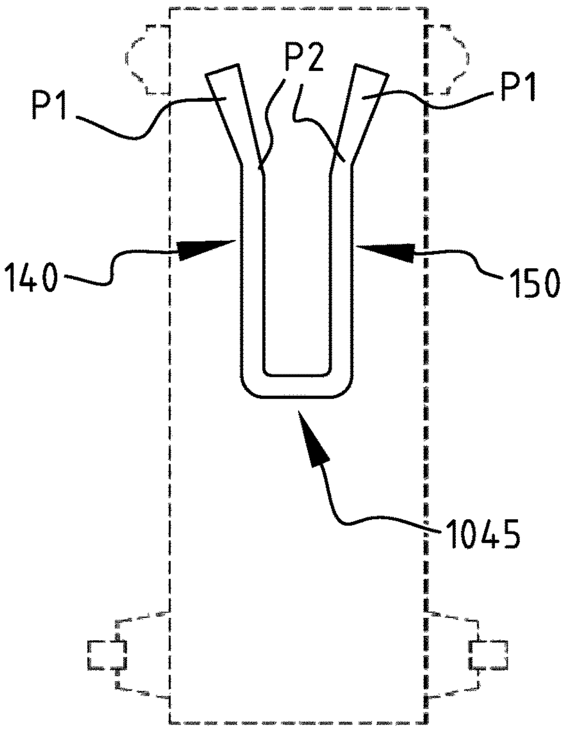
Figure 25J:
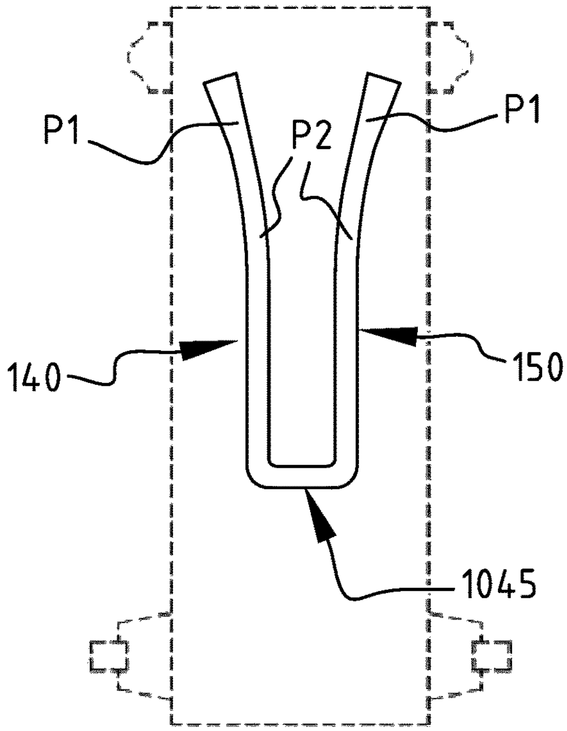
Figure 25K:
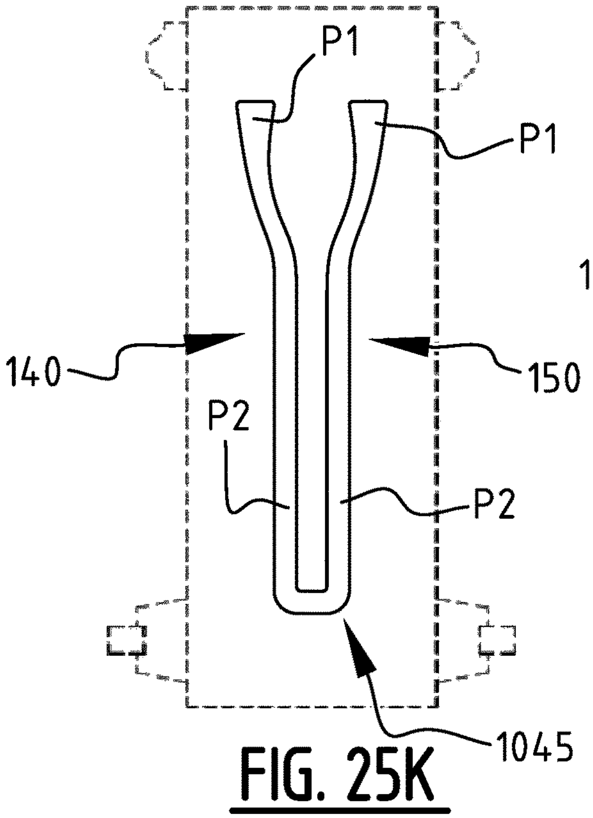
Figure 25L:
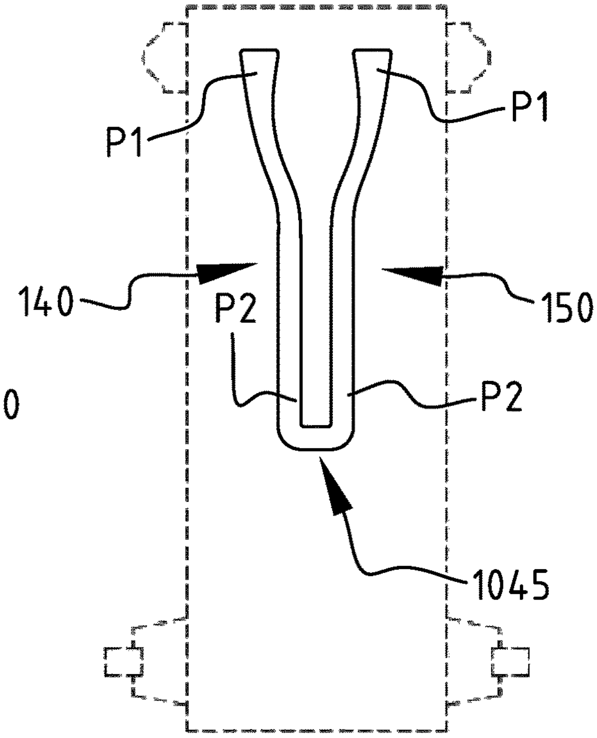
Figure 25M:
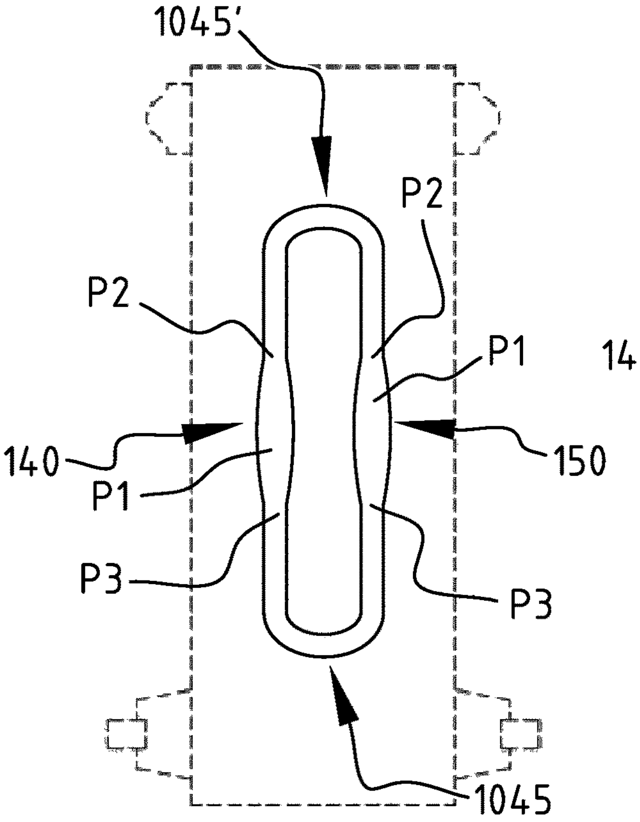
Figure 25N:
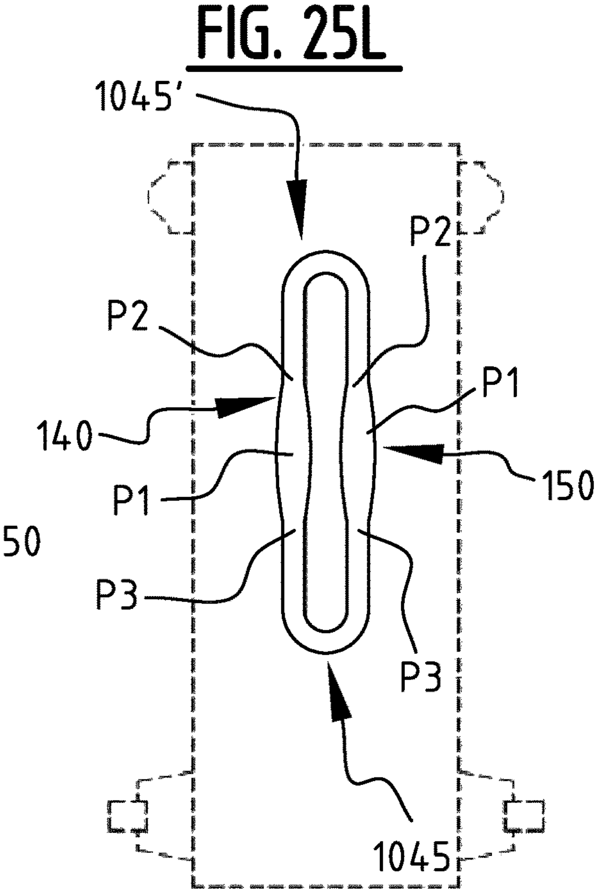
Figure 25O:
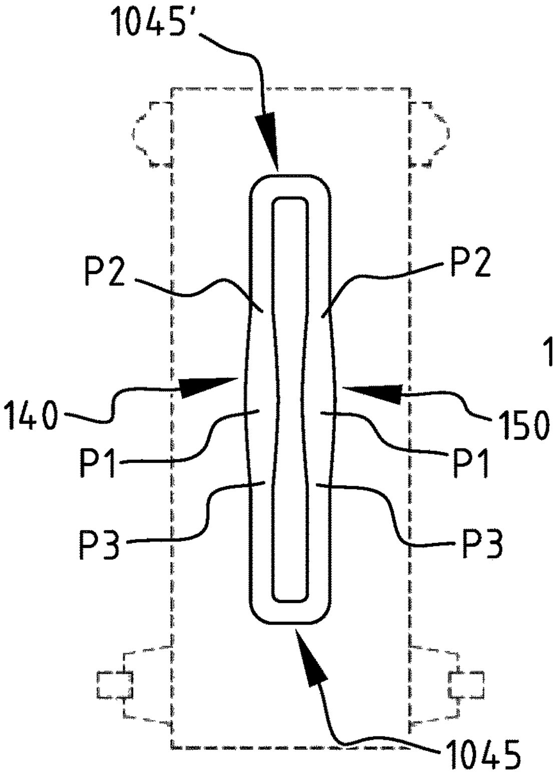
Figure 25P:
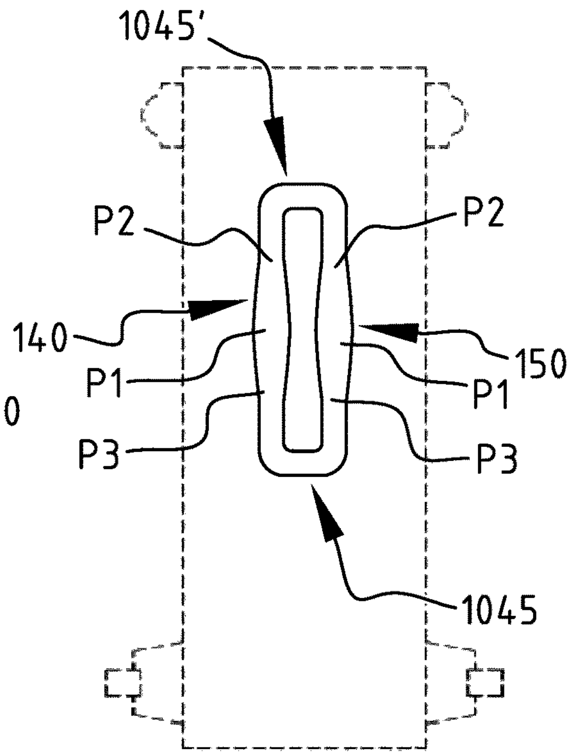
Figure 25Q:
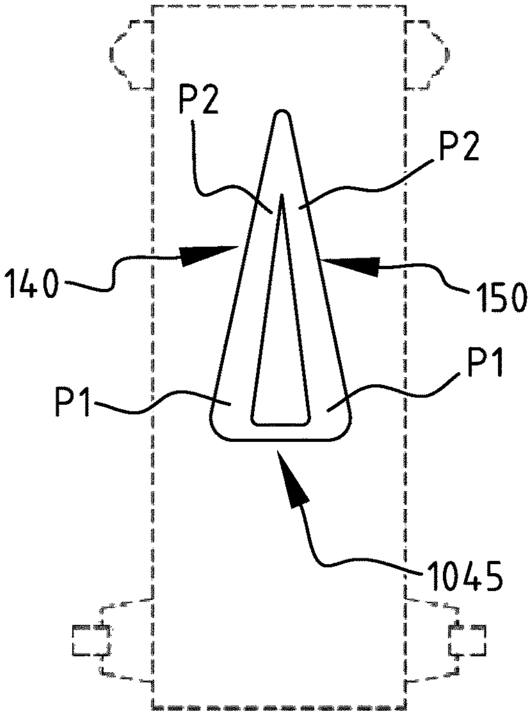
Figure 25R:
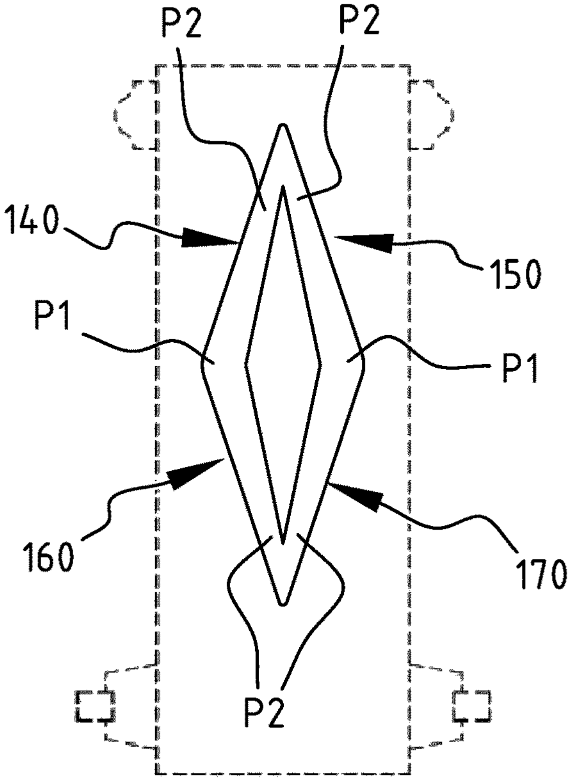
Figure 25S:
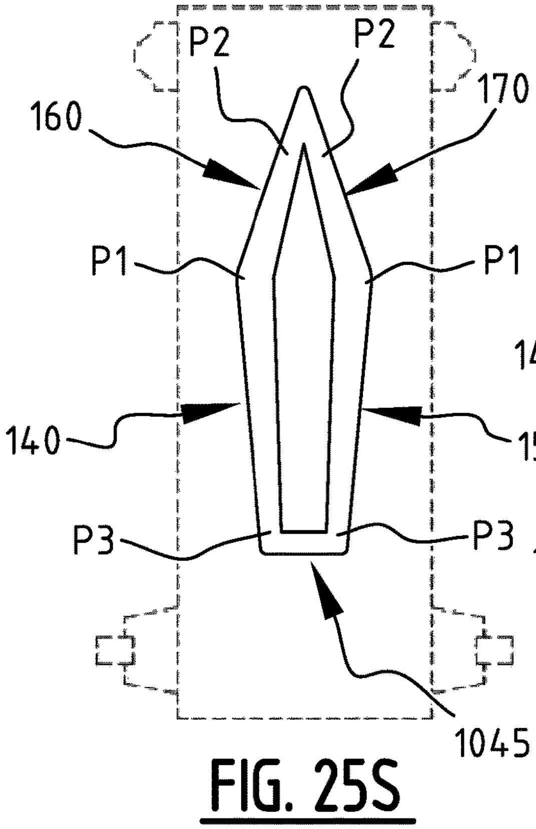
Figure 25T:
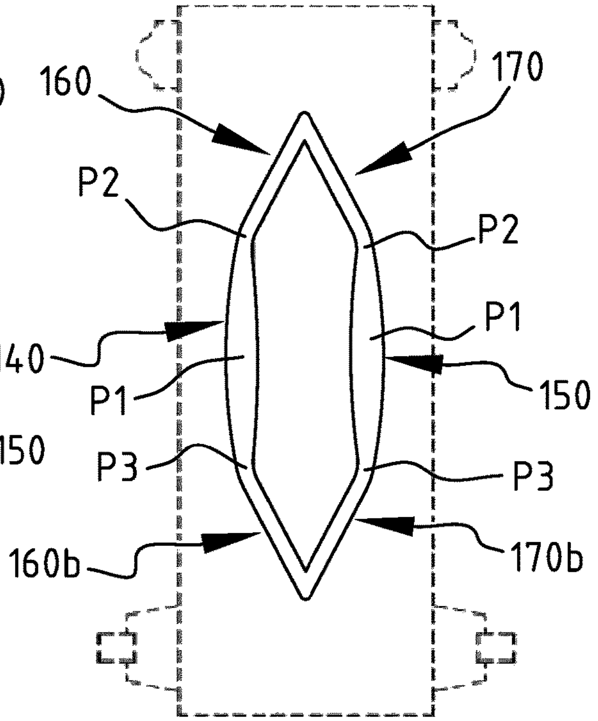
Figure 25U:
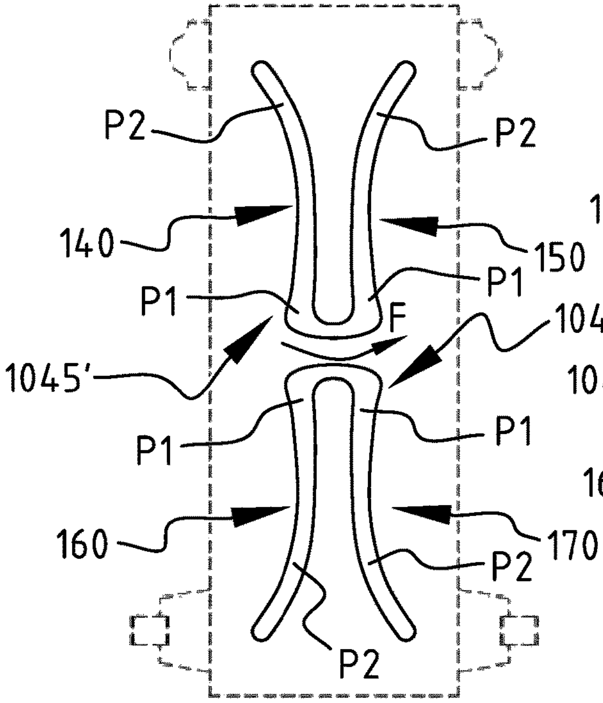
Figure 25V:
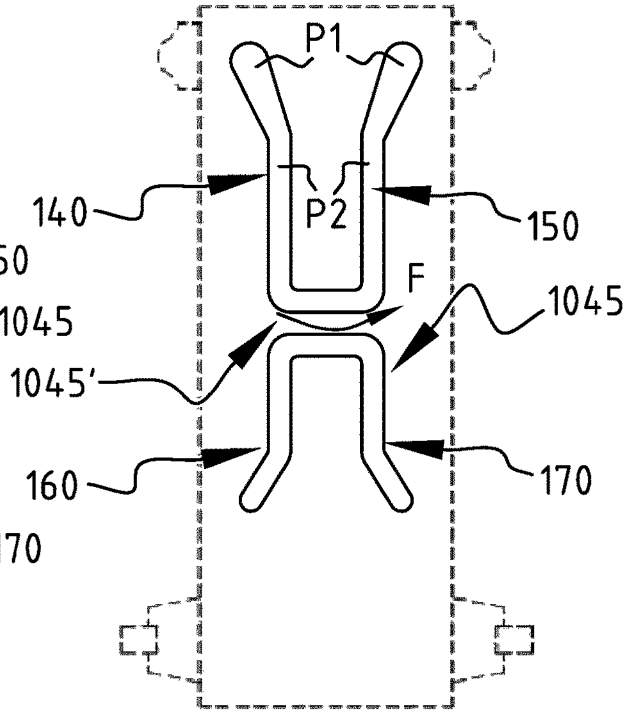

The connecting between the longitudinal channels need not be done with a transversal channel, but may also be achieved by shaping the longitudinal channels in a specific way. For example, in the embodiment of FIG. 25R, the four longitudinal attachment zones 140, 150, 160, 170 collectively form a diamond shape. Likewise, in the embodiment of FIG. 25T, six longitudinal attachment zones 140, 150, 160*a*, 170*a*, 160*b*, 170*c* are so connected as to form an elongated hexagon shape. Combinations of these two methods of connecting channels are also possible. In the embodiment of FIG. 25Q, the longitudinal attachment zones 140, 150 are connected at their front ends by a transversal attachment zone 1045 and converge to meet at their back ends. In the embodiment of FIG. 25S, longitudinal attachment zones 140 and 150 are connected by a transversal attachment zone 1045, while longitudinal attachment zones 160, 170, which are connected to zones 140, 150 respectively, converge at their back ends. The skilled person will be capable of envisaging other combinations and variations of the depicted embodiments.

The advantageous effect may be achieved even in cases wherein the longitudinal attachment zones are not directly connected, but merely approach each other in certain places. For example, in the embodiments of FIG. 22Z, 23J, 23T, the front ends of longitudinal attachment zones 140, 150 are connected by transversal attachment zone 1045, and the back ends of longitudinal attachment zones 160, 170 are shaped such that they approach one another. In other embodiments, such as the ones of FIG. 23U, 23Y, 24A-24C, the longitudinal attachment zones 140, 150, 160, 170 approach one another either at the ends or along their path, and this may, depending on the specific configuration, be sufficient to allow for liquid to go from one channel to another.

FIGS. 27A-27Z and FIGS. 26A-26T illustrate embodiments in which the dimensions of the longitudinal attachments zones 140, 150, 160, 170, 180 in the longitudinal direction have been reduced as compared to previously illustrated embodiments. Regarding the illustrated configurations of the shorter longitudinal attachments zones 140, 150, 160, 170, central attachments zones 180, 180*a*, 180*b*, 180*c* and transversal attachment zones 1045, 1045*a*, 1045*b*, 1045*c* as illustrated in FIGS. 27A-27Z and FIGS. 28A-28T, it is clear to the skilled person that the above described technical considerations and advantages in view of longer longitudinal attachments zones 140, 150, 160, 170, central attachments zones 180, 180*a*, 180*b*, 180*c* and transversal attachment zones 1045, 1045*a*, 1045*b*, 1045*c* as illustrated in the previous figures apply in a similar way, mutatis mutandis.

Figure 26A:
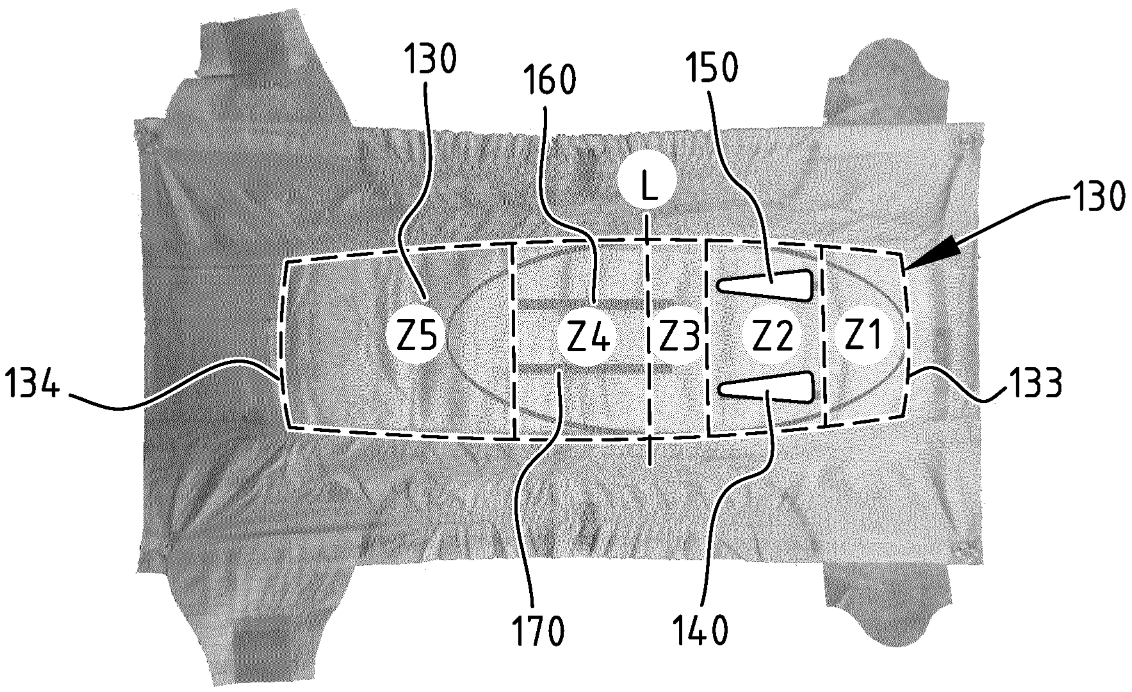
FIGS. 26A-26C are photographs of an exemplary embodiment of a diaper in a dry and wetted state.
Figure 26B:
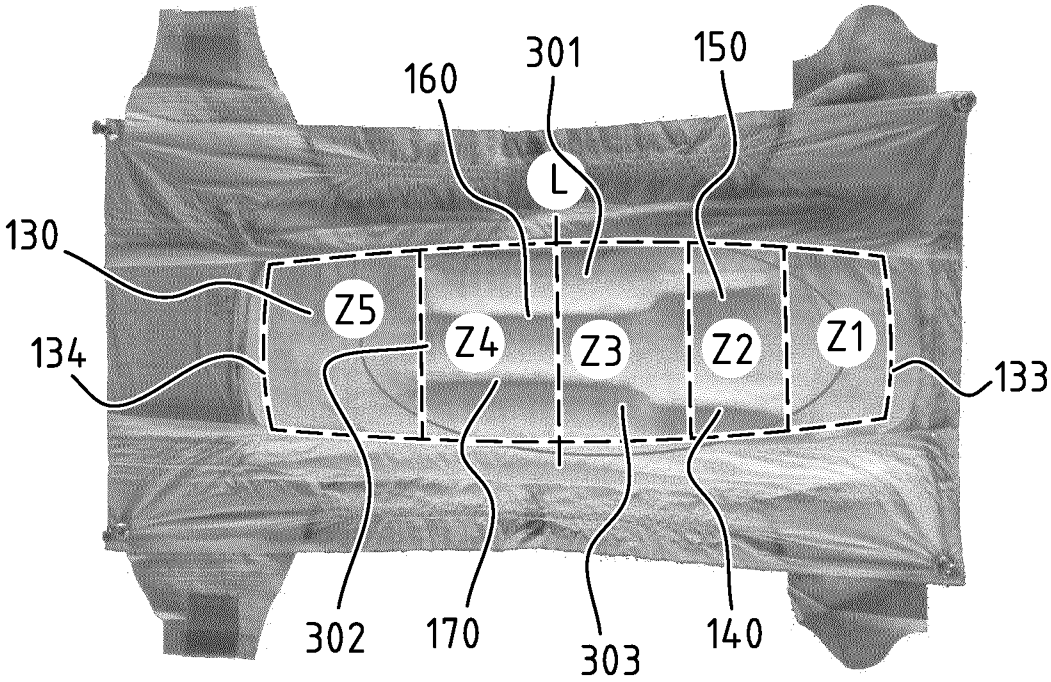
Figure 26C:
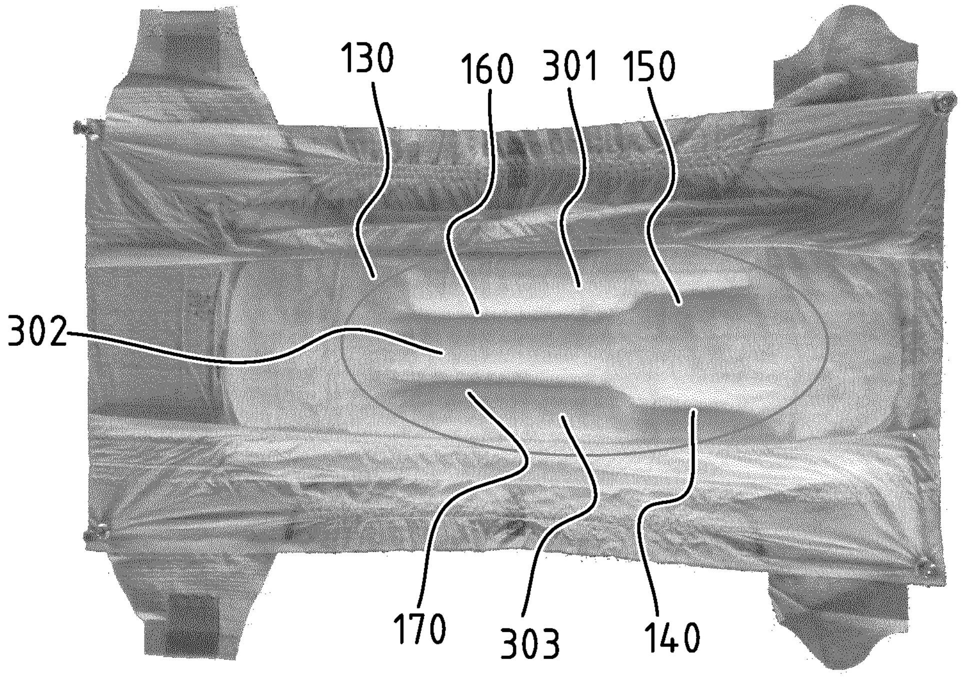
Figure 27A:
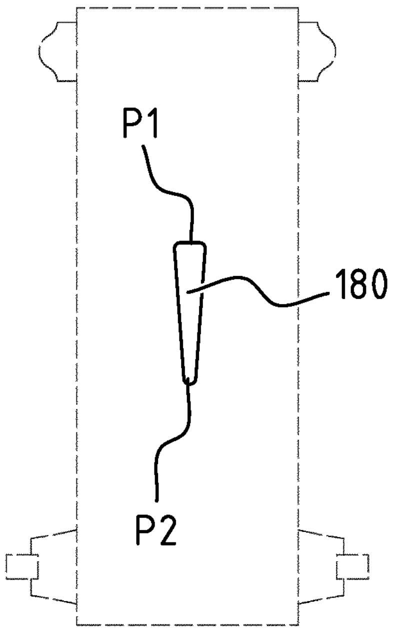
FIGS. 27A-27Z illustrate yet other exemplary embodiments of an absorbent core according to the invention.
Figure 27B:
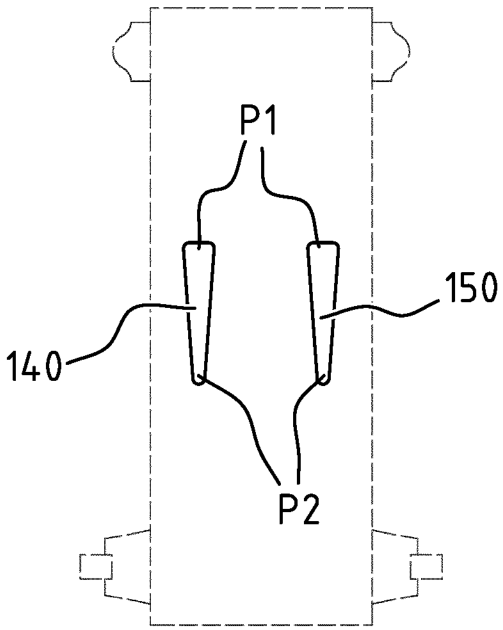
Figure 27C:
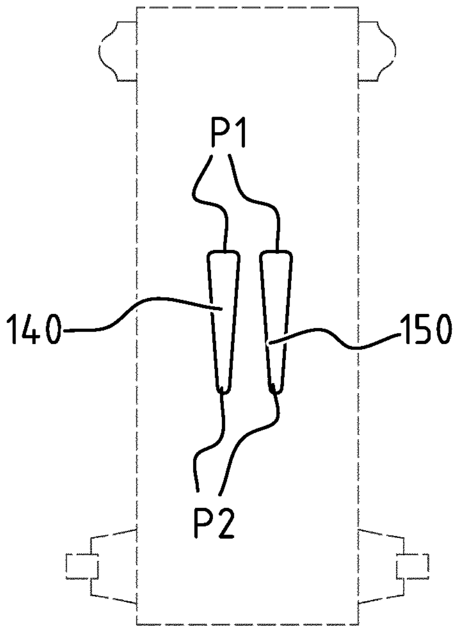
Figure 27D:
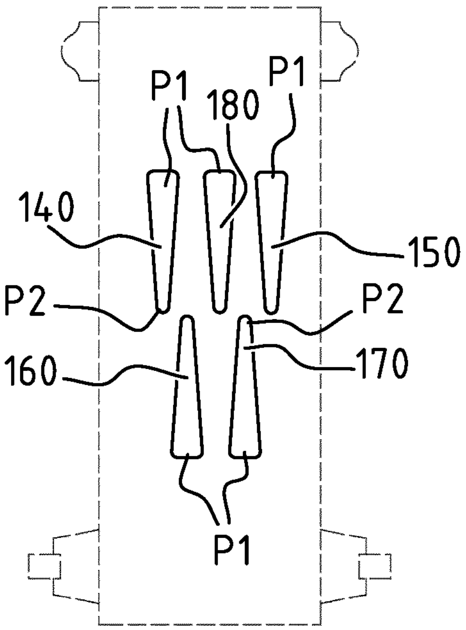
Figure 27E:
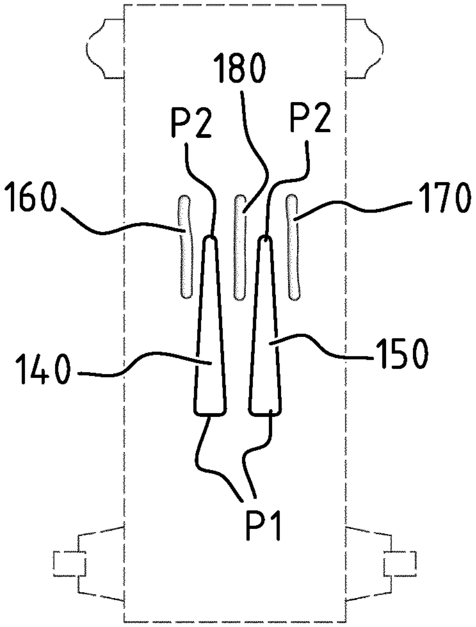
Figure 27F:
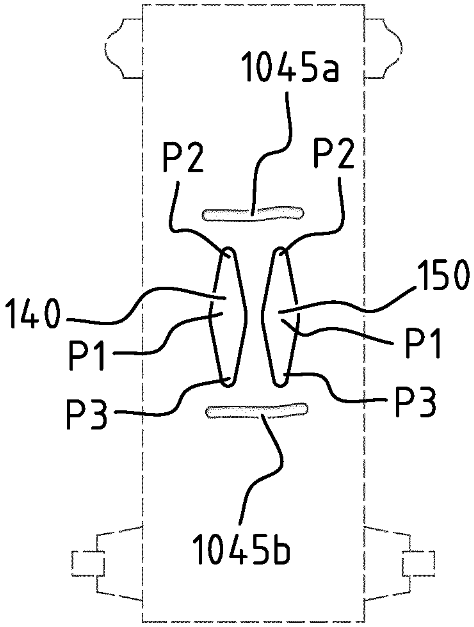
Figure 27G:
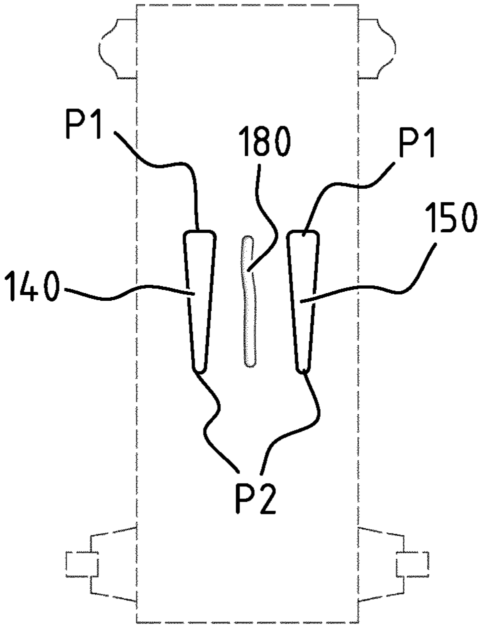
Figure 27H:
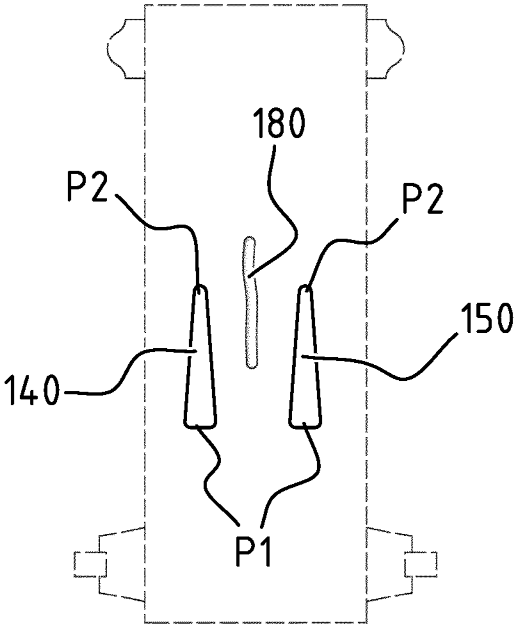
Figure 27I:
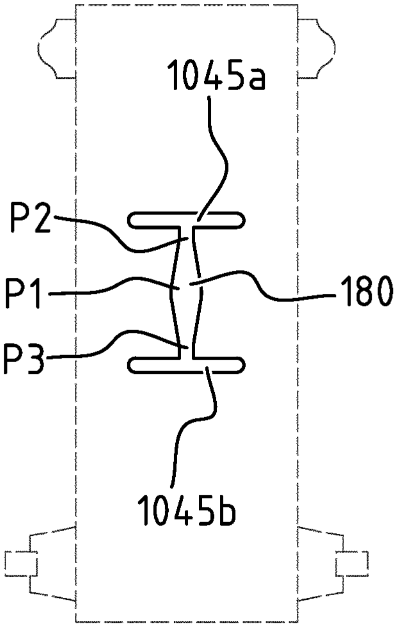
Figure 27J:
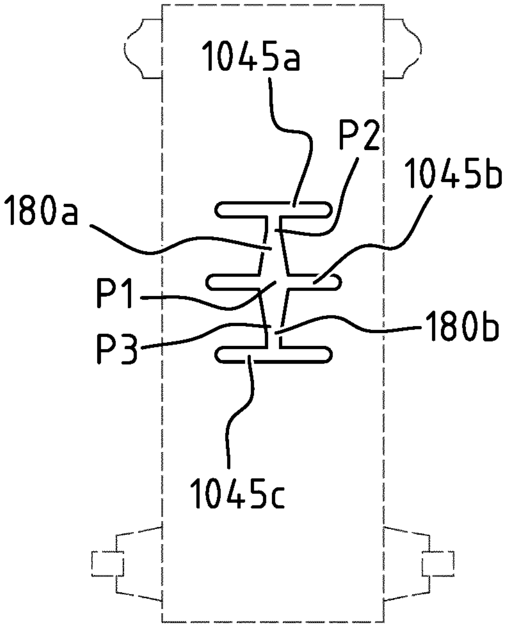
Figure 27K:
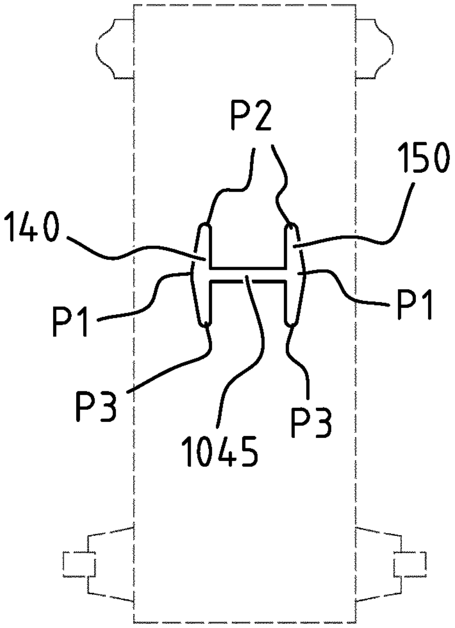
Figure 27L:
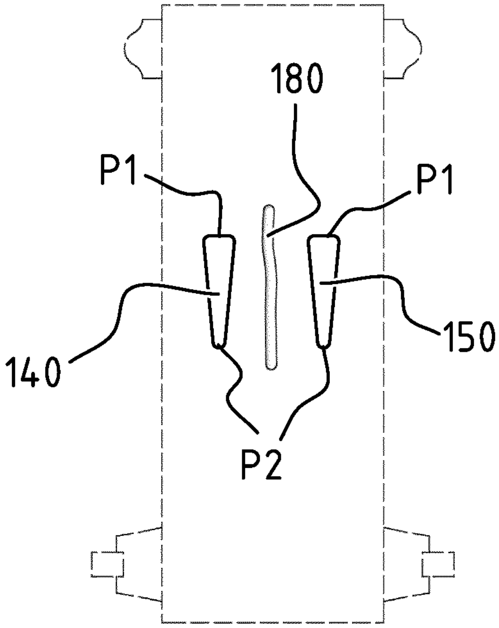
Figure 27M:
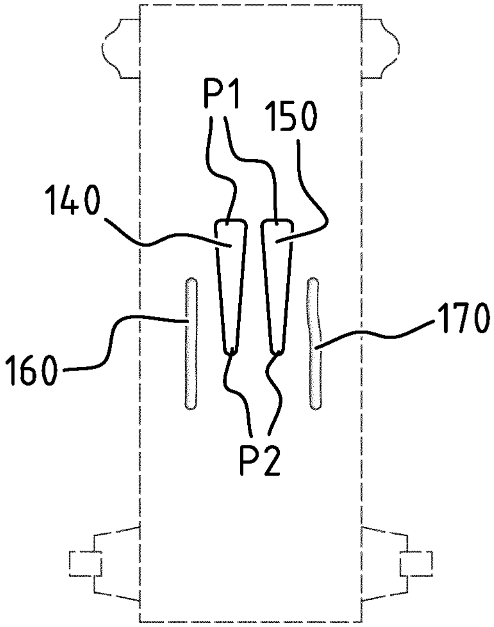
Figure 27N:
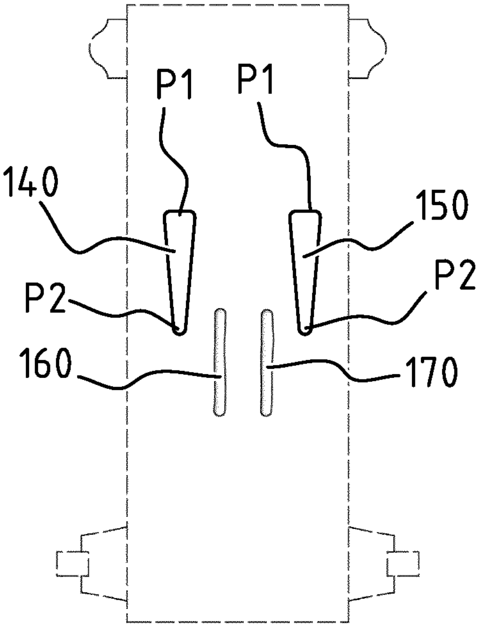
Figure 27O:
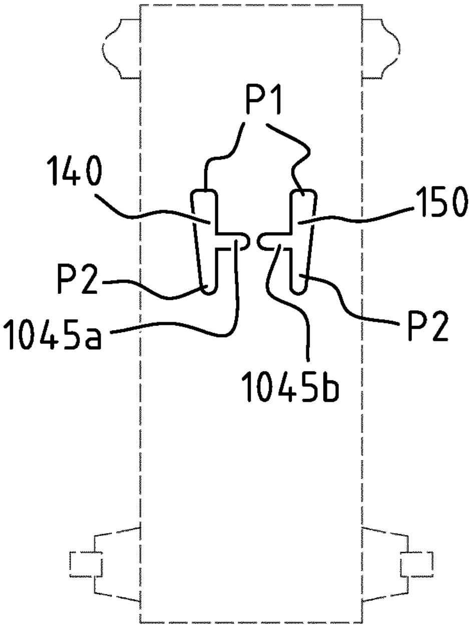
Figure 27P:
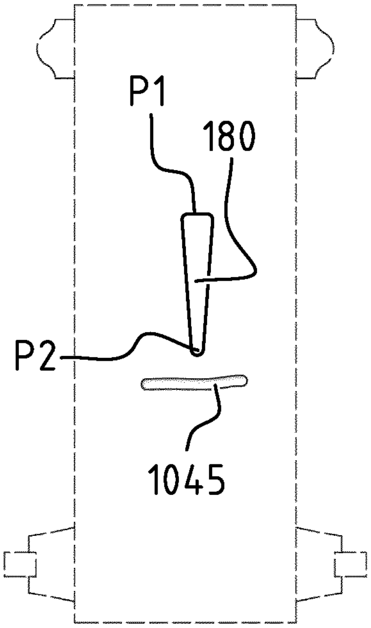
Figure 27Q:
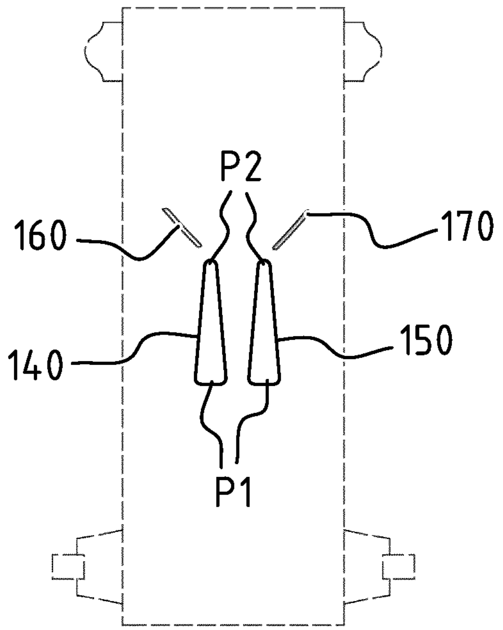
Figure 27R:
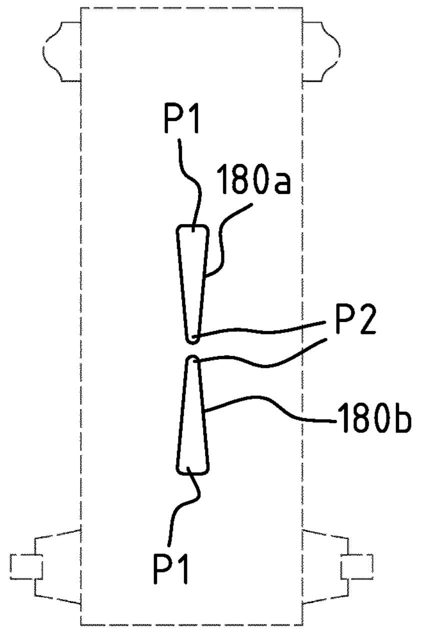
Figure 27S:
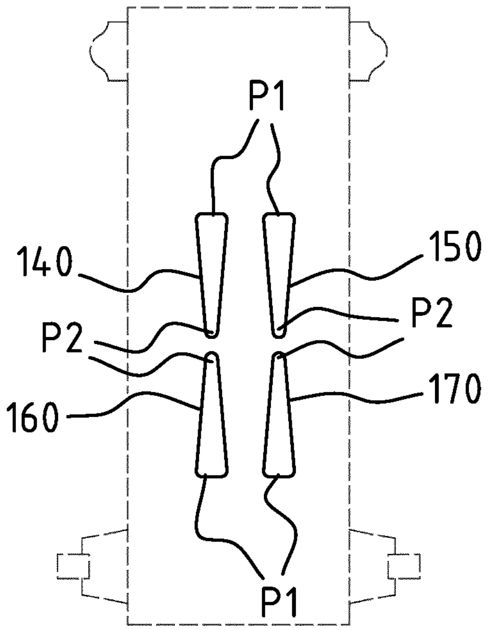
Figure 27T:
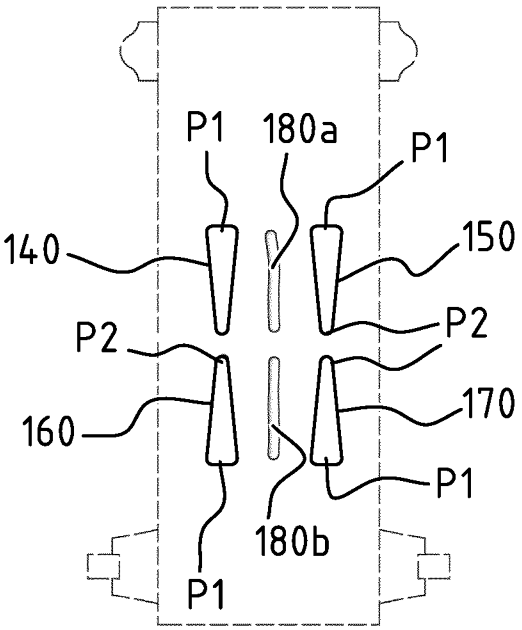
Figure 27U:
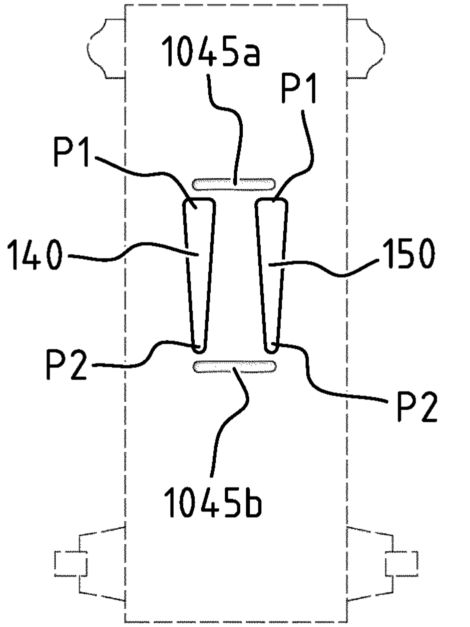
Figure 27V:
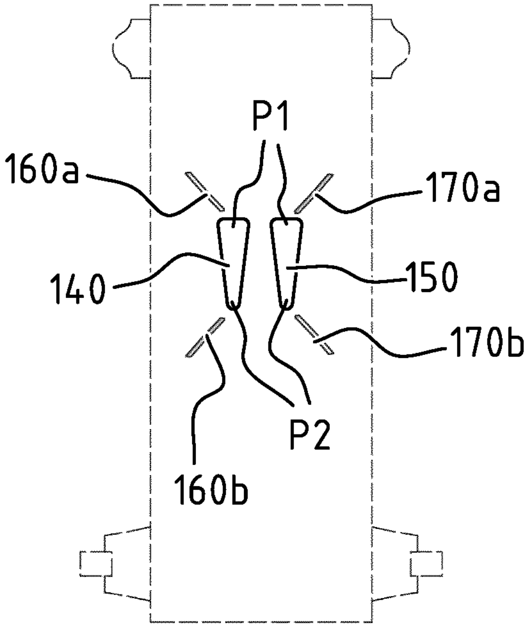
Figure 27W:
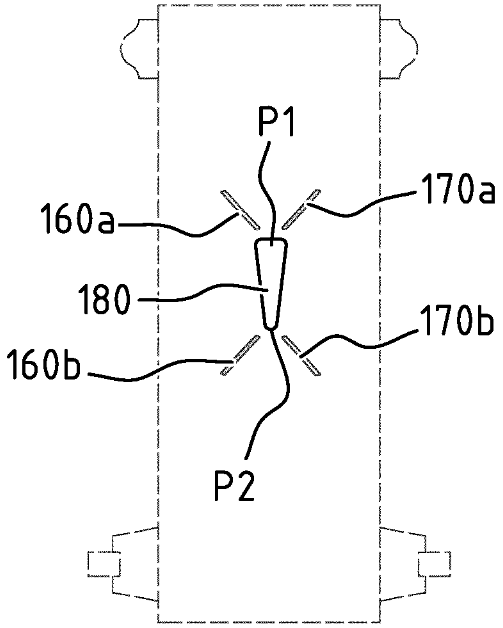
Figure 27X:
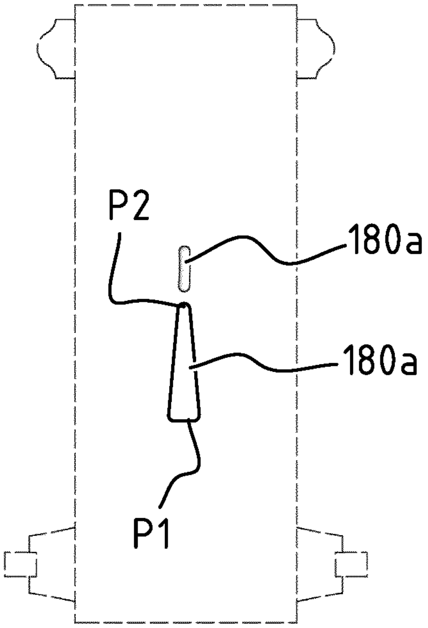
Figure 27Y:
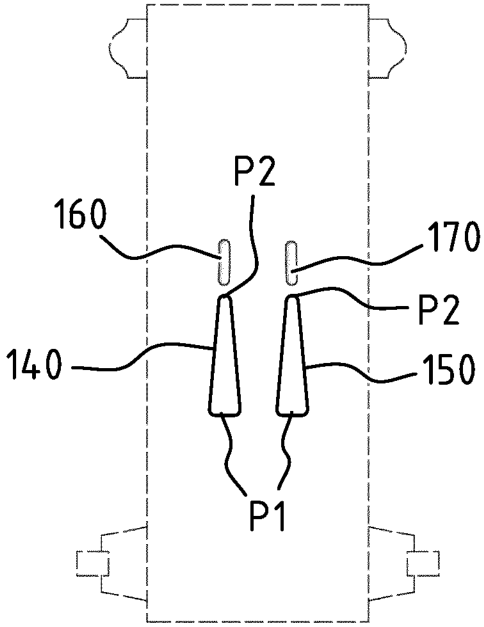
Figure 27Z:
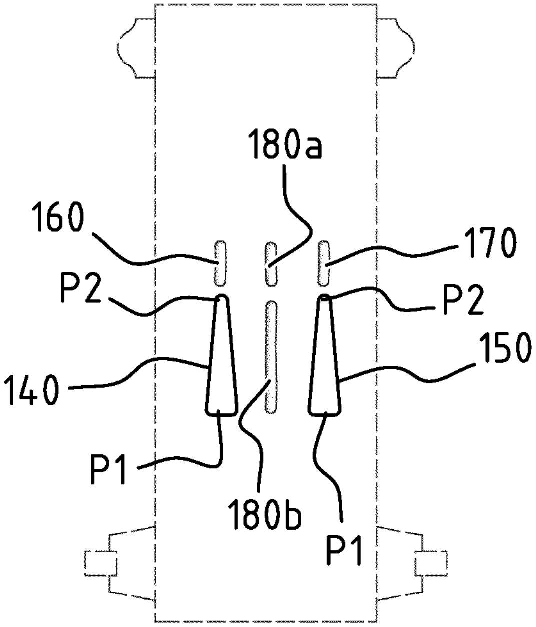

In addition to the perspective view as shown in FIG. 14, FIGS. 26A-C are photographs representing an absorbent article comprising an exemplary embodiment of an absorbent core of the invention. FIG. 26A illustrates the absorbent article when the absorbent core is in a dry state, whereas FIGS. 26B and 26C illustrate the absorbent article when the absorbent core is in a wetted state. In FIG. 26A attachments zones 140, 150, 160 and 170 wherein substantially no absorbent material is present, can be distinguished. However, in the illustrated photograph 26A the attachment zones 140, 150, 160 and 170 have been slightly darkened in order to better illustrate the position thereof, since due to quality restraints of the photograph 26A a part of this visual information has been lost. FIGS. 26B and 26C are photographs of the absorbent article in a wetted state, wherein tubes 301, 302, 303 have formed, which leads to the attachment zones 140, 150, 160 and 170 becoming more visible as channels. Thanks to the attachment zones and associated channels 140, 150, 160 and 170 the liquid is evenly spread, resulting in the formation of tubes 301, 302, 303 which provide a tub shape to the absorbent core 130. Such a tub shape adapts perfectly to the body and can be seen, at least partially, in FIG. 26C where the absorbent article is not attached to a bottom surface at the corners of the absorbent article, which is the case in FIGS. 26A and 26B. Further, compared to prior art solutions, the liquid is kept in an improved manner absorbed in the absorbent core 130, and the risk on leakage is reduced. Also, because of the creation of the channels 140, 150, 160, 170, the liquid is absorbed faster. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5. The zones may have the features of any one of the embodiments above.

Figure 29A:
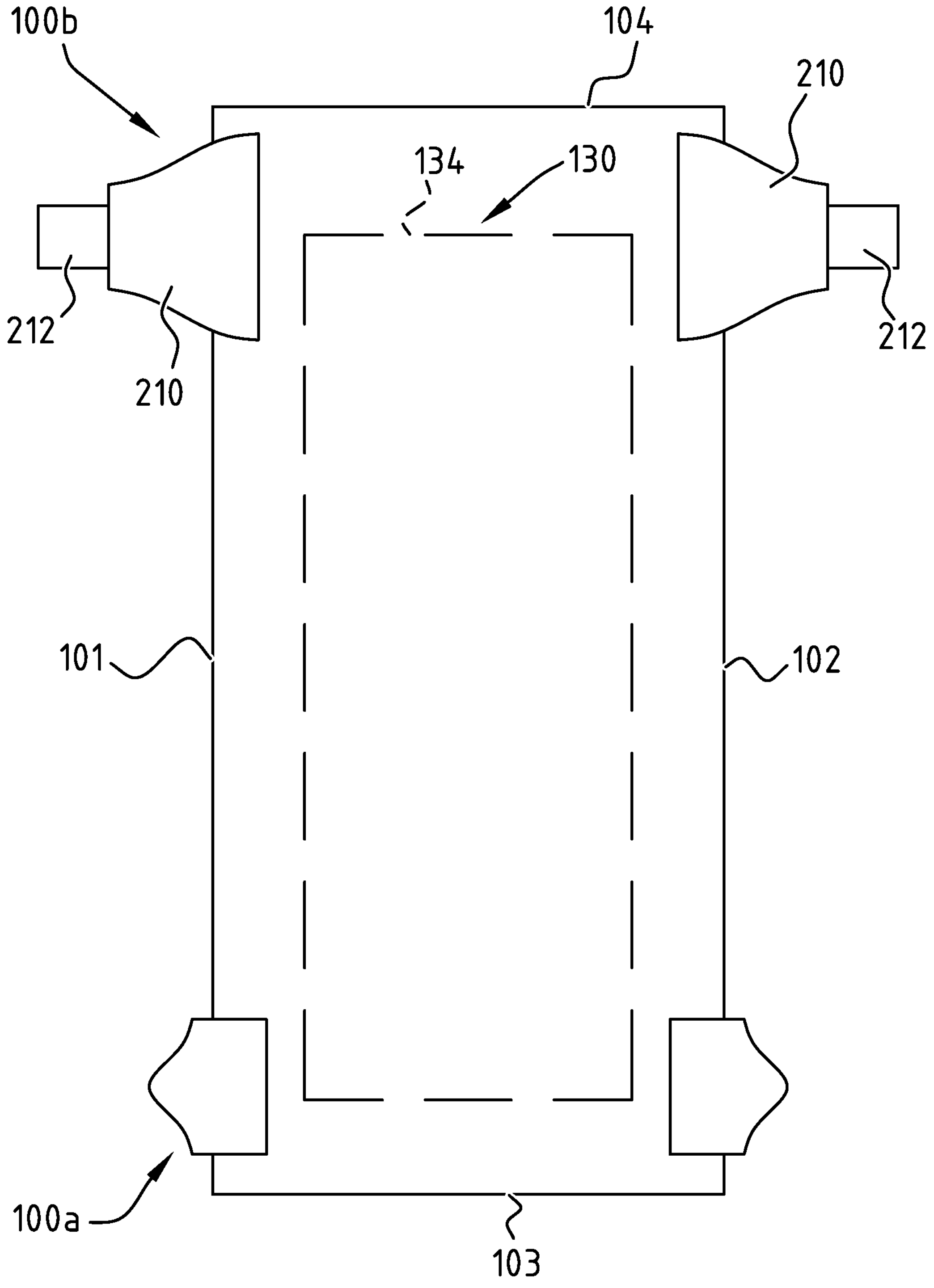
FIGS. 29A and 29B illustrate another exemplary embodiment of an absorbent article according to the invention.

FIG. 29A illustrates a top view of an absorbent article, here a diaper 100, in its flat out, un-contracted state with the wearer side facing the viewer. The skilled person understands that the absorbent article may also be a pant or an adult incontinence garment or the like. Preferably the chassis includes side panels or ears 210, elasticized leg cuffs and elastic waist elements. A front end portion of diaper 100 is configured as a front waist region 100*a*. The opposite rear end portion is configured as a back waist region 100*b* of diaper 100. Waist regions 100*a* and 100*b* may include elastic waist elements such that they gather about the waist of the wearer to provide improved fit and containment. The periphery of diaper 100 is defined by the outer edges of the diaper 100 in which longitudinal edges 101, 102 run generally parallel to a longitudinal axis of diaper 100 and transverse end edges 103, 104 run between the longitudinal edges 101, 102 generally parallel to a transverse axis of diaper 100. The chassis also comprises a fastening system, which may include at least one fastening or securing member 212 and at least one landing zone (not visible). The various components within diaper 100 may be bound, joined or secured by any method known in the art, for example by adhesives in uniform continuous layers, patterned layers or arrays of separate lines, spirals or spots. Top core wrap sheet, topsheet, back core wrap sheet, backsheet, absorbent material and other components may be assembled in a variety of well-known configurations and are well known in the art.

Figure 29B:
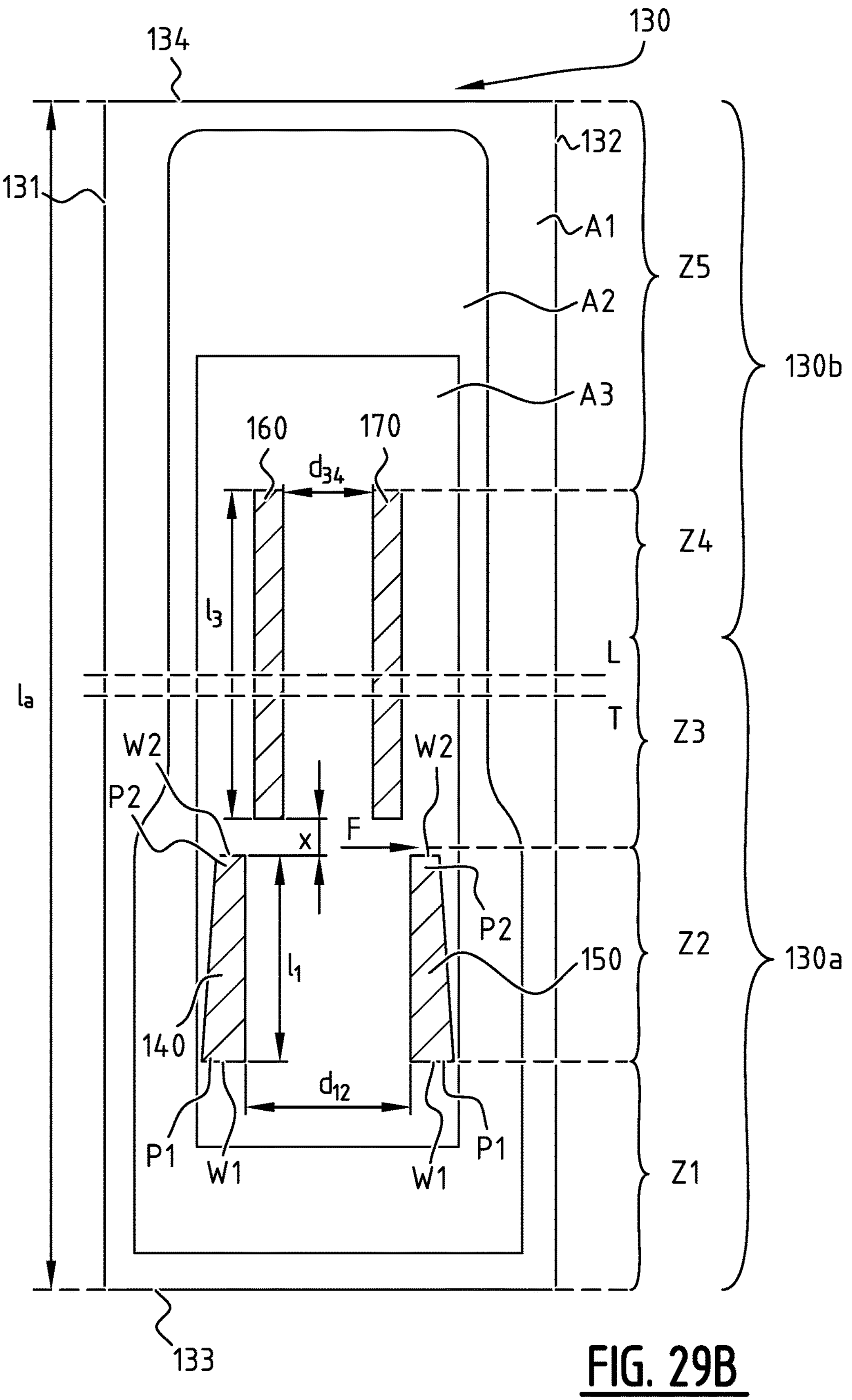

FIG. 29B illustrates the absorbent core 130 of the absorbent article of FIG. 29A. The absorbent article 100 comprises a liquid pervious topsheet, a liquid impervious backsheet, and the absorbent core 130 positioned in between the topsheet and the backsheet. The absorbent core 130 comprises absorbent material between a top core wrap sheet and a back core wrap sheet, in a similar manner as described in the other embodiments. Absorbent core 130 has a first and second side edge 131, 132, a front edge 133 and a rear edge 134, wherein the absorbent core is provided with a plurality of attachment zones 140, 150, 160, 170 where the top core wrap sheet is attached to the back core wrap sheet, and where preferably substantially no absorbent material is present. The first and second attachment zone 140, 150 has a first width w1 at a first position P1 and a second width w2 at a second position P2. The first width is larger than the second width, and the width of the first attachment zone increases from the second position to the first position. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130*a* extending between the front edge 133 and a transverse crotch line L of the absorbent core, and a rear portion 130*b* extending between the rear edge 134 and the transverse crotch line L of the absorbent core 130. The first, second and third zone Z1, Z2, Z3 extend in the front portion of the absorbent core and the fourth and fifth zone Z4, Z5 extend in the rear portion. Preferably, in said first and fifth zone substantially no permanent attachment zones are present. The second zone Z2 comprises a first and a second permanent elongate front attachment zone 130, 140, said first and second front attachment zones 130, 140 extending from an edge of the first zone Z1 in the direction of the third zone Z3.

The fourth and third zone comprises a first and second rear elongate attachment zone 160, 170, said first and second rear attachment zone extending from an edge of the fifth zone Z5 in the direction of the third zone Z3. At least one of said second, third and fourth zone comprises a bridge zone B allowing a liquid flow F between the first and the second side edge 131, 132 by capillary action through the absorbent material. The bridge zone B extends between the first front attachment zone 140 and the first rear attachment zone 160, such that upon wetting of the absorbent material, a front and rear channel are created at said first front and rear attachment zone 140, 160, respectively, wherein the bridge zone B extends between said front and rear channel. Preferably a minimum distance x between the first front attachment zone 140 and the first rear attachment zone 160 is larger than 3 mm more preferably larger than 5 mm. The bridge zone B further extends between the second front attachment zone 150 and the second rear attachment zone 170, such that upon wetting of the absorbent material, a front and rear channel are created at said second front and rear attachment zone 150, 170, respectively, wherein the bridge zone B further extends between said front and rear channel. Preferably a minimum distance x between the second front attachment zone 150 and the second rear attachment zone 170 is larger than 3 mm more preferably larger than 5 mm.

The first and second rear elongate attachment zones 160, 170 extend from the fourth zone into the third zone Z3 so that an absorbent article is formed that fits well to the body of the wearer. Preferably a distance between the transverse crotch line L and a transverse center line T extending perpendicular on the longitudinal direction of the absorbent core, through the middle of the absorbent core, is smaller than 10%, more preferably smaller than 5% of the length of the absorbent core.

The first zone Z1 extends over a length corresponding with at least 5%, preferably at least 10% of the length la of the absorbent core seen in the longitudinal direction, e.g. between 10% and 20%. The fifth zone Z5 extends over a length corresponding with at least 10% of the length la of the absorbent core seen in the longitudinal direction, preferably at least 20%, more preferably at least 25%, e.g. between 20% and 40%.

Preferably the second, the third and/or the fourth zone Z1, Z2, Z3 each extends over a length corresponding with at least 10% of the length la of the absorbent core seen in the longitudinal direction, preferably at least 15%, e.g. between 10% and 20% of the length of the absorbent core.

Preferably the first front attachment zone 140 and the second front attachment zone 150 are arranged symmetrically with respect to a longitudinal center axis CL of the absorbent core 130. Preferably the distance d12 between the first and the second attachment zone is between 20 mm and 70 mm, more preferably between 30 mm and 60 mm, even more preferably between 40 mm and 55 mm. As explained in the summary, such a configuration is especially suitable for male persons.

Preferably the first rear attachment zone 160 and the second rear attachment zone 170 are arranged symmetrically with respect to the longitudinal center axis CL of the absorbent core. Preferably the distance d34 between the first and the second rear attachment zone 160, 170 is between 10 mm and 50 mm, more preferably between 15 mm and 40 mm, even more preferably between 20 mm and 30 mm.

The bridge zone B extends from a first portion of the absorbent core, in the second and/or third zone Z2, Z3, to a second portion of the absorbent core, in the second and/or third zone, wherein the first portion is defined between the first side edge 131 and the longitudinal center axis CL of the absorbent core 130 and the second portion is defined between the second side edge 132 and the longitudinal center axis CL of the absorbent core 130. The bridge zone B may comprise temporary attachments between the top and back core wrap sheet which are configured to detach when wetted.

A first smallest distance d12 between the first and the second front attachment zone 140, 150 is bigger than a second smallest distance d34 between the first and the second rear attachment zone 160, 170. The first and the second front attachment zone 140, 150 extend in a longitudinal direction of the absorbent core over a length l1 which is less than the length l3 of the first and second rear attachment zone. Preferably, the length of the first and second front attachment zone 140, 150 is larger than 30 mm, more preferably larger than 40 mm, even more preferably larger than 50 mm.

The plurality of attachment zones 140, 150, 160, 170 may be permanent attachment zones which remain attached when wetted. The plurality of attachment zones may extend, seen in the transverse direction of the absorbent core, over the transverse distance which is at least 1 mm, preferably at least 3 mm, more preferably at least 4 mm, even more preferably at least 5 mm, most preferably at least 6 mm.

Preferably, the length of the first/second front attachment zone 140, 150 is larger than 5% of the length of the absorbent core; preferably larger than 10%, more preferably larger than 15%; and/or wherein the length of the first/second rear attachment zone 160, 170 is larger than 5% of the length of the absorbent core, preferably larger than 10%, more preferably larger than 15%. Preferably the length of the first/second front attachment zone is at least 10%, more preferably at least 25%, even more preferably at least 35%, or even at least 50 or 75% of the length of the first rear attachment zone.

Preferably the distance between the first and the second front attachment zone 140, 150 is between 15 and 70% of the width of the absorbent core (measured perpendicular on the length la), more preferably between 20 and 50%. Preferably the distance between the first and the second rear attachment zone 160, 170 is between 5 and 60% of the width of the absorbent core, more preferably between 10 and 40%.

The areas A1, A2, A3 indicated in FIG. 29B may have a different amount of absorbent material/absorbent capacity per surface area. Preferably the central area A3 has a larger amount of absorbent material/capacity per surface area than the intermediate area A2. Preferably, the intermediate area A2 has a larger amount of absorbent material/capacity per surface area than a circumferential area A1.

Features described above for other embodiments described above may apply in a similar manner for the embodiment of FIGS. 29A and 29B.

Figure 30A:
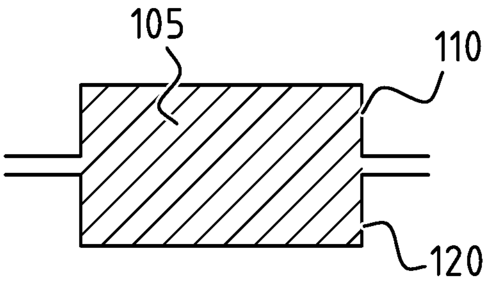
FIGS. 30A-30F illustrate different embodiments of a top core wrap sheet and/or bottom core wrap sheet of an absorbent core.
Figure 30B:
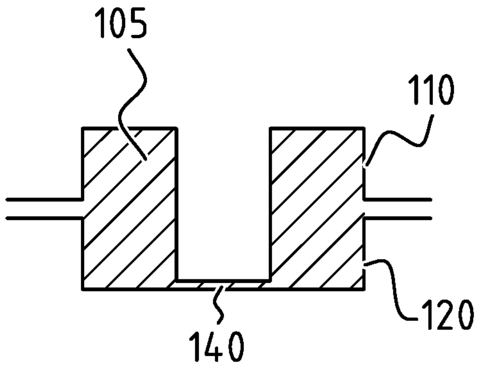
Figure 30C:
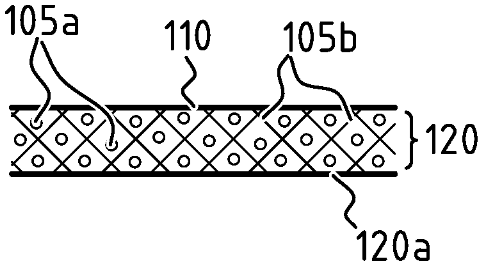
Figure 30D:
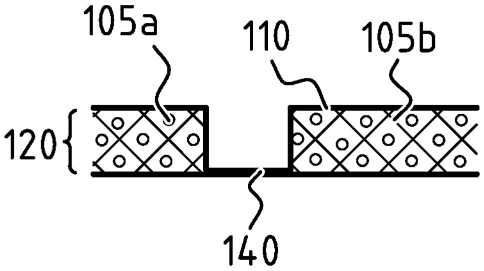
Figure 30E:
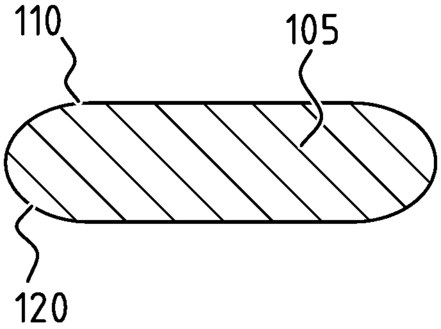
Figure 30F:
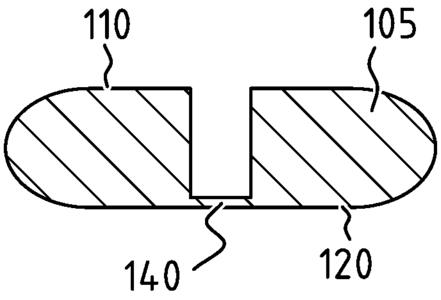

FIGS. 30A, 30C and 30E illustrate different embodiments of a top core wrap sheet 110 and/or bottom core wrap sheet 120 of an absorbent core. FIGS. 30B, 30D and 30F illustrate schematically how attachment zones may be provided by attaching the top core wrap sheet 110 to the bottom core wrap sheet 120 in the corresponding embodiments of FIGS. 30A, 30C and 30E. FIG. 30A illustrates an embodiment wherein a separate top core wrap sheet 110 and separate bottom core wrap sheet 120 are provided and wherein between the top core wrap sheet 110 and bottom core wrap sheet 120 absorbent material 105 is present. FIG. 30B illustrates the embodiment of FIG. 30A wherein the top core wrap sheet 110 is attached to the bottom core wrap sheet 120 at attachment 140. This corresponds with the embodiments as illustrated in FIGS. 3C and 3D. FIG. 30C illustrates an embodiment wherein first core wrap sheet 110 is used in combination with a second core wrap sheet 120 wherein the second core wrap sheet 120 comprises a fibrous substrate layer 120*a* and absorbent material 105*a* embedded within the fibers 105*b* of substrate layer 120*a*. In other words, in the embodiment of FIG. 30B the absorbent material is an integral part of the second core wrap sheet 120. It is clear to the skilled person that the first core wrap sheet 110 may correspond to the top core wrap sheet and the second core wrap sheet 120 may correspond to the bottom core wrap sheet, or vice versa. FIG. 30D illustrates the embodiment of FIG. 30C wherein the top core wrap sheet 110 is attached to the bottom core wrap sheet 120 at attachment 140. FIG. 30E illustrates an embodiment wherein the top core wrap sheet 110 and bottom core wrap sheet 120 are made of one piece of sheet material. In other words, the top core wrap sheet 110 is formed integrally with the bottom core wrap sheet 120. The piece of sheet material 110, 120 is wrapped around the absorbent material 105 such that an upper portion of the sheet material can be considered to be the top core wrap sheet 110 and a bottom portion of the sheet material can be considered to be the bottom core wrap sheet 120. FIG. 30F illustrates the embodiment of FIG. 30E wherein the top core wrap sheet 110 is attached to the bottom core wrap sheet 120 at attachment 140. Preferably the attachment 140 between the top core wrap sheet 110 and the bottom core wrap sheet 120 is realized by any one of the following or a combination thereof: pressure bonding, thermo-bonding, sonic bonding, chemical bonding, adhesive, mechanical bonding. It is clear to the skilled person, that when attachment zones are described within this disclosure, the attachment between the top core wrap sheet and back core wrap sheet may be interpreted to be formed according to any one of the above described embodiments or combinations thereof.

Figure 31A:
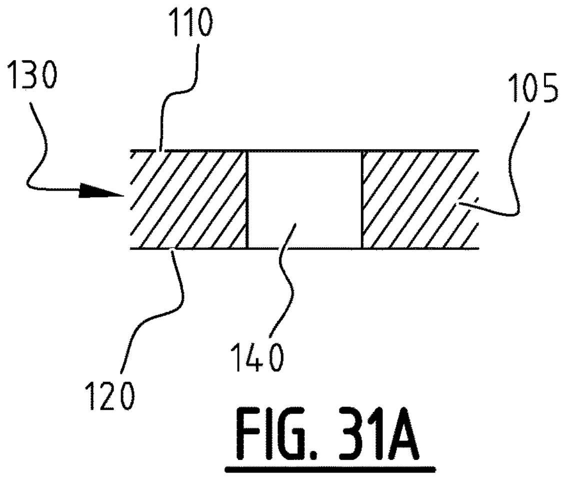
FIGS. 31A-31D schematically illustrate different embodiments of a channel zone in an absorbent core.
Figure 31B:
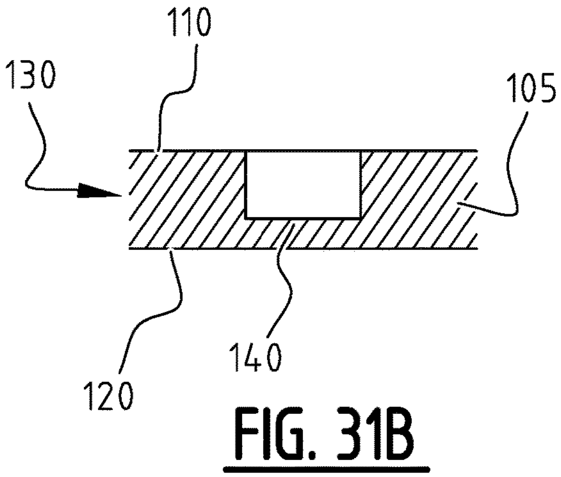
Figure 31C:
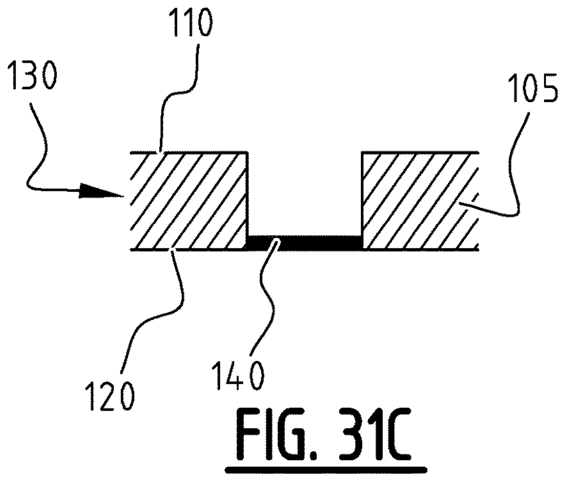
Figure 31D:
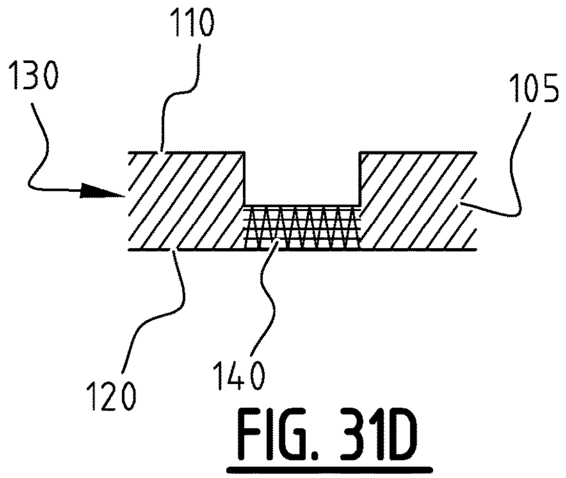

FIGS. 31A, 31B, 31C and 31D illustrate different embodiments of a channel zone 140 in an absorbent core 130, wherein absorbent material 105 is present between a top core wrap sheet 110 and a bottom core wrap sheet 120. FIG. 31A illustrates an embodiment wherein substantially no absorbent material 105 is present in or at the channel zone 140, and wherein the top core wrap sheet 110 is not attached to the bottom core wrap sheet 120 in the channel zone 140. FIG. 31B illustrates an embodiment wherein less absorbent material 105 is present in or at the channel zone 140 as compared to other regions of the absorbent core 130, and wherein the top core wrap sheet 110 is not attached to the bottom core wrap sheet 120 in the channel zone 140. For the sake of completeness it is noted that FIGS. 31A and 31B merely are schematic illustrations, and that although the top core wrap sheet 110 is drawn as a straight line at the position of the channel zone 140, it is clear to the skilled person that the top core wrap sheet 110 may be slightly curved towards the bottom core wrap sheet 120 at the location of the channel zone 140 wherein less or substantially no absorbent material is present. FIG. 31C illustrates an embodiment wherein substantially no absorbent material 105 is present in or at the channel zone 140, and wherein the channel zone 140 is an attachment zone 140 wherein the top core wrap sheet 110 is attached to the bottom core wrap sheet 120 in the channel zone 140. This attachment zone may be a permanent attachment zone or a semi-permanent attachment zone. FIG. 31D illustrates an embodiment wherein less absorbent material 105 is present in or at the channel zone 140, and wherein the channel zone 140 is an attachment zone 140 wherein the top core wrap sheet 110 is attached to the bottom core wrap sheet 120 in the channel zone 140. This attachment zone may be a permanent attachment zone or a semi-permanent attachment zone.

The majority of the embodiments as illustrated in the figures and described in the description correspond to embodiments wherein one or more channel zones are described as being attachment zones, wherein the top core wrap sheet is attached to the bottom core wrap sheet at the location of the one or more attachment zones. However, it is clear to the skilled person that in these embodiments the attachment zones may be replaced by any one of the channel zones as illustrated in FIGS. 31A-31D without departing from the scope of the invention.

Whilst the principles of the invention have been set out above in connection with specific embodiments, it is to be understood that this description is merely made by way of example and not as a limitation of the scope of protection which is determined by the appended claims.

The invention claimed is:

1. An absorbent core having a length, the absorbent core comprising an absorbent material between a top core wrap sheet and a back core wrap sheet, said absorbent core having a first and second longitudinal edge and a first and second transverse edge, wherein the first transverse edge is a front edge intended to be positioned at a front side of a person, and the second transverse edge is a rear edge intended to be positioned at a rear side of a person;

wherein the absorbent core has a front portion near said front edge, a rear portion near said rear edge and a crotch portion in between said front portion and said rear portion;

wherein the crotch portion constitutes about 50% of the length of the absorbent core;

wherein the absorbent core is provided with an elongated channel zone;

wherein said elongated channel zone is formed by an elongated attachment zone where the top core wrap sheet is attached to the back core wrap sheet and wherein substantially no absorbent material is present at the elongated attachment zone between the top core wrap sheet and the back core wrap sheet;

wherein said elongated attachment zone has a length that is larger than 30% of the length of the absorbent core and wherein said elongated attachment zone has a first width at a first position and a second width at a second position, wherein the first width is 10% larger than the second width;

wherein the second position is in the crotch portion of the absorbent core and wherein the first position is in the front portion of the absorbent core;

wherein the width and the length are measured between outer boundaries of the elongated attachment zone; and wherein the elongated attachment zone is formed by a continuous attachment zone;

wherein said absorbent material is disposed adjacent said elongated channel zone such that, as seen from a top view, the elongated channel zone is entirely surrounded by said absorbent material.

2. The absorbent core according to claim 1, wherein the width of said elongated attachment zone increases from the second position to the first position; and wherein the first position is at a first longitudinal outermost end of the elongated attachment zone and the second position is at a second longitudinal outermost end of the elongated attachment zone.

3. The absorbent core according to claim 2, wherein the width of said elongated attachment zone is measured perpendicularly to a center line of the elongated attachment zone; preferably the center line of the channel zone is a straight line, or a curve, or a polyline; and wherein the first longitudinal outermost and the second longitudinal outermost end are surrounded by absorbent material.

4. The absorbent core according to claim 2, wherein the distance between the first position at the first longitudinal outermost end and the second position at the second longitudinal outermost end, as measured along a center line of the channel zone is larger than 40% of the length of the absorbent core.

5. The absorbent core according to claim 1, wherein said channel zone is further configured for liquid distribution and further has a third width at a third position, wherein the second position is located between the first position and the third position, wherein the third width is larger than the second width, and the width of the attachment zone increases from the second position to the third position, wherein said third position is in the rear portion.

6. The absorbent core of claim 1, wherein the elongated attachment zone is asymmetrical with respect to a transversal centre line of the article, wherein a contour of said elongated attachment zone is adjacent to absorbent material; wherein the elongated attachment zone is formed by a continuous attachment zone; and wherein the absorbent material is present along the whole contour of the elongated attachment.

7. An absorbent article comprising a liquid pervious topsheet, a liquid impervious backsheet, and the absorbent core according to claim 1.

8. The absorbent core of claim 1, wherein the first width is at least 3 mm and the second width is at least 2 mm.

9. The absorbent core of claim 1, wherein said elongated attachment zone having said first and second width is a permanent attachment zone which remains attached when wetted.

10. The absorbent core according to claim 1, wherein the absorbent core is provided with a further elongated channel zone, wherein said elongated channel zone and said further elongated channel zone extend next to each other from the crotch portion in the direction of the first and/or the second transverse edge.

11. The absorbent core according to claim 10, wherein the elongated channel zone is connected to the further elongated channel zone through at least one semi-permanent channel zone, preferably extending in a transverse direction, wherein said semi-permanent channel zone connects the elongated channel zone and the further elongated channel zone so as to allow a liquid mass flow between said elongated channel zone and the further elongated channel zone.

12. The absorbent core according to claim 10, wherein the elongated channel zone is connected to the further elongated channel zone through at least a permanent or semi-permanent attached channel zone as a bridge zone, wherein said bridge zone connects the elongated channel zone and the further elongated channel zone so as to allow a liquid mass flow between the elongated channel zone and the further elongated channel zone; and wherein said further elongated channel has a further first width at a further first position in the front region and a further second width at a further second position in the crotch region, wherein the further first width is larger than the further second width;

wherein the bridge zone connects the second position of the elongated channel zone to the second position of the further elongated channel zone.

13. The absorbent core according to claim 1, wherein a contour of the elongated attachment zone is adjacent to absorbent material and wherein said elongated attachment zone is continuous to allow continuous liquid distribution throughout the elongated channel zone;

wherein the first position is at a first end of the attachment zone and wherein the channel zone further has a third width at a third position, wherein the third position is at a second end of the attachment zone, wherein the second position is located between the first position and the third position, wherein the third width is larger than the second width.

14. An absorbent core comprising an absorbent material between a top core wrap sheet and a back core wrap sheet, said absorbent core having a first and second longitudinal edge and a first and second transverse edge, wherein the absorbent core is provided with an elongated channel zone having a center line, wherein said elongated channel zone has a first width at a first position that is a first end of said channel zone and a second width at a second position that is a second end of said channel zone;

wherein said first width and said second width of said channel zone are measured perpendicularly to the center line of said channel zone; and wherein the elongated channel zone is formed by a continuous attachment zone with substantially no absorbent material present between the top core wrap sheet and the back core wrap sheet; and wherein the width of said channel zone increases from said second position to said first position such that the first width is larger than the second width, wherein the first transverse edge is a front edge intended to be positioned at a front side of a person, and the second transverse edge is a rear edge intended to be positioned at a rear side of a person;

wherein the absorbent core has a front portion near said front edge, a rear portion near said rear edge and a crotch portion in between said front portion and said rear portion;

wherein the second position is in the crotch portion of the absorbent core and wherein the first position is in the front portion of the absorbent core.

* * * * *